US012767705B2

(12) United States Patent
Liu et al.

(10) Patent No.: US 12,767,705 B2
(45) Date of Patent: Oct. 20, 2026

(54) ANTIGEN BINDING PROTEINS TO CLASS 5 ETEC ADHESINS

(71) Applicant: United States of America as Represented by the Secretary of the Navy, Silver Spring, MD (US)

(72) Inventors: Yang Liu, North Potomac, MD (US); Stephen Savarino, Saylorsburg, PA (US)

(73) Assignee: United States of America as Represented by the Secretary of the Navy, Silver Spring, MD (US)

( * ) Notice: Subject to any disclaimer, the term of this patent is extended or adjusted under 35 U.S.C. 154(b) by 1057 days.

(21) Appl. No.: 17/915,870

(22) PCT Filed: Mar. 31, 2021

(86) PCT No.: PCT/US2021/025254
§ 371 (c)(1),
(2) Date: Sep. 29, 2022

(87) PCT Pub. No.: WO2021/202798
PCT Pub. Date: Oct. 7, 2021

(65) Prior Publication Data

US 2023/0192824 A1 Jun. 22, 2023

Related U.S. Application Data

(60) Provisional application No. 63/004,002, filed on Apr. 2, 2020.

(51) Int. Cl.
*C07K 16/1232* (2026.01)
*A61P 31/04* (2006.01)
*G01N 33/569* (2006.01)
*A61K 39/00* (2006.01)

(52) U.S. Cl.
CPC .......... *C07K 16/1232* (2013.01); *A61P 31/04* (2018.01); *G01N 33/56916* (2013.01); *A61K 39/00* (2013.01); *C07K 2317/21* (2013.01); *C07K 2317/24* (2013.01); *C07K 2317/33* (2013.01); *C07K 2317/622* (2013.01); *C07K 2317/92* (2013.01); *G01N 2333/245* (2013.01); *G01N 2469/10* (2013.01)

(58) Field of Classification Search
None
See application file for complete search history.

(56) References Cited

U.S. PATENT DOCUMENTS

2014/0127209 A1* 5/2014 Grabstein ............... A61P 19/02
530/387.3
2024/0067720 A1* 2/2024 Liu .......................... A61K 9/19

FOREIGN PATENT DOCUMENTS

WO WO-2020097627 A1 * 5/2020 .............. A61P 31/04

OTHER PUBLICATIONS

Seo et al (Plos One, 14(5):e0216076:1-16, 2019).*
Lloyd et al (Protein Engineering, Design & Selection, 22:159-168, 2009).*
Edwards et al (J Mol Biol, 14;334(1):103-118, 2003).*
Almagro et al (Frontiers in Immunology (2018) 8: 1751, pp. 1-19).*
Sela-Culang et al (Frontiers in Immunology (2013) 4: 302, pp. 1-13).*
Ni (The Protein Journal (2024) 43: 683-696).*

* cited by examiner

*Primary Examiner* — Brad Duffy
(74) *Attorney, Agent, or Firm* — Ning Yang; Anthony Vu

(57) ABSTRACT

Antigen binding proteins that interact with class 5 ETEC adhesins, compositions comprising said antigen binding proteins, and methods of preventing or treating ETEC related disorders in a subject in need thereof comprising administering to said subject a therapeutically effective amount of one or more of said compositions are described.

9 Claims, 98 Drawing Sheets

Specification includes a Sequence Listing.

anti-CotD mAb P12A2

FIG. 9

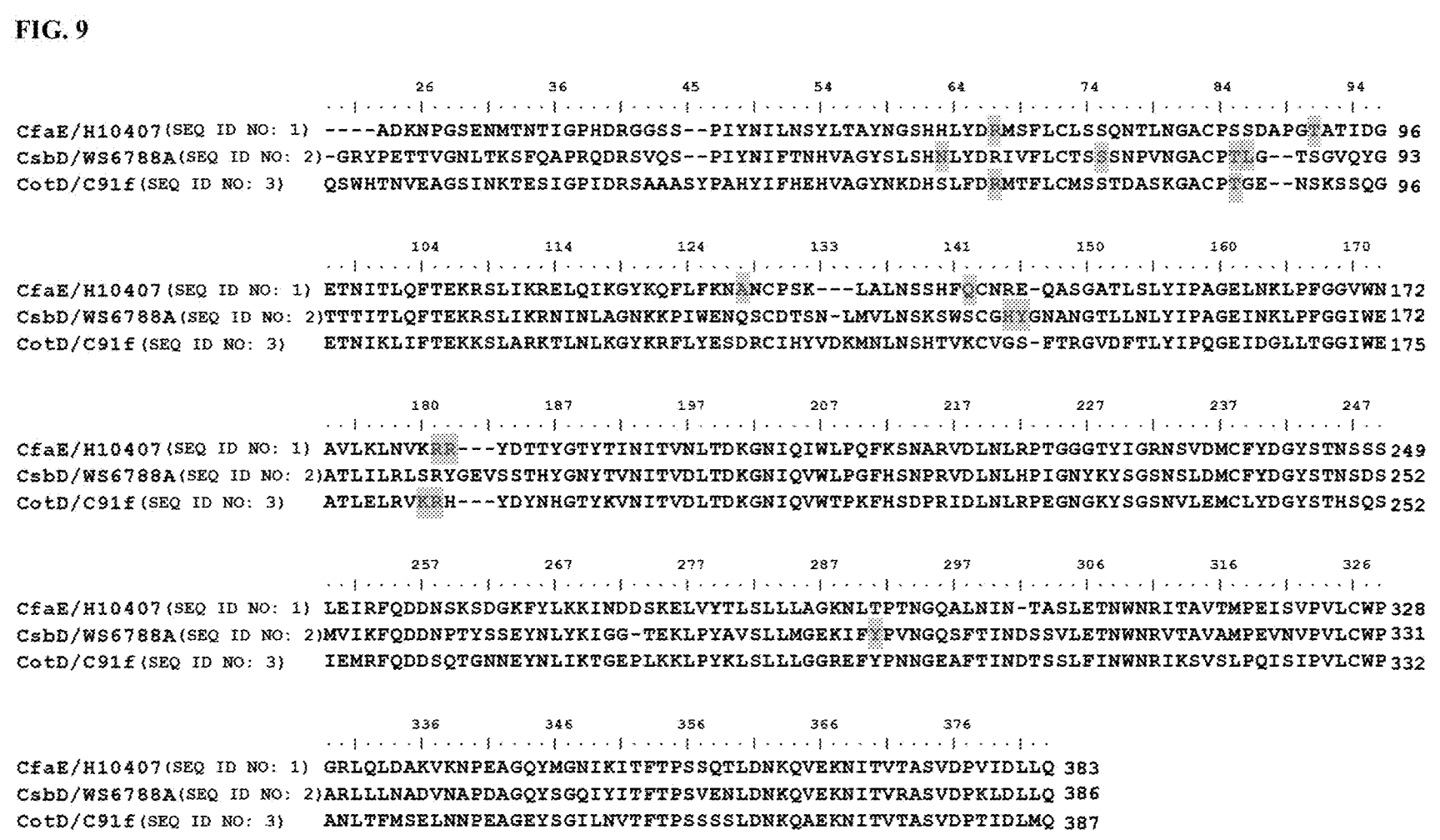

```
                                               26        36        45        54        64        74        84        94
                                            ..|....|....|....|....|....|....|....|....|....|....|....|....|....|....|..
CfaE/H10407(SEQ ID NO: 1) ----ADKNPGSENMTNTIGPHDRGGSS--PIYNILNSYLTAYNGSHHLYD[illegible]MSFLCLSSQNTLNGACPSSDAPG[illegible]ATIDG 96
CsbD/WS6788A(SEQ ID NO: 2)-GRYPETTVGNLTKSFQAPRQDRSVQS--PIYNIFTNHVAGYSLSH[illegible]LYDRIVFLCTS[illegible]SNPVNGACP[illegible][illegible]G--TSGVQYG 93
CotD/C91f(SEQ ID NO: 3)   QSWHTNVEAGSINKTESIGPIDRSAAASYPAHYIFHEHVAGYNKDHSLFD[illegible]MTFLCMSSTDASKGACP[illegible]GE--NSKSSQG 96

                                              104       114       124       133       141       150       160       170
                                            ..|....|....|....|....|....|....|....|....|....|....|....|....|....|..
CfaE/H10407(SEQ ID NO: 1) ETNITLQFTEKRSLIKRELQIKGYKQFLFKN[illegible]NCPSK---LALNSSHF[illegible]CNRE-QASGATLSLYIPAGELNKLPFGGVWN 172
CsbD/WS6788A(SEQ ID NO: 2)TTTITLQFTEKRSLIKRNINLAGNKKPIWENQSCDTSN-LMVLNSKSWSCG[illegible][illegible]GNANGTLLNLYIPAGEINKLPFGGIWE 172
CotD/C91f(SEQ ID NO: 3)   ETNIKLIFTEKKSLARKTLNLKGYKRFLYESDRCIHYVDKMNLNSHTVKCVGS-FTRGVDFTLYIPQGEIDGLLTGGIWE 175

                                              180       187       197       207       217       227       237       247
                                            ..|....|....|....|....|....|....|....|....|....|....|....|....|....|..
CfaE/H10407(SEQ ID NO: 1) AVLKLNVK[illegible][illegible]---YDTTYGTYTINITVNLTDKGNIQIWLPQFKSNARVDLNLRPTGGGTYIGRNSVDMCFYDGYSTNSSS 249
CsbD/WS6788A(SEQ ID NO: 2)ATLILRLSRYGEVSSTHYGNYTVNITVDLTDKGNIQVWLPGFHSNPRVDLNLHPIGNYKYSGSNSLDMCFYDGYSTNSDS 252
CotD/C91f(SEQ ID NO: 3)   ATLELRV[illegible][illegible]H---YDYNHGTYKVNITVDLTDKGNIQVWTPKFHSDPRIDLNLRPEGNGKYSGSNVLEMCLYDGYSTHSQS 252

                                              257       267       277       287       297       306       316       326
                                            ..|....|....|....|....|....|....|....|....|....|....|....|....|....|..
CfaE/H10407(SEQ ID NO: 1) LEIRFQDDNSKSDGKFYLKKINDDSKELVYTLSLLLAGKNLTPTNGQALNIN-TASLETNWNRITAVTMPEISVPVLCWP 328
CsbD/WS6788A(SEQ ID NO: 2)MVIKFQDDNPTYSSEYNLYKIGG-TEKLPYAVSLLMGEKIF[illegible]PVNGQSFTINDSSVLETNWNRVTAVAMPEVNVPVLCWP 331
CotD/C91f(SEQ ID NO: 3)   IEMRFQDDSQTGNNEYNLIKTGEPLKKLPYKLSLLLGGREFYPNNGEAFTINDTSSLFINWNRIKSVSLPQISIPVLCWP 332

                                              336       346       356       366       376
                                            ..|....|....|....|....|....|....|....|....|....|..
CfaE/H10407(SEQ ID NO: 1) GRLQLDAKVKNPEAGQYMGNIKITFTPSSQTLDNKQVEKNITVTASVDPVIDLLQ 383
CsbD/WS6788A(SEQ ID NO: 2)ARLLLNADVNAPDAGQYSGQIYITFTPSVENLDNKQVEKNITVRASVDPKLDLLQ 386
CotD/C91f(SEQ ID NO: 3)   ANLTFMSELNNPEAGEYSGILNVTFTPSSSSLDNKQAEKNITVTASVDPTIDLMQ 387
```

FIG. 12(A)

$dsc_{19}$CfaE6xhis (H10407)

Signal sequence-mature protein-*tag from vector*

ATGAATAAAATTTTATTTATTTTTACATTGTTTTTTTCTTCAGGGTTTTTTACATTTGCCGTATCGGCAGATAAAAA
TCCCGGAAGTGAAAACATGACTAATACTATTGGTCCCCATGACAGGGGGGGATCTTCCCCCATATATAATATCTTAAATT
CCTATCTTACAGCATACAATGGAAGCCATCATCTGTATGATAGGATGAGTTTTTATGTTTGTCTTCTCAAAATACACTG
AATGGAGCATGCCCAAGCAGTGATGCCCCTGGCACTGCTACAATTGATGGCGAAACAAATATAACATTACAATTTACGG
AAAAAAGAAGTCTAATTAAAAGAGAACTGCAAATTAAAGGCTATAAACAATTTTTGTTCAAAAATGCTAATTGCCCATC
TAAACTAGCACTTAACTCATCTCATTTTCAATGTAATAGAGAACAAGCTTCAGGTGCTACTTTATCGTTATACATACCAG
CTGGTGAATTAAATAAATTACCTTTTGGGGGGGTCTGGAATGCCGTTCTGAAGCTAAATGTAAAAAGACGATATGATAC
AACCTATGGGACTTACACTATAAACATCACAGTTAATTTAACTGATAAGGGAAATATTCAGATATGGTTACCACAGTTC
AAAAGTAACGCTCGTGTCGATCTTAACTTGCGTCCAACTGGTGGTGGTACATATATCGGAAGAAATTCTGTTGATATGTG
CTTTTATGATGGATATAGTACTAACAGCAGCTCTTTAGAGATAAGATTTCAGGATGATAATTCTAAATCTGATGGAAAAT
TTTATCTAAAGAAAATAAATGATGACTCCAAAGAACTTGTATACACTTTGTCACTTCTCCTGGCAGGTAAAAATTTAACA
CCAACAAATGGACAGGCATTAAATATTAACACTGCTTCTCTGGAAACAAACTGGAATAGAATTACAGCTGTCACCATGC
CAGAAATCAGTGTTCCGGTGTTGTGTTGGCCTGGACGTTTGCAATTGGATGCAAAAGTGAAAAATCCCGAGGCTGGACA
ATATATGGGGAATATTAAAATTACTTTCACACCAAGTAGTCAAACACTCGACAATAAACAAGTAGAGAAAAATATTACT
GTAACAGCTAGTGTTGATCCTGTGATTGATCTTTTGCAA*CTCGAGCACCACCACCACCACCACTGA* (SEQ ID NO: 4)

MNKILFIFTLFFSSGFFTFAVSADKNPGSENMTNTIGPHDRGGSSPIYNILNSYLTAYNGSHHLYDRMSFLCLSSQNTLNGAC
PSSDAPGTATIDGETNITLQFTEKRSLIKRELQIKGYKQFLFKNANCPSKLALNSSHFQCNREQASGATLSLYIPAGELNKLPFG
GVWNAVLKLNVKRRYDTTYGTYTINITVNLTDKGNIQIWLPQFKSNARVDLNLRPTGGGTYIGRNSVDMCFYDGYSTNSSS
LEIRFQDDNSKSDGKFYLKKINDDSKELVYTLSLLLAGKNLTPTNGQALNINTASLETNWNRITAVTMPEISVPVLCWPGRLQ
LDAKVKNPEAGQYMGNIKITFTPSSQTLDNKQVEKNITVTASVDPVIDLLQ*LEHHHHHH* (SEQ ID NO: 5)

FIG. 12(B)

dsc$_{19}$CsbD6xhis (WS6788A)

Signal sequence-mature protein-*tag from vector*

ATGAAAAAGATATTTATTTTTTTGTCTATCATATTTTCTGCGGTGGTCAGTGCCGGGCGATACCCGGAAACTACAG
TAGGTAATCTGACGAAGAGTTTTCAAGCCCCTCGTCAGGATAGAAGCGTACAATCACCAATATATAACATCTTTACGAA
TCATGTGGCTGGATATAGTTTGAGTCATAACTTATATGACAGGATTGTTTTTTATGTACATCCTCGTCGAATCCGGTTA
ATGGTGCTTGCCCAACCCTTGGAACATCTGGAGTTCAATACGGTACTACAACCATAACCTTGCAGTTTACAGAAAAAAG
AAGTCTGATAAAAAGAAATATTAATCTTGCAGGTAATAAGAAACCAATATGGGAGAATCAGAGTTGCGACACTAGCAA
TCTAATGGTGTTGAATTCGAAGTCTTGGTCCTGTGGGCATTACGGAAATGCTAACGGAACACTTCTAAATCTGTATATC
CCTGCAGGAGAAATCAACAAATTGCCTTTTGGAGGGATATGGGAGGCAACTCTGATCTTACGCTTATCAAGATATGGCG
AAGTCAGTAGCACCCATTACGGCAATTATACCGTAAATATTACGGTTGATTTAACTGATAAAGGTAATATTCAGGTATG
GCTTCCAGGGTTTCACAGCAACCCGCGTGTAGACCTGAATCTGCACCCTATCGGTAATTATAAATATAGTGGTAGTAAT
TCACTCGACATGTGTTTCTATGATGGATATAGTACAAACAGTGATAGCATGGTAATAAAGTTCCAGGATGATAATCCTA
CCTATTCATCTGAATATAATCTTTATAAGATAGGGGGCACTGAAAAATTACCATATGCTGTTTCACTGCTTATGGGAGA
AAAAATATTTTATCCAGTGAATGGTCAATCATTTACTATCAATGACAGTAGTGTACTCGAAACAAACTGGAATCGAGTA
ACCGCAGTTGCTATGCCGGAAGTTAATGTTCCAGTATTATGCTGGCCAGCAAGATTGCTATTAAATGCTGATGTAAATG
CTCCCGATGCAGGACAGTATTCAGGACAGATATATATAACATTTACACCCAGTGTCGAAAATTTAGACAATAAACAAG
TCGAAAAAAATATTACTGTGAGGGCAAGTGTTGACCCTAAACTTGATCTTCTGCAA*CTCGAGCACCACCACCACCACCAC*
*TGA* (SEQ ID NO: 6)

MKKIFIFLSIIFSAVVSAGRYPETTVGNLTKSFQAPRQDRSVQSPIYNIFTNHVAGYSLSHNLYDRIVFLCTSSSNPVNGACPT
LGTSGVQYGTTTITLQFTEKRSLIKRNINLAGNKKPIWENQSCDTSNLMVLNSKSWSCGHYGNANGTLLNLYIPAGEINKLPF
GGIWEATLILRLSRYGEVSSTHYGNYTVNITVDLTDKGNIQVWLPGFHSNPRVDLNLHPIGNYKYSGSNSLDMCFYDGYSTN
SDSMVIKFQDDNPTYSSEYNLYKIGGTEKLPYAVSLLMGEKIFYPVNGQSFTINDSSVLETNWNRVTAVAMPEVNVPVLCWP
ARLLLNADVNAPDAGQYSGQIYITFTPSVENLDNKQVEKNITVRASVDPKLDLLQ*LEHHHHHH* (SEQ ID NO: 7)

FIG. 12(C) dsc$_{19}$CotD6xhis (C91f)

Signal sequence-mature protein-*tag from vector*

ATGAAAAAAGTGATTTTTGTTTTATCCATGTTTCTATGTTCTCAGGTTTACGGGCAATCATGGCATACGAACGTAG
AGGCTGGTTCAATAAATAAAACAGAGTCGATAGGCCCCATAGACCGAAGTGCTGCTGCATCGTATCCTGCTCATTATAT
ATTTCATGAACATGTTGCTGGTTACAATAAAGATCACTCTCTTTTTGACAGGATGACGTTTTTATGTATGTCATCAACAG
ATGCATCTAAAGGTGCATGTCCGACAGGAGAAAACTCCAAATCCTCTCAAGGGGAGACTAATATTAAGCTAATATTTA
CTGAAAAGAAAAGTCTGGCCAGAAAAACATTAAACTTAAAAGGATATAAGAGATTTTTATATGAATCAGATAGATGCA
TTCATTATGTCGATAAAATGAATCTCAATTCTCATACTGTTAAATGTGTAGGTTCATTCACAAGAGGAGTAGATTTCACT
TTATATATCCCACAAGGTGAAATTGATGGGCTTCTAACTGGAGGTATATGGGAGGCAACACTAGAGTTACGAGTCAAA
AGGCATTACGACTATAATCATGGTACTTACAAAGTTAATATCACAGTTGATTTGACAGACAAAGGAAATATTCAGGTCT
GGACACCAAAGTTTCATAGCGATCCTAGAATTGATCTGAATTTACGTCCTGAAGGTAATGGTAAATATTCTGGTAGTAA
CGTGCTTGAGATGTGTCTCTATGATGGCTATAGTACACATAGTCAAAGTATAGAAATGAGGTTTCAGGATGACTCACAA
ACAGGAAATAATGAATATAATCTTATAAAAACTGGAGAGCCATTAAAAAAATTGCCATATAAACTTTCTCTTCTTTTAG
GAGGACGAGAGTTTTATCCAAATAATGGAGAGGCTTTTACTATTAATGATACTTCGTCATTGTTTATAAACTGGAATCG
TATTAAGTCTGTATCCTTACCACAGATTAGTATTCCAGTACTATGCTGGCCAGCAAACTTGACATTTATGTCAGAGCTAA
ATAATCCAGAAGCGGGTGAGTATTCAGGAATACTTAACGTAACATTTACTCCTAGTAGTTCAAGTCTGGACAATAAACA
AGCCGAGAAAAATATCACTGTAACTGCTAGCGTTGATCCAACTATCGATCTGATGCAA*CTCGAGCACCACCACCACCACC*
*ACTGA* (SEQ ID NO: 8)

MKKVIFVLSMFLCSQVYGQSWHTNVEAGSINKTESIGPIDRSAAASYPAHYIFHEHVAGYNKDHSLFDRMTFLCMSSTDAS
KGACPTGENSKSSQGETNIKLIFTEKKSLARKTLNLKGYKRFLYESDRCIHYVDKMNLNSHTVKCVGSFTRGVDFTLYIPQGE
IDGLLTGGIWEATLELRVKRHYDYNHGTYKVNITVDLTDKGNIQVWTPKFHSDPRIDLNLRPEGNGKYSGSNVLEMCLYDG
YSTHSQSIEMRFQDDSQTGNNEYNLIKTGEPLKKLPYKLSLLLGGREFYPNNGEAFTINDTSSLFINWNRIKSVSLPQISIPVLC
WPANLTFMSELNNPEAGEYSGILNVTFTPSSSSLDNKQAEKNITVTASVDPTIDLMQ*LEHHHHHH* (SEQ ID NO: 9)

FIG. 13(A)

P8D10

Heavy chain: DNA sequence (420 bp)

Signal sequence-FR1-CDR1-FR2-CDR2-FR3-CDR3-FR4

ATGGCTTGGGTGTGGACCTTGCTATTCCTGATGGCAGCTGCCCAAAGTGCCCAAGCACAGATCCAGTTGGTGCAGTCTGGACCT
GAGCTGAAGAAGCCTGGAGAGACAGTCAAGATCTCCTGCAAGGCTTCTGGGTATACCTTCACAAACTATGGAATGAACTGG
GTGAAGCAGGCTCCAGGAAAGGGTTTAAAGTGGATGGGCTGGATAAACACCTACACTGGACAGTCAACATATGCTGATGACTT
CAAGGGACGCTTTGCCTTCTCTTTGGAAACCTCTGCCAGCACTGCCCATTTGCAGATCAGCAACCTCAAAAATGAGGACGC
GGCTACATATTTCTGTGCAAGAATGGAGTATGGTAACTACGAAAATGCTTTGGATTACTGGGGTCAAGGAACCTCAGTCACCG
TCTCCTCA (SEQ ID NO: 10)

Heavy chain: Amino acid sequence (140 aa)

Signal peptide-FR1-CDR1-FR2-CDR2-FR3-CDR3-FR4

MAWVWTLLFLMAAAQSAQAQIQLVQSGPELKKPGETVKISCKASGYTFTNYGMNWVKQAPGKGLKWMGWINTYTGQSTYADD
FKGRFAFSLETSASTAHLQISNLKNEDAATYFCARMEYGNYENALDYWGQGTSVTVSS (SEQ ID NO: 11)

Light chain: DNA sequence (381 bp)

Signal sequence-FR1-CDR1-FR2-CDR2-FR3-CDR3-FR4

ATGGAGTCACAGATTCAGGTCTTTGTATTCGTGTTTCTCTGGTTGTCTGGTGTTGACGGAGACATTGTGATGACCCAGTCTCACAA
ATTCATGTCCACATCAATAGGAGACAGGGTCAGCATCACCTGCAAGGCCAGTCAGGATGTGAGTACTGCTGTAGTCTGGTATC
AACAGAAACCAGGACACTCTCCTAAACTACTGATTTATTCGGCATCCTACCGGTACACTGGAGTCCCTGATCGCTTCACTGGC
AGTGGATCTGGGACGGATTTCACTTTCACCATCAGCAGTGTGCAGGCTGAAGACCTGGCAGTTTATTACTGTCTACAACATT
TTAGTACTCCTCGGACGTTCGGTGGAGGCACCAACCTGGAAATCAAA (SEQ ID NO: 12)

Light chain: Amino acid sequence (127 aa)

Signal peptide-FR1-CDR1-FR2-CDR2-FR3-CDR3-FR4

MESQIQVFVFVFLWLSGVDGDIVMTQSHKFMSTSIGDRVSITCKASQDVSTAVVWYQQKPGHSPKLLIYSASYRYTGVPDRFTGSGS
GTDFTFTISSVQAEDLAVYYCCLQHFSTPRTFGGGTNLEIK (SEQ ID NO: 13)

FIG. 13(B) P5C7

Heavy chain: DNA sequence (420 bp)

Signal sequence-FR1-CDR1-FR2-CDR2-FR3-CDR3-FR4

ATGGCTTGGGTGTGGACCTTGCTATTCCTGATGGCAGCTGCCCAAAGTGCCCAAGCACAGATCCAGTTGGTGCAGTCTGGACCT
GAGCTGAAGAAGCCTGGAGAGACAGTCAAGATCTCCTGCAAGGCTTCTGGGTATACCTTCACAAACTATGGAATGAACTGG
GTGAAGCAGGCTCCAGGAAAGGGTTTAAAGTGGATGGGCTGGATAAACACCTACACTGGAGAGCCAACATATACTGATGACTT
CAAGGGACGGTTTGCCTTCTCTTTGGAAACCTCTGCCAGCACTGCCTATTTGCAGATCAACAGCCTCAAAACTGAGGACAC
GGCTACATATTTCTGTGCAAGAATGGAGTATGGTAACTACGAAAATGCTATGGACTCCTGGGGTCAAGGAACCTCAGTCACCG
TCTCCTCA (SEQ ID NO: 14)

Heavy chain: Amino acid sequence (140 aa)

Signal peptide-FR1-CDR1-FR2-CDR2-FR3-CDR3-FR4

MAWVWTLLFLMAAAQSAQAQIQLVQSGPELKKPGETVKISCKASGYTFTNYGMNWVKQAPGKGLKWMGWINTYTGEPTYTDDF
KGRFAFSLETSASTAYLQINSLKTEDTATYFCARMEYGNYENAMDSWGQGTSVTVSS (SEQ ID NO: 15)

Light chain: DNA sequence (381 bp)

Signal sequence-FR1-CDR1-FR2-CDR2-FR3-CDR3-FR4

ATGGAGTCACAGATTCAGGTCTTTGTATTCGTGTTTCTCTGGTTGTCTGGTGTTGACGGAGACACTGTGATGACCCAGTCTCACA
AATTCATGTCCACATCAGTTGGAGACAGGGTCAGCATCACCTGCAAGGCCAGTCAGGATGTGAGTACTGCTGTTGTCTGGTAT
CAACAAAAACCAGGACAATCTCCTAAGCTGCTGATTTACTCGGCATCCTACCGGTACACTGGAGTCCCTGATCGCTTCACTGG
CAGTGGATCTGGGACGGATTTCACTTTCACCATCAGCAGTGTGCAGGCTGAAGACCTGGCAGTTTATTACTGTCTCCAACAT
TTTAATATTCCTCGGACGTTCGGTGGGGGCACCAAGCTGGAAATCAAA (SEQ ID NO: 16)

Light chain: Amino acid sequence (127 aa)

Signal peptide-FR1-CDR1-FR2-CDR2-FR3-CDR3-FR4
MESQIQVFVFVFLWLSGVDGDTVMTQSHKFMSTSVGDRVSITCKASQDVSTAVVWYQQKPGQSPKLLIYSASYRYTGVPDRFTGSG
SGTDFTFTISSVQAEDLAVYYCLQHFNIPRTFGGGTKLEIK (SEQ ID NO: 17)

FIG. 13(C) P9A5

Heavy chain: DNA sequence (414 bp)
Signal sequence-FR1-CDR1-FR2-CDR2-FR3-CDR3-FR4

ATGGAATGGAGCTGGATCTTTCTCTTTCTCCTGTCAGGAACTGCAGGTGTCCTCTCTGAGGTCCAATTGCAACAGTTTGGAGCTG
AGGTGGTGAAGCCTGGGGCTTCAGTGAAGATATCCTGCAAGGCTTCTGGCTACACATTCACTGACTACAACATAGACTGGG
TGAAGCAGAGCCATGGAGAGAGTCTTGAATGGATTGGAGATATTAGTCCTAATTCTGAGGGTACTACCTACAACCAGAAGTTT
AAGGGACAGGCCACATTGACTATAGACAAGTCCTCCACCACAGCCTACATGGAGCTCCGCAGCCTGACATCTGAGGACAGT
GCAGTCTATTACTGTGCAAGAGGGAGCGGGATCTGGAATGGTTTGGACTACTGGGGTCAAGGAACCTCTGTCACCGTCTCCTC
A (SEQ ID NO: 18)

Heavy chain: Amino acid sequence (138 aa)
Signal peptide-FR1-CDR1-FR2-CDR2-FR3-CDR3-FR4

MEWSWIFLFLLSGTAGVLSEVQLQQFGAEVVKPGASVKISCKASGYTFTDYNIDWVKQSHGESLEWIGDISPNSEGTTYNQKFKGQA
TLTIDKSSTTAYMELRSLTSEDSAVYYCARGSGIWNGLDYWGQGTSVTVSS (SEQ ID NO: 19)

Light chain: DNA sequence (381 bp)
Signal sequence-FR1-CDR1-FR2-CDR2-FR3-CDR3-FR4

ATGGAGTCACAGATTCAGGTCTTTGTATTCGTGTTTCTCTGGTTGTCTGGTGTTGACGGAGACATTGTGATGACCCAGTCTCACAA
ATTCATGTCCACATCAGTAGGAGACAGGGTCAGCATCACCTGCAAGGCCAGTCAGGATGTGAGTACTGCTGTAGCCTGGTATC
AACAGAAACCAGGACAATCTCCTCAATTACTGATTTATTCGTCATCCTACCGGTATGTTGGAGTCCCTGATCGCTTCACTGGC
AGTGGATCTGGGACGGACTTCACTTTCACCATCAGCAGTGTGCAGGCTGAAGACCTGGCAGTTTATTACTGTCACCAACATT
ATAGTCTCCCGTACACGTTCGGAGGGGGGACCAAGCTGGAAATAAAA (SEQ ID NO: 20)

Light chain: Amino acid sequence (127 aa)
Signal peptide-FR1-CDR1-FR2-CDR2-FR3-CDR3-FR4

MESQIQVFVFVFLWLSGVDGDIVMTQSHKFMSTSVGDRVSITCKASQDVSTAVAWYQQKPGQSPQLLIYSSSYRYVGVPDRFTGSG
SGTDFTFTISSVQAEDLAVYYCHQHYSLPYTFGGGTKLEIK (SEQ ID NO: 21)

FIG. 13(D)

P6B8

Heavy chain: DNA sequence (423 bp)
Signal sequence-FR1-CDR1-FR2-CDR2-FR3-CDR3-FR4

ATGGGCAGGCTTACTTCTTCATTCTTGCTACTGATTGTCCCTGCATATGTCCTGTCC**CAGGTTACTCTGAAAGAGTCTGGCCCTGG
GATATTGCAGCCCTCCCAGACCCTCAGTCTGACTTGTTCTTTCTCTGGGTTTTCACTGAGT**ACTTCTGGTATGGGTGTAGGCT
GGATTCGTCAGCCTTCAGGGAAGGGTCTGGAGTGGCTGTCACACATTTGGTGGGATGATGAGAAGCGCTATAACCCAGCCCTG
AAGAGC**CGACTGACAATCTCCAAGGATACCTCCAGCAACCAGGTATTCCTCAAGATCGCCAGTGTGGACACTGCAGATACT
GCCACATACTACTGTGCTCGAATAGGGGACAGGTCGGGCCACGCGGGGTTTGTTTACTGGGGCCAAGGGACTCTGGTCACTGT**
CTCTGCA (SEQ ID NO: 22)

Heavy chain: Amino acid sequence (141 aa)
Signal peptide-FR1-CDR1-FR2-CDR2-FR3-CDR3-FR4

MGRLTSSFLLLIVPAYVLSQVTLKESGPGILQPSQTLSLTCSFSGFSLSTSGMGVGWIRQPSGKGLEWLSHIWWDDEKRYNPALKS**RL
TISKDTSSNQVFLKIASVDTADTATYYCARIGDRSGHAGFVYWGQGTLVTVSA (SEQ ID NO: 23)**

Light chain: DNA sequence (381 bp)
Signal sequence-FR1-CDR1-FR2-CDR2-FR3-CDR3-FR4

ATGAGGACCCCTGCTCAGTTTCTTGGAATCTTATTACTCTGGTTTCCAGGTATCAAATGT**GACATCAAGATGACCCAGTCTCCATC
TTCCATGTATGCATCTCTAGGAGAGAGAGTCACTATCACTTGCAAGGCGAGTCAGGACATTAATAGCTATTTAAGCTGGTTCC
AGCAGAAACCAGGGAAATCTCCTAAGACCCTGATCTATCGTGCAAACAGATTGGTAGATGGGGTCCCATCAAGGTTCAGTGG
CAGTGGATCTGGGCAAGATTATTCTCTCACCATCAGCAGCCTGGAGTATGAAGATATGGGAACTTATTATTGT**CTACAGTAT
GATGAGTTTCCGTACACGTTCGGAGGGGGGACCAAGCTGGAAATAAAA (SEQ ID NO: 24)

Light chain: Amino acid sequence (127 aa)
Signal peptide-FR1-CDR1-FR2-CDR2-FR3-CDR3-FR4

MRTPAQFLGILLLWFPGIKCDIKMTQSPSSMYASLGERVTITCKASQDINSYLSWFQQKPGKSPKTLIYRANRLVD**GVPSRFSGSGSG
QDYSLTISSLEYEDMGTYYCCLQYDEFPYTFGGGTKLEIK (SEQ ID NO: 25)**

FIG. 13(E)

P7C2

Heavy chain: DNA sequence (417 bp)
Signal sequence-FR1-CDR1-FR2-CDR2-FR3-CDR3-FR4

ATGTACTTGGGACTGAACTATGTATTCATTGTTTTTCTCTTAAATGGTGTCCAGAGTGAAGTGAAGCTTGAGGAGTCTGGAGGAG
GCTTGGTGCAACCTGGAGGATCCATGAAACTCTCTTGTGCTGCCTCTGGATTCACTTTTAGTGACGCCTGGATGGACTGGGT
CCGCCAGTCTCCAGAGAAGGGGCTTGAATGGGTTGGTAAAATTAGAAGTGAAATTAATGATCATGCAACATACTATGCTGAGT
CTGTGAAAGGGAGGTTCACCATCTCAAGAGATGATTCCAAAAGTGGTGTCTACCTGCAAATGAACAACTTAAGAGCTGAAGA
CACTGGCATTTATTACTGTGCCAGGGATGGTTACTACGGTGCTATGGACTACTGGGGTCAAGGAACGTCAGTCACCGTCTCCT
CA (SEQ ID NO: 26)

Heavy chain: Amino acid sequence (139 aa)
Signal peptide-FR1-CDR1-FR2-CDR2-FR3-CDR3-FR4

MYLGLNYVFIVFLLNGVQSEVKLEESGGGLVQPGGSMKLSCAASGFTFSDAWMDWVRQSPEKGLEWVGKIRSEINDHATYYAESV
KGRFTISRDDSKSGVYLQMNNLRAEDTGIYYCARDGYYGAMDYWGQGTSVTVSS (SEQ ID NO: 27)

Light chain: DNA sequence (381 bp)
Signal sequence-FR1-CDR1-FR2-CDR2-FR3-CDR3-FR4

ATGAGGTTCCAGGTTCAGGTTCTGGGGCTCCTTCTGCTCTGGATATCAGGTGCCCAGTGTGATGTTCAGATAACCCAGTCTCCAT
CTTATCTTGCTGCATCTCCTGGAGAAACCATTACTATTAATTGCAGGTCAAATAAGAGCATTAGCAGATATTTAGCCTGGTATC
AAGAGAAACCTGGGAAAACTAATAAGCTTCTTATCTACTCTGGATCCACTTTGCAATCTGGAATTCCATCAAGGTTCAGTGGC
AGTGGATCTAATACAGATTTCACTCTCACCATCAGTAGCCTGGAGCCTGAAGATTTTGCAATGTATTACTGTCAACAGCATA
ATGAATACCCGTACACGTTCGGCTCGGGGACAAAATTGGAAATAAAA (SEQ ID NO: 28)

Light chain: Amino acid sequence (127 aa)
Signal peptide-FR1-CDR1-FR2-CDR2-FR3-CDR3-FR4

MRFQVQVLGLLLLWISGAQCDVQITQSPSYLAASPGETITINCRSNKSISRYLAWYQEKPGKTNKLLIYSGSTLQSGIPSRFSGSGSNT
DFTLTISSLEPEDFAMYYCQQHNEYPYTFGSGTKLEIK (SEQ ID NO: 29)

FIG. 13(F) P1F9

Heavy chain: DNA sequence (414 bp)
Signal sequence-FR1-CDR1-FR2-CDR2-FR3-CDR3-FR4

ATGGGATGGAGCTGTATCATCCTCTTCTTGGTATCAACAGGTACAGGTGTCCACTCCCAGGTCCAACTGCAGCAGCCTGGGGCT
GAGCTTGTGAAGCCTGGGGCTTCAGTGAAGCTGTCCTGCAAGGCTTCTGGCTACACCTTCACCAGCTACTGGATGCACTGGG
TGAGGCAGAGGCCTGGACAAGGCCTTGACTGGATCGGAGAGATTGATCCTTCTGATAGTTATATTAACTACAATCAAAAGTTC
AAGGGCAAGGCCACATTGACTGTAGACAAATCCTCCAGCACAGCCTACATGCAGCTCAGCAGCCTGACATCTGAGGACTCT
GCGGTCTATTACTGTGGAAGAAAGAGTCTGGGTGTCTCCGTGTTAGCTTACTGGGGCCAAGGGACTCCGGTCACTGTCTCTGC
A (SEQ ID NO: 30)

Heavy chain: Amino acid sequence (138 aa)
Signal peptide-FR1-CDR1-FR2-CDR2-FR3-CDR3-FR4

MGWSCIILFLVSTGTGVHSQVQLQQPGAELVKPGASVKLSCKASGYTFTSYWMHWVRQRPGQGLDWIGEIDPSDSYINYNQKFKG
KATLTVDKSSSTAYMQLSSLTSEDSAVYYCGRKSLGVSVLAYWGQGTPVTVSA (SEQ ID NO: 31)

Light chain: DNA sequence (381 bp)
Signal sequence-FR1-CDR1-FR2-CDR2-FR3-CDR3-FR4

ATGGAGTCACAGATTCAGGCATTTGTATTCGTGTTTCTCTGGTTGTCTGGTGTTGACGGAGACATTGTGATGACCCAGTCTCACA
AATTCATGTCCACATCAGTAGGAGACAGGGTCAGCATCTCCTGCACGGCCAGTCAGGATGTGAATGCTGCTGTAGCCTGGTAT
CAACAAAAACCAGGGCAATCTCCCAAACTACTGATTTACTGGGCATCCACCCGGCACACTGGAGTCCCTGATCGCTTCACAG
GCAGTGGATCTGGGACAGATTATACTCTCACCATCAGCAGTGTGCAGGCTGAAGACCTGGCACTTTATTACTGTCAGCAAC
ATTATAGCACTCCGCTCACGTTCGGTGCTGGGACCAAGCTGGAGCTGAAA (SEQ ID NO: 32)

Light chain: Amino acid sequence (127 aa)
Signal peptide-FR1-CDR1-FR2-CDR2-FR3-CDR3-FR4

MESQIQAFVFVFLWLSGVDGDIVMTQSHKFMSTSVGDRVSISCTASQDVNAAVAWYQQKPGQSPKLLIYWASTRHTGVPDRFTGSG
SGTDYTLTISSVQAEDLALYYCQQHYSTPLTFGAGTKLELK (SEQ ID NO: 33)

FIG. 14(A) P8D10

Heavy chain: DNA sequence (420 bp)

Signal sequence-FR1-CDR1-FR2-CDR2-FR3-CDR3-FR4

ATGGCTTGGGTGTGGACCTTGCTATTCCTGATGGCAGCTGCCCAAAGTGCCCAAGCACAGATCCAGTTGGTGCAGTCTGGACCT
GAGCTGAAGAAGCCTGGAGAGACAGTCAAGATCTCCTGCAAGGCTTCTGGGTATACCTTCACAAACTATGGAATGAACTGGG
TGAAGCAGGCTCCAGGAAAGGGTTTAAAGTGGATGGGCTGGATAAACACCTACACTGGACAGTCAACATATGCTGATGACTT
CAAGGGACGCTTTGCCTTCTCTTTGGAAACCTCTGCCAGCACTGCCCATTTGCAGATCAGCAACCTCAAAAATGAGGACGC
GGCTACATATTTCTGTGCAAGAATGGAGTATGGTAACTACGAAAATGCTTTGGATTACTGGGGTCAAGGAACCTCAGTCACCG
TCTCCTCA (SEQ ID NO: 34)

Heavy chain: Amino acid sequence (140 aa)

Signal peptide-FR1-CDR1-FR2-CDR2-FR3-CDR3-FR4

MAWVWTLLFLMAAAQSAQAQIQLVQSGPELKKPGETVKISCKASGYTFTNYGMNWVKQAPGKGLKWMGWINTYTGQSTYADD
FKGRFAFSLETSASTAHLQISNLKNEDAATYFCARMEYGNYENALDYWGQGTSVTVSS (SEQ ID NO: 35)

Light chain: DNA sequence (381 bp)

Signal sequence-FR1-CDR1-FR2-CDR2-FR3-CDR3-FR4

ATGGAGTCACAGATTCAGGTCTTTGTATTCGTGTTTCTCTGGTTGTCTGGTGTTGACGGAGACATTGTGATGACCCAGTCTCACAA
ATTCATGTCCACATCAATAGGAGACAGGGTCAGCATCACCTGCAAGGCCAGTCAGGATGTGAGTACTGCTGTAGTCTGGTAT
CAACAGAAACCAGGACACTCTCCTAAACTACTGATTTATTCGGCATCCTACCGGTACACTGGAGTCCCTGATCGCTTCACTG
GCAGTGGATCTGGGACGGATTTCACTTTCACCATCAGCAGTGTGCAGGCTGAAGACCTGGCAGTTTATTACTGTCTACAAC
ATTTTAGTACTCCTCGGACGTTCGGTGGAGGCACCAACCTGGAAATCAAA (SEQ ID NO: 36)

Light chain: Amino acid sequence (127 aa)

Signal peptide-FR1-CDR1-FR2-CDR2-FR3-CDR3-FR4

MESQIQVFVFVFLWLSGVDGDIVMTQSHKFMSTSIGDRVSITCKASQDVSTAVVWYQQKPGHSPKLLIYSASYRYTGVPDRFTGSG
SGTDFTFTISSVQAEDLAVYYCLQHFSTPRTFGGGTNLEIK (SEQ ID NO: 37)

FIG. 14(B) P5C7

Heavy chain: DNA sequence (420 bp)
Signal sequence-FR1-CDR1-FR2-CDR2-FR3-CDR3-FR4

ATGGCTTGGGTGTGGACCTTGCTATTCCTGATGGCAGCTGCCCAAAGTGCCCAAGCACAGATCCAGTTGGTGCAGTCTGGACCT
GAGCTGAAGAAGCCTGGAGAGACAGTCAAGATCTCCTGCAAGGCTTCTGGGTATACCTTCACAAACTATGGAATGAACTGGG
TGAAGCAGGCTCCAGGAAAGGGTTTAAAGTGGATGGGCTGGATAAACACCTACACTGGAGAGCCAACATATACTGATGACTT
CAAGGGACGGTTTGCCTTCTCTTTGGAAACCTCTGCCAGCACTGCCTATTTGCAGATCAACAGCCTCAAAACTGAGGACAC
GGCTACATATTTCTGTGCAAGAATGGAGTATGGTAACTACGAAAATGCTATGGACTCCTGGGGTCAAGGAACCTCAGTCACCG
TCTCCTCA (SEQ ID NO: 38)

Heavy chain: Amino acid sequence (140 aa)
Signal peptide-FR1-CDR1-FR2-CDR2-FR3-CDR3-FR4

MAWVWTLLFLMAAAQSAQAQIQLVQSGPELKKPGETVKISCKASGYTFTNYGMNWVKQAPGKGLKWMGWINTYTGEPTYTDDF
KGRFAFSLETSASTAYLQINSLKTEDTATYFCARMEYGNYENAMDSWGQGTSVTVSS (SEQ ID NO: 39)

Light chain: DNA sequence (381 bp)
Signal sequence-FR1-CDR1-FR2-CDR2-FR3-CDR3-FR4

ATGGAGTCACAGATTCAGGTCTTTGTATTCGTGTTTCTCTGGTTGTCTGGTGTTGACGGAGACACTGTGATGACCCAGTCTCACA
AATTCATGTCCACATCAGTTGGAGACAGGGTCAGCATCACCTGCAAGGCCAGTCAGGATGTGAGTACTGCTGTTGTCTGGTA
TCAACAAAAACCAGGACAATCTCCTAAGCTGCTGATTTACTCGGCATCCTACCGGTACACTGGAGTCCCTGATCGCTTCACT
GGCAGTGGATCTGGGACGGATTTCACTTTCACCATCAGCAGTGTGCAGGCTGAAGACCTGGCAGTTTATTACTGTCTCCAA
CATTTTAATATTCCTCGGACGTTCGGTGGGGGCACCAAGCTGGAAATCAAA (SEQ ID NO: 40)

Light chain: Amino acid sequence (127 aa)
Signal peptide-FR1-CDR1-FR2-CDR2-FR3-CDR3-FR4

MESQIQVFVFVFLWLSGVDGDTVMTQSHKFMSTSVGDRVSITCKASQDVSTAVVWYQQKPGQSPKLLIYSASYRYTGVPDRFTGS
GSGTDFTFTISSVQAEDLAVYYCLQHFNIPRTFGGGTKLEIK (SEQ ID NO: 41)

FIG.14(C) P9A5

Heavy chain: DNA sequence (414 bp)
Signal sequence-FR1-CDR1-FR2-CDR2-FR3-CDR3-FR4

ATGGAATGGAGCTGGATCTTTCTCTTTCTCCTGTCAGGAACTGCAGGTGTCCTCTCTGAGGTCCAATTGCAACAGTTTGGAGCTG AGGTGGTGAAGCCTGGGGCTTCAGTGAAGATATCCTGCAAGGCTTCTGGCTACACATTCACTGACTACAACATAGACTGGGT GAAGCAGAGCCATGGAGAGAGTCTTGAATGGATTGGAGATATTAGTCCTAATTCTGAGGGTACTACCTACAACCAGAAGTTT AAGGGACAGGCCACATTGACTATAGACAAGTCCTCCACCACAGCCTACATGGAGCTCCGCAGCCTGACATCTGAGGACAGT GCAGTCTATTACTGTGCAAGAGGGAGCGGGATCTGGAATGGTTTGGACTACTGGGGTCAAGGAACCTCTGTCACCGTCTCCTC A (SEQ ID NO: 42)

Heavy chain: Amino acid sequence (138 aa)
Signal peptide-FR1-CDR1-FR2-CDR2-FR3-CDR3-FR4

MEWSWIFLFLLSGTAGVLSEVQLQQFGAEVVKPGASVKISCKASGYTFTDYNIDWVKQSHGESLEWIGDISPNSEGTTYNQKFKGQ ATLTIDKSSTTAYMELRSLTSEDSAVYYCARGSGIWNGLDYWGQGTSVTVSS (SEQ ID NO: 43)

Light chain: DNA sequence (381 bp)
Signal sequence-FR1-CDR1-FR2-CDR2-FR3-CDR3-FR4

ATGGAGTCACAGATTCAGGTCTTTGTATTCGTGTTTCTCTGGTTGTCTGGTGTTGACGGAGACATTGTGATGACCCAGTCTCACAA ATTCATGTCCACATCAGTAGGAGACAGGGTCAGCATCACCTGCAAGGCCAGTCAGGATGTGAGTACTGCTGTAGCCTGGTAT CAACAGAAACCAGGACAATCTCCTCAATTACTGATTTATTCGTCATCCTACCGGTATGTTGGAGTCCCTGATCGCTTCACTG GCAGTGGATCTGGGACGGACTTCACTTTCACCATCAGCAGTGTGCAGGCTGAAGACCTGGCAGTTTATTACTGTCACCAAC ATTATAGTCTCCCGTACACGTTCGGAGGGGGGACCAAGCTGGAAATAAAA (SEQ ID NO: 44)

Light chain: Amino acid sequence (127 aa)
Signal peptide-FR1-CDR1-FR2-CDR2-FR3-CDR3-FR4

MESQIQVFVFVFLWLSGVDGDIVMTQSHKFMSTSVGDRVSITCKASQDVSTAVAWYQQKPGQSPQLLIYSSSYRYVGVPDRFTGSG SGTDFTFTISSVQAEDLAVYYCCHQHYSLPYTFGGGTKLEIK (SEQ ID NO: 45)

FIG. 14(D) P6B8

Heavy chain: DNA sequence (423 bp)
Signal sequence-FR1-CDR1-FR2-CDR2-FR3-CDR3-FR4

ATGGGCAGGCTTACTTCTTCATTCTTGCTACTGATTGTCCCTGCATATGTCCTGTCCCAGGTTACTCTGAAAGAGTCTGGCC
CTGGGATATTGCAGCCCTCCCAGACCCTCAGTCTGACTTGTTCTTTCTCTGGGTTTTCACTGAGTACTTCTGGTATGGGT
GTAGGCTGGATTCGTCAGCCTTCAGGGAAGGGTCTGGAGTGGCTGTCACACATTTGGTGGGATGATGAGAAGCGCTAT
AACCCAGCCCTGAAGAGCCGACTGACAATCTCCAAGGATACCTCCAGCAACCAGGTATTCCTCAAGATCGCCAGTGT
GGACACTGCAGATACTGCCACATACTACTGTGCTCGAATAGGGGACAGGTCGGGCCACGCGGGGTTTGTTTACTGGGGC
CAAGGGACTCTGGTCACTGTCTCTGCA (SEQ ID NO: 46)

Heavy chain: Amino acid sequence (141 aa)
Signal peptide-FR1-CDR1-FR2-CDR2-FR3-CDR3-FR4

MGRLTSSFLLLIVPAYVLSQVTLKESGPGILQPSQTLSLTCSFSGFSLSTSGMGVGWIRQPSGKGLEWLSHIWWDDEKRYNPAL
KSRLTISKDTSSNQVFLKIASVDTADTATYYCARIGDRSGHAGFVYWGQGTLVTVSA (SEQ ID NO: 47)

Light chain: DNA sequence (381 bp)
Signal sequence-FR1-CDR1-FR2-CDR2-FR3-CDR3-FR4

ATGAGGACCCCTGCTCAGTTTCTTGGAATCTTATTACTCTGGTTTCCAGGTATCAAATGTGACATCAAGATGACCCAGTCTC
CATCTTCCATGTATGCATCTCTAGGAGAGAGAGTCACTATCACTTGCAAGGCGAGTCAGGACATTAATAGCTATTTAAG
CTGGTTCCAGCAGAAACCAGGGAAATCTCCTAAGACCCTGATCTATCGTGCAAACAGATTGGTAGATGGGGTCCCATC
AAGGTTCAGTGGCAGTGGATCTGGGCAAGATTATTCTCTCACCATCAGCAGCCTGGAGTATGAAGATATGGGAACTT
ATTATTGTCTACAGTATGATGAGTTTCCGTACACGTTCGGAGGGGGGACCAAGCTGGAAATAAAA (SEQ ID NO: 48)

Light chain: Amino acid sequence (127 aa)
Signal peptide-FR1-CDR1-FR2-CDR2-FR3-CDR3-FR4

MRTPAQFLGILLLWFPGIKCDIKMTQSPSSMYASLGERVTITCKASQDINSYLSWFQQKPGKSPKTLIYRANRLVDGVPSRFSG
SGSGQDYSLTISSLEYEDMGTYYCLQYDEFPYTFGGGTKLEIK (SEQ ID NO: 49)

FIG. 14(E) P7C2

Heavy chain: DNA sequence (417 bp)
Signal sequence-FR1-CDR1-FR2-CDR2-FR3-CDR3-FR4

ATGTACTTGGGACTGAACTATGTATTCATTGTTTTTCTCTTAAATGGTGTCCAGAGT**GAAGTGAAGCTTGAGGAGTCTGGAGGAG
GCTTGGTGCAACCTGGAGGATCCATGAAACTCTCTTGTGCTGCCTCTGGATTCACTTTTAGTGACGCCTGGATGGACTGGGTC
CGCCAGTCTCCAGAGAAGGGGCTTGAATGGGTTGGTAAAATTAGAAGTGAAATTAATGATCATGCAACATACTATGCTGAGT
CTGTGAAAGGGAGGTTCACCATCTCAAGAGATGATTCCAAAAGTGGTGTCTACCTGCAAATGAACAACTTAAGAGCTGAAG
ACACTGGCATTTATTACTGTGCCAGGGATGGTTACTACGGTGCTATGGACTACTGGGGTCAAGGAACGTCAGTCACCGTCTCC
TCA (SEQ ID NO: 50)**

Heavy chain: Amino acid sequence (139 aa)
Signal peptide-FR1-CDR1-FR2-CDR2-FR3-CDR3-FR4

MYLGLNYVFIVFLLNGVQSEVKLEESGGGLVQPGGSMKLSCAASGFTFSDAWMDWVRQSPEKGLEWVGKIRSEINDHAT**YYAESV
KGRFTISRDDSKSGVYLQMNNLRAEDTGIYYCARDGYYGAMDYWGQGTSVTVSS (SEQ ID NO: 51)**

Light chain: DNA sequence (381 bp)
Signal sequence-FR1-CDR1-FR2-CDR2-FR3-CDR3-FR4

ATGAGGTTCCAGGTTCAGGTTCTGGGGCTCCTTCTGCTCTGGATATCAGGTGCCCAGTGT**GATGTTCAGATAACCCAGTCTCCAT
CTTATCTTGCTGCATCTCCTGGAGAAACCATTACTATTAATTGCAGGTCAAATAAGAGCATTAGCAGATATTTAGCCTGGTAT
CAAGAGAAACCTGGGAAAACTAATAAGCTTCTTATCTACTCTGGATCCACTTTGCAATCTGGAATTCCATCAAGGTTCAGTG
GCAGTGGATCTAATACAGATTTCACTCTCACCATCAGTAGCCTGGAGCCTGAAGATTTTGCAATGTATTACTGT**CAACAGCA
TAATGAATACCCGTACACGTTCGGCTCGGGGACAAAATTGGAAATAAAA (SEQ ID NO: 52)

Light chain: Amino acid sequence (127 aa)
Signal peptide-FR1-CDR1-FR2-CDR2-FR3-CDR3-FR4

MRFQVQVLGLLLLWISGAQCDVQITQSPSYLAASPGETITINCRSNKSISRYLAWYQEKPGKTNKLLIYSGSTLQS**GIPSRFSGSGSNT
DFTLTISSLEPEDFAMYYCCQQHNEYPYTFGSGTKLEIK (SEQ ID NO: 53)**

FIG.14(F) P1F9

Heavy chain: DNA sequence (414 bp)
Signal sequence-FR1-CDR1-FR2-CDR2-FR3-CDR3-FR4

ATGGGATGGAGCTGTATCATCCTCTTCTTGGTATCAACAGGTACAGGTGTCCACTCCCAGGTCCAACTGCAGCAGCCTGGGGCT
GAGCTTGTGAAGCCTGGGGCTTCAGTGAAGCTGTCCTGCAAGGCTTCTGGCTACACCTTCACCAGCTACTGGATGCACTGGG
TGAGGCAGAGGCCTGGACAAGGCCTTGACTGGATCGGAGAGATTGATCCTTCTGATAGTTATATTAACTACAATCAAAAGTTC
AAGGGCAAGGCCACATTGACTGTAGACAAATCCTCCAGCACAGCCTACATGCAGCTCAGCAGCCTGACATCTGAGGACTCT
GCGGTCTATTACTGTGGAAGAAAGAGTCTGGGTGTCTCCGTGTTAGCTTACTGGGGCCAAGGGACTCCGGTCACTGTCTCTGC
A (SEQ ID NO: 54)

Heavy chain: Amino acid sequence (138 aa)
Signal peptide-FR1-CDR1-FR2-CDR2-FR3-CDR3-FR4

MGWSCIILFLVSTGTGVHSQVQLQQPGAELVKPGASVKLSCKASGYTFTSYWMHWVRQRPGQGLDWIGEIDPSDSYINYNQKFKG
KATLTVDKSSSTAYMQLSSLTSEDSAVYYCGRKSLGVSVLAYWGQGTPVTVSA (SEQ ID NO: 55)

Light chain: DNA sequence (381 bp)
Signal sequence-FR1-CDR1-FR2-CDR2-FR3-CDR3-FR4

ATGGAGTCACAGATTCAGGCATTTGTATTCGTGTTTCTCTGGTTGTCTGGTGTTGACGGAGACATTGTGATGACCCAGTCTCACA
AATTCATGTCCACATCAGTAGGAGACAGGGTCAGCATCTCCTGCACGGCCAGTCAGGATGTGAATGCTGCTGTAGCCTGGTA
TCAACAAAAACCAGGGCAATCTCCCAAACTACTGATTTACTGGGCATCCACCCGGCACACTGGAGTCCCTGATCGCTTCACA
GGCAGTGGATCTGGGACAGATTATACTCTCACCATCAGCAGTGTGCAGGCTGAAGACCTGGCACTTTATTACTGTCAGCAA
CATTATAGCACTCCGCTCACGTTCGGTGCTGGGACCAAGCTGGAGCTGAAA (SEQ ID NO: 56)

Light chain: Amino acid sequence (127 aa)
Signal peptide-FR1-CDR1-FR2-CDR2-FR3-CDR3-FR4

MESQIQAFVFVFLWLSGVDGDIVMTQSHKFMSTSVGDRVSISCTASQDVNAAVAWYQQKPGQSPKLLIYWASTRHTGVPDRFTGS
GSGTDYTLTISSVQAEDLALYYCCQQHYSTPLTFGAGTKLELK (SEQ ID NO:57)

FIG. 15(A)

| P8D10 SEQUENCE | V-GENE and allele | Functionality | V-REGION identity % (nt) | J-GENE and allele | D-GENE and allele | AA Junction | Junction frame |
|---|---|---|---|---|---|---|---|
| $V_H$ | Musmus IGHV9-3-1*01 F | productive | 97.92% (282/288 nt) | Musmus IGHJ4*01 F | Musmus IGHD2-10*02 F | CARMEYGNYENALDYW (SEQ ID NO: 58) | in-frame |
| $V_L$ | Musmus IGKV6-17*01 F | productive | 97.49% (272/279 nt) | Musmus IGKJ1*01 F | - | CLQHFSTPRTF (SEQ ID NO: 59) | in-frame |

FIG. 15(B)

| P5C7 SEQUENCE | V-GENE and allele | Functionality | V-REGION identity% (nt) | J-GENE and allele | D-GENE and allele | AA Junction | Junction frame |
|---|---|---|---|---|---|---|---|
| $V_H$ | Musmus IGHV9-3-1*01 F | productive | 98.96% (285/288 nt) | Musmus IGHJ4*01 F | Musmus IGHD2-10*02 F | CARMEYGNYENAMDSW (SEQ ID NO: 60) | in-frame |
| $V_L$ | Musmus IGKV6-17*01 F | productive | 96.06% (268/279 nt) | Musmus IGKJ1*01 F | - | CLQHFNIPRTF (SEQ ID NO: 61) | in-frame |

FIG. 15(C)

| P9A5 SEQUENCE | V-GENE and allele | Functionality | V-REGION identity % (nt) | J-GENE and allele | D-GENE and allele | AA Junction | Junction frame |
|---|---|---|---|---|---|---|---|
| $V_H$ | Musmus IGHV1-18*01 F | productive | 91.67% (264/288 nt) | Musmus IGHJ4*01 F | Musmus IGHD1-3*01 F | CARGSGIWNGLDYW (SEQ ID NO: 62) | in-frame |
| $V_L$ | Musmus IGKV6-17*01 F | productive | 96.77% (270/279 nt) | Musmus IGKJ2*01 F | - | CHQHYSLPYTF (SEQ ID NO: 63) | in-frame |

FIG. 15(D)

| P6B8 SEQUENCE | V-GENE and allele | Functionality | V-REGION identity % (nt) | J-GENE and allele | D-GENE and allele | AA Junction | Junction frame |
|---|---|---|---|---|---|---|---|
| $V_H$ | Musmus IGHV8-8*01 F | productive | 95.88% (279/291 nt) | Musmus IGHJ3*01 F | Musmus IGHD3-1*01 F | CARIGDRSGHAGFVYW (SEQ ID NO: 64) | in-frame |
| $V_L$ | Musmus IGKV14-111*01 F | productive | 99.64% (278/279 nt) | Musmus IGKJ2*01 F | - | CLQYDEFPYTF (SEQ ID NO: 65) | in-frame |

FIG. 15(E)

| P7C2 SEQUENCE | V-GENE and allele | Functionality | V-REGION identity % (nt) | J-GENE and allele | D-GENE and allele | AA Junction | Junction frame |
|---|---|---|---|---|---|---|---|
| $V_H$ | Musmus IGHV6-6*01 F | productive | 96.26% (283/294 nt) | Musmus IGHJ4*01 F | Musmus IGHD2-3*01 F | CARDGYYGAMDYW (SEQ ID NO: 66) | in-frame |
| $V_L$ | Musmus IGKV16-104*01 F | productive | 97.85% (273/279 nt) | Musmus IGKJ4*01 F, or Musmus IGKJ4*02 F | - | CQQHNEYPYTF (SEQ ID NO: 67) | in-frame |

FIG. 15(F)

| P1F9 SEQUENCE | V-GENE and allele | Functionality | V-REGION identity % (nt) | J-GENE and allele | D-GENE and allele | AA Junction | Junction frame |
|---|---|---|---|---|---|---|---|
| $V_H$ | Musmus IGHV1-69*02 F | productive | 98.96% (285/288 nt) | Musmus IGHJ3*01 F | Musmus IGHD2-10*02 F | CGRKSLGVSVLAYW (SEQ ID NO: 68) | in-frame |
| $V_L$ | Musmus IGKV6-25*01 F | productive | 98.21% (274/279 nt) | Musmus IGKJ5*01 F | - | CQQHYSTPLTF (SEQ ID NO: 69) | in-frame |

FIG. 16(A)

Heavy chain DNA sequence (1413 base pairs)
P6B8 heavy chain signal sequence-P6B8 heavy chain variable region-human IgG1 heavy chain constant region ATGGGCAGGCTTACTTCTTCATTCTTGCTACTGATTGTCCCTGCATATGTCCTGTCCCAGGTTACTCTGAAAGAGTCTGGCCCTGG
GATATTGCAGCCCTCCCAGACCCTCAGTCTGACTTGTTCTTTCTCTGGGTTTTCACTGAGTACTTCTGGTATGGGTGTAGGC
TGGATTCGTCAGCCTTCAGGGAAGGGTCTGGAGTGGCTGTCACACATTTGGTGGGATGATGAGAAGCGCTATAACCCAGC
CCTGAAGAGCCGACTGACAATCTCCAAGGATACCTCCAGCAACCAGGTATTCCTCAAGATCGCCAGTGTGGACACTGCAGA
TACTGCCACATACTACTGTGCTCGAATAGGGGACAGGTCGGGCCACGCGGGGTTTGTTTACTGGGGCCAAGGGACTCTGG
TCACTGTCTCTGCAGCTAGCACCAAGGGCCCATCGGTCTTCCCCCTGGCACCCTCCTCCAAGAGCACCTCTGGGGGCACAGCGGC
CCTGGGCTGCCTGGTCAAGGACTACTTCCCCGAACCGGTGACGGTGTCGTGGAACTCAGGCGCCCTGACCAGCGGCGTGCACACCT
TCCCGGCTGTCCTACAGTCCTCAGGACTCTACTCCCTCAGCAGCGTGGTGACCGTGCCCTCCAGCAGCTTGGGCACCCAGACCTAC
ATCTGCAACGTGAATCACAAGCCCAGCAACACCAAGGTGGACAAGAAAGTTGAGCCCAAATCTTGTGACAAAACTCACACATGCC
CACCGTGCCCAGCACCTGAACTCCTGGCGGGACCGGACGTCTTCCTCTTCCCCCCAAAACCCAAGGACACCCTCATGATCTCCCGG
ACCCCTGAGGTCACATGCGTGGTGGTGGACGTGAGCCACGAAGACCCTGAGGTCAAGTTCAACTGGTACGTGGACGGCGTGGAGG
TGCATAATGCCAAGACAAAGCCGCGGGAGGAGCAGTACAACAGCACGTACCGTGTGGTCAGCGTCCTCACCGTCCTGCACCAGGA
CTGGCTGAATGGCAAGGAGTACAAGTGCAAGGTCTCCAACAAAGCCCTCCCAGCCCCCGAGGAGAAAACCATCTCCAAAGCCAAA
GGGCAGCCCCGAGAACCACAGGTGTACACCCTGCCCCCATCCCGGGAGGAGATGACCAAGAACCAGGTCAGCCTGACCTGCCTGG
TCAAAGGCTTCTATCCCAGCGACATCGCCGTGGAGTGGGAGAGCAATGGGCAGCCGGAGAACAACTACAAGACCACGCCTCCCGT
GCTGGACTCCGACGGCTCCTTCTTCCTCTACAGCAAGCTCACCGTGGACAAGAGCAGGTGGCAGCAGGGGAACGTCTTCTCATGCT
CCGTGATGCACGAGGCTCTGCACAACCACTACACGCAGAAGAGCCTCTCCCTGTCTCCGGGTAAA (SEQ ID NO: 70)

Heavy chain amino acid sequence (471 amino acids)

P6B8 heavy chain signal sequence-P6B8 heavy chain variable region-human IgG1 heavy chain constant region MGRLTSSFLLLIVPAYVLSQVTLKESGPGILQPSQTLSLTCSFSGFSLSTSGMGVGWIRQPSGKGLEWLSHIWWDDEKRYNPALKS
RLTISKDTSSNQVFLKIASVDTADTATYYCARIGDRSGHAGFVYWGQGTLVTVSAASTKGPSVFPLAPSSKSTSGGTAALGCLVKDY
FPEPVTVSWNSGALTSGVHTFPAVLQSSGLYSLSSVVTVPSSSLGTQTYICNVNHKPSNTKVDKKVEPKSCDKTHTCPPCPAPELLAGPDV
FLFPPKPKDTLMISRTPEVTCVVVDVSHEDPEVKFNWYVDGVEVHNAKTKPREEQYNSTYRVVSVLTVLHQDWLNGKEYKCKVSNKA
LPAPEEKTISKAKGQPREPQVYTLPPSREEMTKNQVSLTCLVKGFYPSDIAVEWESNGQPENNYKTTPPVLDSDGSFFLYSKLTVDKSRW
QQGNVFSCSVMHEALHNHYTQKSLSLSPGK (SEQ ID NO:71)

FIG. 16(B)

Light chain DNA sequence (699 base pairs)

P6B8 light chain signal sequence-P6B8 light chain variable region-human immunoglobulin kappa light chain constant region ATGAGGACCCCTGCTCAGTTTCTTGGAATCTTATTACTCTGGTTTCCAGGTATCAAATGTGACATCAAGATGACCCAGT
CTCCATCTTCCATGTATGCATCTCTAGGAGAGAGAGTCACTATCACTTGCAAGGCGAGTCAGGACATTAATAGCT
ATTTAAGCTGGTTCCAGCAGAAACCAGGGAAATCTCCTAAGACCCTGATCTATCGTGCAAACAGATTGGTAGAT
GGGGTCCCATCAAGGTTCAGTGGCAGTGGATCTGGGCAAGATTATTCTCTCACCATCAGCAGCCTGGAGTATGA
AGATATGGGAACTTATTATTGTCTACAGTATGATGAGTTTCCGTACACGTTCGGAGGGGGGACCAAGCTGGAAA
TAAAAACGGTGGCTGCACCATCTGTCTTCATCTTCCCGCCATCTGATGAGCAGTTGAAATCTGGAACTGCCTCTGTTGTG
TGCCTGCTGAATAACTTCTATCCCAGAGAGGCCAAAGTACAGTGGAAGGTGGATAACGCCCTCCAATCGGGTAACTCC
CAGGAGAGTGTCACAGAGCAGGACAGCAAGGACAGCACCTACAGCCTCAGCAGCACCCTGACGCTGAGCAAAGCAGA
CTACGAGAAACACAAAGTCTACGCCTGCGAAGTCACCCATCAGGGCCTGAGCTCGCCCGTCACAAAGAGCTTCAACAG
GGGAGAGTGT (SEQ ID NO:72)

Light chain amino acid sequence (233 amino acids)

P6B8 light chain signal sequence-P6B8 light chain variable region-human immunoglobulin kappa light chain constant region MRTPAQFLGILLLWFPGIKCDIKMTQSPSSMYASLGERVTITCKASQDINSYLSWFQQKPGKSPKTLIYRANRLVDGVPS
RFSGSGSGQDYSLTISSLEYEDMGTYYCLQYDEFPYTFGGGTKLEIKTVAAPSVFIFPPSDEQLKSGTASVVCLLNNFYPR
EAKVQWKVDNALQSGNSQESVTEQDSKDSTYSLSSTLTLSKADYEKHKVYACEVTHQGLSSPVTKSFNRGEC (SEQ ID NO:73)

FIG. 18(A)

Heavy chain DNA sequence (1410 base pairs)
P5C7 heavy chain signal sequence-P5C7 heavy chain variable region-human IgG1 heavy chain constant region ATGGCTTGGGTGTGGACCTTGCTATTCCTGATGGCAGCTGCCCAAAGTGCCCAAGCACAGATCCAGTTGGTGCAGTCTGGACCT
GAGCTGAAGAAGCCTGGAGAGACAGTCAAGATCTCCTGCAAGGCTTCTGGGTATACCTTCACAAACTATGGAATGAACTGG
GTGAAGCAGGCTCCAGGAAAGGGTTTAAAGTGGATGGGCTGGATAAACACCTACACTGGAGAGCCAACATATACTGATGA
CTTCAAGGGACGGTTTGCCTTCTCTTTGGAAACCTCTGCCAGCACTGCCTATTTGCAGATCAACAGCCTCAAAACTGAGGA
CACGGCTACATATTTCTGTGCAAGAATGGAGTATGGTAACTACGAAAATGCTATGGACTCCTGGGGTCAAGGAACCTCAGT
CACCGTCTCCTCAGCTAGCACCAAGGGCCCATCGGTCTTCCCCCTGGCACCCTCCTCCAAGAGCACCTCTGGGGGCACAGCGGCC
CTGGGCTGCCTGGTCAAGGACTACTTCCCCGAACCGGTGACGGTGTCGTGGAACTCAGGCGCCCTGACCAGCGGCGTGCACACCTT
CCCGGCTGTCCTACAGTCCTCAGGACTCTACTCCCTCAGCAGCGTGGTGACCGTGCCCTCCAGCAGCTTGGGCACCCAGACCTACA
TCTGCAACGTGAATCACAAGCCCAGCAACACCAAGGTGGACAAGAAAGTTGAGCCCAAATCTTGTGACAAAACTCACACATGCCC
ACCGTGCCCAGCACCTGAACTCCTGGCGGGACCGGACGTCTTCCTCTTCCCCCCAAAACCCAAGGACACCCTCATGATCTCCCGGA
CCCCTGAGGTCACATGCGTGGTGGTGGACGTGAGCCACGAAGACCCTGAGGTCAAGTTCAACTGGTACGTGGACGGCGTGGAGGT
GCATAATGCCAAGACAAAGCCGCGGGAGGAGCAGTACAACAGCACGTACCGTGTGGTCAGCGTCCTCACCGTCCTGCACCAGGAC
TGGCTGAATGGCAAGGAGTACAAGTGCAAGGTCTCCAACAAAGCCCTCCCAGCCCCCGAGGAGAAAACCATCTCCAAAGCCAAAG
GGCAGCCCCGAGAACCACAGGTGTACACCCTGCCCCCATCCCGGGAGGAGATGACCAAGAACCAGGTCAGCCTGACCTGCCTGGT
CAAAGGCTTCTATCCCAGCGACATCGCCGTGGAGTGGGAGAGCAATGGGCAGCCGGAGAACAACTACAAGACCACGCCTCCCGTG
CTGGACTCCGACGGCTCCTTCTTCCTCTACAGCAAGCTCACCGTGGACAAGAGCAGGTGGCAGCAGGGGAACGTCTTCTCATGCTC
CGTGATGCACGAGGCTCTGCACAACCACTACACGCAGAAGAGCCTCTCCCTGTCTCCGGGTAAA (SEQ ID NO: 74)

Heavy chain amino acid sequence (470 amino acids)

P5C7 heavy chain signal sequence-P5C7 heavy chain variable region-human IgG1 heavy chain constant region MAWVWTLLFLMAAAQSAQAQIQLVQSGPELKKPGETVKISCKASGYTFTNYGMNWVKQAPGKGLKWMGWINTYTGEPTYTDD
FKGRFAFSLETSASTAYLQINSLKTEDTATYFCARMEYGNYENAMDSWGQGTSVTVSSASTKGPSVFPLAPSSKSTSGGTAALGCLV
KDYFPEPVTVSWNSGALTSGVHTFPAVLQSSGLYSLSSVVTVPSSSLGTQTYICNVNHKPSNTKVDKKVEPKSCDKTHTCPPCPAPELLA
GPDVFLFPPKPKDTLMISRTPEVTCVVVDVSHEDPEVKFNWYVDGVEVHNAKTKPREEQYNSTYRVVSVLTVLHQDWLNGKEYKCKV
SNKALPAPEEKTISKAKGQPREPQVYTLPPSREEMTKNQVSLTCLVKGFYPSDIAVEWESNGQPENNYKTTPPVLDSDGSFFLYSKLTVD
KSRWQQGNVFSCSVMHEALHNHYTQKSLSLSPGK (SEQ ID NO:75)

FIG. 18(B)
Light chain DNA sequence (699 base pairs)

P5C7 light chain signal sequence-P5C7 light chain variable region-human immunoglobulin kappa light chain constant region ATGGAGTCACAGATTCAGGTCTTTGTATTCGTGTTTCTCTGGTTGTCTGGTGTTGACGGAGACACTGTGATGACCCAGT
CTCACAAATTCATGTCCACATCAGTTGGAGACAGGGTCAGCATCACCTGCAAGGCCAGTCAGGATGTGAGTACT
GCTGTTGTCTGGTATCAACAAAAACCAGGACAATCTCCTAAGCTGCTGATTTACTCGGCATCCTACCGGTACACT
GGAGTCCCTGATCGCTTCACTGGCAGTGGATCTGGGACGGATTTCACTTTCACCATCAGCAGTGTGCAGGCTGA
AGACCTGGCAGTTTATTACTGTCTCCAACATTTTAATATTCCTCGGACGTTCGGTGGGGGCACCAAGCTGGAAAT
CAAAACGGTGGCTGCACCATCTGTCTTCATCTTCCCGCCATCTGATGAGCAGTTGAAATCTGGAACTGCCTCTGTTGTGT
GCCTGCTGAATAACTTCTATCCCAGAGAGGCCAAAGTACAGTGGAAGGTGGATAACGCCCTCCAATCGGGTAACTCCC
AGGAGAGTGTCACAGAGCAGGACAGCAAGGACAGCACCTACAGCCTCAGCAGCACCCTGACGCTGAGCAAAGCAGAC
TACGAGAAACACAAAGTCTACGCCTGCGAAGTCACCCATCAGGGCCTGAGCTCGCCCGTCACAAAGAGCTTCAACAGG
GGAGAGTGT (SEQ ID NO:76)

Light chain amino acid sequence (233 amino acids)

P5C7 light chain signal sequence-P5C7 light chain variable region-human immunoglobulin kappa light chain constant region MESQIQVFVFVFLWLSGVDGDTVMTQSHKFMSTSVGDRVSITCKASQDVSTAVVWYQQKPGQSPKLLIYSASYRYTGV
PDRFTGSGSGTDFTFTISSVQAEDLAVYYCLQHFNIPRTFGGGTKLEIKTVAAPSVFIFPPSDEQLKSGTASVVCLLNNFYP
REAKVQWKVDNALQSGNSQESVTEQDSKDSTYSLSSTLTLSKADYEKHKVYACEVTHQGLSSPVTKSFNRGEC (SEQ ID NO:77)

FIG. 19(A)

P8D10 scFv DNA sequence (795 base pairs):

pelB leader sequence-P8D10 heavy chain variable domain-*linker sequence*-P8D10 light chain variable domain

ATGAAATACCTATTGCCTACGGCAGCCGCTGGATTGTTATTACTCGCGGCCCAGCCGGCGATGGCCCAGATCCAGTTG
GTGCAGTCTGGACCTGAGCTGAAGAAGCCTGGAGAGACAGTCAAGATCTCCTGCAAGGCTTCTGGGTATACCTT
CACAAACTATGGAATGAACTGGGTGAAGCAGGCTCCAGGAAAGGGTTTAAAGTGGATGGGCTGGATAAACACCT
ACACTGGACAGTCAACATATGCTGATGACTTCAAGGGACGCTTTGCCTTCTCTTTGGAAACCTCTGCCAGCACTG
CCCATTTGCAGATCAGCAACCTCAAAAATGAGGACGCGGCTACATATTTCTGTGCAAGAATGGAGTATGGTAAC
TACGAAAATGCTTTGGATTACTGGGGTCAAGGAACCTCAGTCACCGTCTCCTCA*GGTGGCGGTGGCAGCGGCGGC*
*GGTGGTAGCGGTGGTGGCGGCAGC*GACATTGTGATGACCCAGTCTCACAAATTCATGTCCACATCAATAGGAGACA
GGGTCAGCATCACCTGCAAGGCCAGTCAGGATGTGAGTACTGCTGTAGTCTGGTATCAACAGAAACCAGGACAC
TCTCCTAAACTACTGATTTATTCGGCATCCTACCGGTACACTGGAGTCCCTGATCGCTTCACTGGCAGTGGATCT
GGGACGGATTTCACTTTCACCATCAGCAGTGTGCAGGCTGAAGACCTGGCAGTTTATTACTGTCTACAACATTTT
AGTACTCCTCGGACGTTCGGTGGAGGCACCAACCTGGAAATCAAA (SEQ ID NO:78)

P8D10 scFv amino acid sequence (265 amino acids):

pelB leader sequence-P8D10 heavy chain variable domain-*linker sequence*-P8D10 light chain variable domain

MKYLLPTAAAGLLLLAAQPAMAQIQLVQSGPELKKPGETVKISCKASGYTFTNYGMNWVKQAPGKGLKWMGWINTY
TGQSTYADDFKGRFAFSLETSASTAHLQISNLKNEDAATYFCARMEYGNYENALDYWGQGTSVTVSS*GGGGSGGGGS*
*GGGGS*DIVMTQSHKFMSTSIGDRVSITCKASQDVSTAVVWYQQKPGHSPKLLIYSASYRYTGVPDRFTGSGSGTDFTFT
ISSVQAEDLAVYYCLQHFSTPRTFGGGTNLEIK (SEQ ID NO: 79)

FIG. 19(B)

Mouse P8D10 (VH-VL) scFv DNA sequence (795 base pairs):

pelB leader sequence-P8D10 heavy chain variable domain-*linker sequence*-P8D10 light chain variable domain

ATGAAATACCTATTGCCTACGGCAGCCGCTGGATTGTTATTACTCGCGGCCCAGCCGGCGATGGCCCAGATCCAGTTG
GTGCAGTCTGGACCTGAGCTGAAGAAGCCTGGAGAGACAGTCAAGATCTCCTGCAAGGCTTCTGGGTATACCTT
CACAAACTATGGAATGAACTGGGTGAAGCAGGCTCCAGGAAAGGGTTTAAAGTGGATGGGCTGGATAAACACCT
ACACTGGACAGTCAACCTATGCTGATGACTTCAAGGGACGCTTTGCCTTCTCTTTGGAAACCTCTGCCAGCACTG
CCCATTTGCAGATCAGCAACCTCAAAAATGAGGACGCGGCTACATATTTCTGTGCAAGAATGGAGTATGGTAAC
TACGAAAATGCTTTGGATTACTGGGGTCAAGGAACCTCAGTCACCGTCTCCTCA*GGTGGCGGTGGCAGCGGCGGC*
*GGTGGTAGCGGTGGTGGCGGCAGC*GACATTGTGATGACCCAGTCTCACAAATTCATGTCCACATCAATAGGAGACA
GGGTCAGCATCACCTGCAAGGCCAGTCAGGATGTGAGTACTGCTGTAGTCTGGTATCAACAGAAACCAGGACAC
TCTCCTAAACTACTGATTTATTCGGCATCCTACCGGTACACTGGAGTCCCTGATCGCTTCACTGGCAGTGGATCT
GGGACGGATTTCACTTTCACCATCAGCAGTGTGCAGGCTGAAGACCTGGCAGTTTATTACTGTCTACAACATTTT
AGTACTCCTCGGACGTTCGGTGGAGGCACCAACCTGGAAATCAAA (SEQ ID NO:107)

Mouse P8D10 (VH-VL) scFv amino acid sequence (265 amino acids):

pelB leader sequence-P8D10 heavy chain variable domain-*linker sequence*-P8D10 light chain variable domain

MKYLLPTAAAGLLLLAAQPAMAQIQLVQSGPELKKPGETVKISCKASGYTFTNYGMNWVKQAPGKGLKWMGWINTY
TGQSTYADDFKGRFAFSLETSASTAHLQISNLKNEDAATYFCARMEYGNYENALDYWGQGTSVTVSS*GGGGSGGGGS*
*GGGGS*DIVMTQSHKFMSTSIGDRVSITCKASQDVSTAVVWYQQKPGHSPKLLIYSASYRYTGVPDRFTGSGSGTDFTFT
ISSVQAEDLAVYYCLQHFSTPRTFGGGTNLEIK (SEQ ID NO: 108)

FIG. 26(A)

Sequence alignment of P8D10_H and 1IAI_H (88.43% identity)

```
P8D10H    QIQLVQSGPELKKPGETVKISCKASGYTFTNYGMNWVKQAPGKGLKWMGWINTYTGQSTY    60
1IAIH     QIQLVQSGPELKKPGETVKISCKASGYTFTNYGMNWVKQAPGKGLKWMAWINTYTGEPTY    60
          ***********************************************.*******: **

P8D10H    ADDFKGRFAFSLETSASTAHLQISNLKNEDAATYFCARMEYGNYENALDYWGQGTSVTVS    120
1IAIH     ADDFKGRFAFSLETSASTAYLQINNLKNEDTATYFCARDGYYENYYAMDYWGQGTSVTVS    120
          *******************:***.******:*******  *     *:************

P8D10H    S        121   (SEQ ID NO: 80)
1IAIH     S        121   (SEQ ID NO: 81)
          *
```

FIG. 26(B)

Sequence alignment of P8D10_L and 1IAI_L (89.72% identity)

```
P8D10L    DIVMTQSHKFMSTSIGDRVSITCKASQDVSTAVVWYQQKPGHSPKLLIYSASYRYTGVPD    60
1IAIL     DIVMTQSHKFMSTSVGDRVSITCKASQDVSTAVAWYQQKPGQSPKLLIYSASYQYTGVPD    60
          **************:******************.*******:***********:******

P8D10L    RFTGSGSGTDFTFTISSVQAEDLAVYYCLQHFSTPRTFGGGTNLEIK    107   (SEQ ID NO: 82)
1IAIL     RFTGSGSRTDFTFTINSVQAEDLAVYYCHQHYSTPFTFGSGTKLEIK    107   (SEQ ID NO: 83)
          ******* *******.************ **:*** ***.**:****
```

FIG. 27(A)

```
• P8D10H    QIQLVQSGPELKKPGETVKISCKASGYTFTNYGMNWVKQAPGKGLKWMGWINTYTGQSTY   60
• hIg       QVQLVQSGSELKKPGASVKVSCKASGYTFTSYAMNWVRQAPGQGLEWMGWINTNTGNPTY   60
• hIgA      QVQLVQSGSELKKPGASVKVSCKASGYTFTSYAMNWVRQAPGQGLEWMGWINTNTGNPTY   60
• hIgM      QVQLVQSGSELKKPGASVKVSCKASGYTFTSYAMNWVRQAPGQGLEWMGWINTNTGNPTY   60
•           *:****** ****** :**:**********.*.****:****:**:******* **: **
•
• P8D10H    ADDFKGRFAFSLETSASTAHLQISNLKNEDAATYFCARMEYGNYENALDYWGQGTSVTVS   120
• hIg       AQGFTGRFVFSLDTSVSTAYLQISSLKAEDTAVYYCARDVATIDENWFDPWGQGTLVTVS   120
• hIgA      AQGFTGRFVFSLDTSVSTAYLQISSLKAEDTAVYYCARV-QWFGEYFFDYWGQGTLVTVS   119
• hIgM      AQGFTGRFVFSLDTSVSTAYLQISSLKAEDTAVYYCARL-QWMGMNYFDYWGQGTLVTVS   119
•           *:.*.***.***:**.***:****.** **:*.*:***          :* ***** ****
•
• P8D10H    S     121   (SEQ ID NO: 80)
• hIg       S     121   (SEQ ID NO: 84)
• hIgA      S     120   (SEQ ID NO: 85)
• hIgM      S     120   (SEQ ID NO: 86)
            *
```

FIG. 27(B)

```
• hLkappa3    DIQMTQSPSSLSASLGDRVTITCRASQTISSYLNWYQQKPGKAPKLLIYAASTLQSGVPS   60
• hLkappa1    DIVMTQSPSSLSASVGDRVTITCRASQSISSYLNWYQQKPGKAPKLLIYAASSLQSGVPS   60
• hLkappa2    DIVMTQSPSSLSASVGDRVTITCRASQSISNYLNWYQQKPGKAPKLLIYAASSLQSGVPS   60
• P8D10L      DIVMTQSHKFMSTSIGDRVSITCKASQDVSTAVVWYQQKPGHSPKLLIYSASYRYTGVPD   60
•             ** ****  .  :*:*:****:***:***  :*. :  *******::******:**    :***.
•
• hLkappa3    RFSGSGSGTDFTLTISSLQAEDFATYYCQQSYSTPRTFGGGTKVEIK   107   (SEQ ID NO: 87)
• hLkappa1    RFSGSGSGTDFTLTISSLQPEDFATYYCQQSYSTPRTFGGGTKVEIK   107   (SEQ ID NO: 88)
• hLkappa2    RFSGSGSGTDFTLTISSLQPEDFATYYCQQSYSTPRTFGQGTKLEIK   107   (SEQ ID NO: 89)
• P8D10L      RFTGSGSGTDFTFTISSVQAEDLAVYYCLQHFSTPRTFGGGTNLEIK   107   (SEQ ID NO: 82)
•             **:*********:****:*  **:*.*** *  :******* **::***
```

pelB leader seq
Variable domain of humanized P8D10 heavy chain
linker
Variable domain of humanized P8D10 light chain
pelB leader seq
Variable domain of humanized P8D10 light chain
linker
Variable domain of humanized P8D10 heavy chain

FIG. 28(A)
QIQLVQSGSELKKPGASVKVSCKASGYTFTNYGMNWVKQAPGQGLKWMGWINTYTGQSTY
ADDFKGRFAFSLDTSVSTAYLQISSLKAEDTAVYFCARMEYGNYENALDYWGQGTLVTVSS
(SEQ ID NO: 90)
FIG. 28(B)
DIVMTQSPSSLSASVGDRVTITCKASQDVSTAVVWYQQKPGKAPKLLIYSASYRYTGVPD
RFTGSGSGTDFTLTISSLQAEDFATYYCLQHFSTPRTFGGGTKLEIK (SEQ ID NO: 91)
FIG. 28(C)
Humanized P8D10 scFv (VH-VL):
Humanized P8D10 scFv (VL-VH):

FIG. 28(D)

Humanized P8D10 scFv (VH-VL) DNA sequence (795 base pairs):

pelB leader sequence-humanized P8D10 heavy chain variable domain-*linker sequence*-humanized P8D10 light chain variable domain

ATGAAATACCTATTGCCTACGGCAGCCGCTGGATTGTTATTACTCGCGGCCCAGCCGGCGATGGCCCAGATCCAGTTG GTGCAGTCTGGATCTGAGCTGAAGAAGCCTGGAGCGTCAGTCAAGGTCTCCTGCAAGGCTTCTGGGTATACCTT CACAAACTATGGAATGAACTGGGTGAAGCAGGCTCCAGGACAGGGTTTAAAGTGGATGGGCTGGATAAACACCT ACACTGGACAGTCAACCTATGCTGATGACTTCAAGGGACGCTTTGCCTTCTCTTTGGATACCTCTGTCAGCACTG CCTATTTGCAGATCAGCAGCCTCAAAGCTGAGGACACGGCTGTGTATTTCTGTGCAAGAATGGAGTATGGTAAC TACGAAAATGCTTTGGATTACTGGGGTCAAGGAACCTTAGTCACCGTCTCCTCA*GGTGGCGGTGGCAGCGGCGGC GGTGGTAGCGGTGGTGGCGGCAGC*GACATTGTGATGACCCAGTCTCCCAGCTCCCTGTCCGCATCAGTAGGAGACA GGGTCACCATCACCTGCAAGGCCAGTCAGGATGTGAGTACTGCTGTAGTCTGGTATCAACAGAAACCAGGAAAA GCTCCTAAACTACTGATTTATTCGGCATCCTACCGGTACACTGGAGTCCCTGATCGCTTCACTGGCAGTGGATCT GGGACGGATTTCACTTTGACCATCAGCAGTCTGCAGGCTGAAGACTTCGCAACCTATTACTGTCTACAACATTTT AGTACTCCTCGGACGTTCGGTGGAGGCACCAAACTGGAAATCAAA (SEQ ID NO:109)

Humanized P8D10 scFv (VH-VL) amino acid sequence (265 amino acids):

pelB leader sequence-humanized P8D10 heavy chain variable domain-*linker sequence*-humanized P8D10 light chain variable domain

MKYLLPTAAAGLLLLAAQPAMAQIQLVQSGSELKKPGASVKVSCKASGYTFTNYGMNWVKQAPGQGLKWMGWINT YTGQSTYADDFKGRFAFSLDTSVSTAYLQISSLKAEDTAVYFCARMEYGNYENALDYWGQGTLVTVSS*GGGGSGGGG SGGGGS*DIVMTQSPSSLSASVGDRVTITCKASQDVSTAVVWYQQKPGKAPKLLIYSASYRYTGVPDRFTGSGSGTDFTL TISSLQAEDFATYYCLQHFSTPRTFGGGTKLEIK (SEQ ID NO: 110)

FIG. 28(E)

Humanized P8D10 scFv (VL-VH) DNA sequence (795 base pairs):

pelB leader sequence-humanized P8D10 light chain variable domain-*linker sequence*-humanized P8D10 heavy chain variable domain

ATGAAATACCTATTGCCTACGGCAGCCGCTGGATTGTTATTACTCGCGGCCCAGCCGGCGATGGCCGACATTGTGATG
ACCCAGTCTCCCAGCTCCCTGTCCGCATCAGTAGGAGACAGGGTCACCATCACCTGCAAGGCCAGTCAGGATGT
GAGTACTGCTGTAGTCTGGTATCAACAGAAACCAGGAAAAGCTCCTAAACTACTGATTTATTCGGCATCCTACCG
GTACACTGGAGTCCCTGATCGCTTCACTGGCAGTGGATCTGGGACGGATTTCACTTTGACCATCAGCAGTCTGC
AGGCTGAAGACTTCGCAACCTATTACTGTCTACAACATTTTAGTACTCCTCGGACGTTCGGTGGAGGCACCAAA
CTGGAAATCAAA*GGTGGCGGTGGCAGCGGCGGCGGTGGTAGCGGTGGTGGCGGCAGC*CAGATCCAGTTGGTGCAGTC
TGGATCTGAGCTGAAGAAGCCTGGAGCGTCAGTCAAGGTCTCCTGCAAGGCTTCTGGGTATACCTTCACAAACT
ATGGAATGAACTGGGTGAAGCAGGCTCCAGGACAGGGTTTAAAGTGGATGGGCTGGATAAACACCTACACTGG
ACAGTCAACCTATGCTGATGACTTCAAGGGACGCTTTGCCTTCTCTTTGGATACCTCTGTCAGCACTGCCTATTT
GCAGATCAGCAGCCTCAAAGCTGAGGACACGGCTGTGTATTTCTGTGCAAGAATGGAGTATGGTAACTACGAAA
ATGCTTTGGATTACTGGGGTCAAGGAACCTTAGTCACCGTCTCCTCA (SEQ ID NO: 111)

Humanized P8D10 scFv (VL-VH) amino acid sequence (265 amino acids):

pelB leader sequence-humanized P8D10 light chain variable domain-*linker sequence*-humanized P8D10 heavy chain variable domain

MKYLLPTAAAGLLLLAAQPAMADIVMTQSPSSLSASVGDRVTITCKASQDVSTAVVWYQQKPGKAPKLLIYSASYRYT
GVPDRFTGSGSGTDFTLTISSLQAEDFATYYCLQHFSTPRTFGGGTKLEIK*GGGGSGGGGSGGGGS*QIQLVQSGSELKK
PGASVKVSCKASGYTFTNYGMNWVKQAPGQGLKWMGWINTYTGQSTYADDFKGRFAFSLDTSVSTAYLQISSLKAE
DTAVYFCARMEYGNYENALDYWGQGTLVTVSS (SEQ ID NO: 112)

FIG. 31
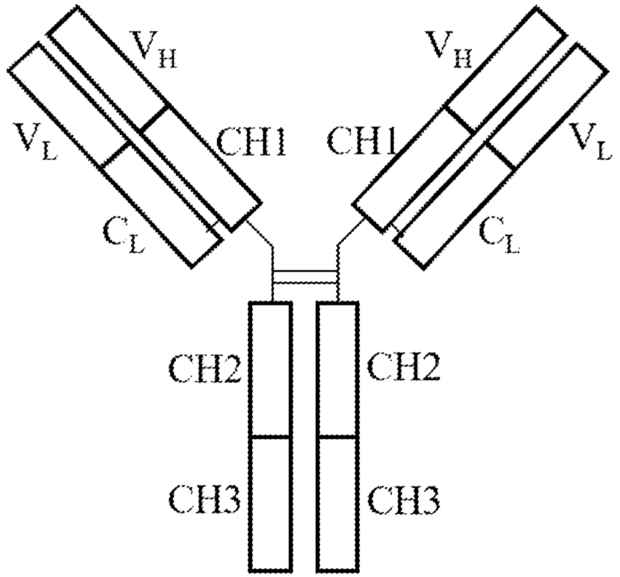
Full length P8D10 mouse mAb
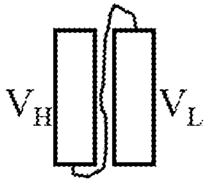
P8D10 mouse $V_HV_L$ scFv
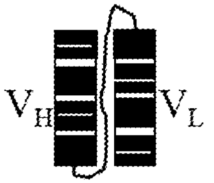
P8D10 humanized $V_HV_L$ scFv
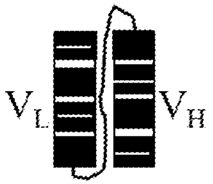
P8D10 humanized $V_LV_H$ scFv
| Antibody | MIC (Minimum inhibition concentration) |
|---|---|
| Full length P8D10 mouse mAb | 0.74 ug/ml |
| P8D10 mouse $V_HV_L$ scFv | 6.5 ug/ml |
| P8D10 humanized $V_HV_L$ scFv | 2.93 ug/ml |
| P8D10 humanized $V_LV_H$ scFv | 1.70 ug/ml |

FIG. 33(A)

Heavy chain DNA sequence (1410 base pairs)
P8D10 heavy chain signal sequence-P8D10 humanized heavy chain variable region-human IgG1 heavy chain constant region ATGGCTTGGGTGTGGACCTTGCTATTCCTGATGGCAGCTGCCCAAAGTGCCCAAGCACAGATCCAGTTGGTGCAGTCTGGATCT
GAGCTGAAGAAGCCTGGAGCGTCAGTCAAGGTCTCCTGCAAGGCTTCTGGGTATACCTTCACAAACTATGGAATGAACTGG
GTGAAGCAGGCTCCAGGACAGGGTTTAAAGTGGATGGGCTGGATAAACACCTACACTGGACAGTCAACCTATGCTGATGA
CTTCAAGGGACGCTTTGCCTTCTCTTTGGATACCTCTGTCAGCACTGCCTATTTGCAGATCAGCAGCCTCAAAGCTGAGGA
CACGGCTGTGTATTTCTGTGCAAGAATGGAGTATGGTAACTACGAAAATGCTTTGGATTACTGGGGTCAAGGAACCTTAGT
CACCGTCTCCTCAGCTAGCACCAAGGGCCCATCGGTCTTCCCCCTGGCACCCTCCTCCAAGAGCACCTCTGGGGGCACAGCGGCC
CTGGGCTGCCTGGTCAAGGACTACTTCCCCGAACCGGTGACGGTGTCGTGGAACTCAGGCGCCCTGACCAGCGGCGTGCACACCTT
CCCGGCTGTCCTACAGTCCTCAGGACTCTACTCCCTCAGCAGCGTGGTGACCGTGCCCTCCAGCAGCTTGGGCACCCAGACCTACA
TCTGCAACGTGAATCACAAGCCCAGCAACACCAAGGTGGACAAGAAAGTTGAGCCCAAATCTTGTGACAAAACTCACACATGCCC
ACCGTGCCCAGCACCTGAACTCCTGGCGGGACCGGACGTCTTCCTCTTCCCCCCAAAACCCAAGGACACCCTCATGATCTCCCGGA
CCCCTGAGGTCACATGCGTGGTGGTGGACGTGAGCCACGAAGACCCTGAGGTCAAGTTCAACTGGTACGTGGACGGCGTGGAGGT
GCATAATGCCAAGACAAAGCCGCGGGAGGAGCAGTACAACAGCACGTACCGTGTGGTCAGCGTCCTCACCGTCCTGCACCAGGAC
TGGCTGAATGGCAAGGAGTACAAGTGCAAGGTCTCCAACAAAGCCCTCCCAGCCCCCGAGGAGAAAACCATCTCCAAAGCCAAAG
GGCAGCCCCGAGAACCACAGGTGTACACCCTGCCCCCATCCCGGGAGGAGATGACCAAGAACCAGGTCAGCCTGACCTGCCTGGT
CAAAGGCTTCTATCCCAGCGACATCGCCGTGGAGTGGGAGAGCAATGGGCAGCCGGAGAACAACTACAAGACCACGCCTCCCGTG
CTGGACTCCGACGGCTCCTTCTTCCTCTACAGCAAGCTCACCGTGGACAAGAGCAGGTGGCAGCAGGGGAACGTCTTCTCATGCTC
CGTGATGCACGAGGCTCTGCACAACCACTACACGCAGAAGAGCCTCTCCCTGTCTCCGGGTAAA (SEQ ID NO: 113)

Heavy chain amino acid sequence (470 amino acids)

P8D10 heavy chain signal sequence-P8D10 humanized heavy chain variable region-human IgG1 heavy chain constant region MAWVWTLLFLMAAAQSAQAQIQLVQSGSELKKPGASVKVSCKASGYTFTNYGMNWVKQAPGQGLKWMGWINTYTGQSTYAD
DFKGRFAFSLDTSVSTAYLQISSLKAEDTAVYFCARMEYGNYENALDYWGQGTLVTVSSASTKGPSVFPLAPSSKSTSGGTAALGCL
VKDYFPEPVTVSWNSGALTSGVHTFPAVLQSSGLYSLSSVVTVPSSSLGTQTYICNVNHKPSNTKVDKKVEPKSCDKTHTCPPCPAPELL
AGPDVFLFPPKPKDTLMISRTPEVTCVVVDVSHEDPEVKFNWYVDGVEVHNAKTKPREEQYNSTYRVVSVLTVLHQDWLNGKEYKCK
VSNKALPAPEEKTISKAKGQPREPQVYTLPPSREEMTKNQVSLTCLVKGFYPSDIAVEWESNGQPENNYKTTPPVLDSDGSFFLYSKLTV
DKSRWQQGNVFSCSVMHEALHNHYTQKSLSLSPGK (SEQ ID NO:114)

FIG. 33(B)

Light chain DNA sequence (699 base pairs)
P8D10 light chain signal sequence-P8D10 humanized light chain variable region-human immunoglobulin kappa light chain constant region ATGGAGTCACAGATTCAGGTCTTTGTATTCGTGTTTCTCTGGTTGTCTGGTGTTGACGGAGACATTGTGATGACCCAGT
CTCCCAGCTCCCTGTCCGCATCAGTAGGAGACAGGGTCACCATCACCTGCAAGGCCAGTCAGGATGTGAGTACT
GCTGTAGTCTGGTATCAACAGAAACCAGGAAAAGCTCCTAAACTACTGATTTATTCGGCATCCTACCGGTACACT
GGAGTCCCTGATCGCTTCACTGGCAGTGGATCTGGGACGGATTTCACTTTGACCATCAGCAGTCTGCAGGCTGA
AGACTTCGCAACCTATTACTGTCTACAACATTTTAGTACTCCTCGGACGTTCGGTGGAGGCACCAAACTGGAAAT
CAAAACGGTGGCTGCACCATCTGTCTTCATCTTCCCGCCATCTGATGAGCAGTTGAAATCTGGAACTGCCTCTGTTGTGT
GCCTGCTGAATAACTTCTATCCCAGAGAGGCCAAAGTACAGTGGAAGGTGGATAACGCCCTCCAATCGGGTAACTCCC
AGGAGAGTGTCACAGAGCAGGACAGCAAGGACAGCACCTACAGCCTCAGCAGCACCCTGACGCTGAGCAAAGCAGAC
TACGAGAAACACAAAGTCTACGCCTGCGAAGTCACCCATCAGGGCCTGAGCTCGCCCGTCACAAAGAGCTTCAACAGG
GGAGAGTGT (SEQ ID NO:115)

Light chain amino acid sequence (233 amino acids)

P8D10 light chain signal sequence-P8D10 humanized light chain variable region-human immunoglobulin kappa light chain constant region MESQIQVFVFVFLWLSGVDGDIVMTQSPSSLSASVGDRVTITCKASQDVSTAVVWYQQKPGKAPKLLIYSASYRYTGVP
DRFTGSGSGTDFTLTISSLQAEDFATYYCLQHFSTPRTFGGGTKLEIKTVAAPSVFIFPPSDEQLKSGTASVVCLLNNFYPR
EAKVQWKVDNALQSGNSQESVTEQDSKDSTYSLSSTLTLSKADYEKHKVYACEVTHQGLSSPVTKSFNRGEC (SEQ ID
NO:116)

SEQUENCE LISTING

```
<160> NUMBER OF SEQ ID NOS: 122

<210> SEQ ID NO 1
<211> LENGTH: 361
<212> TYPE: PRT
<213> ORGANISM: Escherichia coli

<400> SEQUENCE: 1

Ala Asp Lys Asn Pro Gly Ser Glu Asn Met Thr Asn Thr Ile Gly Pro
1               5                   10                  15

His Asp Arg Gly Gly Ser Ser Pro Ile Tyr Asn Ile Leu Asn Ser Tyr
            20                  25                  30

Leu Thr Ala Tyr Asn Gly Ser His His Leu Tyr Asp Arg Met Ser Phe
        35                  40                  45

Leu Cys Leu Ser Ser Gln Asn Thr Leu Asn Gly Ala Cys Pro Ser Ser
    50                  55                  60

Asp Ala Pro Gly Thr Ala Thr Ile Asp Gly Glu Thr Asn Ile Thr Leu
65                  70                  75                  80

Gln Phe Thr Glu Lys Arg Ser Leu Ile Lys Arg Glu Leu Gln Ile Lys
                85                  90                  95

Gly Tyr Lys Gln Phe Leu Phe Lys Asn Ala Asn Cys Pro Ser Lys Leu
            100                 105                 110

Ala Leu Asn Ser Ser His Phe Gln Cys Asn Arg Glu Gln Ala Ser Gly
        115                 120                 125

Ala Thr Leu Ser Leu Tyr Ile Pro Ala Gly Glu Leu Asn Lys Leu Pro
    130                 135                 140

Phe Gly Gly Val Trp Asn Ala Val Leu Lys Leu Asn Val Lys Arg Arg
145                 150                 155                 160
```

```
Tyr Asp Thr Thr Tyr Gly Thr Tyr Thr Ile Asn Ile Thr Val Asn Leu
                165                 170                 175

Thr Asp Lys Gly Asn Ile Gln Ile Trp Leu Pro Gln Phe Lys Ser Asn
            180                 185                 190

Ala Arg Val Asp Leu Asn Leu Arg Pro Thr Gly Gly Gly Thr Tyr Ile
        195                 200                 205

Gly Arg Asn Ser Val Asp Met Cys Phe Tyr Asp Gly Tyr Ser Thr Asn
    210                 215                 220

Ser Ser Ser Leu Glu Ile Arg Phe Gln Asp Asp Asn Ser Lys Ser Asp
225                 230                 235                 240

Gly Lys Phe Tyr Leu Lys Lys Ile Asn Asp Asp Ser Lys Glu Leu Val
                245                 250                 255

Tyr Thr Leu Ser Leu Leu Leu Ala Gly Lys Asn Leu Thr Pro Thr Asn
            260                 265                 270

Gly Gln Ala Leu Asn Ile Asn Thr Ala Ser Leu Glu Thr Asn Trp Asn
        275                 280                 285

Arg Ile Thr Ala Val Thr Met Pro Glu Ile Ser Val Pro Val Leu Cys
    290                 295                 300

Trp Pro Gly Arg Leu Gln Leu Asp Ala Lys Val Lys Asn Pro Glu Ala
305                 310                 315                 320

Gly Gln Tyr Met Gly Asn Ile Lys Ile Thr Phe Thr Pro Ser Ser Gln
                325                 330                 335

Thr Leu Asp Asn Lys Gln Val Glu Lys Asn Ile Thr Val Thr Ala Ser
            340                 345                 350

Val Asp Pro Val Ile Asp Leu Leu Gln
        355                 360


<210> SEQ ID NO 2
<211> LENGTH: 368
<212> TYPE: PRT
<213> ORGANISM: Escherichia coli

<400> SEQUENCE: 2

Gly Arg Tyr Pro Glu Thr Thr Val Gly Asn Leu Thr Lys Ser Phe Gln
1               5                   10                  15

Ala Pro Arg Gln Asp Arg Ser Val Gln Ser Pro Ile Tyr Asn Ile Phe
            20                  25                  30

Thr Asn His Val Ala Gly Tyr Ser Leu Ser His Asn Leu Tyr Asp Arg
        35                  40                  45

Ile Val Phe Leu Cys Thr Ser Ser Ser Asn Pro Val Asn Gly Ala Cys
    50                  55                  60

Pro Thr Leu Gly Thr Ser Gly Val Gln Tyr Gly Thr Thr Thr Ile Thr
65                  70                  75                  80

Leu Gln Phe Thr Glu Lys Arg Ser Leu Ile Lys Arg Asn Ile Asn Leu
                85                  90                  95

Ala Gly Asn Lys Lys Pro Ile Trp Glu Asn Gln Ser Cys Asp Thr Ser
            100                 105                 110

Asn Leu Met Val Leu Asn Ser Lys Ser Trp Ser Cys Gly His Tyr Gly
        115                 120                 125

Asn Ala Asn Gly Thr Leu Leu Asn Leu Tyr Ile Pro Ala Gly Glu Ile
    130                 135                 140

Asn Lys Leu Pro Phe Gly Gly Ile Trp Glu Ala Thr Leu Ile Leu Arg
145                 150                 155                 160

Leu Ser Arg Tyr Gly Glu Val Ser Ser Thr His Tyr Gly Asn Tyr Thr
```

```
                165                 170                 175

Val Asn Ile Thr Val Asp Leu Thr Asp Lys Gly Asn Ile Gln Val Trp
            180                 185                 190

Leu Pro Gly Phe His Ser Asn Pro Arg Val Asp Leu Asn Leu His Pro
        195                 200                 205

Ile Gly Asn Tyr Lys Tyr Ser Gly Ser Asn Ser Leu Asp Met Cys Phe
    210                 215                 220

Tyr Asp Gly Tyr Ser Thr Asn Ser Asp Ser Met Val Ile Lys Phe Gln
225                 230                 235                 240

Asp Asp Asn Pro Thr Tyr Ser Ser Glu Tyr Asn Leu Tyr Lys Ile Gly
                245                 250                 255

Gly Thr Glu Lys Leu Pro Tyr Ala Val Ser Leu Leu Met Gly Glu Lys
            260                 265                 270

Ile Phe Tyr Pro Val Asn Gly Gln Ser Phe Thr Ile Asn Asp Ser Ser
        275                 280                 285

Val Leu Glu Thr Asn Trp Asn Arg Val Thr Ala Val Ala Met Pro Glu
    290                 295                 300

Val Asn Val Pro Val Leu Cys Trp Pro Ala Arg Leu Leu Leu Asn Ala
305                 310                 315                 320

Asp Val Asn Ala Pro Asp Ala Gly Gln Tyr Ser Gly Gln Ile Tyr Ile
                325                 330                 335

Thr Phe Thr Pro Ser Val Glu Asn Leu Asp Asn Lys Gln Val Glu Lys
            340                 345                 350

Asn Ile Thr Val Arg Ala Ser Val Asp Pro Lys Leu Asp Leu Leu Gln
        355                 360                 365


<210> SEQ ID NO 3
<211> LENGTH: 369
<212> TYPE: PRT
<213> ORGANISM: Escherichia coli

<400> SEQUENCE: 3

Gln Ser Trp His Thr Asn Val Glu Ala Gly Ser Ile Asn Lys Thr Glu
1               5                   10                  15

Ser Ile Gly Pro Ile Asp Arg Ser Ala Ala Ala Ser Tyr Pro Ala His
            20                  25                  30

Tyr Ile Phe His Glu His Val Ala Gly Tyr Asn Lys Asp His Ser Leu
        35                  40                  45

Phe Asp Arg Met Thr Phe Leu Cys Met Ser Ser Thr Asp Ala Ser Lys
    50                  55                  60

Gly Ala Cys Pro Thr Gly Glu Asn Ser Lys Ser Ser Gln Gly Glu Thr
65                  70                  75                  80

Asn Ile Lys Leu Ile Phe Thr Glu Lys Lys Ser Leu Ala Arg Lys Thr
                85                  90                  95

Leu Asn Leu Lys Gly Tyr Lys Arg Phe Leu Tyr Glu Ser Asp Arg Cys
            100                 105                 110

Ile His Tyr Val Asp Lys Met Asn Leu Asn Ser His Thr Val Lys Cys
        115                 120                 125

Val Gly Ser Phe Thr Arg Gly Val Asp Phe Thr Leu Tyr Ile Pro Gln
    130                 135                 140

Gly Glu Ile Asp Gly Leu Leu Thr Gly Gly Ile Trp Glu Ala Thr Leu
145                 150                 155                 160

Glu Leu Arg Val Lys Arg His Tyr Asp Tyr Asn His Gly Thr Tyr Lys
                165                 170                 175
```

```
Val Asn Ile Thr Val Asp Leu Thr Asp Lys Gly Asn Ile Gln Val Trp
            180                 185                 190

Thr Pro Lys Phe His Ser Asp Pro Arg Ile Asp Leu Asn Leu Arg Pro
        195                 200                 205

Glu Gly Asn Gly Lys Tyr Ser Gly Ser Asn Val Leu Glu Met Cys Leu
    210                 215                 220

Tyr Asp Gly Tyr Ser Thr His Ser Gln Ser Ile Glu Met Arg Phe Gln
225                 230                 235                 240

Asp Asp Ser Gln Thr Gly Asn Asn Glu Tyr Asn Leu Ile Lys Thr Gly
                245                 250                 255

Glu Pro Leu Lys Lys Leu Pro Tyr Lys Leu Ser Leu Leu Leu Gly Gly
            260                 265                 270

Arg Glu Phe Tyr Pro Asn Asn Gly Glu Ala Phe Thr Ile Asn Asp Thr
        275                 280                 285

Ser Ser Leu Phe Ile Asn Trp Asn Arg Ile Lys Ser Val Ser Leu Pro
    290                 295                 300

Gln Ile Ser Ile Pro Val Leu Cys Trp Pro Ala Asn Leu Thr Phe Met
305                 310                 315                 320

Ser Glu Leu Asn Asn Pro Glu Ala Gly Glu Tyr Ser Gly Ile Leu Asn
                325                 330                 335

Val Thr Phe Thr Pro Ser Ser Ser Ser Leu Asp Asn Lys Gln Ala Glu
            340                 345                 350

Lys Asn Ile Thr Val Thr Ala Ser Val Asp Pro Thr Ile Asp Leu Met
        355                 360                 365

Gln
```

<210> SEQ ID NO 4
<211> LENGTH: 1176
<212> TYPE: DNA
<213> ORGANISM: Artificial Sequence
<220> FEATURE:
<223> OTHER INFORMATION: dsc19CfaE6xHis (H10407)

<400> SEQUENCE: 4

```
atgaataaaa ttttatttat ttttacattg tttttttctt cagggttttt tacatttgcc     60

gtatcggcag ataaaaatcc cggaagtgaa aacatgacta atactattgg tccccatgac    120

aggggggat cttcccccat atataatatc ttaaattcct atcttacagc atacaatgga    180

agccatcatc tgtatgatag gatgagtttt ttatgtttgt cttctcaaaa tacactgaat    240

ggagcatgcc caagcagtga tgcccctggc actgctacaa ttgatggcga aacaaatata    300

acattacaat ttacggaaaa aagaagtcta attaaaagag aactgcaaat taaaggctat    360

aaacaatttt tgttcaaaaa tgctaattgc ccatctaaac tagcacttaa ctcatctcat    420

tttcaatgta atagagaaca agcttcaggt gctactttat cgttatacat accagctggt    480

gaattaaata aattaccttt tggggggtc tggaatgccg ttctgaagct aaatgtaaaa    540

agacgatatg atacaaccta tgggacttac actataaaca tcacagttaa tttaactgat    600

aagggaaata ttcagatatg gttaccacag ttcaaaagta acgctcgtgt cgatcttaac    660

ttgcgtccaa ctggtggtgg tacatatatc ggaagaaatt ctgttgatat gtgcttttat    720

gatggatata gtactaacag cagctcttta gagataagat ttcaggatga taattctaaa    780

tctgatggaa aattttatct aaagaaaata aatgatgact ccaaagaact tgtatacact    840

ttgtcacttc tcctggcagg taaaaattta acaccaacaa atggacaggc attaaatatt    900

aacactgctt ctctggaaac aaactggaat agaattacag ctgtcaccat gccagaaatc    960
```

```
agtgttccgg tgttgtgttg gcctggacgt ttgcaattgg atgcaaaagt gaaaaatccc   1020

gaggctggac aatatatggg gaatattaaa attactttca caccaagtag tcaaacactc   1080

gacaataaac aagtagagaa aaatattact gtaacagcta gtgttgatcc tgtgattgat   1140

cttttgcaac tcgagcacca ccaccaccac cactga                             1176
```

<210> SEQ ID NO 5
<211> LENGTH: 391
<212> TYPE: PRT
<213> ORGANISM: Artificial Sequence
<220> FEATURE:
<223> OTHER INFORMATION: dsc19CfaE6xHis (H10407)

<400> SEQUENCE: 5

```
Met Asn Lys Ile Leu Phe Ile Phe Thr Leu Phe Phe Ser Ser Gly Phe
1               5                   10                  15

Phe Thr Phe Ala Val Ser Ala Asp Lys Asn Pro Gly Ser Glu Asn Met
            20                  25                  30

Thr Asn Thr Ile Gly Pro His Asp Arg Gly Gly Ser Ser Pro Ile Tyr
        35                  40                  45

Asn Ile Leu Asn Ser Tyr Leu Thr Ala Tyr Asn Gly Ser His His Leu
    50                  55                  60

Tyr Asp Arg Met Ser Phe Leu Cys Leu Ser Ser Gln Asn Thr Leu Asn
65                  70                  75                  80

Gly Ala Cys Pro Ser Ser Asp Ala Pro Gly Thr Ala Thr Ile Asp Gly
                85                  90                  95

Glu Thr Asn Ile Thr Leu Gln Phe Thr Glu Lys Arg Ser Leu Ile Lys
            100                 105                 110

Arg Glu Leu Gln Ile Lys Gly Tyr Lys Gln Phe Leu Phe Lys Asn Ala
        115                 120                 125

Asn Cys Pro Ser Lys Leu Ala Leu Asn Ser Ser His Phe Gln Cys Asn
    130                 135                 140

Arg Glu Gln Ala Ser Gly Ala Thr Leu Ser Leu Tyr Ile Pro Ala Gly
145                 150                 155                 160

Glu Leu Asn Lys Leu Pro Phe Gly Gly Val Trp Asn Ala Val Leu Lys
                165                 170                 175

Leu Asn Val Lys Arg Arg Tyr Asp Thr Thr Tyr Gly Thr Tyr Thr Ile
            180                 185                 190

Asn Ile Thr Val Asn Leu Thr Asp Lys Gly Asn Ile Gln Ile Trp Leu
        195                 200                 205

Pro Gln Phe Lys Ser Asn Ala Arg Val Asp Leu Asn Leu Arg Pro Thr
    210                 215                 220

Gly Gly Gly Thr Tyr Ile Gly Arg Asn Ser Val Asp Met Cys Phe Tyr
225                 230                 235                 240

Asp Gly Tyr Ser Thr Asn Ser Ser Ser Leu Glu Ile Arg Phe Gln Asp
                245                 250                 255

Asp Asn Ser Lys Ser Asp Gly Lys Phe Tyr Leu Lys Lys Ile Asn Asp
            260                 265                 270

Asp Ser Lys Glu Leu Val Tyr Thr Leu Ser Leu Leu Leu Ala Gly Lys
        275                 280                 285

Asn Leu Thr Pro Thr Asn Gly Gln Ala Leu Asn Ile Asn Thr Ala Ser
    290                 295                 300

Leu Glu Thr Asn Trp Asn Arg Ile Thr Ala Val Thr Met Pro Glu Ile
305                 310                 315                 320
```

```
Ser Val Pro Val Leu Cys Trp Pro Gly Arg Leu Gln Leu Asp Ala Lys
                325                 330                 335

Val Lys Asn Pro Glu Ala Gly Gln Tyr Met Gly Asn Ile Lys Ile Thr
            340                 345                 350

Phe Thr Pro Ser Ser Gln Thr Leu Asp Asn Lys Gln Val Glu Lys Asn
        355                 360                 365

Ile Thr Val Thr Ala Ser Val Asp Pro Val Ile Asp Leu Leu Gln Leu
    370                 375                 380

Glu His His His His His His
385                 390


<210> SEQ ID NO 6
<211> LENGTH: 1185
<212> TYPE: DNA
<213> ORGANISM: Artificial Sequence
<220> FEATURE:
<223> OTHER INFORMATION: dsc19CsbD6xHis (WS6788A)

<400> SEQUENCE: 6

atgaaaaaga tatttatttt tttgtctatc atattttctg cggtggtcag tgccgggcga     60

tacccggaaa ctacagtagg taatctgacg aagagttttc aagcccctcg tcaggataga    120

agcgtacaat caccaatata taacatcttt acgaatcatg tggctggata tagtttgagt    180

cataacttat atgacaggat tgttttttta tgtacatcct cgtcgaatcc ggttaatggt    240

gcttgcccaa cccttggaac atctggagtt caatacggta ctacaaccat aaccttgcag    300

tttacagaaa aaagaagtct gataaaaaga aatattaatc ttgcaggtaa taagaaacca    360

atatgggaga atcagagttg cgacactagc aatctaatgg tgttgaattc gaagtcttgg    420

tcctgtgggc attacggaaa tgctaacgga acacttctaa atctgtatat ccctgcagga    480

gaaatcaaca aattgccttt tggagggata tgggaggcaa ctctgatctt acgcttatca    540

agatatggcg aagtcagtag cacccattac ggcaattata ccgtaaatat tacggttgat    600

ttaactgata aaggtaatat tcaggtatgg cttccagggt ttcacagcaa cccgcgtgta    660

gacctgaatc tgcaccctat cggtaattat aaatatagtg gtagtaattc actcgacatg    720

tgtttctatg atggatatag tacaaacagt gatagcatgg taataaagtt ccaggatgat    780

aatcctacct attcatctga atataatctt tataagatag ggggcactga aaaattacca    840

tatgctgttt cactgcttat gggagaaaaa atattttatc cagtgaatgg tcaatcattt    900

actatcaatg acagtagtgt actcgaaaca aactggaatc gagtaaccgc agttgctatg    960

ccggaagtta atgttccagt attatgctgg ccagcaagat tgctattaaa tgctgatgta   1020

aatgctcccg atgcaggaca gtattcagga cagatatata taacatttac acccagtgtc   1080

gaaaatttag acaataaaca agtcgaaaaa aatattactg tgagggcaag tgttgaccct   1140

aaacttgatc ttctgcaact cgagcaccac caccaccacc actga                   1185


<210> SEQ ID NO 7
<211> LENGTH: 394
<212> TYPE: PRT
<213> ORGANISM: Artificial Sequence
<220> FEATURE:
<223> OTHER INFORMATION: dsc19CsbD6xHis (WS6788A)

<400> SEQUENCE: 7

Met Lys Lys Ile Phe Ile Phe Leu Ser Ile Ile Phe Ser Ala Val Val
1               5                   10                  15

Ser Ala Gly Arg Tyr Pro Glu Thr Thr Val Gly Asn Leu Thr Lys Ser
```

20 25 30

Phe Gln Ala Pro Arg Gln Asp Arg Ser Val Gln Ser Pro Ile Tyr Asn
35 40 45

Ile Phe Thr Asn His Val Ala Gly Tyr Ser Leu Ser His Asn Leu Tyr
50 55 60

Asp Arg Ile Val Phe Leu Cys Thr Ser Ser Ser Asn Pro Val Asn Gly
65 70 75 80

Ala Cys Pro Thr Leu Gly Thr Ser Gly Val Gln Tyr Gly Thr Thr Thr
85 90 95

Ile Thr Leu Gln Phe Thr Glu Lys Arg Ser Leu Ile Lys Arg Asn Ile
100 105 110

Asn Leu Ala Gly Asn Lys Lys Pro Ile Trp Glu Asn Gln Ser Cys Asp
115 120 125

Thr Ser Asn Leu Met Val Leu Asn Ser Lys Ser Trp Ser Cys Gly His
130 135 140

Tyr Gly Asn Ala Asn Gly Thr Leu Leu Asn Leu Tyr Ile Pro Ala Gly
145 150 155 160

Glu Ile Asn Lys Leu Pro Phe Gly Gly Ile Trp Glu Ala Thr Leu Ile
165 170 175

Leu Arg Leu Ser Arg Tyr Gly Glu Val Ser Ser Thr His Tyr Gly Asn
180 185 190

Tyr Thr Val Asn Ile Thr Val Asp Leu Thr Asp Lys Gly Asn Ile Gln
195 200 205

Val Trp Leu Pro Gly Phe His Ser Asn Pro Arg Val Asp Leu Asn Leu
210 215 220

His Pro Ile Gly Asn Tyr Lys Tyr Ser Gly Ser Asn Ser Leu Asp Met
225 230 235 240

Cys Phe Tyr Asp Gly Tyr Ser Thr Asn Ser Asp Ser Met Val Ile Lys
245 250 255

Phe Gln Asp Asp Asn Pro Thr Tyr Ser Ser Glu Tyr Asn Leu Tyr Lys
260 265 270

Ile Gly Gly Thr Glu Lys Leu Pro Tyr Ala Val Ser Leu Leu Met Gly
275 280 285

Glu Lys Ile Phe Tyr Pro Val Asn Gly Gln Ser Phe Thr Ile Asn Asp
290 295 300

Ser Ser Val Leu Glu Thr Asn Trp Asn Arg Val Thr Ala Val Ala Met
305 310 315 320

Pro Glu Val Asn Val Pro Val Leu Cys Trp Pro Ala Arg Leu Leu Leu
325 330 335

Asn Ala Asp Val Asn Ala Pro Asp Ala Gly Gln Tyr Ser Gly Gln Ile
340 345 350

Tyr Ile Thr Phe Thr Pro Ser Val Glu Asn Leu Asp Asn Lys Gln Val
355 360 365

Glu Lys Asn Ile Thr Val Arg Ala Ser Val Asp Pro Lys Leu Asp Leu
370 375 380

Leu Gln Leu Glu His His His His His His
385 390

<210> SEQ ID NO 8
<211> LENGTH: 1188
<212> TYPE: DNA
<213> ORGANISM: Artificial Sequence
<220> FEATURE:
<223> OTHER INFORMATION: dsc19CotD6xHis (C91f)

<400> SEQUENCE: 8

```
atgaaaaaag tgatttttgt tttatccatg tttctatgtt ctcaggttta cgggcaatca      60
tggcatacga acgtagaggc tggttcaata aataaaacag agtcgatagg ccccatagac     120
cgaagtgctg ctgcatcgta tcctgctcat tatatatttc atgaacatgt tgctggttac     180
aataaagatc actctctttt tgacaggatg acgtttttat gtatgtcatc aacagatgca     240
tctaaaggtg catgtccgac aggagaaaac tccaaatcct ctcaagggga gactaatatt     300
aagctaatat ttactgaaaa gaaaagtctg gccagaaaaa cattaaactt aaaaggatat     360
aagagatttt tatatgaatc agatagatgc attcattatg tcgataaaat gaatctcaat     420
tctcatactg ttaaatgtgt aggttcattc acaagaggag tagatttcac tttatatatc     480
ccacaaggtg aaattgatgg gcttctaact ggaggtatat gggaggcaac actagagtta     540
cgagtcaaaa ggcattacga ctataatcat ggtacttaca aagttaatat cacagttgat     600
ttgacagaca aaggaaatat tcaggtctgg acaccaaagt ttcatagcga tcctagaatt     660
gatctgaatt tacgtcctga aggtaatggt aaatattctg gtagtaacgt gcttgagatg     720
tgtctctatg atggctatag tacacatagt caaagtatag aaatgaggtt tcaggatgac     780
tcacaaacag gaaataatga atataatctt ataaaaactg gagagccatt aaaaaaattg     840
ccatataaac tttctcttct tttaggagga cgagagtttt atccaaataa tggagaggct     900
tttactatta atgatacttc gtcattgttt ataaactgga atcgtattaa gtctgtatcc     960
ttaccacaga ttagtattcc agtactatgc tggccagcaa acttgacatt tatgtcagag    1020
ctaaataatc cagaagcggg tgagtattca ggaatactta acgtaacatt tactcctagt    1080
agttcaagtc tggacaataa acaagccgag aaaaatatca ctgtaactgc tagcgttgat    1140
ccaactatcg atctgatgca actcgagcac caccaccacc accactga                 1188
```

<210> SEQ ID NO 9
<211> LENGTH: 395
<212> TYPE: PRT
<213> ORGANISM: Artificial Sequence
<220> FEATURE:
<223> OTHER INFORMATION: dsc19CotD6xHis (C91f)

<400> SEQUENCE: 9

```
Met Lys Lys Val Ile Phe Val Leu Ser Met Phe Leu Cys Ser Gln Val
1               5                   10                  15

Tyr Gly Gln Ser Trp His Thr Asn Val Glu Ala Gly Ser Ile Asn Lys
            20                  25                  30

Thr Glu Ser Ile Gly Pro Ile Asp Arg Ser Ala Ala Ala Ser Tyr Pro
        35                  40                  45

Ala His Tyr Ile Phe His Glu His Val Ala Gly Tyr Asn Lys Asp His
    50                  55                  60

Ser Leu Phe Asp Arg Met Thr Phe Leu Cys Met Ser Ser Thr Asp Ala
65                  70                  75                  80

Ser Lys Gly Ala Cys Pro Thr Gly Glu Asn Ser Lys Ser Ser Gln Gly
                85                  90                  95

Glu Thr Asn Ile Lys Leu Ile Phe Thr Glu Lys Lys Ser Leu Ala Arg
            100                 105                 110

Lys Thr Leu Asn Leu Lys Gly Tyr Lys Arg Phe Leu Tyr Glu Ser Asp
        115                 120                 125

Arg Cys Ile His Tyr Val Asp Lys Met Asn Leu Asn Ser His Thr Val
    130                 135                 140
```

Lys Cys Val Gly Ser Phe Thr Arg Gly Val Asp Phe Thr Leu Tyr Ile
145 150 155 160

Pro Gln Gly Glu Ile Asp Gly Leu Leu Thr Gly Gly Ile Trp Glu Ala
165 170 175

Thr Leu Glu Leu Arg Val Lys Arg His Tyr Asp Tyr Asn His Gly Thr
180 185 190

Tyr Lys Val Asn Ile Thr Val Asp Leu Thr Asp Lys Gly Asn Ile Gln
195 200 205

Val Trp Thr Pro Lys Phe His Ser Asp Pro Arg Ile Asp Leu Asn Leu
210 215 220

Arg Pro Glu Gly Asn Gly Lys Tyr Ser Gly Ser Asn Val Leu Glu Met
225 230 235 240

Cys Leu Tyr Asp Gly Tyr Ser Thr His Ser Gln Ser Ile Glu Met Arg
245 250 255

Phe Gln Asp Asp Ser Gln Thr Gly Asn Asn Glu Tyr Asn Leu Ile Lys
260 265 270

Thr Gly Glu Pro Leu Lys Lys Leu Pro Tyr Lys Leu Ser Leu Leu Leu
275 280 285

Gly Gly Arg Glu Phe Tyr Pro Asn Asn Gly Glu Ala Phe Thr Ile Asn
290 295 300

Asp Thr Ser Ser Leu Phe Ile Asn Trp Asn Arg Ile Lys Ser Val Ser
305 310 315 320

Leu Pro Gln Ile Ser Ile Pro Val Leu Cys Trp Pro Ala Asn Leu Thr
325 330 335

Phe Met Ser Glu Leu Asn Asn Pro Glu Ala Gly Glu Tyr Ser Gly Ile
340 345 350

Leu Asn Val Thr Phe Thr Pro Ser Ser Ser Ser Leu Asp Asn Lys Gln
355 360 365

Ala Glu Lys Asn Ile Thr Val Thr Ala Ser Val Asp Pro Thr Ile Asp
370 375 380

Leu Met Gln Leu Glu His His His His His His
385 390 395

<210> SEQ ID NO 10
<211> LENGTH: 420
<212> TYPE: DNA
<213> ORGANISM: mouse

<400> SEQUENCE: 10
atggcttggg tgtggacctt gctattcctg atggcagctg cccaaagtgc ccaagcacag 60
atccagttgg tgcagtctgg acctgagctg aagaagcctg gagagacagt caagatctcc 120
tgcaaggctt ctgggtatac cttcacaaac tatggaatga actgggtgaa gcaggctcca 180
ggaaagggtt taaagtggat gggctggata aacacctaca ctggacagtc aacatatgct 240
gatgacttca agggacgctt tgccttctct ttggaaacct ctgccagcac tgcccatttg 300
cagatcagca acctcaaaaa tgaggacgcg gctacatatt tctgtgcaag aatggagtat 360
ggtaactacg aaaatgcttt ggattactgg ggtcaaggaa cctcagtcac cgtctcctca 420

<210> SEQ ID NO 11
<211> LENGTH: 140
<212> TYPE: PRT
<213> ORGANISM: Mouse

<400> SEQUENCE: 11

Met Ala Trp Val Trp Thr Leu Leu Phe Leu Met Ala Ala Ala Gln Ser

-continued 1 5 10 15

Ala Gln Ala Gln Ile Gln Leu Val Gln Ser Gly Pro Glu Leu Lys Lys
20 25 30

Pro Gly Glu Thr Val Lys Ile Ser Cys Lys Ala Ser Gly Tyr Thr Phe
35 40 45

Thr Asn Tyr Gly Met Asn Trp Val Lys Gln Ala Pro Gly Lys Gly Leu
50 55 60

Lys Trp Met Gly Trp Ile Asn Thr Tyr Thr Gly Gln Ser Thr Tyr Ala
65 70 75 80

Asp Asp Phe Lys Gly Arg Phe Ala Phe Ser Leu Glu Thr Ser Ala Ser
85 90 95

Thr Ala His Leu Gln Ile Ser Asn Leu Lys Asn Glu Asp Ala Ala Thr
100 105 110

Tyr Phe Cys Ala Arg Met Glu Tyr Gly Asn Tyr Glu Asn Ala Leu Asp
115 120 125

Tyr Trp Gly Gln Gly Thr Ser Val Thr Val Ser Ser
130 135 140

<210> SEQ ID NO 12
<211> LENGTH: 381
<212> TYPE: DNA
<213> ORGANISM: Mouse

<400> SEQUENCE: 12
atggagtcac agattcaggt ctttgtattc gtgtttctct ggttgtctgg tgttgacgga 60
gacattgtga tgacccagtc tcacaaattc atgtccacat caataggaga cagggtcagc 120
atcacctgca aggccagtca ggatgtgagt actgctgtag tctggtatca acagaaacca 180
ggacactctc ctaaactact gatttattcg gcatcctacc ggtacactgg agtccctgat 240
cgcttcactg gcagtggatc tgggacggat ttcactttca ccatcagcag tgtgcaggct 300
gaagacctgg cagtttatta ctgtctacaa cattttagta ctcctcggac gttcggtgga 360
ggcaccaacc tggaaatcaa a 381

<210> SEQ ID NO 13
<211> LENGTH: 127
<212> TYPE: PRT
<213> ORGANISM: Mouse

<400> SEQUENCE: 13

Met Glu Ser Gln Ile Gln Val Phe Val Phe Val Phe Leu Trp Leu Ser
1 5 10 15

Gly Val Asp Gly Asp Ile Val Met Thr Gln Ser His Lys Phe Met Ser
20 25 30

Thr Ser Ile Gly Asp Arg Val Ser Ile Thr Cys Lys Ala Ser Gln Asp
35 40 45

Val Ser Thr Ala Val Val Trp Tyr Gln Gln Lys Pro Gly His Ser Pro
50 55 60

Lys Leu Leu Ile Tyr Ser Ala Ser Tyr Arg Tyr Thr Gly Val Pro Asp
65 70 75 80

Arg Phe Thr Gly Ser Gly Ser Gly Thr Asp Phe Thr Phe Thr Ile Ser
85 90 95

Ser Val Gln Ala Glu Asp Leu Ala Val Tyr Tyr Cys Leu Gln His Phe
100 105 110

Ser Thr Pro Arg Thr Phe Gly Gly Gly Thr Asn Leu Glu Ile Lys
115 120 125

<210> SEQ ID NO 14
<211> LENGTH: 420
<212> TYPE: DNA
<213> ORGANISM: Mouse

<400> SEQUENCE: 14

```
atggcttggg tgtggacctt gctattcctg atggcagctg cccaaagtgc ccaagcacag     60

atccagttgg tgcagtctgg acctgagctg aagaagcctg gagagacagt caagatctcc    120

tgcaaggctt ctgggtatac cttcacaaac tatggaatga actgggtgaa gcaggctcca    180

ggaaagggtt taaagtggat gggctggata aacacctaca ctggagagcc aacatatact    240

gatgacttca agggacggtt tgccttctct ttggaaacct ctgccagcac tgcctatttg    300

cagatcaaca gcctcaaaac tgaggacacg gctacatatt tctgtgcaag aatggagtat    360

ggtaactacg aaaatgctat ggactcctgg ggtcaaggaa cctcagtcac cgtctcctca    420
```

<210> SEQ ID NO 15
<211> LENGTH: 140
<212> TYPE: PRT
<213> ORGANISM: Mouse

<400> SEQUENCE: 15

```
Met Ala Trp Val Trp Thr Leu Leu Phe Leu Met Ala Ala Ala Gln Ser
1               5                   10                  15

Ala Gln Ala Gln Ile Gln Leu Val Gln Ser Gly Pro Glu Leu Lys Lys
            20                  25                  30

Pro Gly Glu Thr Val Lys Ile Ser Cys Lys Ala Ser Gly Tyr Thr Phe
        35                  40                  45

Thr Asn Tyr Gly Met Asn Trp Val Lys Gln Ala Pro Gly Lys Gly Leu
    50                  55                  60

Lys Trp Met Gly Trp Ile Asn Thr Tyr Thr Gly Glu Pro Thr Tyr Thr
65                  70                  75                  80

Asp Asp Phe Lys Gly Arg Phe Ala Phe Ser Leu Glu Thr Ser Ala Ser
                85                  90                  95

Thr Ala Tyr Leu Gln Ile Asn Ser Leu Lys Thr Glu Asp Thr Ala Thr
            100                 105                 110

Tyr Phe Cys Ala Arg Met Glu Tyr Gly Asn Tyr Glu Asn Ala Met Asp
        115                 120                 125

Ser Trp Gly Gln Gly Thr Ser Val Thr Val Ser Ser
    130                 135                 140
```

<210> SEQ ID NO 16
<211> LENGTH: 381
<212> TYPE: DNA
<213> ORGANISM: Mouse

<400> SEQUENCE: 16

```
atggagtcac agattcaggt ctttgtattc gtgtttctct ggttgtctgg tgttgacgga     60

gacactgtga tgacccagtc tcacaaattc atgtccacat cagttggaga cagggtcagc    120

atcacctgca aggccagtca ggatgtgagt actgctgttg tctggtatca acaaaaacca    180

ggacaatctc ctaagctgct gatttactcg gcatcctacc ggtacactgg agtccctgat    240

cgcttcactg gcagtggatc tgggacggat ttcactttca ccatcagcag tgtgcaggct    300

gaagacctgg cagtttatta ctgtctccaa cattttaata ttcctcggac gttcggtggg    360

ggcaccaagc tggaaatcaa a                                              381
```

<210> SEQ ID NO 17
<211> LENGTH: 127
<212> TYPE: PRT
<213> ORGANISM: Mouse

<400> SEQUENCE: 17

```
Met Glu Ser Gln Ile Gln Val Phe Val Phe Val Phe Leu Trp Leu Ser
1               5                   10                  15

Gly Val Asp Gly Asp Thr Val Met Thr Gln Ser His Lys Phe Met Ser
            20                  25                  30

Thr Ser Val Gly Asp Arg Val Ser Ile Thr Cys Lys Ala Ser Gln Asp
        35                  40                  45

Val Ser Thr Ala Val Val Trp Tyr Gln Gln Lys Pro Gly Gln Ser Pro
    50                  55                  60

Lys Leu Leu Ile Tyr Ser Ala Ser Tyr Arg Tyr Thr Gly Val Pro Asp
65                  70                  75                  80

Arg Phe Thr Gly Ser Gly Ser Gly Thr Asp Phe Thr Phe Thr Ile Ser
                85                  90                  95

Ser Val Gln Ala Glu Asp Leu Ala Val Tyr Tyr Cys Leu Gln His Phe
            100                 105                 110

Asn Ile Pro Arg Thr Phe Gly Gly Gly Thr Lys Leu Glu Ile Lys
        115                 120                 125
```

<210> SEQ ID NO 18
<211> LENGTH: 414
<212> TYPE: DNA
<213> ORGANISM: Mouse

<400> SEQUENCE: 18

```
atggaatgga gctggatctt tctctttctc ctgtcaggaa ctgcaggtgt cctctctgag      60

gtccaattgc aacagtttgg agctgaggtg gtgaagcctg gggcttcagt gaagatatcc     120

tgcaaggctt ctggctacac attcactgac tacaacatag actgggtgaa gcagagccat     180

ggagagagtc ttgaatggat tggagatatt agtcctaatt ctgagggtac tacctacaac     240

cagaagttta agggacaggc cacattgact atagacaagt cctccaccac agcctacatg     300

gagctccgca gcctgacatc tgaggacagt gcagtctatt actgtgcaag agggagcggg     360

atctggaatg gtttggacta ctggggtcaa ggaacctctg tcaccgtctc ctca           414
```

<210> SEQ ID NO 19
<211> LENGTH: 138
<212> TYPE: PRT
<213> ORGANISM: Mouse

<400> SEQUENCE: 19

```
Met Glu Trp Ser Trp Ile Phe Leu Phe Leu Leu Ser Gly Thr Ala Gly
1               5                   10                  15

Val Leu Ser Glu Val Gln Leu Gln Gln Phe Gly Ala Glu Val Val Lys
            20                  25                  30

Pro Gly Ala Ser Val Lys Ile Ser Cys Lys Ala Ser Gly Tyr Thr Phe
        35                  40                  45

Thr Asp Tyr Asn Ile Asp Trp Val Lys Gln Ser His Gly Glu Ser Leu
    50                  55                  60

Glu Trp Ile Gly Asp Ile Ser Pro Asn Ser Glu Gly Thr Thr Tyr Asn
65                  70                  75                  80

Gln Lys Phe Lys Gly Gln Ala Thr Leu Thr Ile Asp Lys Ser Ser Thr
```

```
                85                  90                  95

Thr Ala Tyr Met Glu Leu Arg Ser Leu Thr Ser Glu Asp Ser Ala Val
            100                 105                 110

Tyr Tyr Cys Ala Arg Gly Ser Gly Ile Trp Asn Gly Leu Asp Tyr Trp
        115                 120                 125

Gly Gln Gly Thr Ser Val Thr Val Ser Ser
    130                 135


<210> SEQ ID NO 20
<211> LENGTH: 381
<212> TYPE: DNA
<213> ORGANISM: Mouse

<400> SEQUENCE: 20

atggagtcac agattcaggt ctttgtattc gtgtttctct ggttgtctgg tgttgacgga     60

gacattgtga tgacccagtc tcacaaattc atgtccacat cagtaggaga cagggtcagc    120

atcacctgca aggccagtca ggatgtgagt actgctgtag cctggtatca acagaaacca    180

ggacaatctc ctcaattact gatttattcg tcatcctacc ggtatgttgg agtccctgat    240

cgcttcactg gcagtggatc tgggacggac ttcactttca ccatcagcag tgtgcaggct    300

gaagacctgg cagtttatta ctgtcaccaa cattatagtc tcccgtacac gttcggaggg    360

gggaccaagc tggaaataaa a                                              381


<210> SEQ ID NO 21
<211> LENGTH: 127
<212> TYPE: PRT
<213> ORGANISM: Mouse

<400> SEQUENCE: 21

Met Glu Ser Gln Ile Gln Val Phe Val Phe Val Phe Leu Trp Leu Ser
1               5                   10                  15

Gly Val Asp Gly Asp Ile Val Met Thr Gln Ser His Lys Phe Met Ser
            20                  25                  30

Thr Ser Val Gly Asp Arg Val Ser Ile Thr Cys Lys Ala Ser Gln Asp
        35                  40                  45

Val Ser Thr Ala Val Ala Trp Tyr Gln Gln Lys Pro Gly Gln Ser Pro
    50                  55                  60

Gln Leu Leu Ile Tyr Ser Ser Ser Tyr Arg Tyr Val Gly Val Pro Asp
65                  70                  75                  80

Arg Phe Thr Gly Ser Gly Ser Gly Thr Asp Phe Thr Phe Thr Ile Ser
                85                  90                  95

Ser Val Gln Ala Glu Asp Leu Ala Val Tyr Tyr Cys His Gln His Tyr
            100                 105                 110

Ser Leu Pro Tyr Thr Phe Gly Gly Gly Thr Lys Leu Glu Ile Lys
        115                 120                 125


<210> SEQ ID NO 22
<211> LENGTH: 423
<212> TYPE: DNA
<213> ORGANISM: Mouse

<400> SEQUENCE: 22

atgggcaggc ttacttcttc attcttgcta ctgattgtcc ctgcatatgt cctgtcccag     60

gttactctga aagagtctgg ccctgggata ttgcagccct cccagaccct cagtctgact    120

tgttctttct ctgggttttc actgagtact tctggtatgg gtgtaggctg gattcgtcag    180
```

```
ccttcaggga agggtctgga gtggctgtca cacatttggt gggatgatga gaagcgctat    240

aacccagccc tgaagagccg actgacaatc tccaaggata cctccagcaa ccaggtattc    300

ctcaagatcg ccagtgtgga cactgcagat actgccacat actactgtgc tcgaataggg    360

gacaggtcgg gccacgcggg gtttgtttac tggggccaag ggactctggt cactgtctct    420

gca                                                                   423


<210> SEQ ID NO 23
<211> LENGTH: 141
<212> TYPE: PRT
<213> ORGANISM: Mouse

<400> SEQUENCE: 23

Met Gly Arg Leu Thr Ser Ser Phe Leu Leu Leu Ile Val Pro Ala Tyr
1               5                   10                  15

Val Leu Ser Gln Val Thr Leu Lys Glu Ser Gly Pro Gly Ile Leu Gln
            20                  25                  30

Pro Ser Gln Thr Leu Ser Leu Thr Cys Ser Phe Ser Gly Phe Ser Leu
        35                  40                  45

Ser Thr Ser Gly Met Gly Val Gly Trp Ile Arg Gln Pro Ser Gly Lys
    50                  55                  60

Gly Leu Glu Trp Leu Ser His Ile Trp Trp Asp Asp Glu Lys Arg Tyr
65                  70                  75                  80

Asn Pro Ala Leu Lys Ser Arg Leu Thr Ile Ser Lys Asp Thr Ser Ser
                85                  90                  95

Asn Gln Val Phe Leu Lys Ile Ala Ser Val Asp Thr Ala Asp Thr Ala
            100                 105                 110

Thr Tyr Tyr Cys Ala Arg Ile Gly Asp Arg Ser Gly His Ala Gly Phe
        115                 120                 125

Val Tyr Trp Gly Gln Gly Thr Leu Val Thr Val Ser Ala
    130                 135                 140


<210> SEQ ID NO 24
<211> LENGTH: 381
<212> TYPE: DNA
<213> ORGANISM: Mouse

<400> SEQUENCE: 24

atgaggaccc ctgctcagtt tcttggaatc ttattactct ggtttccagg tatcaaatgt     60

gacatcaaga tgacccagtc tccatcttcc atgtatgcat ctctaggaga gagagtcact    120

atcacttgca aggcgagtca ggacattaat agctatttaa gctggttcca gcagaaacca    180

gggaaatctc ctaagaccct gatctatcgt gcaaacagat tggtagatgg ggtcccatca    240

aggttcagtg gcagtggatc tgggcaagat tattctctca ccatcagcag cctggagtat    300

gaagatatgg gaacttatta ttgtctacag tatgatgagt ttccgtacac gttcggaggg    360

gggaccaagc tggaaataaa a                                              381


<210> SEQ ID NO 25
<211> LENGTH: 127
<212> TYPE: PRT
<213> ORGANISM: Mouse

<400> SEQUENCE: 25

Met Arg Thr Pro Ala Gln Phe Leu Gly Ile Leu Leu Leu Trp Phe Pro
1               5                   10                  15

Gly Ile Lys Cys Asp Ile Lys Met Thr Gln Ser Pro Ser Ser Met Tyr
```

20 25 30

Ala Ser Leu Gly Glu Arg Val Thr Ile Thr Cys Lys Ala Ser Gln Asp
35 40 45

Ile Asn Ser Tyr Leu Ser Trp Phe Gln Gln Lys Pro Gly Lys Ser Pro
50 55 60

Lys Thr Leu Ile Tyr Arg Ala Asn Arg Leu Val Asp Gly Val Pro Ser
65 70 75 80

Arg Phe Ser Gly Ser Gly Ser Gly Gln Asp Tyr Ser Leu Thr Ile Ser
85 90 95

Ser Leu Glu Tyr Glu Asp Met Gly Thr Tyr Tyr Cys Leu Gln Tyr Asp
100 105 110

Glu Phe Pro Tyr Thr Phe Gly Gly Gly Thr Lys Leu Glu Ile Lys
115 120 125

<210> SEQ ID NO 26
<211> LENGTH: 417
<212> TYPE: DNA
<213> ORGANISM: Mouse

<400> SEQUENCE: 26
atgtacttgg gactgaacta tgtattcatt gtttttctct taaatggtgt ccagagtgaa 60
gtgaagcttg aggagtctgg aggaggcttg gtgcaacctg gaggatccat gaaactctct 120
tgtgctgcct ctggattcac ttttagtgac gcctggatgg actgggtccg ccagtctcca 180
gagaaggggc ttgaatgggt tggtaaaatt agaagtgaaa ttaatgatca tgcaacatac 240
tatgctgagt ctgtgaaagg gaggttcacc atctcaagag atgattccaa aagtggtgtc 300
tacctgcaaa tgaacaactt aagagctgaa gacactggca tttattactg tgccagggat 360
ggttactacg gtgctatgga ctactggggt caaggaacgt cagtcaccgt ctcctca 417

<210> SEQ ID NO 27
<211> LENGTH: 139
<212> TYPE: PRT
<213> ORGANISM: Mouse

<400> SEQUENCE: 27

Met Tyr Leu Gly Leu Asn Tyr Val Phe Ile Val Phe Leu Leu Asn Gly
1 5 10 15

Val Gln Ser Glu Val Lys Leu Glu Glu Ser Gly Gly Gly Leu Val Gln
20 25 30

Pro Gly Gly Ser Met Lys Leu Ser Cys Ala Ala Ser Gly Phe Thr Phe
35 40 45

Ser Asp Ala Trp Met Asp Trp Val Arg Gln Ser Pro Glu Lys Gly Leu
50 55 60

Glu Trp Val Gly Lys Ile Arg Ser Glu Ile Asn Asp His Ala Thr Tyr
65 70 75 80

Tyr Ala Glu Ser Val Lys Gly Arg Phe Thr Ile Ser Arg Asp Asp Ser
85 90 95

Lys Ser Gly Val Tyr Leu Gln Met Asn Asn Leu Arg Ala Glu Asp Thr
100 105 110

Gly Ile Tyr Tyr Cys Ala Arg Asp Gly Tyr Tyr Gly Ala Met Asp Tyr
115 120 125

Trp Gly Gln Gly Thr Ser Val Thr Val Ser Ser
130 135

<210> SEQ ID NO 28

<211> LENGTH: 381
<212> TYPE: DNA
<213> ORGANISM: Mouse

<400> SEQUENCE: 28
atgaggttcc aggttcaggt tctggggctc cttctgctct ggatatcagg tgcccagtgt 60
gatgttcaga taacccagtc tccatcttat cttgctgcat ctcctggaga aaccattact 120
attaattgca ggtcaaataa gagcattagc agatatttag cctggtatca agagaaacct 180
gggaaaacta ataagcttct tatctactct ggatccactt tgcaatctgg aattccatca 240
aggttcagtg gcagtggatc taatacagat ttcactctca ccatcagtag cctggagcct 300
gaagattttg caatgtatta ctgtcaacag cataatgaat acccgtacac gttcggctcg 360
gggacaaaat tggaaataaa a 381

<210> SEQ ID NO 29
<211> LENGTH: 127
<212> TYPE: PRT
<213> ORGANISM: Mouse

<400> SEQUENCE: 29

Met Arg Phe Gln Val Gln Val Leu Gly Leu Leu Leu Leu Trp Ile Ser
1 5 10 15

Gly Ala Gln Cys Asp Val Gln Ile Thr Gln Ser Pro Ser Tyr Leu Ala
20 25 30

Ala Ser Pro Gly Glu Thr Ile Thr Ile Asn Cys Arg Ser Asn Lys Ser
35 40 45

Ile Ser Arg Tyr Leu Ala Trp Tyr Gln Glu Lys Pro Gly Lys Thr Asn
50 55 60

Lys Leu Leu Ile Tyr Ser Gly Ser Thr Leu Gln Ser Gly Ile Pro Ser
65 70 75 80

Arg Phe Ser Gly Ser Gly Ser Asn Thr Asp Phe Thr Leu Thr Ile Ser
85 90 95

Ser Leu Glu Pro Glu Asp Phe Ala Met Tyr Tyr Cys Gln Gln His Asn
100 105 110

Glu Tyr Pro Tyr Thr Phe Gly Ser Gly Thr Lys Leu Glu Ile Lys
115 120 125

<210> SEQ ID NO 30
<211> LENGTH: 414
<212> TYPE: DNA
<213> ORGANISM: Mouse

<400> SEQUENCE: 30
atgggatgga gctgtatcat cctcttcttg gtatcaacag gtacaggtgt ccactcccag 60
gtccaactgc agcagcctgg ggctgagctt gtgaagcctg gggcttcagt gaagctgtcc 120
tgcaaggctt ctggctacac cttcaccagc tactggatgc actgggtgag gcagaggcct 180
ggacaaggcc ttgactggat cggagagatt gatccttctg atagttatat taactacaat 240
caaaagttca agggcaaggc cacattgact gtagacaaat cctccagcac agcctacatg 300
cagctcagca gcctgacatc tgaggactct gcggtctatt actgtggaag aaagagtctg 360
ggtgtctccg tgttagctta ctggggccaa gggactccgg tcactgtctc tgca 414

<210> SEQ ID NO 31
<211> LENGTH: 138
<212> TYPE: PRT
<213> ORGANISM: Mouse

<400> SEQUENCE: 31

```
Met Gly Trp Ser Cys Ile Ile Leu Phe Leu Val Ser Thr Gly Thr Gly
1               5                   10                  15

Val His Ser Gln Val Gln Leu Gln Gln Pro Gly Ala Glu Leu Val Lys
            20                  25                  30

Pro Gly Ala Ser Val Lys Leu Ser Cys Lys Ala Ser Gly Tyr Thr Phe
        35                  40                  45

Thr Ser Tyr Trp Met His Trp Val Arg Gln Arg Pro Gly Gln Gly Leu
    50                  55                  60

Asp Trp Ile Gly Glu Ile Asp Pro Ser Asp Ser Tyr Ile Asn Tyr Asn
65                  70                  75                  80

Gln Lys Phe Lys Gly Lys Ala Thr Leu Thr Val Asp Lys Ser Ser Ser
                85                  90                  95

Thr Ala Tyr Met Gln Leu Ser Ser Leu Thr Ser Glu Asp Ser Ala Val
            100                 105                 110

Tyr Tyr Cys Gly Arg Lys Ser Leu Gly Val Ser Val Leu Ala Tyr Trp
        115                 120                 125

Gly Gln Gly Thr Pro Val Thr Val Ser Ala
    130                 135
```

<210> SEQ ID NO 32
<211> LENGTH: 381
<212> TYPE: DNA
<213> ORGANISM: Mouse

<400> SEQUENCE: 32

```
atggagtcac agattcaggc atttgtattc gtgtttctct ggttgtctgg tgttgacgga     60

gacattgtga tgacccagtc tcacaaattc atgtccacat cagtaggaga cagggtcagc    120

atctcctgca cggccagtca ggatgtgaat gctgctgtag cctggtatca acaaaaacca    180

gggcaatctc ccaaactact gatttactgg gcatccaccc ggcacactgg agtccctgat    240

cgcttcacag gcagtggatc tgggacagat tatactctca ccatcagcag tgtgcaggct    300

gaagacctgg cactttatta ctgtcagcaa cattatagca ctccgctcac gttcggtgct    360

gggaccaagc tggagctgaa a                                              381
```

<210> SEQ ID NO 33
<211> LENGTH: 127
<212> TYPE: PRT
<213> ORGANISM: Mouse

<400> SEQUENCE: 33

```
Met Glu Ser Gln Ile Gln Ala Phe Val Phe Val Phe Leu Trp Leu Ser
1               5                   10                  15

Gly Val Asp Gly Asp Ile Val Met Thr Gln Ser His Lys Phe Met Ser
            20                  25                  30

Thr Ser Val Gly Asp Arg Val Ser Ile Ser Cys Thr Ala Ser Gln Asp
        35                  40                  45

Val Asn Ala Ala Val Ala Trp Tyr Gln Gln Lys Pro Gly Gln Ser Pro
    50                  55                  60

Lys Leu Leu Ile Tyr Trp Ala Ser Thr Arg His Thr Gly Val Pro Asp
65                  70                  75                  80

Arg Phe Thr Gly Ser Gly Ser Gly Thr Asp Tyr Thr Leu Thr Ile Ser
                85                  90                  95

Ser Val Gln Ala Glu Asp Leu Ala Leu Tyr Tyr Cys Gln Gln His Tyr
```

```
            100                 105                 110

Ser Thr Pro Leu Thr Phe Gly Ala Gly Thr Lys Leu Glu Leu Lys
        115                 120                 125
```

<210> SEQ ID NO 34
<211> LENGTH: 420
<212> TYPE: DNA
<213> ORGANISM: Mouse

<400> SEQUENCE: 34

```
atggcttggg tgtggacctt gctattcctg atggcagctg cccaaagtgc ccaagcacag     60

atccagttgg tgcagtctgg acctgagctg aagaagcctg gagagacagt caagatctcc    120

tgcaaggctt ctgggtatac cttcacaaac tatggaatga actgggtgaa gcaggctcca    180

ggaaagggtt taaagtggat gggctggata aacacctaca ctggacagtc aacatatgct    240

gatgacttca agggacgctt tgccttctct ttggaaacct ctgccagcac tgcccatttg    300

cagatcagca acctcaaaaa tgaggacgcg gctacatatt tctgtgcaag aatggagtat    360

ggtaactacg aaaatgcttt ggattactgg ggtcaaggaa cctcagtcac cgtctcctca    420
```

<210> SEQ ID NO 35
<211> LENGTH: 140
<212> TYPE: PRT
<213> ORGANISM: Mouse

<400> SEQUENCE: 35

```
Met Ala Trp Val Trp Thr Leu Leu Phe Leu Met Ala Ala Ala Gln Ser
1               5                   10                  15

Ala Gln Ala Gln Ile Gln Leu Val Gln Ser Gly Pro Glu Leu Lys Lys
            20                  25                  30

Pro Gly Glu Thr Val Lys Ile Ser Cys Lys Ala Ser Gly Tyr Thr Phe
        35                  40                  45

Thr Asn Tyr Gly Met Asn Trp Val Lys Gln Ala Pro Gly Lys Gly Leu
    50                  55                  60

Lys Trp Met Gly Trp Ile Asn Thr Tyr Thr Gly Gln Ser Thr Tyr Ala
65                  70                  75                  80

Asp Asp Phe Lys Gly Arg Phe Ala Phe Ser Leu Glu Thr Ser Ala Ser
                85                  90                  95

Thr Ala His Leu Gln Ile Ser Asn Leu Lys Asn Glu Asp Ala Ala Thr
            100                 105                 110

Tyr Phe Cys Ala Arg Met Glu Tyr Gly Asn Tyr Glu Asn Ala Leu Asp
        115                 120                 125

Tyr Trp Gly Gln Gly Thr Ser Val Thr Val Ser Ser
    130                 135                 140
```

<210> SEQ ID NO 36
<211> LENGTH: 381
<212> TYPE: DNA
<213> ORGANISM: Mouse

<400> SEQUENCE: 36

```
atggagtcac agattcaggt ctttgtattc gtgtttctct ggttgtctgg tgttgacgga     60

gacattgtga tgacccagtc tcacaaattc atgtccacat caataggaga cagggtcagc    120

atcacctgca aggccagtca ggatgtgagt actgctgtag tctggtatca acagaaacca    180

ggacactctc ctaaactact gatttattcg gcatcctacc ggtacactgg agtccctgat    240

cgcttcactg gcagtggatc tgggacggat ttcactttca ccatcagcag tgtgcaggct    300
```

gaagacctgg cagtttatta ctgtctacaa cattttagta ctcctcggac gttcggtgga 360
ggcaccaacc tggaaatcaa a 381

<210> SEQ ID NO 37
<211> LENGTH: 127
<212> TYPE: PRT
<213> ORGANISM: Mouse

<400> SEQUENCE: 37

Met Glu Ser Gln Ile Gln Val Phe Val Phe Val Phe Leu Trp Leu Ser
1 5 10 15

Gly Val Asp Gly Asp Ile Val Met Thr Gln Ser His Lys Phe Met Ser
20 25 30

Thr Ser Ile Gly Asp Arg Val Ser Ile Thr Cys Lys Ala Ser Gln Asp
35 40 45

Val Ser Thr Ala Val Val Trp Tyr Gln Gln Lys Pro Gly His Ser Pro
50 55 60

Lys Leu Leu Ile Tyr Ser Ala Ser Tyr Arg Tyr Thr Gly Val Pro Asp
65 70 75 80

Arg Phe Thr Gly Ser Gly Ser Gly Thr Asp Phe Thr Phe Thr Ile Ser
85 90 95

Ser Val Gln Ala Glu Asp Leu Ala Val Tyr Tyr Cys Leu Gln His Phe
100 105 110

Ser Thr Pro Arg Thr Phe Gly Gly Gly Thr Asn Leu Glu Ile Lys
115 120 125

<210> SEQ ID NO 38
<211> LENGTH: 420
<212> TYPE: DNA
<213> ORGANISM: Mouse

<400> SEQUENCE: 38
atggcttggg tgtggacctt gctattcctg atggcagctg cccaaagtgc ccaagcacag 60
atccagttgg tgcagtctgg acctgagctg aagaagcctg gagagacagt caagatctcc 120
tgcaaggctt ctgggtatac cttcacaaac tatggaatga actgggtgaa gcaggctcca 180
ggaaagggtt taaagtggat gggctggata aacacctaca ctggagagcc aacatatact 240
gatgacttca agggacggtt tgccttctct ttggaaacct ctgccagcac tgcctatttg 300
cagatcaaca gcctcaaaac tgaggacacg gctacatatt tctgtgcaag aatggagtat 360
ggtaactacg aaaatgctat ggactcctgg ggtcaaggaa cctcagtcac cgtctcctca 420

<210> SEQ ID NO 39
<211> LENGTH: 140
<212> TYPE: PRT
<213> ORGANISM: Mouse

<400> SEQUENCE: 39

Met Ala Trp Val Trp Thr Leu Leu Phe Leu Met Ala Ala Ala Gln Ser
1 5 10 15

Ala Gln Ala Gln Ile Gln Leu Val Gln Ser Gly Pro Glu Leu Lys Lys
20 25 30

Pro Gly Glu Thr Val Lys Ile Ser Cys Lys Ala Ser Gly Tyr Thr Phe
35 40 45

Thr Asn Tyr Gly Met Asn Trp Val Lys Gln Ala Pro Gly Lys Gly Leu
50 55 60

```
Lys Trp Met Gly Trp Ile Asn Thr Tyr Thr Gly Glu Pro Thr Tyr Thr
65                  70                  75                  80

Asp Asp Phe Lys Gly Arg Phe Ala Phe Ser Leu Glu Thr Ser Ala Ser
                85                  90                  95

Thr Ala Tyr Leu Gln Ile Asn Ser Leu Lys Thr Glu Asp Thr Ala Thr
            100                 105                 110

Tyr Phe Cys Ala Arg Met Glu Tyr Gly Asn Tyr Glu Asn Ala Met Asp
        115                 120                 125

Ser Trp Gly Gln Gly Thr Ser Val Thr Val Ser Ser
    130                 135                 140


<210> SEQ ID NO 40
<211> LENGTH: 381
<212> TYPE: DNA
<213> ORGANISM: Mouse

<400> SEQUENCE: 40

atggagtcac agattcaggt ctttgtattc gtgtttctct ggttgtctgg tgttgacgga      60

gacactgtga tgacccagtc tcacaaattc atgtccacat cagttggaga cagggtcagc     120

atcacctgca aggccagtca ggatgtgagt actgctgttg tctggtatca acaaaaacca     180

ggacaatctc ctaagctgct gatttactcg gcatcctacc ggtacactgg agtccctgat     240

cgcttcactg gcagtggatc tgggacggat ttcactttca ccatcagcag tgtgcaggct     300

gaagacctgg cagtttatta ctgtctccaa cattttaata ttcctcggac gttcggtggg     360

ggcaccaagc tggaaatcaa a                                               381


<210> SEQ ID NO 41
<211> LENGTH: 127
<212> TYPE: PRT
<213> ORGANISM: Mouse

<400> SEQUENCE: 41

Met Glu Ser Gln Ile Gln Val Phe Val Phe Val Phe Leu Trp Leu Ser
1               5                   10                  15

Gly Val Asp Gly Asp Thr Val Met Thr Gln Ser His Lys Phe Met Ser
            20                  25                  30

Thr Ser Val Gly Asp Arg Val Ser Ile Thr Cys Lys Ala Ser Gln Asp
        35                  40                  45

Val Ser Thr Ala Val Val Trp Tyr Gln Gln Lys Pro Gly Gln Ser Pro
    50                  55                  60

Lys Leu Leu Ile Tyr Ser Ala Ser Tyr Arg Tyr Thr Gly Val Pro Asp
65                  70                  75                  80

Arg Phe Thr Gly Ser Gly Ser Gly Thr Asp Phe Thr Phe Thr Ile Ser
                85                  90                  95

Ser Val Gln Ala Glu Asp Leu Ala Val Tyr Tyr Cys Leu Gln His Phe
            100                 105                 110

Asn Ile Pro Arg Thr Phe Gly Gly Gly Thr Lys Leu Glu Ile Lys
        115                 120                 125


<210> SEQ ID NO 42
<211> LENGTH: 414
<212> TYPE: DNA
<213> ORGANISM: Mouse

<400> SEQUENCE: 42

atggaatgga gctggatctt tctctttctc ctgtcaggaa ctgcaggtgt cctctctgag      60
```

```
gtccaattgc aacagtttgg agctgaggtg gtgaagcctg gggcttcagt gaagatatcc    120

tgcaaggctt ctggctacac attcactgac tacaacatag actgggtgaa gcagagccat    180

ggagagagtc ttgaatggat tggagatatt agtcctaatt ctgagggtac tacctacaac    240

cagaagttta agggacaggc cacattgact atagacaagt cctccaccac agcctacatg    300

gagctccgca gcctgacatc tgaggacagt gcagtctatt actgtgcaag agggagcggg    360

atctggaatg gtttggacta ctggggtcaa ggaacctctg tcaccgtctc ctca          414
```

<210> SEQ ID NO 43
<211> LENGTH: 138
<212> TYPE: PRT
<213> ORGANISM: Mouse

<400> SEQUENCE: 43

```
Met Glu Trp Ser Trp Ile Phe Leu Phe Leu Leu Ser Gly Thr Ala Gly
1               5                   10                  15

Val Leu Ser Glu Val Gln Leu Gln Gln Phe Gly Ala Glu Val Val Lys
            20                  25                  30

Pro Gly Ala Ser Val Lys Ile Ser Cys Lys Ala Ser Gly Tyr Thr Phe
        35                  40                  45

Thr Asp Tyr Asn Ile Asp Trp Val Lys Gln Ser His Gly Glu Ser Leu
    50                  55                  60

Glu Trp Ile Gly Asp Ile Ser Pro Asn Ser Glu Gly Thr Thr Tyr Asn
65                  70                  75                  80

Gln Lys Phe Lys Gly Gln Ala Thr Leu Thr Ile Asp Lys Ser Ser Thr
                85                  90                  95

Thr Ala Tyr Met Glu Leu Arg Ser Leu Thr Ser Glu Asp Ser Ala Val
            100                 105                 110

Tyr Tyr Cys Ala Arg Gly Ser Gly Ile Trp Asn Gly Leu Asp Tyr Trp
        115                 120                 125

Gly Gln Gly Thr Ser Val Thr Val Ser Ser
    130                 135
```

<210> SEQ ID NO 44
<211> LENGTH: 381
<212> TYPE: DNA
<213> ORGANISM: Mouse

<400> SEQUENCE: 44

```
atggagtcac agattcaggt ctttgtattc gtgtttctct ggttgtctgg tgttgacgga     60

gacattgtga tgacccagtc tcacaaattc atgtccacat cagtaggaga cagggtcagc    120

atcacctgca aggccagtca ggatgtgagt actgctgtag cctggtatca acagaaacca    180

ggacaatctc ctcaattact gatttattcg tcatcctacc ggtatgttgg agtccctgat    240

cgcttcactg gcagtggatc tgggacggac ttcactttca ccatcagcag tgtgcaggct    300

gaagacctgg cagtttatta ctgtcaccaa cattatagtc tcccgtacac gttcggaggg    360

gggaccaagc tggaaataaa a                                              381
```

<210> SEQ ID NO 45
<211> LENGTH: 127
<212> TYPE: PRT
<213> ORGANISM: Mouse

<400> SEQUENCE: 45

```
Met Glu Ser Gln Ile Gln Val Phe Val Phe Val Phe Leu Trp Leu Ser
1               5                   10                  15
```

```
Gly Val Asp Gly Asp Ile Val Met Thr Gln Ser His Lys Phe Met Ser
            20                  25                  30

Thr Ser Val Gly Asp Arg Val Ser Ile Thr Cys Lys Ala Ser Gln Asp
        35                  40                  45

Val Ser Thr Ala Val Ala Trp Tyr Gln Gln Lys Pro Gly Gln Ser Pro
    50                  55                  60

Gln Leu Leu Ile Tyr Ser Ser Ser Tyr Arg Tyr Val Gly Val Pro Asp
65                  70                  75                  80

Arg Phe Thr Gly Ser Gly Ser Gly Thr Asp Phe Thr Phe Thr Ile Ser
                85                  90                  95

Ser Val Gln Ala Glu Asp Leu Ala Val Tyr Tyr Cys His Gln His Tyr
            100                 105                 110

Ser Leu Pro Tyr Thr Phe Gly Gly Gly Thr Lys Leu Glu Ile Lys
        115                 120                 125


<210> SEQ ID NO 46
<211> LENGTH: 423
<212> TYPE: DNA
<213> ORGANISM: Mouse

<400> SEQUENCE: 46

atgggcaggc ttacttcttc attcttgcta ctgattgtcc ctgcatatgt cctgtcccag      60

gttactctga aagagtctgg ccctgggata ttgcagccct cccagaccct cagtctgact     120

tgttctttct ctgggttttc actgagtact tctggtatgg gtgtaggctg gattcgtcag     180

ccttcaggga agggtctgga gtggctgtca cacatttggt gggatgatga gaagcgctat     240

aacccagccc tgaagagccg actgacaatc tccaaggata cctccagcaa ccaggtattc     300

ctcaagatcg ccagtgtgga cactgcagat actgccacat actactgtgc tcgaataggg     360

gacaggtcgg gccacgcggg gtttgtttac tggggccaag ggactctggt cactgtctct     420

gca                                                                   423


<210> SEQ ID NO 47
<211> LENGTH: 141
<212> TYPE: PRT
<213> ORGANISM: Mouse

<400> SEQUENCE: 47

Met Gly Arg Leu Thr Ser Ser Phe Leu Leu Leu Ile Val Pro Ala Tyr
1               5                   10                  15

Val Leu Ser Gln Val Thr Leu Lys Glu Ser Gly Pro Gly Ile Leu Gln
            20                  25                  30

Pro Ser Gln Thr Leu Ser Leu Thr Cys Ser Phe Ser Gly Phe Ser Leu
        35                  40                  45

Ser Thr Ser Gly Met Gly Val Gly Trp Ile Arg Gln Pro Ser Gly Lys
    50                  55                  60

Gly Leu Glu Trp Leu Ser His Ile Trp Trp Asp Asp Glu Lys Arg Tyr
65                  70                  75                  80

Asn Pro Ala Leu Lys Ser Arg Leu Thr Ile Ser Lys Asp Thr Ser Ser
                85                  90                  95

Asn Gln Val Phe Leu Lys Ile Ala Ser Val Asp Thr Ala Asp Thr Ala
            100                 105                 110

Thr Tyr Tyr Cys Ala Arg Ile Gly Asp Arg Ser Gly His Ala Gly Phe
        115                 120                 125

Val Tyr Trp Gly Gln Gly Thr Leu Val Thr Val Ser Ala
```

```
130                 135                 140

<210> SEQ ID NO 48
<211> LENGTH: 381
<212> TYPE: DNA
<213> ORGANISM: Mouse

<400> SEQUENCE: 48

atgaggaccc ctgctcagtt tcttggaatc ttattactct ggtttccagg tatcaaatgt      60

gacatcaaga tgacccagtc tccatcttcc atgtatgcat ctctaggaga gagagtcact     120

atcacttgca aggcgagtca ggacattaat agctatttaa gctggttcca gcagaaacca     180

gggaaatctc ctaagaccct gatctatcgt gcaaacagat tggtagatgg ggtcccatca     240

aggttcagtg gcagtggatc tgggcaagat tattctctca ccatcagcag cctggagtat     300

gaagatatgg gaacttatta ttgtctacag tatgatgagt ttccgtacac gttcggaggg     360

gggaccaagc tggaaataaa a                                               381

<210> SEQ ID NO 49
<211> LENGTH: 127
<212> TYPE: PRT
<213> ORGANISM: Mouse

<400> SEQUENCE: 49

Met Arg Thr Pro Ala Gln Phe Leu Gly Ile Leu Leu Leu Trp Phe Pro
1               5                   10                  15

Gly Ile Lys Cys Asp Ile Lys Met Thr Gln Ser Pro Ser Ser Met Tyr
            20                  25                  30

Ala Ser Leu Gly Glu Arg Val Thr Ile Thr Cys Lys Ala Ser Gln Asp
        35                  40                  45

Ile Asn Ser Tyr Leu Ser Trp Phe Gln Gln Lys Pro Gly Lys Ser Pro
    50                  55                  60

Lys Thr Leu Ile Tyr Arg Ala Asn Arg Leu Val Asp Gly Val Pro Ser
65                  70                  75                  80

Arg Phe Ser Gly Ser Gly Ser Gly Gln Asp Tyr Ser Leu Thr Ile Ser
                85                  90                  95

Ser Leu Glu Tyr Glu Asp Met Gly Thr Tyr Tyr Cys Leu Gln Tyr Asp
            100                 105                 110

Glu Phe Pro Tyr Thr Phe Gly Gly Gly Thr Lys Leu Glu Ile Lys
        115                 120                 125

<210> SEQ ID NO 50
<211> LENGTH: 417
<212> TYPE: DNA
<213> ORGANISM: Mouse

<400> SEQUENCE: 50

atgtacttgg gactgaacta tgtattcatt gtttttctct taaatggtgt ccagagtgaa      60

gtgaagcttg aggagtctgg aggaggcttg gtgcaacctg gaggatccat gaaactctct     120

tgtgctgcct ctggattcac ttttagtgac gcctggatgg actgggtccg ccagtctcca     180

gagaaggggc ttgaatgggt tggtaaaatt agaagtgaaa ttaatgatca tgcaacatac     240

tatgctgagt ctgtgaaagg gaggttcacc atctcaagag atgattccaa aagtggtgtc     300

tacctgcaaa tgaacaactt aagagctgaa gacactggca tttattactg tgccagggat     360

ggttactacg gtgctatgga ctactggggt caaggaacgt cagtcaccgt ctcctca        417
```

<210> SEQ ID NO 51
<211> LENGTH: 139
<212> TYPE: PRT
<213> ORGANISM: Mouse

<400> SEQUENCE: 51

```
Met Tyr Leu Gly Leu Asn Tyr Val Phe Ile Val Phe Leu Leu Asn Gly
1               5                   10                  15

Val Gln Ser Glu Val Lys Leu Glu Glu Ser Gly Gly Gly Leu Val Gln
            20                  25                  30

Pro Gly Gly Ser Met Lys Leu Ser Cys Ala Ala Ser Gly Phe Thr Phe
        35                  40                  45

Ser Asp Ala Trp Met Asp Trp Val Arg Gln Ser Pro Glu Lys Gly Leu
    50                  55                  60

Glu Trp Val Gly Lys Ile Arg Ser Glu Ile Asn Asp His Ala Thr Tyr
65                  70                  75                  80

Tyr Ala Glu Ser Val Lys Gly Arg Phe Thr Ile Ser Arg Asp Asp Ser
                85                  90                  95

Lys Ser Gly Val Tyr Leu Gln Met Asn Asn Leu Arg Ala Glu Asp Thr
            100                 105                 110

Gly Ile Tyr Tyr Cys Ala Arg Asp Gly Tyr Tyr Gly Ala Met Asp Tyr
        115                 120                 125

Trp Gly Gln Gly Thr Ser Val Thr Val Ser Ser
    130                 135
```

<210> SEQ ID NO 52
<211> LENGTH: 381
<212> TYPE: DNA
<213> ORGANISM: Mouse

<400> SEQUENCE: 52

```
atgaggttcc aggttcaggt tctggggctc cttctgctct ggatatcagg tgcccagtgt      60

gatgttcaga taacccagtc tccatcttat cttgctgcat ctcctggaga aaccattact     120

attaattgca ggtcaaataa gagcattagc agatatttag cctggtatca agagaaacct     180

gggaaaacta ataagcttct tatctactct ggatccactt tgcaatctgg aattccatca     240

aggttcagtg gcagtggatc taatacagat ttcactctca ccatcagtag cctggagcct     300

gaagattttg caatgtatta ctgtcaacag cataatgaat acccgtacac gttcggctcg     360

gggacaaaat tggaaataaa a                                               381
```

<210> SEQ ID NO 53
<211> LENGTH: 127
<212> TYPE: PRT
<213> ORGANISM: Mouse

<400> SEQUENCE: 53

```
Met Arg Phe Gln Val Gln Val Leu Gly Leu Leu Leu Leu Trp Ile Ser
1               5                   10                  15

Gly Ala Gln Cys Asp Val Gln Ile Thr Gln Ser Pro Ser Tyr Leu Ala
            20                  25                  30

Ala Ser Pro Gly Glu Thr Ile Thr Ile Asn Cys Arg Ser Asn Lys Ser
        35                  40                  45

Ile Ser Arg Tyr Leu Ala Trp Tyr Gln Glu Lys Pro Gly Lys Thr Asn
    50                  55                  60

Lys Leu Leu Ile Tyr Ser Gly Ser Thr Leu Gln Ser Gly Ile Pro Ser
65                  70                  75                  80
```

```
Arg Phe Ser Gly Ser Gly Ser Asn Thr Asp Phe Thr Leu Thr Ile Ser
            85                  90                  95

Ser Leu Glu Pro Glu Asp Phe Ala Met Tyr Tyr Cys Gln Gln His Asn
            100                 105                 110

Glu Tyr Pro Tyr Thr Phe Gly Ser Gly Thr Lys Leu Glu Ile Lys
        115                 120                 125
```

<210> SEQ ID NO 54
<211> LENGTH: 414
<212> TYPE: DNA
<213> ORGANISM: Mouse

<400> SEQUENCE: 54

```
atgggatgga gctgtatcat cctcttcttg gtatcaacag gtacaggtgt ccactcccag      60

gtccaactgc agcagcctgg ggctgagctt gtgaagcctg gggcttcagt gaagctgtcc     120

tgcaaggctt ctggctacac cttcaccagc tactggatgc actgggtgag gcagaggcct     180

ggacaaggcc ttgactggat cggagagatt gatccttctg atagttatat taactacaat     240

caaaagttca agggcaaggc cacattgact gtagacaaat cctccagcac agcctacatg     300

cagctcagca gcctgacatc tgaggactct gcggtctatt actgtggaag aaagagtctg     360

ggtgtctccg tgttagctta ctggggccaa gggactccgg tcactgtctc tgca           414
```

<210> SEQ ID NO 55
<211> LENGTH: 138
<212> TYPE: PRT
<213> ORGANISM: Mouse

<400> SEQUENCE: 55

```
Met Gly Trp Ser Cys Ile Ile Leu Phe Leu Val Ser Thr Gly Thr Gly
1               5                   10                  15

Val His Ser Gln Val Gln Leu Gln Gln Pro Gly Ala Glu Leu Val Lys
            20                  25                  30

Pro Gly Ala Ser Val Lys Leu Ser Cys Lys Ala Ser Gly Tyr Thr Phe
        35                  40                  45

Thr Ser Tyr Trp Met His Trp Val Arg Gln Arg Pro Gly Gln Gly Leu
    50                  55                  60

Asp Trp Ile Gly Glu Ile Asp Pro Ser Asp Ser Tyr Ile Asn Tyr Asn
65                  70                  75                  80

Gln Lys Phe Lys Gly Lys Ala Thr Leu Thr Val Asp Lys Ser Ser Ser
            85                  90                  95

Thr Ala Tyr Met Gln Leu Ser Ser Leu Thr Ser Glu Asp Ser Ala Val
            100                 105                 110

Tyr Tyr Cys Gly Arg Lys Ser Leu Gly Val Ser Val Leu Ala Tyr Trp
        115                 120                 125

Gly Gln Gly Thr Pro Val Thr Val Ser Ala
    130                 135
```

<210> SEQ ID NO 56
<211> LENGTH: 381
<212> TYPE: DNA
<213> ORGANISM: Mouse

<400> SEQUENCE: 56

```
atggagtcac agattcaggc atttgtattc gtgtttctct ggttgtctgg tgttgacgga      60

gacattgtga tgacccagtc tcacaaattc atgtccacat cagtaggaga cagggtcagc     120

atctcctgca cggccagtca ggatgtgaat gctgctgtag cctggtatca acaaaaacca     180
```

```
gggcaatctc ccaaactact gatttactgg gcatccaccc ggcacactgg agtccctgat    240

cgcttcacag gcagtggatc tgggacagat tatactctca ccatcagcag tgtgcaggct    300

gaagacctgg cactttatta ctgtcagcaa cattatagca ctccgctcac gttcggtgct    360

gggaccaagc tggagctgaa a                                              381
```

```
<210> SEQ ID NO 57
<211> LENGTH: 127
<212> TYPE: PRT
<213> ORGANISM: Mouse

<400> SEQUENCE: 57

Met Glu Ser Gln Ile Gln Ala Phe Val Phe Val Phe Leu Trp Leu Ser
1               5                   10                  15

Gly Val Asp Gly Asp Ile Val Met Thr Gln Ser His Lys Phe Met Ser
            20                  25                  30

Thr Ser Val Gly Asp Arg Val Ser Ile Ser Cys Thr Ala Ser Gln Asp
        35                  40                  45

Val Asn Ala Ala Val Ala Trp Tyr Gln Gln Lys Pro Gly Gln Ser Pro
    50                  55                  60

Lys Leu Leu Ile Tyr Trp Ala Ser Thr Arg His Thr Gly Val Pro Asp
65                  70                  75                  80

Arg Phe Thr Gly Ser Gly Ser Gly Thr Asp Tyr Thr Leu Thr Ile Ser
                85                  90                  95

Ser Val Gln Ala Glu Asp Leu Ala Leu Tyr Tyr Cys Gln Gln His Tyr
            100                 105                 110

Ser Thr Pro Leu Thr Phe Gly Ala Gly Thr Lys Leu Glu Leu Lys
        115                 120                 125


<210> SEQ ID NO 58
<211> LENGTH: 16
<212> TYPE: PRT
<213> ORGANISM: Mouse

<400> SEQUENCE: 58

Cys Ala Arg Met Glu Tyr Gly Asn Tyr Glu Asn Ala Leu Asp Tyr Trp
1               5                   10                  15


<210> SEQ ID NO 59
<211> LENGTH: 11
<212> TYPE: PRT
<213> ORGANISM: Mouse

<400> SEQUENCE: 59

Cys Leu Gln His Phe Ser Thr Pro Arg Thr Phe
1               5                   10


<210> SEQ ID NO 60
<211> LENGTH: 16
<212> TYPE: PRT
<213> ORGANISM: Mouse

<400> SEQUENCE: 60

Cys Ala Arg Met Glu Tyr Gly Asn Tyr Glu Asn Ala Met Asp Ser Trp
1               5                   10                  15


<210> SEQ ID NO 61
<211> LENGTH: 11
<212> TYPE: PRT
<213> ORGANISM: Mouse
```

<400> SEQUENCE: 61

Cys Leu Gln His Phe Asn Ile Pro Arg Thr Phe
1 5 10

<210> SEQ ID NO 62
<211> LENGTH: 14
<212> TYPE: PRT
<213> ORGANISM: Mouse

<400> SEQUENCE: 62

Cys Ala Arg Gly Ser Gly Ile Trp Asn Gly Leu Asp Tyr Trp
1 5 10

<210> SEQ ID NO 63
<211> LENGTH: 11
<212> TYPE: PRT
<213> ORGANISM: Mouse

<400> SEQUENCE: 63

Cys His Gln His Tyr Ser Leu Pro Tyr Thr Phe
1 5 10

<210> SEQ ID NO 64
<211> LENGTH: 16
<212> TYPE: PRT
<213> ORGANISM: Mouse

<400> SEQUENCE: 64

Cys Ala Arg Ile Gly Asp Arg Ser Gly His Ala Gly Phe Val Tyr Trp
1 5 10 15

<210> SEQ ID NO 65
<211> LENGTH: 11
<212> TYPE: PRT
<213> ORGANISM: Mouse

<400> SEQUENCE: 65

Cys Leu Gln Tyr Asp Glu Phe Pro Tyr Thr Phe
1 5 10

<210> SEQ ID NO 66
<211> LENGTH: 13
<212> TYPE: PRT
<213> ORGANISM: Mouse

<400> SEQUENCE: 66

Cys Ala Arg Asp Gly Tyr Tyr Gly Ala Met Asp Tyr Trp
1 5 10

<210> SEQ ID NO 67
<211> LENGTH: 11
<212> TYPE: PRT
<213> ORGANISM: Mouse

<400> SEQUENCE: 67

Cys Gln Gln His Asn Glu Tyr Pro Tyr Thr Phe
1 5 10

<210> SEQ ID NO 68
<211> LENGTH: 14
<212> TYPE: PRT
<213> ORGANISM: Mouse

<400> SEQUENCE: 68

Cys Gly Arg Lys Ser Leu Gly Val Ser Val Leu Ala Tyr Trp
1 5 10

<210> SEQ ID NO 69
<211> LENGTH: 11
<212> TYPE: PRT
<213> ORGANISM: Mouse

<400> SEQUENCE: 69

Cys Gln Gln His Tyr Ser Thr Pro Leu Thr Phe
1 5 10

<210> SEQ ID NO 70
<211> LENGTH: 1413
<212> TYPE: DNA
<213> ORGANISM: Artificial Sequence
<220> FEATURE:
<223> OTHER INFORMATION: chimeric mAb

<400> SEQUENCE: 70
atgggcaggc ttacttcttc attcttgcta ctgattgtcc ctgcatatgt cctgtcccag 60
gttactctga aagagtctgg ccctgggata ttgcagccct cccagaccct cagtctgact 120
tgttctttct ctgggttttc actgagtact tctggtatgg gtgtaggctg gattcgtcag 180
ccttcaggga agggtctgga gtggctgtca cacatttggt gggatgatga gaagcgctat 240
aacccagccc tgaagagccg actgacaatc tccaaggata cctccagcaa ccaggtattc 300
ctcaagatcg ccagtgtgga cactgcagat actgccacat actactgtgc tcgaataggg 360
gacaggtcgg gccacgcggg gtttgtttac tggggccaag ggactctggt cactgtctct 420
gcagctagca ccaagggccc atcggtcttc cccctggcac cctcctccaa gagcacctct 480
gggggcacag cggccctggg ctgcctggtc aaggactact tccccgaacc ggtgacggtg 540
tcgtggaact caggcgccct gaccagcggc gtgcacacct tcccggctgt cctacagtcc 600
tcaggactct actccctcag cagcgtggtg accgtgccct ccagcagctt gggcacccag 660
acctacatct gcaacgtgaa tcacaagccc agcaacacca aggtggacaa gaaagttgag 720
cccaaatctt gtgacaaaac tcacacatgc ccaccgtgcc cagcacctga actcctggcg 780
ggaccggacg tcttcctctt ccccccaaaa cccaaggaca ccctcatgat ctcccggacc 840
cctgaggtca catgcgtggt ggtggacgtg agccacgaag accctgaggt caagttcaac 900
tggtacgtgg acggcgtgga ggtgcataat gccaagacaa agccgcggga ggagcagtac 960
aacagcacgt accgtgtggt cagcgtcctc accgtcctgc accaggactg gctgaatggc 1020
aaggagtaca agtgcaaggt ctccaacaaa gccctcccag cccccgagga gaaaaccatc 1080
tccaaagcca aagggcagcc ccgagaacca caggtgtaca ccctgccccc atcccgggag 1140
gagatgacca agaaccaggt cagcctgacc tgcctggtca aaggcttcta tcccagcgac 1200
atcgccgtgg agtgggagag caatgggcag ccggagaaca actacaagac cacgcctccc 1260
gtgctggact ccgacggctc cttcttcctc tacagcaagc tcaccgtgga caagagcagg 1320
tggcagcagg ggaacgtctt ctcatgctcc gtgatgcacg aggctctgca caaccactac 1380
acgcagaaga gcctctccct gtctccgggt aaa 1413

<210> SEQ ID NO 71
<211> LENGTH: 471
<212> TYPE: PRT
<213> ORGANISM: Artificial Sequence
<220> FEATURE:

<223> OTHER INFORMATION: chimeric mAb

<400> SEQUENCE: 71

Met Gly Arg Leu Thr Ser Ser Phe Leu Leu Leu Ile Val Pro Ala Tyr
1 5 10 15

Val Leu Ser Gln Val Thr Leu Lys Glu Ser Gly Pro Gly Ile Leu Gln
20 25 30

Pro Ser Gln Thr Leu Ser Leu Thr Cys Ser Phe Ser Gly Phe Ser Leu
35 40 45

Ser Thr Ser Gly Met Gly Val Gly Trp Ile Arg Gln Pro Ser Gly Lys
50 55 60

Gly Leu Glu Trp Leu Ser His Ile Trp Trp Asp Asp Glu Lys Arg Tyr
65 70 75 80

Asn Pro Ala Leu Lys Ser Arg Leu Thr Ile Ser Lys Asp Thr Ser Ser
85 90 95

Asn Gln Val Phe Leu Lys Ile Ala Ser Val Asp Thr Ala Asp Thr Ala
100 105 110

Thr Tyr Tyr Cys Ala Arg Ile Gly Asp Arg Ser Gly His Ala Gly Phe
115 120 125

Val Tyr Trp Gly Gln Gly Thr Leu Val Thr Val Ser Ala Ala Ser Thr
130 135 140

Lys Gly Pro Ser Val Phe Pro Leu Ala Pro Ser Ser Lys Ser Thr Ser
145 150 155 160

Gly Gly Thr Ala Ala Leu Gly Cys Leu Val Lys Asp Tyr Phe Pro Glu
165 170 175

Pro Val Thr Val Ser Trp Asn Ser Gly Ala Leu Thr Ser Gly Val His
180 185 190

Thr Phe Pro Ala Val Leu Gln Ser Ser Gly Leu Tyr Ser Leu Ser Ser
195 200 205

Val Val Thr Val Pro Ser Ser Ser Leu Gly Thr Gln Thr Tyr Ile Cys
210 215 220

Asn Val Asn His Lys Pro Ser Asn Thr Lys Val Asp Lys Lys Val Glu
225 230 235 240

Pro Lys Ser Cys Asp Lys Thr His Thr Cys Pro Pro Cys Pro Ala Pro
245 250 255

Glu Leu Leu Ala Gly Pro Asp Val Phe Leu Phe Pro Pro Lys Pro Lys
260 265 270

Asp Thr Leu Met Ile Ser Arg Thr Pro Glu Val Thr Cys Val Val Val
275 280 285

Asp Val Ser His Glu Asp Pro Glu Val Lys Phe Asn Trp Tyr Val Asp
290 295 300

Gly Val Glu Val His Asn Ala Lys Thr Lys Pro Arg Glu Glu Gln Tyr
305 310 315 320

Asn Ser Thr Tyr Arg Val Val Ser Val Leu Thr Val Leu His Gln Asp
325 330 335

Trp Leu Asn Gly Lys Glu Tyr Lys Cys Lys Val Ser Asn Lys Ala Leu
340 345 350

Pro Ala Pro Glu Glu Lys Thr Ile Ser Lys Ala Lys Gly Gln Pro Arg
355 360 365

Glu Pro Gln Val Tyr Thr Leu Pro Pro Ser Arg Glu Glu Met Thr Lys
370 375 380

Asn Gln Val Ser Leu Thr Cys Leu Val Lys Gly Phe Tyr Pro Ser Asp
385 390 395 400

```
Ile Ala Val Glu Trp Glu Ser Asn Gly Gln Pro Glu Asn Asn Tyr Lys
                405                 410                 415

Thr Thr Pro Pro Val Leu Asp Ser Asp Gly Ser Phe Phe Leu Tyr Ser
            420                 425                 430

Lys Leu Thr Val Asp Lys Ser Arg Trp Gln Gln Gly Asn Val Phe Ser
        435                 440                 445

Cys Ser Val Met His Glu Ala Leu His Asn His Tyr Thr Gln Lys Ser
    450                 455                 460

Leu Ser Leu Ser Pro Gly Lys
465                 470


<210> SEQ ID NO 72
<211> LENGTH: 699
<212> TYPE: DNA
<213> ORGANISM: Artificial Sequence
<220> FEATURE:
<223> OTHER INFORMATION: chimeric antibody

<400> SEQUENCE: 72

atgaggaccc ctgctcagtt tcttggaatc ttattactct ggtttccagg tatcaaatgt      60

gacatcaaga tgacccagtc tccatcttcc atgtatgcat ctctaggaga gagagtcact     120

atcacttgca aggcgagtca ggacattaat agctatttaa gctggttcca gcagaaacca     180

gggaaatctc ctaagaccct gatctatcgt gcaaacagat tggtagatgg ggtcccatca     240

aggttcagtg gcagtggatc tgggcaagat tattctctca ccatcagcag cctggagtat     300

gaagatatgg gaacttatta ttgtctacag tatgatgagt ttccgtacac gttcggaggg     360

gggaccaagc tggaaataaa aacggtggct gcaccatctg tcttcatctt cccgccatct     420

gatgagcagt tgaaatctgg aactgcctct gttgtgtgcc tgctgaataa cttctatccc     480

agagaggcca aagtacagtg gaaggtggat aacgccctcc aatcgggtaa ctcccaggag     540

agtgtcacag agcaggacag caaggacagc acctacagcc tcagcagcac cctgacgctg     600

agcaaagcag actacgagaa acacaaagtc tacgcctgcg aagtcaccca tcagggcctg     660

agctcgcccg tcacaaagag cttcaacagg ggagagtgt                            699


<210> SEQ ID NO 73
<211> LENGTH: 233
<212> TYPE: PRT
<213> ORGANISM: Artificial Sequence
<220> FEATURE:
<223> OTHER INFORMATION: mouse-human chimeric antibody

<400> SEQUENCE: 73

Met Arg Thr Pro Ala Gln Phe Leu Gly Ile Leu Leu Leu Trp Phe Pro
1               5                   10                  15

Gly Ile Lys Cys Asp Ile Lys Met Thr Gln Ser Pro Ser Ser Met Tyr
            20                  25                  30

Ala Ser Leu Gly Glu Arg Val Thr Ile Thr Cys Lys Ala Ser Gln Asp
        35                  40                  45

Ile Asn Ser Tyr Leu Ser Trp Phe Gln Gln Lys Pro Gly Lys Ser Pro
    50                  55                  60

Lys Thr Leu Ile Tyr Arg Ala Asn Arg Leu Val Asp Gly Val Pro Ser
65                  70                  75                  80

Arg Phe Ser Gly Ser Gly Ser Gly Gln Asp Tyr Ser Leu Thr Ile Ser
                85                  90                  95

Ser Leu Glu Tyr Glu Asp Met Gly Thr Tyr Tyr Cys Leu Gln Tyr Asp
            100                 105                 110
```

```
Glu Phe Pro Tyr Thr Phe Gly Gly Gly Thr Lys Leu Glu Ile Lys Thr
        115                 120                 125

Val Ala Ala Pro Ser Val Phe Ile Phe Pro Pro Ser Asp Glu Gln Leu
    130                 135                 140

Lys Ser Gly Thr Ala Ser Val Val Cys Leu Leu Asn Asn Phe Tyr Pro
145                 150                 155                 160

Arg Glu Ala Lys Val Gln Trp Lys Val Asp Asn Ala Leu Gln Ser Gly
                165                 170                 175

Asn Ser Gln Glu Ser Val Thr Glu Gln Asp Ser Lys Asp Ser Thr Tyr
            180                 185                 190

Ser Leu Ser Ser Thr Leu Thr Leu Ser Lys Ala Asp Tyr Glu Lys His
        195                 200                 205

Lys Val Tyr Ala Cys Glu Val Thr His Gln Gly Leu Ser Ser Pro Val
    210                 215                 220

Thr Lys Ser Phe Asn Arg Gly Glu Cys
225                 230
```

<210> SEQ ID NO 74
<211> LENGTH: 1410
<212> TYPE: DNA
<213> ORGANISM: Artificial Sequence
<220> FEATURE:
<223> OTHER INFORMATION: mouse-human chimeric antibody

<400> SEQUENCE: 74

```
atggcttggg tgtggacctt gctattcctg atggcagctg cccaaagtgc ccaagcacag      60

atccagttgg tgcagtctgg acctgagctg aagaagcctg gagagacagt caagatctcc     120

tgcaaggctt ctgggtatac cttcacaaac tatggaatga actgggtgaa gcaggctcca     180

ggaaagggtt taaagtggat gggctggata aacacctaca ctggagagcc aacatatact     240

gatgacttca agggacggtt tgccttctct ttggaaacct ctgccagcac tgcctatttg     300

cagatcaaca gcctcaaaac tgaggacacg gctacatatt tctgtgcaag aatggagtat     360

ggtaactacg aaaatgctat ggactcctgg ggtcaaggaa cctcagtcac cgtctcctca     420

gctagcacca agggcccatc ggtcttcccc ctggcaccct cctccaagag cacctctggg     480

ggcacagcgg ccctgggctg cctggtcaag gactacttcc ccgaaccggt gacggtgtcg     540

tggaactcag gcgccctgac cagcggcgtg cacaccttcc cggctgtcct acagtcctca     600

ggactctact ccctcagcag cgtggtgacc gtgccctcca gcagcttggg cacccagacc     660

tacatctgca acgtgaatca caagcccagc aacaccaagg tggacaagaa agttgagccc     720

aaatcttgtg acaaaactca cacatgccca ccgtgcccag cacctgaact cctggcggga     780

ccggacgtct tcctcttccc cccaaaaccc aaggacaccc tcatgatctc ccggacccct     840

gaggtcacat gcgtggtggt ggacgtgagc cacgaagacc ctgaggtcaa gttcaactgg     900

tacgtggacg gcgtggaggt gcataatgcc aagacaaagc cgcgggagga gcagtacaac     960

agcacgtacc gtgtggtcag cgtcctcacc gtcctgcacc aggactggct gaatggcaag    1020

gagtacaagt gcaaggtctc caacaaagcc ctcccagccc ccgaggagaa aaccatctcc    1080

aaagccaaag ggcagccccg agaaccacag gtgtacaccc tgcccccatc ccgggaggag    1140

atgaccaaga accaggtcag cctgacctgc ctggtcaaag gcttctatcc cagcgacatc    1200

gccgtggagt gggagagcaa tgggcagccg gagaacaact acaagaccac gcctcccgtg    1260

ctggactccg acggctcctt cttcctctac agcaagctca ccgtggacaa gagcaggtgg    1320
```

cagcagggga acgtcttctc atgctccgtg atgcacgagg ctctgcacaa ccactacacg 1380
cagaagagcc tctccctgtc tccgggtaaa 1410

<210> SEQ ID NO 75
<211> LENGTH: 470
<212> TYPE: PRT
<213> ORGANISM: Artificial Sequence
<220> FEATURE:
<223> OTHER INFORMATION: mouse-human chimeric antibody

<400> SEQUENCE: 75

Met Ala Trp Val Trp Thr Leu Leu Phe Leu Met Ala Ala Ala Gln Ser
1 5 10 15

Ala Gln Ala Gln Ile Gln Leu Val Gln Ser Gly Pro Glu Leu Lys Lys
20 25 30

Pro Gly Glu Thr Val Lys Ile Ser Cys Lys Ala Ser Gly Tyr Thr Phe
35 40 45

Thr Asn Tyr Gly Met Asn Trp Val Lys Gln Ala Pro Gly Lys Gly Leu
50 55 60

Lys Trp Met Gly Trp Ile Asn Thr Tyr Thr Gly Glu Pro Thr Tyr Thr
65 70 75 80

Asp Asp Phe Lys Gly Arg Phe Ala Phe Ser Leu Glu Thr Ser Ala Ser
85 90 95

Thr Ala Tyr Leu Gln Ile Asn Ser Leu Lys Thr Glu Asp Thr Ala Thr
100 105 110

Tyr Phe Cys Ala Arg Met Glu Tyr Gly Asn Tyr Glu Asn Ala Met Asp
115 120 125

Ser Trp Gly Gln Gly Thr Ser Val Thr Val Ser Ser Ala Ser Thr Lys
130 135 140

Gly Pro Ser Val Phe Pro Leu Ala Pro Ser Ser Lys Ser Thr Ser Gly
145 150 155 160

Gly Thr Ala Ala Leu Gly Cys Leu Val Lys Asp Tyr Phe Pro Glu Pro
165 170 175

Val Thr Val Ser Trp Asn Ser Gly Ala Leu Thr Ser Gly Val His Thr
180 185 190

Phe Pro Ala Val Leu Gln Ser Ser Gly Leu Tyr Ser Leu Ser Ser Val
195 200 205

Val Thr Val Pro Ser Ser Ser Leu Gly Thr Gln Thr Tyr Ile Cys Asn
210 215 220

Val Asn His Lys Pro Ser Asn Thr Lys Val Asp Lys Lys Val Glu Pro
225 230 235 240

Lys Ser Cys Asp Lys Thr His Thr Cys Pro Pro Cys Pro Ala Pro Glu
245 250 255

Leu Leu Ala Gly Pro Asp Val Phe Leu Phe Pro Pro Lys Pro Lys Asp
260 265 270

Thr Leu Met Ile Ser Arg Thr Pro Glu Val Thr Cys Val Val Val Asp
275 280 285

Val Ser His Glu Asp Pro Glu Val Lys Phe Asn Trp Tyr Val Asp Gly
290 295 300

Val Glu Val His Asn Ala Lys Thr Lys Pro Arg Glu Glu Gln Tyr Asn
305 310 315 320

Ser Thr Tyr Arg Val Val Ser Val Leu Thr Val Leu His Gln Asp Trp
325 330 335

Leu Asn Gly Lys Glu Tyr Lys Cys Lys Val Ser Asn Lys Ala Leu Pro
340 345 350

```
Ala Pro Glu Glu Lys Thr Ile Ser Lys Ala Lys Gly Gln Pro Arg Glu
        355                 360                 365

Pro Gln Val Tyr Thr Leu Pro Pro Ser Arg Glu Glu Met Thr Lys Asn
    370                 375                 380

Gln Val Ser Leu Thr Cys Leu Val Lys Gly Phe Tyr Pro Ser Asp Ile
385                 390                 395                 400

Ala Val Glu Trp Glu Ser Asn Gly Gln Pro Glu Asn Asn Tyr Lys Thr
                405                 410                 415

Thr Pro Pro Val Leu Asp Ser Asp Gly Ser Phe Phe Leu Tyr Ser Lys
            420                 425                 430

Leu Thr Val Asp Lys Ser Arg Trp Gln Gln Gly Asn Val Phe Ser Cys
        435                 440                 445

Ser Val Met His Glu Ala Leu His Asn His Tyr Thr Gln Lys Ser Leu
    450                 455                 460

Ser Leu Ser Pro Gly Lys
465                 470


<210> SEQ ID NO 76
<211> LENGTH: 699
<212> TYPE: DNA
<213> ORGANISM: Artificial Sequence
<220> FEATURE:
<223> OTHER INFORMATION: mouse-human chimeric antibody

<400> SEQUENCE: 76

atggagtcac agattcaggt ctttgtattc gtgtttctct ggttgtctgg tgttgacgga     60

gacactgtga tgacccagtc tcacaaattc atgtccacat cagttggaga cagggtcagc    120

atcacctgca aggccagtca ggatgtgagt actgctgttg tctggtatca acaaaaacca    180

ggacaatctc ctaagctgct gatttactcg gcatcctacc ggtacactgg agtccctgat    240

cgcttcactg gcagtggatc tgggacggat ttcactttca ccatcagcag tgtgcaggct    300

gaagacctgg cagtttatta ctgtctccaa cattttaata ttcctcggac gttcggtggg    360

ggcaccaagc tggaaatcaa aacggtggct gcaccatctg tcttcatctt cccgccatct    420

gatgagcagt tgaaatctgg aactgcctct gttgtgtgcc tgctgaataa cttctatccc    480

agagaggcca aagtacagtg gaaggtggat aacgccctcc aatcgggtaa ctcccaggag    540

agtgtcacag agcaggacag caaggacagc acctacagcc tcagcagcac cctgacgctg    600

agcaaagcag actacgagaa acacaaagtc tacgcctgcg aagtcaccca tcagggcctg    660

agctcgcccg tcacaaagag cttcaacagg ggagagtgt                           699


<210> SEQ ID NO 77
<211> LENGTH: 233
<212> TYPE: PRT
<213> ORGANISM: Artificial Sequence
<220> FEATURE:
<223> OTHER INFORMATION: mouse-human chimeric antibody

<400> SEQUENCE: 77

Met Glu Ser Gln Ile Gln Val Phe Val Phe Val Phe Leu Trp Leu Ser
1               5                   10                  15

Gly Val Asp Gly Asp Thr Val Met Thr Gln Ser His Lys Phe Met Ser
            20                  25                  30

Thr Ser Val Gly Asp Arg Val Ser Ile Thr Cys Lys Ala Ser Gln Asp
        35                  40                  45

Val Ser Thr Ala Val Val Trp Tyr Gln Gln Lys Pro Gly Gln Ser Pro
```

```
    50                  55                  60

Lys Leu Leu Ile Tyr Ser Ala Ser Tyr Arg Tyr Thr Gly Val Pro Asp
65                  70                  75                  80

Arg Phe Thr Gly Ser Gly Ser Gly Thr Asp Phe Thr Phe Thr Ile Ser
                85                  90                  95

Ser Val Gln Ala Glu Asp Leu Ala Val Tyr Tyr Cys Leu Gln His Phe
            100                 105                 110

Asn Ile Pro Arg Thr Phe Gly Gly Gly Thr Lys Leu Glu Ile Lys Thr
        115                 120                 125

Val Ala Ala Pro Ser Val Phe Ile Phe Pro Pro Ser Asp Glu Gln Leu
    130                 135                 140

Lys Ser Gly Thr Ala Ser Val Val Cys Leu Leu Asn Asn Phe Tyr Pro
145                 150                 155                 160

Arg Glu Ala Lys Val Gln Trp Lys Val Asp Asn Ala Leu Gln Ser Gly
                165                 170                 175

Asn Ser Gln Glu Ser Val Thr Glu Gln Asp Ser Lys Asp Ser Thr Tyr
            180                 185                 190

Ser Leu Ser Ser Thr Leu Thr Leu Ser Lys Ala Asp Tyr Glu Lys His
        195                 200                 205

Lys Val Tyr Ala Cys Glu Val Thr His Gln Gly Leu Ser Ser Pro Val
    210                 215                 220

Thr Lys Ser Phe Asn Arg Gly Glu Cys
225                 230
```

<210> SEQ ID NO 78
<211> LENGTH: 795
<212> TYPE: DNA
<213> ORGANISM: Artificial Sequence
<220> FEATURE:
<223> OTHER INFORMATION: scFv

<400> SEQUENCE: 78

```
atgaaatacc tattgcctac ggcagccgct ggattgttat tactcgcggc ccagccggcg      60

atggcccaga tccagttggt gcagtctgga cctgagctga agaagcctgg agagacagtc     120

aagatctcct gcaaggcttc tgggtatacc ttcacaaact atggaatgaa ctgggtgaag     180

caggctccag gaaagggttt aaagtggatg ggctggataa acacctacac tggacagtca     240

acatatgctg atgacttcaa gggacgcttt gccttctctt tggaaacctc tgccagcact     300

gcccatttgc agatcagcaa cctcaaaaat gaggacgcgg ctacatattt ctgtgcaaga     360

atggagtatg gtaactacga aaatgctttg gattactggg gtcaaggaac ctcagtcacc     420

gtctcctcag gtggcggtgg cagcggcggc ggtggtagcg gtggtggcgg cagcgacatt     480

gtgatgaccc agtctcacaa attcatgtcc acatcaatag gagacagggt cagcatcacc     540

tgcaaggcca gtcaggatgt gagtactgct gtagtctggt atcaacagaa accaggacac     600

tctcctaaac tactgattta ttcggcatcc taccggtaca ctggagtccc tgatcgcttc     660

actggcagtg gatctgggac ggatttcact ttcaccatca gcagtgtgca ggctgaagac     720

ctggcagttt attactgtct acaacatttt agtactcctc ggacgttcgg tggaggcacc     780

aacctggaaa tcaaa                                                      795
```

<210> SEQ ID NO 79
<211> LENGTH: 265
<212> TYPE: PRT
<213> ORGANISM: Artificial Sequence
<220> FEATURE:

```
<223> OTHER INFORMATION: scFv

<400> SEQUENCE: 79

Met Lys Tyr Leu Leu Pro Thr Ala Ala Ala Gly Leu Leu Leu Leu Ala
1               5                   10                  15

Ala Gln Pro Ala Met Ala Gln Ile Gln Leu Val Gln Ser Gly Pro Glu
            20                  25                  30

Leu Lys Lys Pro Gly Glu Thr Val Lys Ile Ser Cys Lys Ala Ser Gly
        35                  40                  45

Tyr Thr Phe Thr Asn Tyr Gly Met Asn Trp Val Lys Gln Ala Pro Gly
    50                  55                  60

Lys Gly Leu Lys Trp Met Gly Trp Ile Asn Thr Tyr Thr Gly Gln Ser
65                  70                  75                  80

Thr Tyr Ala Asp Asp Phe Lys Gly Arg Phe Ala Phe Ser Leu Glu Thr
                85                  90                  95

Ser Ala Ser Thr Ala His Leu Gln Ile Ser Asn Leu Lys Asn Glu Asp
            100                 105                 110

Ala Ala Thr Tyr Phe Cys Ala Arg Met Glu Tyr Gly Asn Tyr Glu Asn
        115                 120                 125

Ala Leu Asp Tyr Trp Gly Gln Gly Thr Ser Val Thr Val Ser Ser Gly
    130                 135                 140

Gly Gly Gly Ser Gly Gly Gly Gly Ser Gly Gly Gly Gly Ser Asp Ile
145                 150                 155                 160

Val Met Thr Gln Ser His Lys Phe Met Ser Thr Ser Ile Gly Asp Arg
                165                 170                 175

Val Ser Ile Thr Cys Lys Ala Ser Gln Asp Val Ser Thr Ala Val Val
            180                 185                 190

Trp Tyr Gln Gln Lys Pro Gly His Ser Pro Lys Leu Leu Ile Tyr Ser
        195                 200                 205

Ala Ser Tyr Arg Tyr Thr Gly Val Pro Asp Arg Phe Thr Gly Ser Gly
    210                 215                 220

Ser Gly Thr Asp Phe Thr Phe Thr Ile Ser Ser Val Gln Ala Glu Asp
225                 230                 235                 240

Leu Ala Val Tyr Tyr Cys Leu Gln His Phe Ser Thr Pro Arg Thr Phe
                245                 250                 255

Gly Gly Gly Thr Asn Leu Glu Ile Lys
            260                 265


<210> SEQ ID NO 80
<211> LENGTH: 121
<212> TYPE: PRT
<213> ORGANISM: Mouse

<400> SEQUENCE: 80

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Asn Tyr
            20                  25                  30

Gly Met Asn Trp Val Lys Gln Ala Pro Gly Lys Gly Leu Lys Trp Met
        35                  40                  45

Gly Trp Ile Asn Thr Tyr Thr Gly Gln Ser Thr Tyr Ala Asp Asp Phe
    50                  55                  60

Lys Gly Arg Phe Ala Phe Ser Leu Glu Thr Ser Ala Ser Thr Ala His
65                  70                  75                  80

Leu Gln Ile Ser Asn Leu Lys Asn Glu Asp Ala Ala Thr Tyr Phe Cys
```

```
                85                  90                  95

Ala Arg Met Glu Tyr Gly Asn Tyr Glu Asn Ala Leu Asp Tyr Trp Gly
            100                 105                 110

Gln Gly Thr Ser Val Thr Val Ser Ser
        115                 120


<210> SEQ ID NO 81
<211> LENGTH: 121
<212> TYPE: PRT
<213> ORGANISM: Human

<400> SEQUENCE: 81

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Asn Tyr
            20                  25                  30

Gly Met Asn Trp Val Lys Gln Ala Pro Gly Lys Gly Leu Lys Trp Met
        35                  40                  45

Ala Trp Ile Asn Thr Tyr Thr Gly Glu Pro Thr Tyr Ala Asp Asp Phe
    50                  55                  60

Lys Gly Arg Phe Ala Phe Ser Leu Glu Thr Ser Ala Ser Thr Ala Tyr
65                  70                  75                  80

Leu Gln Ile Asn Asn Leu Lys Asn Glu Asp Thr Ala Thr Tyr Phe Cys
                85                  90                  95

Ala Arg Asp Gly Tyr Tyr Glu Asn Tyr Tyr Ala Met Asp Tyr Trp Gly
            100                 105                 110

Gln Gly Thr Ser Val Thr Val Ser Ser
        115                 120


<210> SEQ ID NO 82
<211> LENGTH: 107
<212> TYPE: PRT
<213> ORGANISM: Mouse

<400> SEQUENCE: 82

Asp Ile Val Met Thr Gln Ser His Lys Phe Met Ser Thr Ser Ile Gly
1               5                   10                  15

Asp Arg Val Ser Ile Thr Cys Lys Ala Ser Gln Asp Val Ser Thr Ala
            20                  25                  30

Val Val Trp Tyr Gln Gln Lys Pro Gly His Ser Pro Lys Leu Leu Ile
        35                  40                  45

Tyr Ser Ala Ser Tyr Arg Tyr Thr Gly Val Pro Asp Arg Phe Thr Gly
    50                  55                  60

Ser Gly Ser Gly Thr Asp Phe Thr Phe Thr Ile Ser Ser Val Gln Ala
65                  70                  75                  80

Glu Asp Leu Ala Val Tyr Tyr Cys Leu Gln His Phe Ser Thr Pro Arg
                85                  90                  95

Thr Phe Gly Gly Gly Thr Asn Leu Glu Ile Lys
            100                 105


<210> SEQ ID NO 83
<211> LENGTH: 107
<212> TYPE: PRT
<213> ORGANISM: Human

<400> SEQUENCE: 83

Asp Ile Val Met Thr Gln Ser His Lys Phe Met Ser Thr Ser Val Gly
1               5                   10                  15
```

```
Asp Arg Val Ser Ile Thr Cys Lys Ala Ser Gln Asp Val Ser Thr Ala
            20                  25                  30

Val Ala Trp Tyr Gln Gln Lys Pro Gly Gln Ser Pro Lys Leu Leu Ile
        35                  40                  45

Tyr Ser Ala Ser Tyr Gln Tyr Thr Gly Val Pro Asp Arg Phe Thr Gly
    50                  55                  60

Ser Gly Ser Arg Thr Asp Phe Thr Phe Thr Ile Asn Ser Val Gln Ala
65                  70                  75                  80

Glu Asp Leu Ala Val Tyr Tyr Cys His Gln His Tyr Ser Thr Pro Phe
                85                  90                  95

Thr Phe Gly Ser Gly Thr Lys Leu Glu Ile Lys
            100                 105
```

<210> SEQ ID NO 84
<211> LENGTH: 121
<212> TYPE: PRT
<213> ORGANISM: Human

<400> SEQUENCE: 84

```
Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Ser Tyr
            20                  25                  30

Ala Met Asn Trp Val Arg Gln Ala Pro Gly Gln Gly Leu Glu Trp Met
        35                  40                  45

Gly Trp Ile Asn Thr Asn Thr Gly Asn Pro Thr Tyr Ala Gln Gly Phe
    50                  55                  60

Thr Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Ala Arg Asp Val Ala Thr Ile Asp Glu Asn Trp Phe Asp Pro Trp Gly
            100                 105                 110

Gln Gly Thr Leu Val Thr Val Ser Ser
        115                 120
```

<210> SEQ ID NO 85
<211> LENGTH: 120
<212> TYPE: PRT
<213> ORGANISM: Human

<400> SEQUENCE: 85

```
Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Ser Tyr
            20                  25                  30

Ala Met Asn Trp Val Arg Gln Ala Pro Gly Gln Gly Leu Glu Trp Met
        35                  40                  45

Gly Trp Ile Asn Thr Asn Thr Gly Asn Pro Thr Tyr Ala Gln Gly Phe
    50                  55                  60

Thr Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Ala Arg Val Gln Trp Phe Gly Glu Tyr Phe Phe Asp Tyr Trp Gly Gln
            100                 105                 110
```

```
Gly Thr Leu Val Thr Val Ser Ser
        115                 120


<210> SEQ ID NO 86
<211> LENGTH: 120
<212> TYPE: PRT
<213> ORGANISM: Human

<400> SEQUENCE: 86

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Ser Tyr
            20                  25                  30

Ala Met Asn Trp Val Arg Gln Ala Pro Gly Gln Gly Leu Glu Trp Met
        35                  40                  45

Gly Trp Ile Asn Thr Asn Thr Gly Asn Pro Thr Tyr Ala Gln Gly Phe
    50                  55                  60

Thr Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Ala Arg Leu Gln Trp Met Gly Met Asn Tyr Phe Asp Tyr Trp Gly Gln
            100                 105                 110

Gly Thr Leu Val Thr Val Ser Ser
        115                 120


<210> SEQ ID NO 87
<211> LENGTH: 107
<212> TYPE: PRT
<213> ORGANISM: Human

<400> SEQUENCE: 87

Asp Ile Gln Met Thr Gln Ser Pro Ser Ser Leu Ser Ala Ser Leu Gly
1               5                   10                  15

Asp Arg Val Thr Ile Thr Cys Arg Ala Ser Gln Thr Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Ala
65                  70                  75                  80

Glu Asp Phe Ala Thr Tyr Tyr Cys Gln Gln Ser Tyr Ser Thr Pro Arg
                85                  90                  95

Thr Phe Gly Gly Gly Thr Lys Val Glu Ile Lys
            100                 105


<210> SEQ ID NO 88
<211> LENGTH: 107
<212> TYPE: PRT
<213> ORGANISM: Human

<400> SEQUENCE: 88

Asp Ile Val Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30
```

Leu Asn Trp Tyr Gln Gln Lys Pro Gly Lys Ala Pro Lys Leu Leu Ile
35 40 45

Tyr Ala Ala Ser Ser Leu Gln Ser Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Gln Gln Ser Tyr Ser Thr Pro Arg
85 90 95

Thr Phe Gly Gly Gly Thr Lys Val Glu Ile Lys
100 105

<210> SEQ ID NO 89
<211> LENGTH: 107
<212> TYPE: PRT
<213> ORGANISM: Human

<400> SEQUENCE: 89

Asp Ile Val Met Thr Gln Ser Pro Ser Ser Leu Ser Ala Ser Val Gly
1 5 10 15

Asp Arg Val Thr Ile Thr Cys Arg Ala Ser Gln Ser Ile Ser Asn Tyr
20 25 30

Leu Asn Trp Tyr Gln Gln Lys Pro Gly Lys Ala Pro Lys Leu Leu Ile
35 40 45

Tyr Ala Ala Ser Ser Leu Gln Ser Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Gln Gln Ser Tyr Ser Thr Pro Arg
85 90 95

Thr Phe Gly Gln Gly Thr Lys Leu Glu Ile Lys
100 105

<210> SEQ ID NO 90
<211> LENGTH: 121
<212> TYPE: PRT
<213> ORGANISM: Artificial Sequence
<220> FEATURE:
<223> OTHER INFORMATION: scFv

<400> SEQUENCE: 90

Gln Ile Gln Leu Val Gln Ser Gly Ser Glu Leu Lys Lys Pro Gly Ala
1 5 10 15

Ser Val Lys Val Ser Cys Lys Ala Ser Gly Tyr Thr Phe Thr Asn Tyr
20 25 30

Gly Met Asn Trp Val Lys Gln Ala Pro Gly Gln Gly Leu Lys Trp Met
35 40 45

Gly Trp Ile Asn Thr Tyr Thr Gly Gln Ser Thr Tyr Ala Asp Asp Phe
50 55 60

Lys Gly Arg Phe Ala Phe Ser Leu Asp Thr Ser Val Ser Thr Ala Tyr
65 70 75 80

Leu Gln Ile Ser Ser Leu Lys Ala Glu Asp Thr Ala Val Tyr Phe Cys
85 90 95

Ala Arg Met Glu Tyr Gly Asn Tyr Glu Asn Ala Leu Asp Tyr Trp Gly
100 105 110

Gln Gly Thr Leu Val Thr Val Ser Ser
115 120

<210> SEQ ID NO 91
<211> LENGTH: 107
<212> TYPE: PRT
<213> ORGANISM: Artificial Sequence
<220> FEATURE:
<223> OTHER INFORMATION: scFv

<400> SEQUENCE: 91

```
Asp Ile Val Met Thr Gln Ser Pro Ser Ser Leu Ser Ala Ser Val Gly
1               5                   10                  15

Asp Arg Val Thr Ile Thr Cys Lys Ala Ser Gln Asp Val Ser Thr Ala
            20                  25                  30

Val Val Trp Tyr Gln Gln Lys Pro Gly Lys Ala Pro Lys Leu Leu Ile
        35                  40                  45

Tyr Ser Ala Ser Tyr Arg Tyr Thr Gly Val Pro Asp Arg Phe Thr Gly
    50                  55                  60

Ser Gly Ser Gly Thr Asp Phe Thr Leu Thr Ile Ser Ser Leu Gln Ala
65                  70                  75                  80

Glu Asp Phe Ala Thr Tyr Tyr Cys Leu Gln His Phe Ser Thr Pro Arg
                85                  90                  95

Thr Phe Gly Gly Gly Thr Lys Leu Glu Ile Lys
            100                 105
```

<210> SEQ ID NO 92
<211> LENGTH: 4
<212> TYPE: PRT
<213> ORGANISM: Artificial Sequence
<220> FEATURE:
<223> OTHER INFORMATION: Linker

<400> SEQUENCE: 92

```
Asp Asn Lys Gln
1
```

<210> SEQ ID NO 93
<211> LENGTH: 19
<212> TYPE: PRT
<213> ORGANISM: Escherichia coli

<400> SEQUENCE: 93

```
Val Glu Lys Asn Ile Thr Val Thr Ala Ser Val Asp Pro Val Ile Asp
1               5                   10                  15

Leu Leu Gln
```

<210> SEQ ID NO 94
<211> LENGTH: 8
<212> TYPE: PRT
<213> ORGANISM: Artificial Sequence
<220> FEATURE:
<223> OTHER INFORMATION: 6XHis tag

<400> SEQUENCE: 94

```
Leu Glu His His His His His His
1               5
```

<210> SEQ ID NO 95
<211> LENGTH: 19
<212> TYPE: PRT
<213> ORGANISM: Escherichia coli

<400> SEQUENCE: 95

```
Val Glu Lys Asn Ile Thr Val Arg Ala Ser Val Asp Pro Lys Leu Asp
1               5                   10                  15
```

Leu Leu Gln

<210> SEQ ID NO 96
<211> LENGTH: 19
<212> TYPE: PRT
<213> ORGANISM: Escherichia coli

<400> SEQUENCE: 96

Ala Glu Lys Asn Ile Thr Val Thr Ala Ser Val Asp Pro Thr Ile Asp
1               5                   10                  15

Leu Met Gln

<210> SEQ ID NO 97
<211> LENGTH: 15
<212> TYPE: PRT
<213> ORGANISM: Artificial Sequence
<220> FEATURE:
<223> OTHER INFORMATION: Linker

<400> SEQUENCE: 97

Gly Gly Gly Gly Ser Gly Gly Gly Gly Ser Gly Gly Gly Gly Ser
1               5                   10                  15

<210> SEQ ID NO 98
<211> LENGTH: 18
<212> TYPE: PRT
<213> ORGANISM: Artificial Sequence
<220> FEATURE:
<223> OTHER INFORMATION: Linker

<400> SEQUENCE: 98

Gly Gly Ser Ser Arg Ser Ser Ser Ser Gly Gly Gly Gly Ser Gly Gly
1               5                   10                  15

Gly Gly

<210> SEQ ID NO 99
<211> LENGTH: 20
<212> TYPE: PRT
<213> ORGANISM: Artificial Sequence
<220> FEATURE:
<223> OTHER INFORMATION: Linker

<400> SEQUENCE: 99

Gly Gly Gly Gly Ser Gly Gly Gly Gly Ser Gly Gly Gly Gly Ser Gly
1               5                   10                  15

Gly Gly Gly Ser
            20

<210> SEQ ID NO 100
<211> LENGTH: 22
<212> TYPE: PRT
<213> ORGANISM: Artificial Sequence
<220> FEATURE:
<223> OTHER INFORMATION: pelB leader sequence

<400> SEQUENCE: 100

Met Lys Tyr Leu Leu Pro Thr Ala Ala Ala Gly Leu Leu Leu Leu Ala
1               5                   10                  15

Ala Gln Pro Ala Met Ala
            20

<210> SEQ ID NO 101
<211> LENGTH: 22

<212> TYPE: PRT
<213> ORGANISM: Artificial Sequence
<220> FEATURE:
<223> OTHER INFORMATION: Variant pelB leader sequence

<400> SEQUENCE: 101

Met Lys Tyr Leu Leu Pro Thr Ala Glu Ala Gly Leu Leu Leu Leu Ala
1               5                   10                  15

Ala Gln Pro Ala Met Ala
            20

<210> SEQ ID NO 102
<211> LENGTH: 25
<212> TYPE: PRT
<213> ORGANISM: Artificial Sequence
<220> FEATURE:
<223> OTHER INFORMATION: malE leader sequence

<400> SEQUENCE: 102

Met Lys Lys Thr Gly Ala Arg Ile Leu Ala Leu Ser Ala Leu Thr Thr
1               5                   10                  15

Met Met Phe Ser Ala Ser Ala Leu Ala
            20                  25

<210> SEQ ID NO 103
<211> LENGTH: 25
<212> TYPE: PRT
<213> ORGANISM: Artificial Sequence
<220> FEATURE:
<223> OTHER INFORMATION: Variant malE leader sequence

<400> SEQUENCE: 103

Met Lys Lys Thr Gly Ala Arg Ile Leu Ala Leu Ser Glu Leu Thr Thr
1               5                   10                  15

Met Met Phe Ser Ala Ser Ala Leu Ala
            20                  25

<210> SEQ ID NO 104
<211> LENGTH: 21
<212> TYPE: PRT
<213> ORGANISM: Artificial Sequence
<220> FEATURE:
<223> OTHER INFORMATION: DsbA leader sequence

<400> SEQUENCE: 104

Met Lys Lys Ile Trp Leu Ala Leu Ala Gly Leu Val Leu Ala Phe Ser
1               5                   10                  15

Ala Ser Ala Ala Gln
            20

<210> SEQ ID NO 105
<211> LENGTH: 21
<212> TYPE: PRT
<213> ORGANISM: Artificial Sequence
<220> FEATURE:
<223> OTHER INFORMATION: OmpA leader sequence

<400> SEQUENCE: 105

Met Lys Lys Thr Ala Ile Ala Ile Ala Val Ala Leu Ala Gly Phe Ala
1               5                   10                  15

Thr Val Ala Gln Ala
            20

<210> SEQ ID NO 106

<211> LENGTH: 21
<212> TYPE: PRT
<213> ORGANISM: Artificial Sequence
<220> FEATURE:
<223> OTHER INFORMATION: PhoA leader sequence

<400> SEQUENCE: 106

Val Lys Gln Ser Thr Ile Ala Leu Ala Leu Leu Pro Leu Leu Phe Thr
1 5 10 15

Pro Val Thr Lys Ala
20

<210> SEQ ID NO 107
<211> LENGTH: 795
<212> TYPE: DNA
<213> ORGANISM: Artificial Sequence
<220> FEATURE:
<223> OTHER INFORMATION: scFv

<400> SEQUENCE: 107
atgaaatacc tattgcctac ggcagccgct ggattgttat tactcgcggc ccagccggcg 60
atggcccaga tccagttggt gcagtctgga cctgagctga agaagcctgg agagacagtc 120
aagatctcct gcaaggcttc tgggtatacc ttcacaaact atggaatgaa ctgggtgaag 180
caggctccag gaaagggttt aaagtggatg ggctggataa acacctacac tggacagtca 240
acctatgctg atgacttcaa gggacgcttt gccttctctt tggaaacctc tgccagcact 300
gcccatttgc agatcagcaa cctcaaaaat gaggacgcgg ctacatattt ctgtgcaaga 360
atggagtatg gtaactacga aaatgctttg gattactggg gtcaaggaac ctcagtcacc 420
gtctcctcag gtggcggtgg cagcggcggc ggtggtagcg gtggtggcgg cagcgacatt 480
gtgatgaccc agtctcacaa attcatgtcc acatcaatag gagacagggt cagcatcacc 540
tgcaaggcca gtcaggatgt gagtactgct gtagtctggt atcaacagaa accaggacac 600
tctcctaaac tactgattta ttcggcatcc taccggtaca ctggagtccc tgatcgcttc 660
actggcagtg gatctgggac ggatttcact ttcaccatca gcagtgtgca ggctgaagac 720
ctggcagttt attactgtct acaacatttt agtactcctc ggacgttcgg tggaggcacc 780
aacctggaaa tcaaa 795

<210> SEQ ID NO 108
<211> LENGTH: 265
<212> TYPE: PRT
<213> ORGANISM: Artificial Sequence
<220> FEATURE:
<223> OTHER INFORMATION: scFv

<400> SEQUENCE: 108

Met Lys Tyr Leu Leu Pro Thr Ala Ala Ala Gly Leu Leu Leu Leu Ala
1 5 10 15

Ala Gln Pro Ala Met Ala Gln Ile Gln Leu Val Gln Ser Gly Pro Glu
20 25 30

Leu Lys Lys Pro Gly Glu Thr Val Lys Ile Ser Cys Lys Ala Ser Gly
35 40 45

Tyr Thr Phe Thr Asn Tyr Gly Met Asn Trp Val Lys Gln Ala Pro Gly
50 55 60

Lys Gly Leu Lys Trp Met Gly Trp Ile Asn Thr Tyr Thr Gly Gln Ser
65 70 75 80

Thr Tyr Ala Asp Asp Phe Lys Gly Arg Phe Ala Phe Ser Leu Glu Thr
85 90 95

```
Ser Ala Ser Thr Ala His Leu Gln Ile Ser Asn Leu Lys Asn Glu Asp
            100                 105                 110

Ala Ala Thr Tyr Phe Cys Ala Arg Met Glu Tyr Gly Asn Tyr Glu Asn
        115                 120                 125

Ala Leu Asp Tyr Trp Gly Gln Gly Thr Ser Val Thr Val Ser Ser Gly
    130                 135                 140

Gly Gly Gly Ser Gly Gly Gly Gly Ser Gly Gly Gly Gly Ser Asp Ile
145                 150                 155                 160

Val Met Thr Gln Ser His Lys Phe Met Ser Thr Ser Ile Gly Asp Arg
                165                 170                 175

Val Ser Ile Thr Cys Lys Ala Ser Gln Asp Val Ser Thr Ala Val Val
            180                 185                 190

Trp Tyr Gln Gln Lys Pro Gly His Ser Pro Lys Leu Leu Ile Tyr Ser
        195                 200                 205

Ala Ser Tyr Arg Tyr Thr Gly Val Pro Asp Arg Phe Thr Gly Ser Gly
    210                 215                 220

Ser Gly Thr Asp Phe Thr Phe Thr Ile Ser Ser Val Gln Ala Glu Asp
225                 230                 235                 240

Leu Ala Val Tyr Tyr Cys Leu Gln His Phe Ser Thr Pro Arg Thr Phe
                245                 250                 255

Gly Gly Gly Thr Asn Leu Glu Ile Lys
            260                 265
```

<210> SEQ ID NO 109
<211> LENGTH: 795
<212> TYPE: DNA
<213> ORGANISM: Artificial Sequence
<220> FEATURE:
<223> OTHER INFORMATION: scFv

<400> SEQUENCE: 109

```
atgaaatacc tattgcctac ggcagccgct ggattgttat tactcgcggc ccagccggcg     60

atggcccaga tccagttggt gcagtctgga tctgagctga agaagcctgg agcgtcagtc    120

aaggtctcct gcaaggcttc tgggtatacc ttcacaaact atggaatgaa ctgggtgaag    180

caggctccag gacagggttt aaagtggatg ggctggataa acacctacac tggacagtca    240

acctatgctg atgacttcaa gggacgcttt gccttctctt tggatacctc tgtcagcact    300

gcctatttgc agatcagcag cctcaaagct gaggacacgg ctgtgtattt ctgtgcaaga    360

atggagtatg gtaactacga aaatgctttg gattactggg gtcaaggaac cttagtcacc    420

gtctcctcag gtggcggtgg cagcggcggc ggtggtagcg gtggtggcgg cagcgacatt    480

gtgatgaccc agtctcccag ctccctgtcc gcatcagtag gagacagggt caccatcacc    540

tgcaaggcca gtcaggatgt gagtactgct gtagtctggt atcaacagaa accaggaaaa    600

gctcctaaac tactgattta ttcggcatcc taccggtaca ctggagtccc tgatcgcttc    660

actggcagtg gatctgggac ggatttcact ttgaccatca gcagtctgca ggctgaagac    720

ttcgcaacct attactgtct acaacatttt agtactcctc ggacgttcgg tggaggcacc    780

aaactggaaa tcaaa                                                     795
```

<210> SEQ ID NO 110
<211> LENGTH: 265
<212> TYPE: PRT
<213> ORGANISM: Artificial Sequence
<220> FEATURE:
<223> OTHER INFORMATION: scFv

<400> SEQUENCE: 110

Met Lys Tyr Leu Leu Pro Thr Ala Ala Ala Gly Leu Leu Leu Leu Ala
1 5 10 15

Ala Gln Pro Ala Met Ala Gln Ile Gln Leu Val Gln Ser Gly Ser Glu
20 25 30

Leu Lys Lys Pro Gly Ala Ser Val Lys Val Ser Cys Lys Ala Ser Gly
35 40 45

Tyr Thr Phe Thr Asn Tyr Gly Met Asn Trp Val Lys Gln Ala Pro Gly
50 55 60

Gln Gly Leu Lys Trp Met Gly Trp Ile Asn Thr Tyr Thr Gly Gln Ser
65 70 75 80

Thr Tyr Ala Asp Asp Phe Lys Gly Arg Phe Ala Phe Ser Leu Asp Thr
85 90 95

Ser Val Ser Thr Ala Tyr Leu Gln Ile Ser Ser Leu Lys Ala Glu Asp
100 105 110

Thr Ala Val Tyr Phe Cys Ala Arg Met Glu Tyr Gly Asn Tyr Glu Asn
115 120 125

Ala Leu Asp Tyr Trp Gly Gln Gly Thr Leu Val Thr Val Ser Ser Gly
130 135 140

Gly Gly Gly Ser Gly Gly Gly Gly Ser Gly Gly Gly Gly Ser Asp Ile
145 150 155 160

Val Met Thr Gln Ser Pro Ser Ser Leu Ser Ala Ser Val Gly Asp Arg
165 170 175

Val Thr Ile Thr Cys Lys Ala Ser Gln Asp Val Ser Thr Ala Val Val
180 185 190

Trp Tyr Gln Gln Lys Pro Gly Lys Ala Pro Lys Leu Leu Ile Tyr Ser
195 200 205

Ala Ser Tyr Arg Tyr Thr Gly Val Pro Asp Arg Phe Thr Gly Ser Gly
210 215 220

Ser Gly Thr Asp Phe Thr Leu Thr Ile Ser Ser Leu Gln Ala Glu Asp
225 230 235 240

Phe Ala Thr Tyr Tyr Cys Leu Gln His Phe Ser Thr Pro Arg Thr Phe
245 250 255

Gly Gly Gly Thr Lys Leu Glu Ile Lys
260 265

<210> SEQ ID NO 111
<211> LENGTH: 795
<212> TYPE: DNA
<213> ORGANISM: Artificial Sequence
<220> FEATURE:
<223> OTHER INFORMATION: scFv

<400> SEQUENCE: 111
atgaaatacc tattgcctac ggcagccgct ggattgttat tactcgcggc ccagccggcg 60
atggccgaca ttgtgatgac ccagtctccc agctccctgt ccgcatcagt aggagacagg 120
gtcaccatca cctgcaaggc cagtcaggat gtgagtactg ctgtagtctg gtatcaacag 180
aaaccaggaa aagctcctaa actactgatt tattcggcat cctaccggta cactggagtc 240
cctgatcgct tcactggcag tggatctggg acggatttca ctttgaccat cagcagtctg 300
caggctgaag acttcgcaac ctattactgt ctacaacatt ttagtactcc tcggacgttc 360
ggtggaggca ccaaactgga aatcaaaggt ggcggtggca gcggcggcgg tggtagcggt 420
ggtggcggca gccagatcca gttggtgcag tctggatctg agctgaagaa gcctggagcg 480
tcagtcaagg tctcctgcaa ggcttctggg tataccttca caaactatgg aatgaactgg 540
gtgaagcagg ctccaggaca gggtttaaag tggatgggct ggataaacac ctacactgga 600
cagtcaacct atgctgatga cttcaaggga cgctttgcct tctctttgga tacctctgtc 660
agcactgcct atttgcagat cagcagcctc aaagctgagg acacggctgt gtatttctgt 720
gcaagaatgg agtatggtaa ctacgaaaat gctttggatt actggggtca aggaacctta 780
gtcaccgtct cctca 795

<210> SEQ ID NO 112
<211> LENGTH: 265
<212> TYPE: PRT
<213> ORGANISM: Artificial Sequence
<220> FEATURE:
<223> OTHER INFORMATION: scFv

<400> SEQUENCE: 112

Met Lys Tyr Leu Leu Pro Thr Ala Ala Ala Gly Leu Leu Leu Leu Ala
1 5 10 15

Ala Gln Pro Ala Met Ala Asp Ile Val Met Thr Gln Ser Pro Ser Ser
20 25 30

Leu Ser Ala Ser Val Gly Asp Arg Val Thr Ile Thr Cys Lys Ala Ser
35 40 45

Gln Asp Val Ser Thr Ala Val Val Trp Tyr Gln Gln Lys Pro Gly Lys
50 55 60

Ala Pro Lys Leu Leu Ile Tyr Ser Ala Ser Tyr Arg Tyr Thr Gly Val
65 70 75 80

Pro Asp Arg Phe Thr Gly Ser Gly Ser Gly Thr Asp Phe Thr Leu Thr
85 90 95

Ile Ser Ser Leu Gln Ala Glu Asp Phe Ala Thr Tyr Tyr Cys Leu Gln
100 105 110

His Phe Ser Thr Pro Arg Thr Phe Gly Gly Gly Thr Lys Leu Glu Ile
115 120 125

Lys Gly Gly Gly Gly Ser Gly Gly Gly Gly Ser Gly Gly Gly Gly Ser
130 135 140

Gln Ile Gln Leu Val Gln Ser Gly Ser Glu Leu Lys Lys Pro Gly Ala
145 150 155 160

Ser Val Lys Val Ser Cys Lys Ala Ser Gly Tyr Thr Phe Thr Asn Tyr
165 170 175

Gly Met Asn Trp Val Lys Gln Ala Pro Gly Gln Gly Leu Lys Trp Met
180 185 190

Gly Trp Ile Asn Thr Tyr Thr Gly Gln Ser Thr Tyr Ala Asp Asp Phe
195 200 205

Lys Gly Arg Phe Ala Phe Ser Leu Asp Thr Ser Val Ser Thr Ala Tyr
210 215 220

Leu Gln Ile Ser Ser Leu Lys Ala Glu Asp Thr Ala Val Tyr Phe Cys
225 230 235 240

Ala Arg Met Glu Tyr Gly Asn Tyr Glu Asn Ala Leu Asp Tyr Trp Gly
245 250 255

Gln Gly Thr Leu Val Thr Val Ser Ser
260 265

<210> SEQ ID NO 113
<211> LENGTH: 1410
<212> TYPE: DNA
<213> ORGANISM: Artificial Sequence

```
<220> FEATURE:
<223> OTHER INFORMATION: Humanized antibody

<400> SEQUENCE: 113

atggcttggg tgtggacctt gctattcctg atggcagctg cccaaagtgc ccaagcacag      60

atccagttgg tgcagtctgg atctgagctg aagaagcctg gagcgtcagt caaggtctcc     120

tgcaaggctt ctgggtatac cttcacaaac tatggaatga actgggtgaa gcaggctcca     180

ggacagggtt taaagtggat gggctggata aacacctaca ctggacagtc aacctatgct     240

gatgacttca agggacgctt tgccttctct ttggatacct ctgtcagcac tgcctatttg     300

cagatcagca gcctcaaagc tgaggacacg gctgtgtatt tctgtgcaag aatggagtat     360

ggtaactacg aaaatgcttt ggattactgg ggtcaaggaa ccttagtcac cgtctcctca     420

gctagcacca agggcccatc ggtcttcccc ctggcaccct cctccaagag cacctctggg     480

ggcacagcgg ccctgggctg cctggtcaag gactacttcc ccgaaccggt gacggtgtcg     540

tggaactcag gcgccctgac cagcggcgtg cacaccttcc cggctgtcct acagtcctca     600

ggactctact ccctcagcag cgtggtgacc gtgccctcca gcagcttggg cacccagacc     660

tacatctgca acgtgaatca caagcccagc aacaccaagg tggacaagaa agttgagccc     720

aaatcttgtg acaaaactca cacatgccca ccgtgcccag cacctgaact cctggcggga     780

ccggacgtct tcctcttccc cccaaaaccc aaggacaccc tcatgatctc ccggacccct     840

gaggtcacat gcgtggtggt ggacgtgagc cacgaagacc ctgaggtcaa gttcaactgg     900

tacgtggacg gcgtggaggt gcataatgcc aagacaaagc cgcgggagga gcagtacaac     960

agcacgtacc gtgtggtcag cgtcctcacc gtcctgcacc aggactggct gaatggcaag    1020

gagtacaagt gcaaggtctc caacaaagcc ctcccagccc ccgaggagaa aaccatctcc    1080

aaagccaaag ggcagccccg agaaccacag gtgtacaccc tgcccccatc ccgggaggag    1140

atgaccaaga accaggtcag cctgacctgc ctggtcaaag gcttctatcc cagcgacatc    1200

gccgtggagt gggagagcaa tgggcagccg gagaacaact acaagaccac gcctcccgtg    1260

ctggactccg acggctcctt cttcctctac agcaagctca ccgtggacaa gagcaggtgg    1320

cagcagggga acgtcttctc atgctccgtg atgcacgagg ctctgcacaa ccactacacg    1380

cagaagagcc tctccctgtc tccgggtaaa                                     1410


<210> SEQ ID NO 114
<211> LENGTH: 470
<212> TYPE: PRT
<213> ORGANISM: Artificial Sequence
<220> FEATURE:
<223> OTHER INFORMATION: Humanized antibody

<400> SEQUENCE: 114

Met Ala Trp Val Trp Thr Leu Leu Phe Leu Met Ala Ala Ala Gln Ser
1               5                   10                  15

Ala Gln Ala Gln Ile Gln Leu Val Gln Ser Gly Ser Glu Leu Lys Lys
            20                  25                  30

Pro Gly Ala Ser Val Lys Val Ser Cys Lys Ala Ser Gly Tyr Thr Phe
        35                  40                  45

Thr Asn Tyr Gly Met Asn Trp Val Lys Gln Ala Pro Gly Gln Gly Leu
    50                  55                  60

Lys Trp Met Gly Trp Ile Asn Thr Tyr Thr Gly Gln Ser Thr Tyr Ala
65                  70                  75                  80

Asp Asp Phe Lys Gly Arg Phe Ala Phe Ser Leu Asp Thr Ser Val Ser
```

```
                85                  90                  95

Thr Ala Tyr Leu Gln Ile Ser Ser Leu Lys Ala Glu Asp Thr Ala Val
            100                 105                 110

Tyr Phe Cys Ala Arg Met Glu Tyr Gly Asn Tyr Glu Asn Ala Leu Asp
        115                 120                 125

Tyr Trp Gly Gln Gly Thr Leu Val Thr Val Ser Ser Ala Ser Thr Lys
    130                 135                 140

Gly Pro Ser Val Phe Pro Leu Ala Pro Ser Ser Lys Ser Thr Ser Gly
145                 150                 155                 160

Gly Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
        195                 200                 205

Val Thr Val Pro Ser Ser Ser Leu Gly Thr Gln Thr Tyr Ile Cys Asn
    210                 215                 220

Val Asn His Lys Pro Ser Asn Thr Lys Val Asp Lys Lys Val Glu Pro
225                 230                 235                 240

Lys Ser Cys Asp Lys Thr His Thr Cys Pro Pro Cys Pro Ala Pro Glu
                245                 250                 255

Leu Leu Ala Gly Pro Asp Val Phe Leu Phe Pro Pro Lys Pro Lys Asp
            260                 265                 270

Thr Leu Met Ile Ser Arg Thr Pro Glu Val Thr Cys Val Val Val Asp
        275                 280                 285

Val Ser His Glu Asp Pro Glu Val Lys Phe Asn Trp Tyr Val Asp Gly
    290                 295                 300

Val Glu Val His Asn Ala Lys Thr Lys Pro Arg Glu Glu Gln Tyr Asn
305                 310                 315                 320

Ser Thr Tyr Arg Val Val Ser Val Leu Thr Val Leu His Gln Asp Trp
                325                 330                 335

Leu Asn Gly Lys Glu Tyr Lys Cys Lys Val Ser Asn Lys Ala Leu Pro
            340                 345                 350

Ala Pro Glu Glu Lys Thr Ile Ser Lys Ala Lys Gly Gln Pro Arg Glu
        355                 360                 365

Pro Gln Val Tyr Thr Leu Pro Pro Ser Arg Glu Glu Met Thr Lys Asn
    370                 375                 380

Gln Val Ser Leu Thr Cys Leu Val Lys Gly Phe Tyr Pro Ser Asp Ile
385                 390                 395                 400

Ala Val Glu Trp Glu Ser Asn Gly Gln Pro Glu Asn Asn Tyr Lys Thr
                405                 410                 415

Thr Pro Pro Val Leu Asp Ser Asp Gly Ser Phe Phe Leu Tyr Ser Lys
            420                 425                 430

Leu Thr Val Asp Lys Ser Arg Trp Gln Gln Gly Asn Val Phe Ser Cys
        435                 440                 445

Ser Val Met His Glu Ala Leu His Asn His Tyr Thr Gln Lys Ser Leu
    450                 455                 460

Ser Leu Ser Pro Gly Lys
465                 470
```

<210> SEQ ID NO 115
<211> LENGTH: 699
<212> TYPE: DNA
<213> ORGANISM: Artificial Sequence

```
<220> FEATURE:
<223> OTHER INFORMATION: Humanized antibody

<400> SEQUENCE: 115

atggagtcac agattcaggt ctttgtattc gtgtttctct ggttgtctgg tgttgacgga     60

gacattgtga tgacccagtc tcccagctcc ctgtccgcat cagtaggaga cagggtcacc    120

atcacctgca aggccagtca ggatgtgagt actgctgtag tctggtatca acagaaacca    180

ggaaaagctc ctaaactact gatttattcg gcatcctacc ggtacactgg agtccctgat    240

cgcttcactg gcagtggatc tgggacggat ttcactttga ccatcagcag tctgcaggct    300

gaagacttcg caacctatta ctgtctacaa cattttagta ctcctcggac gttcggtgga    360

ggcaccaaac tggaaatcaa aacggtggct gcaccatctg tcttcatctt cccgccatct    420

gatgagcagt tgaaatctgg aactgcctct gttgtgtgcc tgctgaataa cttctatccc    480

agagaggcca aagtacagtg gaaggtggat aacgccctcc aatcgggtaa ctcccaggag    540

agtgtcacag agcaggacag caaggacagc acctacagcc tcagcagcac cctgacgctg    600

agcaaagcag actacgagaa acacaaagtc tacgcctgcg aagtcaccca tcagggcctg    660

agctcgcccg tcacaaagag cttcaacagg ggagagtgt                           699


<210> SEQ ID NO 116
<211> LENGTH: 233
<212> TYPE: PRT
<213> ORGANISM: Artificial Sequence
<220> FEATURE:
<223> OTHER INFORMATION: Humanized antibody

<400> SEQUENCE: 116

Met Glu Ser Gln Ile Gln Val Phe Val Phe Val Phe Leu Trp Leu Ser
1               5                   10                  15

Gly Val Asp Gly Asp Ile Val Met Thr Gln Ser Pro Ser Ser Leu Ser
            20                  25                  30

Ala Ser Val Gly Asp Arg Val Thr Ile Thr Cys Lys Ala Ser Gln Asp
        35                  40                  45

Val Ser Thr Ala Val Val Trp Tyr Gln Gln Lys Pro Gly Lys Ala Pro
    50                  55                  60

Lys Leu Leu Ile Tyr Ser Ala Ser Tyr Arg Tyr Thr Gly Val Pro Asp
65                  70                  75                  80

Arg Phe Thr Gly Ser Gly Ser Gly Thr Asp Phe Thr Leu Thr Ile Ser
                85                  90                  95

Ser Leu Gln Ala Glu Asp Phe Ala Thr Tyr Tyr Cys Leu Gln His Phe
            100                 105                 110

Ser Thr Pro Arg Thr Phe Gly Gly Gly Thr Lys Leu Glu Ile Lys Thr
        115                 120                 125

Val Ala Ala Pro Ser Val Phe Ile Phe Pro Pro Ser Asp Glu Gln Leu
    130                 135                 140

Lys Ser Gly Thr Ala Ser Val Val Cys Leu Leu Asn Asn Phe Tyr Pro
145                 150                 155                 160

Arg Glu Ala Lys Val Gln Trp Lys Val Asp Asn Ala Leu Gln Ser Gly
                165                 170                 175

Asn Ser Gln Glu Ser Val Thr Glu Gln Asp Ser Lys Asp Ser Thr Tyr
            180                 185                 190

Ser Leu Ser Ser Thr Leu Thr Leu Ser Lys Ala Asp Tyr Glu Lys His
        195                 200                 205

Lys Val Tyr Ala Cys Glu Val Thr His Gln Gly Leu Ser Ser Pro Val
```

210 215 220

Thr Lys Ser Phe Asn Arg Gly Glu Cys
225 230

<210> SEQ ID NO 117
<211> LENGTH: 807
<212> TYPE: DNA
<213> ORGANISM: Artificial Sequence
<220> FEATURE:
<223> OTHER INFORMATION: scFv

<400> SEQUENCE: 117
catatgatga aatacctatt gcctacggca gccgctggat tgttattact cgcggcccag 60
ccggcgatgg cccagatcca gttggtgcag tctggacctg agctgaagaa gcctggagag 120
acagtcaaga tctcctgcaa ggcttctggg tataccttca caaactatgg aatgaactgg 180
gtgaagcagg ctccaggaaa gggtttaaag tggatgggct ggataaacac ctacactgga 240
cagtcaacat atgctgatga cttcaaggga cgctttgcct tctctttgga aacctctgcc 300
agcactgccc atttgcagat cagcaacctc aaaaatgagg acgcggctac atatttctgt 360
gcaagaatgg agtatggtaa ctacgaaaat gctttggatt actggggtca aggaacctca 420
gtcaccgtct cctcaggtgg cggtggcagc ggcggcggtg gtagcggtgg tggcggcagc 480
gacattgtga tgacccagtc tcacaaattc atgtccacat caataggaga cagggtcagc 540
atcacctgca aggccagtca ggatgtgagt actgctgtag tctggtatca acagaaacca 600
ggacactctc ctaaactact gatttattcg gcatcctacc ggtacactgg agtccctgat 660
cgcttcactg gcagtggatc tgggacggat ttcactttca ccatcagcag tgtgcaggct 720
gaagacctgg cagtttatta ctgtctacaa cattttagta ctcctcggac gttcggtgga 780
ggcaccaacc tggaaatcaa actcgag 807

<210> SEQ ID NO 118
<211> LENGTH: 44
<212> TYPE: DNA
<213> ORGANISM: Artificial Sequence
<220> FEATURE:
<223> OTHER INFORMATION: primer

<400> SEQUENCE: 118
cctacactgg acagtcaacc tatgctgatg acttcaaggg acgc 44

<210> SEQ ID NO 119
<211> LENGTH: 44
<212> TYPE: DNA
<213> ORGANISM: Artificial Sequence
<220> FEATURE:
<223> OTHER INFORMATION: Primer

<400> SEQUENCE: 119
gcgtcccttg aagtcatcag cataggttga ctgtccagtg tagg 44

<210> SEQ ID NO 120
<211> LENGTH: 807
<212> TYPE: DNA
<213> ORGANISM: Artificial Sequence
<220> FEATURE:
<223> OTHER INFORMATION: scFv

<400> SEQUENCE: 120
catatgatga aatacctatt gcctacggca gccgctggat tgttattact cgcggcccag 60
ccggcgatgg cccagatcca gttggtgcag tctggacctg agctgaagaa gcctggagag 120
acagtcaaga tctcctgcaa ggcttctggg tataccttca caaactatgg aatgaactgg 180
gtgaagcagg ctccaggaaa gggtttaaag tggatgggct ggataaacac ctacactgga 240
cagtcaacct atgctgatga cttcaaggga cgctttgcct tctctttgga aacctctgcc 300
agcactgccc atttgcagat cagcaacctc aaaaatgagg acgcggctac atatttctgt 360
gcaagaatgg agtatggtaa ctacgaaaat gctttggatt actggggtca aggaacctca 420
gtcaccgtct cctcaggtgg cggtggcagc ggcggcggtg gtagcggtgg tggcggcagc 480
gacattgtga tgacccagtc tcacaaattc atgtccacat caataggaga cagggtcagc 540
atcacctgca aggccagtca ggatgtgagt actgctgtag tctggtatca acagaaacca 600
ggacactctc ctaaactact gatttattcg gcatcctacc ggtacactgg agtccctgat 660
cgcttcactg gcagtggatc tgggacggat ttcactttca ccatcagcag tgtgcaggct 720
gaagacctgg cagtttatta ctgtctacaa cattttagta ctcctcggac gttcggtgga 780
ggcaccaacc tggaaatcaa actcgag 807

<210> SEQ ID NO 121
<211> LENGTH: 807
<212> TYPE: DNA
<213> ORGANISM: Artificial Sequence
<220> FEATURE:
<223> OTHER INFORMATION: scFv

<400> SEQUENCE: 121
catatgatga aatacctatt gcctacggca gccgctggat tgttattact cgcggcccag 60
ccggcgatgg cccagatcca gttggtgcag tctggatctg agctgaagaa gcctggagcg 120
tcagtcaagg tctcctgcaa ggcttctggg tataccttca caaactatgg aatgaactgg 180
gtgaagcagg ctccaggaca gggtttaaag tggatgggct ggataaacac ctacactgga 240
cagtcaacct atgctgatga cttcaaggga cgctttgcct tctctttgga tacctctgtc 300
agcactgcct atttgcagat cagcagcctc aaagctgagg acacggctgt gtatttctgt 360
gcaagaatgg agtatggtaa ctacgaaaat gctttggatt actggggtca aggaacctta 420
gtcaccgtct cctcaggtgg cggtggcagc ggcggcggtg gtagcggtgg tggcggcagc 480
gacattgtga tgacccagtc tcccagctcc ctgtccgcat cagtaggaga cagggtcacc 540
atcacctgca aggccagtca ggatgtgagt actgctgtag tctggtatca acagaaacca 600
ggaaaagctc ctaaactact gatttattcg gcatcctacc ggtacactgg agtccctgat 660
cgcttcactg gcagtggatc tgggacggat ttcactttga ccatcagcag tctgcaggct 720
gaagacttcg caacctatta ctgtctacaa cattttagta ctcctcggac gttcggtgga 780
ggcaccaaac tggaaatcaa actcgag 807

<210> SEQ ID NO 122
<211> LENGTH: 807
<212> TYPE: DNA
<213> ORGANISM: Artificial Sequence
<220> FEATURE:
<223> OTHER INFORMATION: scFv

<400> SEQUENCE: 122
catatgatga aatacctatt gcctacggca gccgctggat tgttattact cgcggcccag 60
ccggcgatgg ccgacattgt gatgacccag tctcccagct ccctgtccgc atcagtagga 120
gacagggtca ccatcacctg caaggccagt caggatgtga gtactgctgt agtctggtat 180

-continued

```
caacagaaac caggaaaagc tcctaaacta ctgatttatt cggcatccta ccggtacact    240
ggagtccctg atcgcttcac tggcagtgga tctgggacgg atttcacttt gaccatcagc    300
agtctgcagg ctgaagactt cgcaacctat tactgtctac aacattttag tactcctcgg    360
acgttcggtg gaggcaccaa actggaaatc aaaggtggcg gtggcagcgg cggcggtggt    420
agcggtggtg gcggcagcca gatccagttg gtgcagtctg gatctgagct gaagaagcct    480
ggagcgtcag tcaaggtctc ctgcaaggct tctgggtata ccttcacaaa ctatggaatg    540
aactgggtga agcaggctcc aggacagggt ttaaagtgga tgggctggat aaacacctac    600
actggacagt caacctatgc tgatgacttc aagggacgct ttgccttctc tttggatacc    660
tctgtcagca ctgcctattt gcagatcagc agcctcaaag ctgaggacac ggctgtgtat    720
ttctgtgcaa gaatggagta tggtaactac gaaaatgctt tggattactg gggtcaagga    780
accttagtca ccgtctcctc actcgag                                         807
```

ANTIGEN BINDING PROTEINS TO CLASS 5 ETEC ADHESINS

CROSS REFERENCE TO RELATED APPLICATIONS

The present application is a national phase entry under 35 U.S.C. § 371 of International Application No. PCT/US21/25254 filed Mar. 31, 2021 published in English, which claims the benefit of U.S. Provisional Patent Application No. 63/004,002 filed Apr. 2, 2020, the entire disclosures of which are incorporated by reference herein.

SEQUENCE LISTING

The instant application contains a Sequence Listing that has been submitted in ASCII format via EFS-Web and is hereby incorporated by reference herein in its entirety. Said ASCII copy, created on Mar. 31, 2021, is named "Sequence_List_NCI 10768PCT_ST25.txt" and is 131 kilobytes in size.

FIELD OF THE INVENTION

The subject matter of the instant invention relates to antigen binding proteins that bind to class 5 enterotoxigenic *Escherichia coli* (ETEC) adhesins, methods of making and using these antigen binding proteins, and ETEC immunogenic compositions and vaccine formulations comprising said antigen binding proteins.

BACKGROUND OF INVENTION

ETEC is a leading diarrheagenic bacterial pathogen among travelers and children in resource-limited regions. ETEC pathogenesis is initiated upon adherence of the bacteria to host intestinal cells using bacterial fimbrial colonization factors (CFs) and the subsequent secretion of enterotoxins. The ETEC class 5 fimbrial family contains some of the most prevalent CFs, and consists of eight members divided into three subclasses: 5a (CFA/I, CS4, CS14), 5b (CS1, CS17, CS19, PCF071) and 5c (CS2). See Table 1 (4,5).

TABLE 1

ETEC Class 5 Fimbrial Colonization Factors and Minor Subunit Adhesins

| ETEC Fimbrial Colonization Factor (fimbria) | Fimbrial Subclass | Subclass 5a Fimbrial Tip Adhesin | Subclass 5b Fimbrial Tip Adhesin | Subclass 5c Fimbrial Tip Adhesin |
|---|---|---|---|---|
| CFA/I | 5a | CfaE | | |
| CS4 | 5a | CsfD | | |
| CS14 | 5a | CsuD | | |
| CS1 | 5b | | CooD | |
| CS17 | 5b | | CsbD | |
| CS19 | 5b | | CsdD | |
| PCF071 | 5b | | CosD | |
| CS2 | 5c | | | CotD |

In the past two decades, the molecular assembly and functional components of the class 5 fimbriae have been characterized, and data indicate that these CFs comprise a stalk-forming major subunit and a tip-localized minor adhesin subunit. Research indicates that the minor adhesin subunits of the class 5 fimbriae are the essential component for bacterial adherence, functioning as the "fimbrial tip adhesins."

Ideally, while a multivalent ETEC vaccine would be directed to as many of the eight class 5 colonization factors as possible, a major challenge to the development of such broadly protective ETEC adhesin-based vaccine is the antigenic and sequence variability among the class 5 adhesins. Previous studies to identify cross-reactive functional epitopes present among the class 5 adhesins include initial experiments with 28 murine monoclonal antibodies generated by immunizing mice with each of three representative class 5 adhesins, CfaE (the CFA/I adhesin), CsbD (the CS17 adhesin) and CotD (the CS2 adhesin) (33,34). Preliminary efforts at epitope mapping using these murine monoclonal antibodies have been reported, however, the amino acid and nucleic acid sequences of these murine Mabs remained uncharacterized (33, 34.) Thus, there exists a need for additional studies to develop these and other anti-adhesin antibodies and particularly, therapeutic antigen binding proteins that bind to one or more ETEC class 5 adhesins for use in methods of preventing or treating an ETEC-related infection in a subject.

SUMMARY OF THE INVENTION

In a first aspect, the invention broadly relates to antigen binding proteins that bind to one or more ETEC class 5 adhesins and thus prevent or reduce the ability of ETEC to infect a subject, e.g., by disrupting the adherence of ETEC CFs to the subject's intestinal cells. In a particular embodiment, the antigen binding protein is an isolated antigen binding protein. In a particular embodiment, the isolated antigen binding protein is a monoclonal antibody (mAb or Mab) to an ETEC class 5 adhesin. In particular embodiments, the isolated antigen binding proteins are the mouse mAbs listed in Table 3, Table 4 and Table 5. In a particular embodiment, the mAb is selected from the group consisting of mouse mAbs P8D10, P6B8, P10A7, P5C7, P2H6 and P7F9.

In another aspect, the invention relates to an antigen binding protein that binds to an ETEC class 5 adhesin, wherein said ETEC class 5 adhesin is selected from the group consisting of ETEC class 5 adhesins encoded by amino acid sequences disclosed in FIGS. 12(A)-12(C) and set forth as SEQ ID NOs: 5, 7, and 9. In a particular embodiment, the ETEC class 5 adhesin is the CfaE sequence from H10407 strain encoded by the amino acid sequence provided as SEQ ID NO: 5 and encoded by the nucleic acid sequence set forth as SEQ ID NO: 4 disclosed in FIG. 12(A), and the CsbD sequence from WS6788A strain encoded by the amino acid sequence provided as SEQ ID NO: 7 and encoded by the nucleic acid sequence set forth as SEQ ID NO: 6 disclosed in FIG. 12(B), and the CotD sequence from C91f strain encoded by the amino acid sequence provided as SEQ ID NO:9 and encoded by the nucleic acid sequence set forth as SEQ ID NO:8 disclosed in FIG. 12(C).

In another aspect, the invention relates to an antigen binding protein, or an immunologically active fragment or derivative thereof, that binds to an ETEC class 5 adhesin, wherein said antigen binding protein comprises one or more variable regions or active fragment thereof selected from the group consisting of the variable regions encoded in the amino acid sequences disclosed in FIGS. 13(A)-13(F) and FIGS. 14(A)-14(F) and set forth as SEQ ID NOs: 11, 13, 15, 17, 19, 21, 23, 25, 27, 29, 31, 33, 35, 37, 39, 41, 43, 45, 47, 49, 51, 53, 55, and 57. In one embodiment, the antigen binding protein is selected from the group consisting of chimeric, humanized, and human monoclonal antibodies. In particular embodiments, the antigen binding protein is a chimeric, humanized, or human monoclonal antibody comprising a human IgG constant region and/or a human immunoglobulin kappa light chain. In a particular embodiment, the human IgG constant region is a human IgG1 constant region. In various embodiments, the antigen binding protein is an isolated antigen binding protein.

In another aspect, the invention relates to an antigen binding protein which is capable of binding an ETEC class 5 adhesin and which comprises heavy chain amino acid complementarity determining region ("CDR") sequences CDR1, CDR2 and CDR3 and light chain amino acid sequences CDR1, CDR2 and CDR3 of a murine mAb variable region disclosed in FIGS. 13(A)-13(F) or FIGS. 14(A)-14(F) and provided in the amino acid sequences set forth therein as SEQ ID NOs: 11, 13, 15, 17, 19, 21, 23, 25, 27, 29, 31, 33, 35, 37, 39, 41, 43, 45, 47, 49, 51, 53, 55, and 57. In a particular embodiment, the antigen binding protein is a single chain variable fragment (scFv) antibody.

In additional embodiments, the antigen binding protein is capable of binding an ETEC class 5 adhesin and comprises the amino acid sequence depicted in FIG. 16(A) (SEQ ID NO: 71) or a functional fragment thereof and/or comprises the amino acid sequence depicted in FIG. 16(B) (SEQ ID NO: 73) or a functional fragment thereof. In another embodiment, the antigen binding protein is capable of binding an ETEC class 5 adhesin and comprises the amino acid sequence depicted in FIG. 18(A) (SEQ ID NO: 75) or a functional fragment thereof and/or comprises the amino acid sequence depicted in FIG. 18(B) (SEQ ID NO: 75) or a functional fragment thereof.

In another embodiment, the antigen binding protein is capable of binding an ETEC class 5 adhesin and comprises the amino acid sequence depicted in FIG. 19(A) (SEQ ID NO: 79) or FIG. 19(B) (SEQ ID NO: 108) or a functional fragment thereof.

In another embodiment, the antigen binding protein is capable of binding an ETEC class 5 adhesin and comprises the amino acid sequence depicted in FIG. 26(A) (SEQ ID NO: 80) or a functional fragment thereof and/or comprises the amino acid sequence depicted in FIG. 26(B) (SEQ ID NO: 82) or a functional fragment thereof.

In another embodiment, the antigen binding protein is capable of binding an ETEC class 5 adhesin and comprises the amino acid sequence depicted in FIG. 28(A) (SEQ ID NO: 90) or a functional fragment thereof and/or comprises the amino acid sequence depicted in FIG. 28(B) (SEQ ID NO: 91) or a functional fragment thereof.

In another embodiment, the antigen binding protein is capable of binding an ETEC class 5 adhesin and comprises the amino acid sequence depicted in FIG. 28(D) (SEQ ID NO: 110) or a functional fragment thereof.

In another embodiment, the antigen binding protein is capable of binding an ETEC class 5 adhesin and comprises the amino acid sequence depicted in FIG. 28(E) (SEQ ID NO: 112) or a functional fragment thereof.

In an additional embodiment, the antigen binding protein is capable of binding an ETEC class 5 adhesin and comprises the amino acid sequence depicted in FIG. 33(A) (SEQ ID NO: 114) or a functional fragment thereof and/or comprises the amino acid sequence depicted in FIG. 33(B) (SEQ ID NO: 116) or a functional fragment thereof.

In additional aspects, the invention relates to nucleic acid molecules comprising a nucleotide sequence encoding one or more of the antigen binding proteins of the instant invention; nucleic acid vectors comprising one or more of said nucleic acid molecules, wherein said nucleic acid molecules are operably linked to a promoter capable of driving the expression of said nucleic acid molecules; and host cells comprising one or more of these nucleic acid vectors. The invention also includes compositions comprising said nucleic acid molecules, nucleic acid vectors, and host cells.

In an additional aspect, the invention relates to compositions comprising one or more of the antigen binding proteins of the instant invention. In a particular embodiment, the composition is a pharmaceutical composition. In particular embodiments, the pharmaceutical composition is selected from the group consisting of an ETEC immunogenic composition and an ETEC vaccine formulation. In additional embodiments, the pharmaceutical composition optionally comprises one or more adjuvants in an amount sufficient to enhance an immune response to the one or more of the antigen binding proteins.

In another aspect, the invention relates to methods of preventing or treating an ETEC-related infection in a subject in need thereof, comprising administering to the subject a therapeutically effective amount of a composition of the instant invention. In a particular embodiment, the composition is a pharmaceutical composition.

In yet another aspect, the invention relates to a kit for detecting ETEC bacteria comprising one or more of the antigen binding proteins of the instant invention.

BRIEF DESCRIPTION OF THE DRAWINGS

FIG. 1(A) depicts mAbs specific to the CFA/I adhesin. FIG. 1(B) depicts mAbs cross-reactive to the CFA/I and CS14 adhesins. FIG. 1(C) depicts mAb cross-reactive to the CFA/I, CS4 and CS14 adhesins. FIG. 1(D) depicts mAbs cross-reactive to the CFA/I, CS1 and CS17 adhesins. FIG. 1(E) depicts mAbs cross-reactive to the CFA/I, CS4, CS14, CS1, CS17 and CS2 adhesins. In these figures, the dashed lines represent the limit of detection in the anti-CfaE mAb ELISA assays, which was calculated as average background of PBS buffer plus three times the standard deviation. All mAbs were produced against the dsc antigen construct disclosed in FIG. 12(A). FIGS. 1(A)-1(E) depict a subset of data provided in FIGS. 5(A)-5(I).

FIG. 2(A) depicts mAbs cross-reactive to the CS17 adhesin and FIG. 2(B) depicts mAbs cross-reactive to the CS1 adhesin. FIG. 2(C) depicts mAb cross-reactive to the CFA/I, CS4, CS14, CS17 and CS1 adhesins. FIG. 2(D) depicts mAb cross-reactive to the CFA/I, CS4, CS14, CS1, CS17 and CS2 adhesins. In these figures, the dashed lines represent the limit of detection in the anti-CsbD mAb ELISA assays, which was calculated as average background of PBS buffer plus three times the standard deviation. All mAbs were produced against the dsc antigen construct disclosed in FIG. 12(B). FIGS. 2(A)-2(D) depict a subset of data provided in FIGS. 6(A)-6(K).

FIG. 3(A) depicts mAbs specific to the CS2 adhesin. FIG. 3(B) depicts mAb cross-reactive to the CFA/I, CS14 and CS2 adhesins. FIG. 3(C) depicts mAb cross-reactive to the CS4, CS14 and CS2 adhesins. FIG.

3(D) depicts mAb cross-reactive to the CFA/I, CS4, CS14 and CS2 adhesins. In these figures, the dashed lines represented the limit of detection in the anti-CotD mAb ELISA assays, which was calculated as average background of PBS buffer plus three times the standard deviation. All mAbs were produced against the dsc antigen construct disclosed in FIG. 12(C). FIGS. 3(A)-3(D) depict a subset of data provided in FIG. 7(A)-7(H).

FIG. 4(A) depicts epitope residues (ball & stick view) of anti-CfaE mAbs P8D10, P6C11, P6H4, P10A7 and P5C7 mapped onto the CfaE crystal structure (ribbon and surface view, PDB ID: 2HB0). The receptor binding site of CfaE is located in the adhesin domain, and includes residues R67 and R181. FIG. 4(B) and FIG. 4(C) depict epitope residues of anti-CsbD mAbs P2H6, P1F7 and P7F9, and anti-CotD mAb P6B8 mapped onto the CsbD and CotD structure models, respectively. As depicted, residues T84, S88, H144, R181, and Y182 are found in the adhesin domain of CsbD, and residues R69 and R184 are present in the adhesin domain of CotD, respectively. All mAbs were produced against the respective dsc antigen constructs disclosed in FIG. 12(A)-(C).

FIG. 5(A) depicts anti-CfaE Mab P8D10 ELISA; FIG. 5(B) depicts anti-CfaE P6C11 ELISA;

FIG. 5(C) depicts anti-CfaE Mab P6H4 ELISA; FIG. 5(D) depicts anti-CfaE Mab P10A7 ELISA; FIG. 5(E) depicts anti-CfaE Mab P5C7 ELISA; FIG. 5(F) depicts anti-CfaE Mab P2E11 ELISA; FIG. 5(G) depicts anti-CfaE Mab P3B2 ELISA; FIG. 5(H) depicts anti-CfaE Mab P13A7 ELISA; and FIG. 5(I) depicts anti-CfaE Mab PIF9 ELISA. All mAbs were produced against the dsc antigen construct disclosed in FIG. 12(A).

FIG. 6(A) depicts anti-CsbD Mab P7C2 ELISA; FIG. 6(B) depicts anti-CsbD Mab P9A5 ELISA; FIG. 6(C) depicts anti-CsbD Mab P2H6 ELISA; FIG. 6(D) depicts anti-CsbD Mab P6G1 ELISA; FIG. 6(E) depicts anti-CsbD Mab P2A9 ELISA; FIG. 6(F) depicts anti-CsbD Mab PIF7 ELISA; FIG. 6(G) depicts anti-CsbD Mab P9E11 ELISA;

FIG. 6(H) depicts anti-CsbD Mab P7F9 ELISA; FIG. 6(I) depicts anti-CsbD Mab P5A12 ELISA: FIG. 6(J) depicts anti-CsbD Mab P9D12 ELISA; and FIG. 6(K) depicts Anti-CsbD Mab P7F12 ELISA. All mAbs were produced against the dsc antigen construct disclosed in FIG. 12(B).

FIG. 7(A) depicts anti-CotD Mab P7F6 ELISA; FIG. 7(B) depicts anti-CotD Mab P3F4 ELISA;

FIG. 7(C) depicts anti-CotD Mab P6B8 ELISA; FIG. 7(D) depicts anti-CotD Mab P3D11 ELISA; FIG. 7(E) depicts anti-CotD Mab P9A10 ELISA; FIG. 7(F) depicts anti-CotD Mab P9G7 ELISA; FIG. 7(G) depicts anti-CotD Mab P2B8 ELISA; FIG. 7(H) depicts anti-CotD mAb P12A2 ELISA. All mAbs were produced against the dsc antigen construct disclosed in FIG. 12(C).

FIG. 8(A) depicts anti-CotD mAb P7F6 ELISA; FIG. 8(B) depicts anti-CotD mAb P3F4 ELISA;

FIG. 8(C) depicts anti-CotD mAb P6B8 ELISA; FIG. 8(D) depicts anti-CotD mAb P3D11 ELISA; FIG. 8(E) depicts anti-CotD mAb P9A10 ELISA; FIG. 8(F) depicts anti-CotD mAb P9G7 ELISA; FIG. 8(G) depicts anti-CotD mAb P21B8 ELISA; FIG. 8(H) depicts anti-CotD mAb P12A2 ELISA. All mAbs were produced against the dsc antigen construct disclosed in FIG. 12(C).

FIG. 9 depicts multiple amino acid sequence alignment of CfaE from CFA/I-expressing H10407 strain (SEQ ID NO:1), CsbD from CS17-expressing WS6788A strain (SEQ ID NO:2), and CotD from CS2-expressing C91f strain (SEQ ID NO:3). Residues with allelic variations and site-directed mutations are highlighted with shaded boxes. The numbers at the top of the sequences indicate amino acid positions in CfaE starting from the leader sequence. The numbers on the right side of the sequences indicate amino acids positions starting from the leader sequences of CfaE, CsbD, and CotD, respectively.

FIGS. 12(A), 12(B), and 12(C) depict the DNA and amino acid sequences of donor strand complemented sequences of CfaE, CsbD, and CotD, used to create the mAbs of the instant invention. Specifically, FIG. 12(A) depicts the DNA (SEQ ID NO:4) and amino acid (SEQ ID NO:5) sequences of the donor strand complemented recombinant CFA/I fimbrial tip adhesin CfaE (prototypical strain H10407) referred to herein as "$dsc_{19}$CfaE6xhis (H10407)". The amino acid sequence depicts the signal sequence in bold, mature CfaE sequence, a DNKQ tetrapeptide linker (SEQ ID NO: 92), an underlined 19-amino acid donor strand from the N-terminal of CfaB (VEKNITVTASVDPVIDLLQ (SEQ ID NO: 93)), and an italicized 6xHis tag of LEHHHHHH (SEQ ID NO: 94)). FIG. 12(B) depicts the DNA (SEQ ID NO:6) and amino acid (SEQ ID NO: 7) sequences of the donor strand complemented recombinant CS17 fimbrial tip adhesin CsbD from ETEC strain WS6788A, referred to herein as "$dsc_{19}$CsbD6xhis (WS6788A)". This sequence contains signal sequence in bold, mature CsbD sequence, a DNKQ tetrapeptide linker (SEQ ID NO:92), an underlined 19-amino acid donor strand from the N-terminal of CsbA, (VEKNITVRASVDPKLDLLQ (SEQ ID NO: 95)), and an italicized 6xHis tag of LEHHHHHH (SEQ ID NO: 94). FIG. 12(C) depicts the DNA (SEQ ID NO:8) and amino acid (SEQ ID NO:9) sequences of the donor strand complemented recombinant CS2 fimbrial tip adhesin CotD from ETEC strain C91f, referred to herein as "$dsc_{19}$CotD6xhis (C91f)". This sequence contains signal sequence in bold, mature CotD sequence, a DNKQ tetrapeptide linker (SEQ ID NO: 92), an underlined 19-amino acid donor strand from the N-terminal of CotA (AEKNITVTASVDPTIDLMQ (SEQ ID NO: 96)), and an italicized 6xHis tag of LEHHHHHH (SEQ ID NO: 94). In FIGS. 12(A)-(C), the DNA and amino acid sequence representing the mature protein is flanked by the signal sequence (bold font) and 6xHis tag (italic font).

FIGS. 13(A)-13(F) provides the nucleotide and amino acid sequence information of the variable regions of the mouse mAbs P8D10, P5C7, P9A5, P6B8, P7C2, and P1F9 obtained using Kabat sequence analysis (SEQ ID NOs: 10-33). FIG. 13(A) depicts data for P8D10; FIG. 13(B) depicts data for P5C7; FIG. 13(C) depicts data for P9A5; FIG. 13(D) depicts data for P6B8; FIG. 13(E) depicts data for P7C2; and FIG. 13(F) depicts data for PIF9. As indicated in the figures, the shaded sequences depict the signal sequence; bold font represents the framework regions ("FR"); and regular font depicts the complementarity-determining regions ("CDR") of the variable regions in the nAb. All mAbs were produced against the respective dsc antigen constructs disclosed in FIGS. 12(A)-12(C). The FR and CDR region predictions were performed by Kabat sequence analysis.

FIGS. 14(A)-14(F) provides the nucleotide and amino acid sequence information of the variable regions of the mAbs P8D10, P5C7, P9A5, P6B8, P7C2, and P1F9 obtained using IMGT/NCBI IgBlast analysis https://wwv.ncbi.nlm-.nih.gov/igblast/(SEQ ID NOs: 34-57). FIG. 14(A) depicts data for P8D10; FIG. 14(B) depicts data for P5C7; FIG. 14(C) depicts data for P9A5; FIG. 14(D) depicts data for P6B8; FIG. 14(E) depicts data for P7C2; and FIG. 14(F) depicts data for PIF9. As indicated in the figures, the shaded sequences depict the signal sequence; bold font represents the framework regions ("FR"); and regular font depicts the complementarity-determining regions ("CDR") of the variable regions in the mAb. All mAbs were produced against the respective dsc antigen constructs disclosed in FIGS. 12(A)-12(C).

FIGS. 15(A)-15(F) depict the IMGT analysis of V(D)J junctions in the mAbs P8D10, P5C7, P9A5, P6B8, P7C2, and PIF9. The amino acid sequence of the respective junctions is set forth as SEQ ID NOs: 58-69. FIG. 15(A) depicts data for P8D10;

FIG. 15(B) depicts data for P5C7; FIG. 15(C) depicts data for P9A5; FIG. 15(D) depicts data for P6B8; FIG. 15(E) depicts data for P7C2; and FIG. 15(F) depicts data for PIF9. As indicated therein, the gene sequences are abbreviated: "V"=variable: "D"=diversity; "J"=joining. All mAbs were produced against the respective dsc antigen constructs disclosed in FIGS. 12(A)-12(C).

FIGS. 16(A) and 16(B) depict the heavy chain DNA (SEQ ID NO: 70) and amino acid (SEQ ID NO: 71) sequences, and light chain DNA (SEQ ID NO: 72) and amino acid (SEQ ID NO: 73) sequences, respectively, of a particular embodiment of a prophetic mouse-human chimeric antibody that may be created by fusion of mouse variable regions of P6B8 nAb with constant regions of human IgG1 heavy chain and human immunoglobulin kappa light chain as described in Example 12. As depicted in FIG. 16(A), the shaded sequences indicate the mAb P6B8 heavy chain signal sequence, the bold sequence is the mAb P6B8 heavy chain variable region, and the regular font represents the human IgG1 heavy chain constant region. As depicted in FIG. 16(B), the shaded sequences indicate the mAb P6B8 light chain signal sequence, the bold sequence is the mAb P6B8 light chain variable region, and the regular font represents the human immunoglobulin kappa light chain constant region.

FIG. 17(A) depicts a capture ELISA scheme using anti-adhesin mAb P10A7 to quantify ETEC proteins (unscaled). As depicted, the CfaEB protein contains a 6xHis tag (triangle), R67 and R181 residues (circles). CfaEB is captured by the anti-His rabbit capture antibody affixed to the plate. R67 and R181 residues in CfaEB are recognized by the anti-CfaE mouse mAb P10A7. The detecting antibody is a horseradish peroxidase (HRP)-conjugated goat anti-mouse IgG antibody. FIG. 17(B) depicts testing of a series concentration from 0.03 ug/ml to 1.0 ug/ml of purified CfaEB using the capture ELISA scheme shown in FIG. 17(A). The OD and CfaEB concentrations are plotted as indicated (black dots). FIG. 17(C) depicts testing of a series concentration from 0.025 ug/ml to 0.2 ug/ml of purified CfaEB using the capture ELISA scheme shown in FIG. 17(A). The OD and CfaEB concentrations are plotted as indicated (black dots). A standard curve was fitted using linear regression. A diluted sample containing CfaEB (black star) was also tested and the CfaEB concentration in the diluted sample was interpolated based on its OD value.

FIGS. 18(A)-18(B) depict the heavy chain DNA (SEQ ID NO: 74) and amino acid (SEQ ID NO: 75) sequences, and light chain DNA (SEQ ID NO: 76) and amino acid (SEQ ID NO: 77) sequences, respectively, of a particular embodiment of a prophetic mouse-human chimeric antibody that may be created by fusion of mouse variable regions of P5C7 mAb with constant regions of human IgG1 heavy chain and human immunoglobulin kappa light chain as described in Example 12. As depicted in FIG. 18(A), the shaded sequences indicate the mAb P5C7 heavy chain signal sequence, the bold sequence is the mAb P5C7 heavy chain variable region, and the regular font represents the human IgG1 heavy chain constant region. As depicted in FIG. 18(B), the shaded sequences indicate the mAb P5C7 light chain signal sequence, the bold sequence is the mAb P5C7 light chain variable region, and the regular font represents the human immunoglobulin kappa light chain constant region.

FIG. 19(A) depicts the DNA (SEQ ID NO: 78) and amino acid (SEQ ID NO: 79) sequences of a prophetic P8D10 VH-VL scFv antibody. As depicted, the scFv antibody design comprises a pelB leader sequence (shaded font) followed by a P8D10 murine mAb heavy chain variable domain and a P8D10 mAb light chain variable domain (bold font) linked together using a 15-mer linker of $(GGGGS)_3$ (italics) (SEQ ID NO: 97). FIG. 19(B) depicts the DNA (SEQ ID NO: 107) and amino acid (SEQ ID NO: 108) sequences of the created mouse P8D10 VH-VL scFv antibody. As depicted, the scFv antibody comprises a pelB leader sequence (shaded font) followed by a P8D10 murine mAb heavy chain variable domain and a P8D10 mAb light chain variable domain (bold font) linked together using a 15-mer linker of $(GGGGS)_3$ (italics) (SEQ ID NO: 97).

FIG. 26(A) depicts the heavy chain sequence alignment of P8D10_H and 1IAI_H (88.43% identity) and FIG. 26(B) depicts the light chain sequence alignment of P8D10_L and 1IAI_L (89.72% identity). Bold residues are predicted to be CDR residues, and underlined residues are mouse framework residues within 5 Å of CDR regions, which have potential to influence antigen-binding activity based on the P8D10 VHVL scFv structural model. As depicted, an asterisk (*) means the residues are identical in the sequence alignment; a colon symbol (;) means the residues in the sequence alignment have a high degree of conservation; a dot (.) means the residues have some degree of conservation; the absence of any symbol means no conservation is present between the aligned residues.

FIGS. 27(A) and 27(B) depict the alignment of mouse P8D10 variable domains with human immunoglobulin sequences. Specifically, FIG. 27(A) depicts the alignment of the P8D10 heavy chain variable domain with the three human immunoglobulin heavy chain variable domains from Ig, IgA and IgM (Genbank IDs: AAC18206.1, AAC09074.1, AAC51710.1, respectively, incorporated by reference herein as present in the database on Mar. 25, 2021). FIG. 27(B) depicts the alignment of the P8D10 light chain variable domain with three human immunoglobulin light chain (kappa) variable domains (Genbank IDs: CAD43020.1, BAH04731.1, QAV56209.1, incorporated by reference herein as present in the database on Mar. 25, 2021). The bold residues are predicted to be CDR residues and the underlined residues are framework residues within 5 Å of CDR regions that have potential to influence antigen-binding activity based on the P8D10 scFv structural model VH-VL depicted in FIG. 25. The italicized and shaded residues are residues in the framework region mutated back to mouse residues in order to maintain antigen-binding activity; in these sequence alignments, the underlined and mouse-specific residues in the P8D10 variable domain sequences (which are italicized and shaded), are the mouse residues in the framework regions having potential to influence antigen-binding activity. Therefore, the italicized and shaded mouse residues in the framework regions (white sticks in the black blocks in Step 3 of FIG. 24), besides the mouse residues in the CDR regions (narrow white blocks in the Step 3 of FIG. 24), are the only mouse residues retained in the humanized P8D10 scFv sequence in the framework region (mutated back to mouse residues), in order to maintain antigen-binding activity. The rest of the humanized P8D10 scFv sequence is from the three human immunoglobulin sequences. As depicted, an asterisk (*) means the residues are identical in the sequence alignment; a colon symbol (;) means the residues in the sequence alignment have a high degree of conservation: a dot (.) means the residues have some degree of conservation; the absence of any symbol means no conservation is present between the aligned residues.

FIG. 28(A)-28(E) depict humanized P8D10 sequences and constructs.

FIG. 28(A) depicts the humanized P8D10 scFv heavy chain sequence after incorporation of residues from human immunoglobulin sequences, mouse CDR (bold residues) and five mouse framework residues retained to maintain antigen-binding activity (italicized and shaded residues) (SEQ ID NO: 90). FIG. 28(B) depicts the humanized P8D10 scFv light chain sequence after incorporation of residues from human immunoglobulin sequences, mouse CDR (bold residues) and two mouse framework residues retained to maintain antigen-binding activity (italicized and shaded residues) (SEQ ID NO: 91). FIG. 28(C) depicts models of two constructs created using the sequences in FIG. 28(A) and FIG. 28(B), VH-linker-VL and VL-linker-VH orientation, respectively, that were created as explained in Example 13. FIG. 28(D) depicts the DNA (SEQ ID NO: 109) and amino acid (SEQ ID NO: 110) sequences of the created humanized P8D10 scFv VH-VL antibody. As depicted, the scFv antibody comprises a pelB leader sequence (shaded font) followed by a humanized P8D10 heavy chain variable domain and a humanized P8D10 mAb light chain variable domain (bold font) linked together using a 15-mer linker of $(GGGGS)_3$ (italics) (SEQ ID NO: 97). FIG. 28(E) depicts the DNA (SEQ ID NO: 111) and amino acid (SEQ ID NO: 112) sequences of the created humanized P8D10 scFv VL-VH antibody. As depicted, the scFv antibody comprises a pelB leader sequence (shaded font) followed by a humanized P8D10 light chain variable domain and a humanized P8D10 heavy chain variable domain (bold font) linked together using a 15-mer linker of $(GGGGS)_3$ (italics) (SEQ ID NO: 97).

FIG. 31 is a cartoon depicting the P8D10 mouse mAb, P8D10 mouse scFv, P8D10 humanized VH-VL scFv, and P8D10 humanized VL-VH scFv and indicates the minimum inhibitory concentrations (MIC) of each in an HAI assay as described in Example 14. As depicted, white blocks and sticks are mouse sequences, black blocks are human sequences.

FIG. 33(A) and FIG. 33(B) depict the heavy chain DNA (SEQ ID NO: 113) and amino acid (SEQ ID NO: 114) sequences, and light chain DNA (SEQ ID NO: 115) and amino acid (SEQ ID NO: 116) sequences, respectively, of a particular embodiment of a prophetic humanized antibody that may be created by fusion of humanized variable regions of P8D10 mAb with constant regions of human IgG1 heavy chain and human immunoglobulin kappa light chain as described in Example 12 and Example 15. As depicted in FIG. 33(A), the shaded sequences indicate the mAb P8D10 heavy chain signal sequence, the bold sequence is the humanized P8D10 heavy chain variable region, and the regular font represents the human IgG1 heavy chain constant region. As depicted in FIG. 33(B), the shaded sequences indicate the mAb P8D10 light chain signal sequence, the bold sequence is the humanized P8D10 light chain variable region, and the regular font represents the human immunoglobulin kappa light chain constant region.

DETAILED DESCRIPTION

Figure 1A:
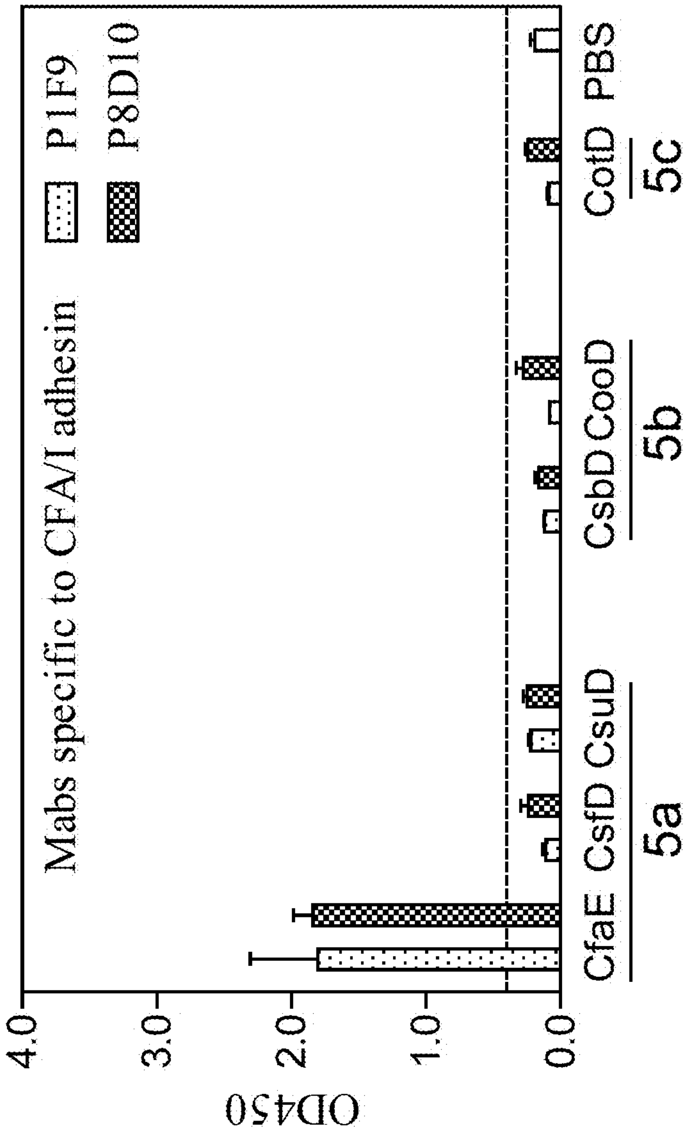
FIGS. 1(A)-1(E) depict anti-CfaE mAb cross-reactivity data revealed in ELISA assays by binding to a panel of class 5 adhesins. In these figures, mAbs with similar cross-reactivity are grouped together. Specifically.
Figure 1B:
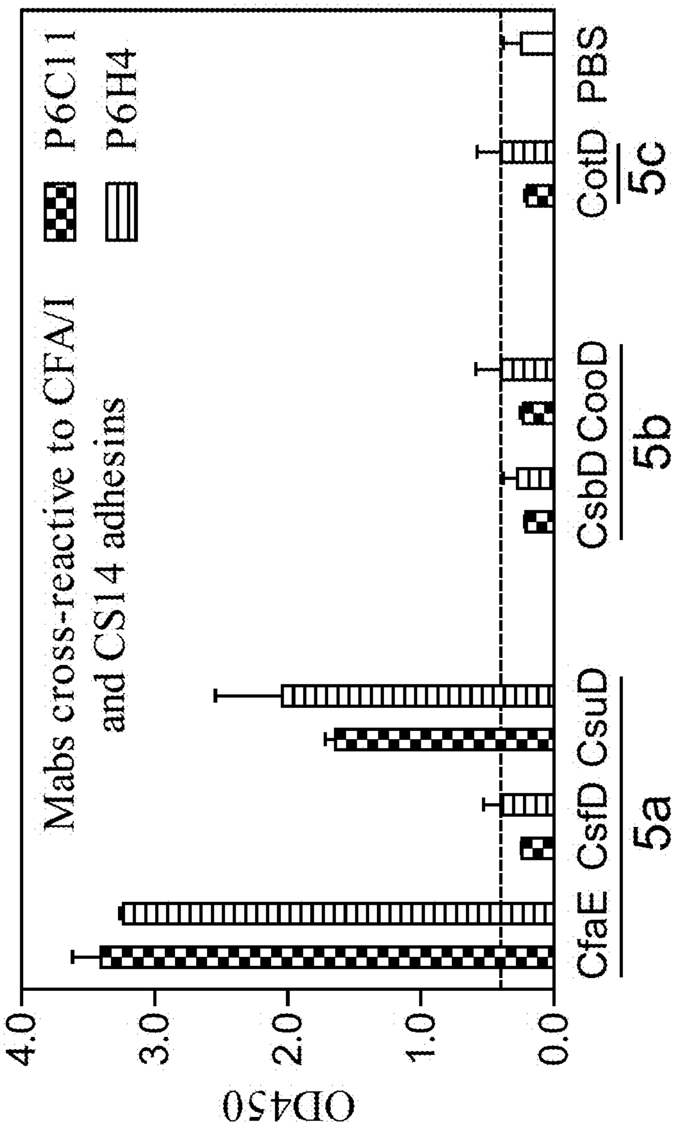
Figure 1C:
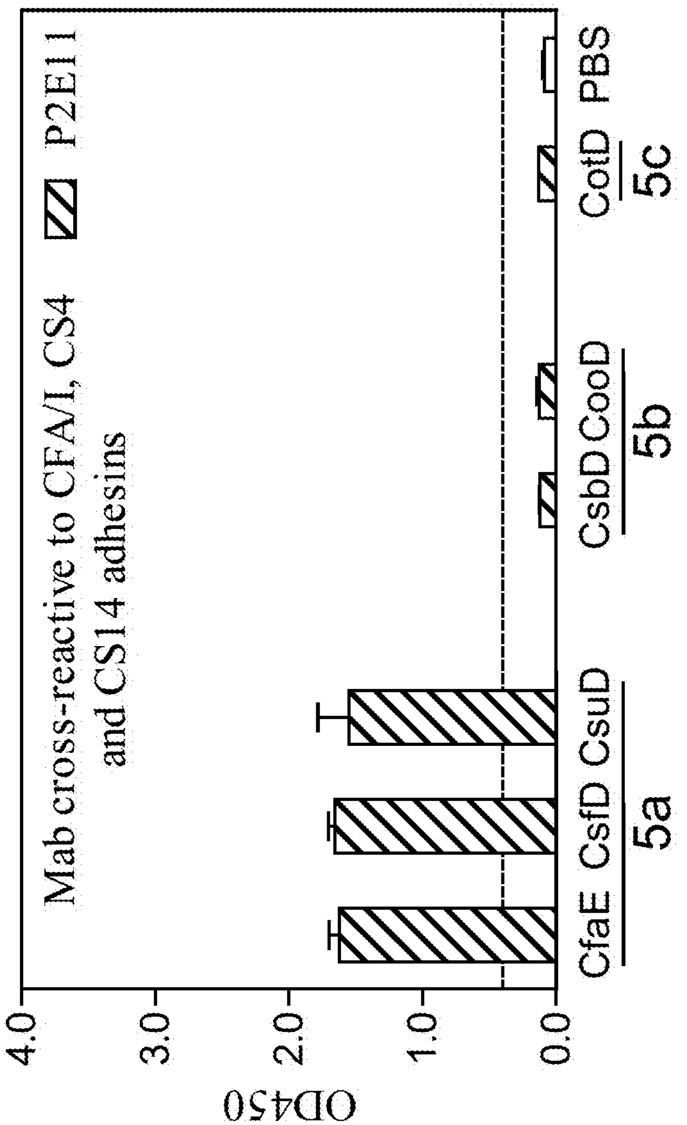
Figure 1D:
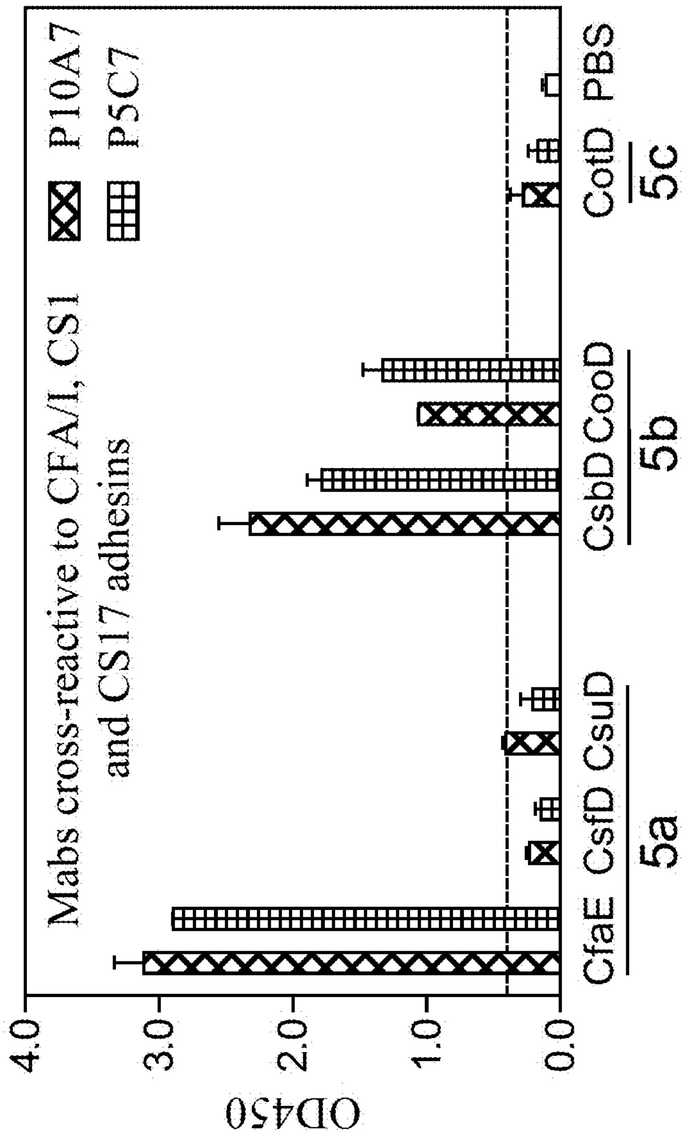
Figure 1E:
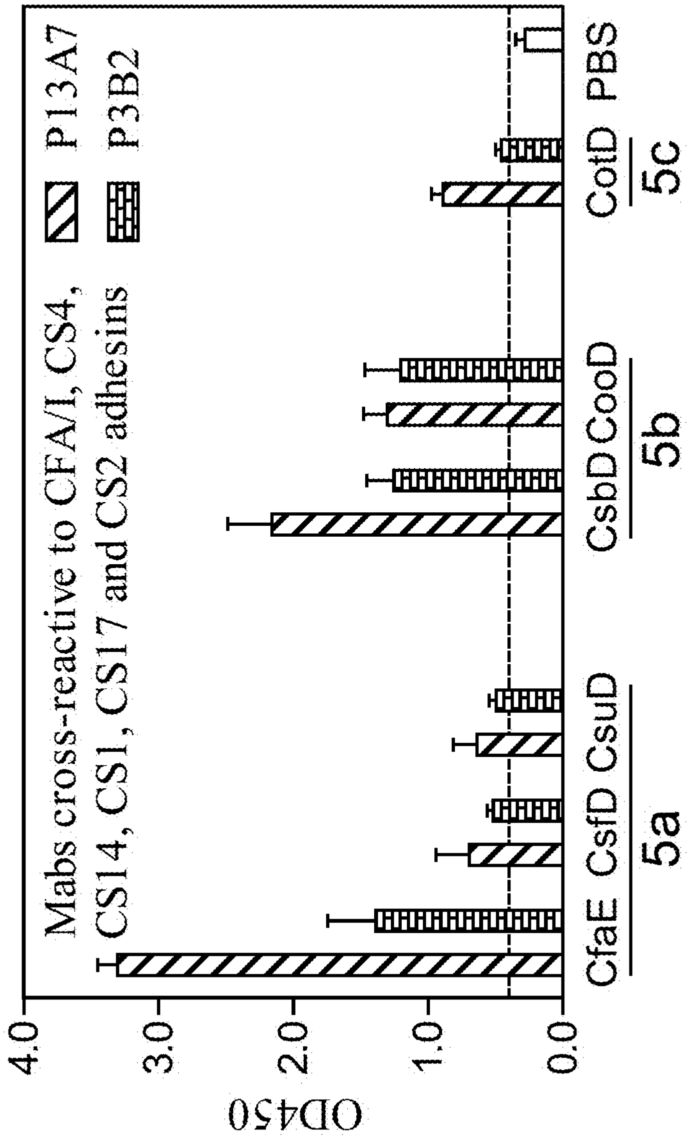
Figure 2A:
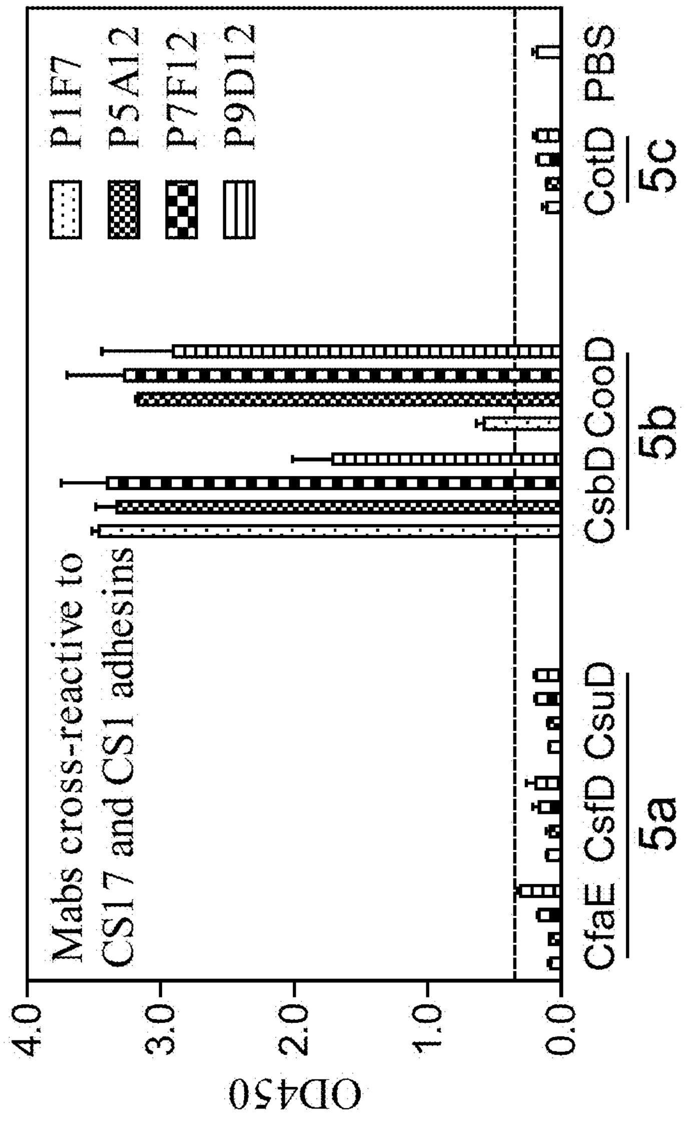
FIGS. 2(A)-2(D) depict anti-CsbD mAb cross-reactivity data revealed in ELISA assays by binding to a panel of class 5 adhesins. In these figures, mAbs with similar cross-reactivity are grouped together.
Figure 2B:
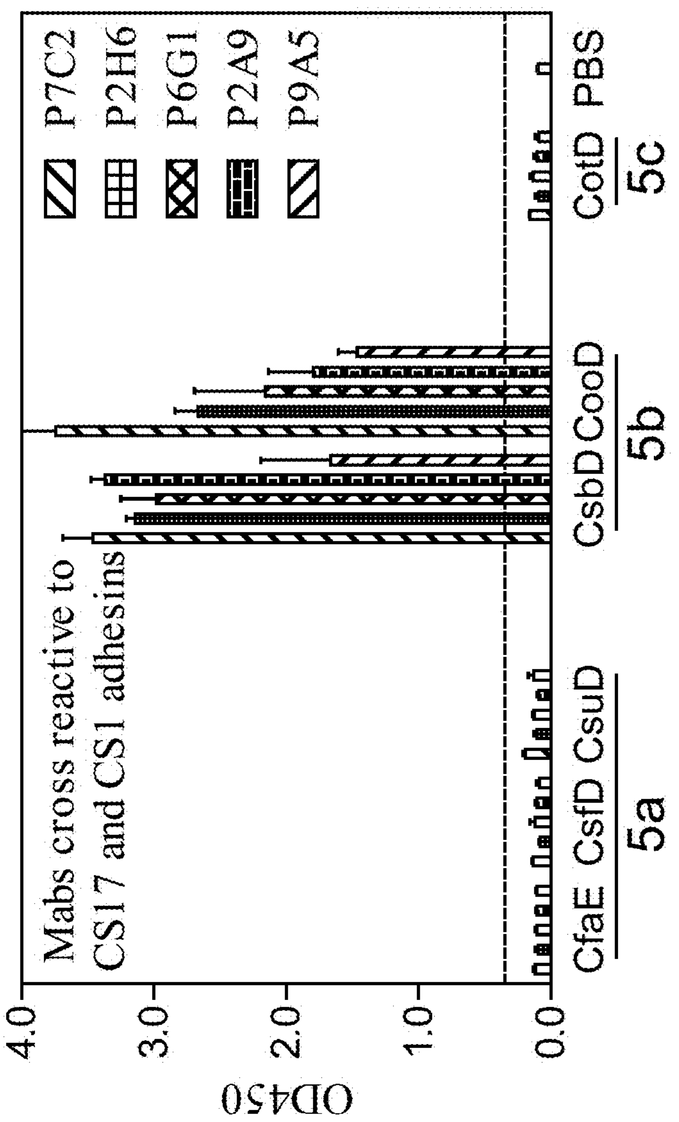
Figure 2C:
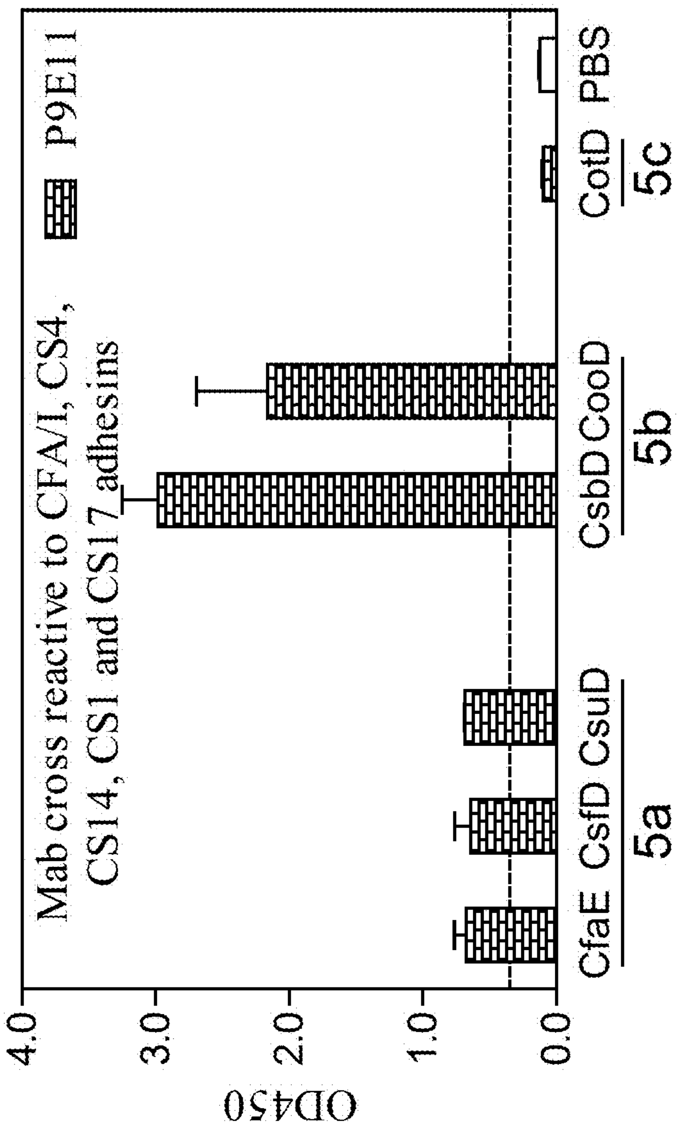
Figure 2D:
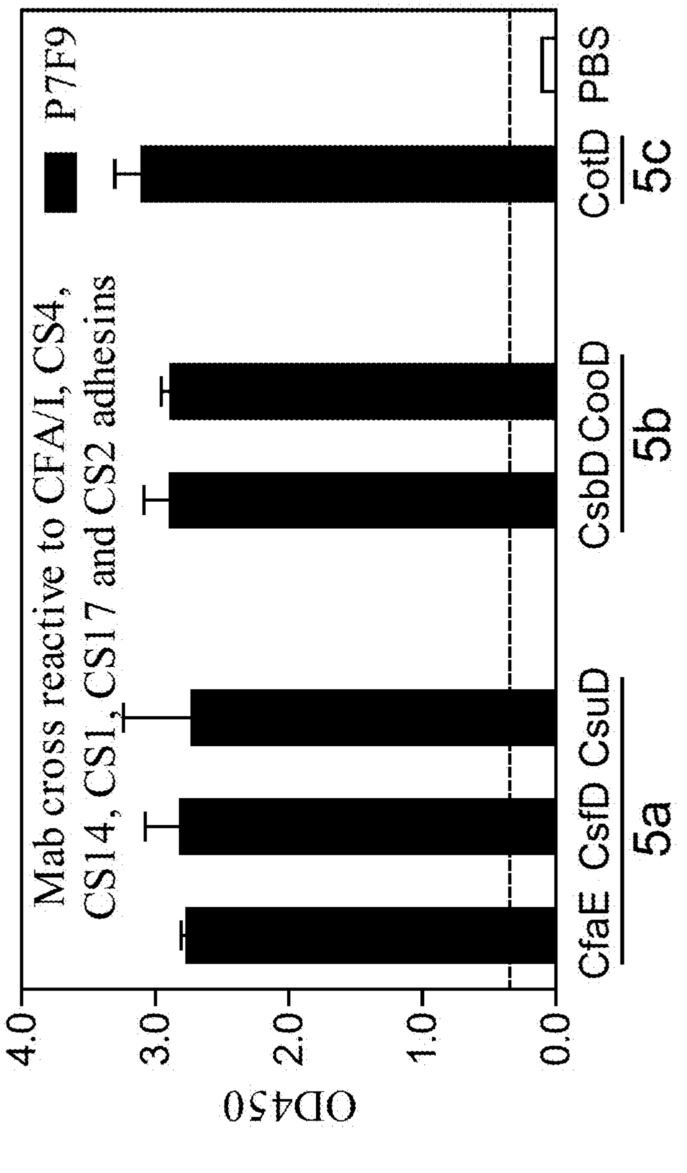
Figure 3A:
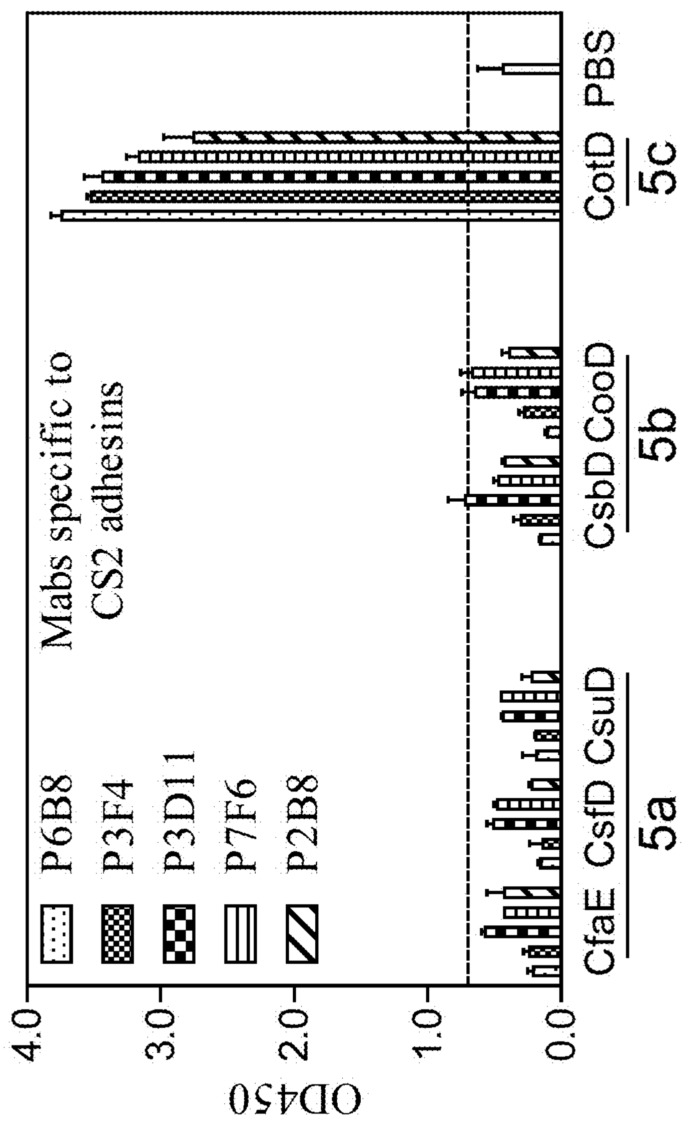
FIGS. 3(A)-3(D) depict anti-CotD mAb cross-reactivity revealed in ELISA assays by binding to a panel of class 5 adhesins. In these figures, mAbs with similar cross-reactivity are grouped together.
Figure 3B:
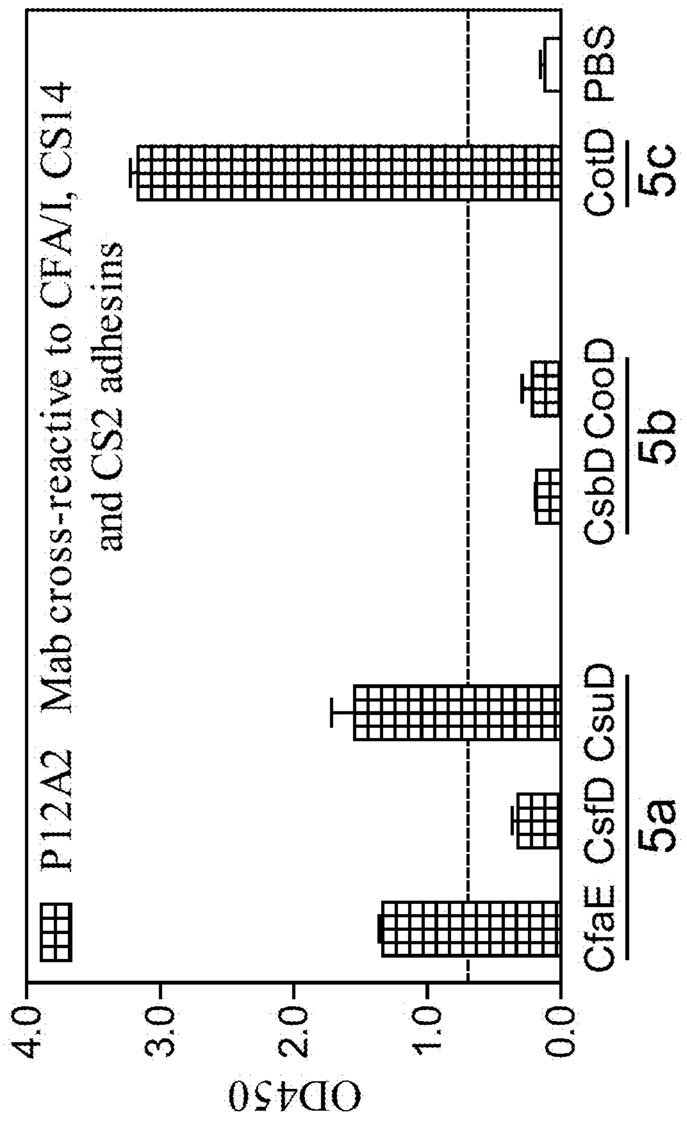
Figure 3C:
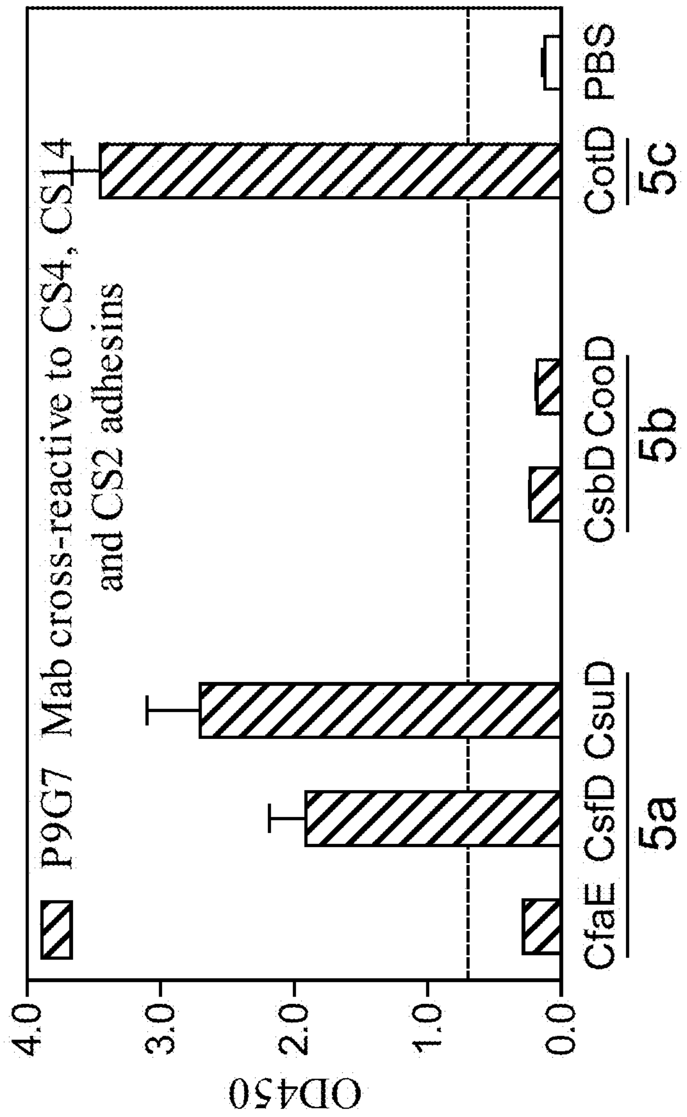
Figure 3D:
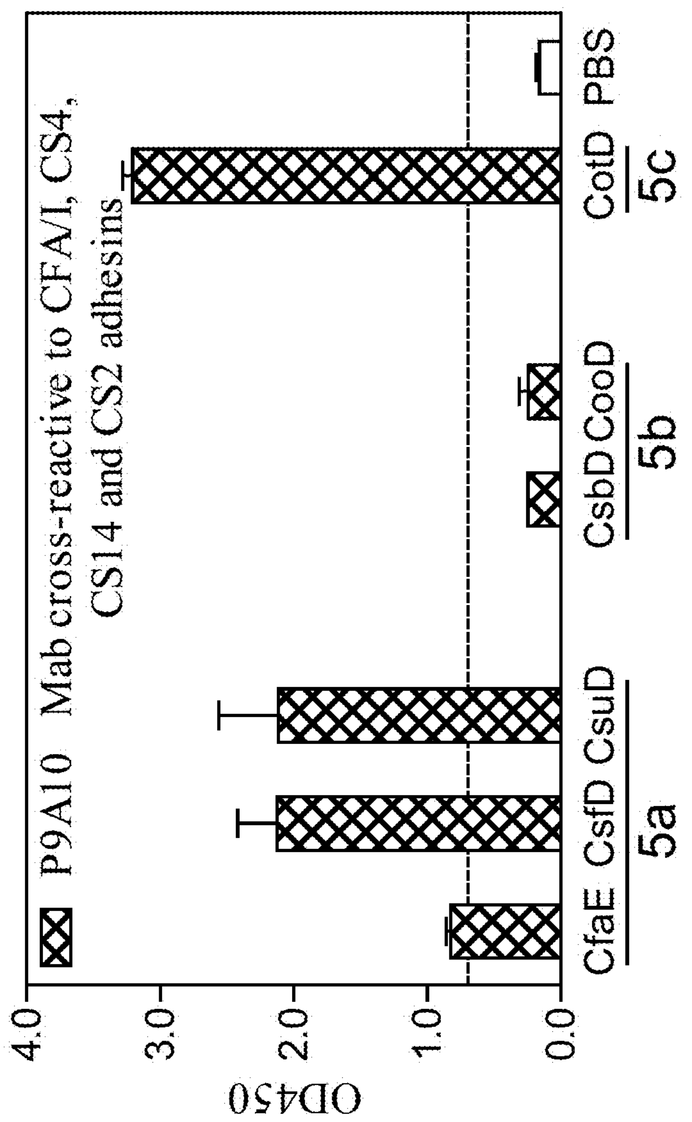

While the specification concludes with the claims particularly pointing out and distinctly claiming the invention, it is believed that the present invention will be better understood from the following description.

All percentages and ratios used herein are by weight of the total composition unless otherwise indicated herein. All temperatures are in degrees Celsius unless specified otherwise. All measurements made are at 25° C. and normal pressure unless otherwise designated. The present invention can "comprise" (open ended) or "consist essentially of" the components of the present invention as well as other ingredients or elements described herein. As used herein, "comprising" means the elements recited, or their equivalent in structure or function, plus any other element or elements which are not recited. The terms "having" and "including" are also to be construed as open ended unless the context suggests otherwise. As used herein, "consisting essentially of" means that the invention may include components in addition to those recited in the claim, but only if the additional components do not materially alter the basic and novel characteristics of the claimed invention.

All ranges recited herein include the endpoints, including those that recite a range "between" two values. Terms such as "about," "generally," "substantially," "approximately" and the like are to be construed as modifying a term or value such that it is not an absolute, but does not read on the prior art. Such terms will be defined by the circumstances and the terms that they modify as those terms are understood by those of skill in the art. This includes, at very least, the degree of expected experimental error, technique error and instrument error for a given technique used to measure a value. Unless otherwise indicated, as used herein, "a" and "an" include the plural, such that, e.g., "a pharmaceutically acceptable agent" can mean at least one pharmaceutically acceptable agent, as well as a plurality of pharmaceutically acceptable agents, i.e., more than one pharmaceutically acceptable agent.

Where used herein, the term "and/or" when used in a list of two or more items means that any one of the listed characteristics can be present, or any combination of two or more of the listed characteristics can be present. For example, if a composition of the instant invention is described as containing characteristics A, B, and/or C, the composition can contain A feature alone; B alone; C alone; A and B in combination; A and C in combination; B and C in combination; or A, B, and C in combination. The entire teachings of any patents, patent applications or other publications referred to herein are incorporated by reference herein as if fully set forth herein.

Therapeutics that can prevent or reduce the ability of ETEC to infect a subject are desired. Thus, in particular aspects, the present invention is directed to antigen binding proteins that bind to class 5 ETEC adhesins, methods of making and using these antigen binding proteins, and compositions comprising these antigen binding proteins, including, e.g., ETEC immunogenic compositions and vaccine formulations comprising these antigen binding proteins. Without intending to be limited to any particular mechanism of action, "preventing or reducing the ability of ETEC to infect a subject" includes the ability of a therapeutic of the instant invention to prevent or reduce the adherence of the ETEC bacteria to host intestinal cells by blocking the action of ETEC fimbrial tip adhesins, and thereby reduce or prevent infection and thus produce a therapeutic benefit to a subject. Specifically, provided herein are data regarding previously isolated mouse mAbs which bind to specific epitopes on ETEC adhesins (33, 34). Subsequent additional studies provided herein focus on additional epitope mapping and reanalysis of these murine mAbs. As explained below, these additional epitope studies reveal various errors and inaccuracies in previously reported data for these mAbs.

One of skill in the art will appreciate that, while useful for various purposes, murine mAbs such as those disclosed herein tend to be highly antigenic in humans. Thus, additional studies first described herein now provide the nucleic acid and amino acid sequence information for these previously reported murine mAbs. It is contemplated herein that the amino acid and nucleic acid sequence information of the variable regions of these mAbs, as well as additional data provided herein regarding cross-reactivity, epitopes, and potency of each murine mAb, may be employed by one of skill in the art using conventional methods to design anti-ETEC therapeutics including but not limited to, antigen binding proteins and compositions comprising these antigen binding proteins, as well as methods of protecting a subject in need thereof against ETEC infection comprising administration of these antigen binding proteins and compositions.

In particular, it is contemplated herein that the nucleic and amino acid sequences of the murine mAbs disclosed herein may be used to create antibodies with reduced antigenicity in human subjects, i.e., antibodies in which immunogenic murine regions have been replaced with non-immunogenic human regions. Specifically, it is contemplated herein that one of skill in the art may use conventional recombinant techniques to design chimeric, humanized, or human antibodies which comprise the antigen binding sequence specificity of the variable regions of the disclosed murine mAbs, or functional variants thereof, and thus create therapeutically effective anti-ETEC antigen binding proteins which present reduced antigenicity when presented to the human immune system. Also contemplated are recombinant nucleic acids encoding these antigen binding proteins as well as vectors and host cells related thereto. Conventional methods for creating these antigen binding proteins and other recombinant materials of the instant invention are discussed below and include, e.g., methods disclosed in Carter P et al., Proc Natl Acad Sci USA. 1992 May 15; 89(10):4285-9; Almagro, J and Fransson, J. Front Biosci. 2008 Jan. 1; 13: 1619-33; Wu H et al, J Mol Biol. 1999 Nov. 19; 294(1):151-62; Morrison, S L et al PNAS USA 1984 November, 81 (21): 6851-5; and Boulianne G L et al., Nature 1984 Dec. 13-19; 312(5995):643-6.

As used herein, the term "antigen binding protein" means any protein that binds to a specified target antigen The term "antigen binding protein" includes but is not limited to antibodies and binding parts thereof, such as immunologically functional fragments, or derivatives thereof.

It is contemplated herein that the antigen binding proteins and Mabs of the instant invention may be isolated antigen binding proteins and isolated Mabs. One of skill in the art will appreciate that an "isolated" antigen binding protein or an "isolated" Mab is one that has been separated and/or recovered from a component of its natural environment. Contaminant components of its natural environment are materials that would interfere with diagnostic or therapeutic uses of the antigen binding proteins and Mabs and may include enzymes, hormones, and other proteinaceous or non-proteinaceous components. Purified forms are contemplated herein, i.e., the isolated antigen binding protein is at least 60% free, preferably at least 75% free, and most preferably at least 90% free from other components with which they are naturally associated. One of skill in the art will appreciate that antigen binding proteins and other polypeptides that are produced outside the organism in which they naturally occur, e.g., through chemical or recombinant means, are considered to be isolated and purified by definition, since they were never present in a natural environment.

In the instant application, the specified "target antigen" is an ETEC adhesin protein or fragment thereof, particularly the class 5 ETEC adhesins listed in Table 1: CfaE, CsfD, CsuD, CooD, CsbD, CsdD, CosD, and CotD. As described herein, because of their demonstrated increased stability, "target antigens" of the instant invention include recombinant "donor strand complemented" antigens based on the adhesins of Table 1, and are discussed in detail below.

One of skill in the art will appreciate that an antibody molecule of the IgG type comprises two light chains and two heavy chains linked via disulfide bonds. Both the light chain and the heavy chain contains a domain of relatively variable amino acid sequences, known as the variable region, which in turn contains hypervariable regions, also known as complementarity-determining regions (CDRs), that are interspersed among relatively conserved framework regions (FRs). Thus, as used herein, the term "variable region" refers to the antigen-binding site or paratope of an antibody which comprises a set of CDRs. Together, the CDR and FR determine the three-dimensional structure of the IgG binding site and thus, the antigen specificity of the antibody.

The complete IgG molecule also contains a domain of relatively conserved amino acid sequences, called the "constant region" consisting of three constant domains (CH1, CH2, and CH3). The IgG molecule is often referred to in terms of its functional fragments. Cleavage of an IgG with the protease papain produces two identical antigen-binding fragments (Fab) and an "Fc" fragment conferring the biological activity of the antibody, such as binding to the first component of the complement cascade or binding to Fc-receptor bearing cells, such as phagocytes, mast cells, neutrophils and natural killer cells. The Fc fragment comprises the heavy constant regions CH2 and CH3, and the Fab fragment comprises the heavy (CH1) and light (CL) constant regions and the variable regions of the heavy (VH) and light (VL) chains. The terms "Fab", "Fab-fragment" and "Fab-region" are used interchangeably herein.

The term "epitope" used herein refers to the part of a protein antigen recognized by the immune system and to which the variable region of an antibody binds.

The term "antibody" as used herein refers to molecules with an immunoglobulin-like domain and includes monoclonal antibodies (for example IgG, IgM, IgA, IgD or IgE.) As understood by one of skill in the art, a monoclonal antibody refers to an antibody secreted by a single antibody-producing cell (clone). As discussed above, the secreted antibody usually contains heavy and light chains, and the variable regions of antibody have the antigen binding property. The terms "mAbs", "Mabs" and like terms are familiar to one of skill in the art and are used interchangeably herein to refer to monoclonal antibodies.

Antigen binding proteins of the instant invention also include various fragments or engineered peptides that may be created by one of skill in the art using conventional methods Such fragments and engineered peptides include, e.g.: a single variable domain (e.g., VH, VHH, VL), a domain antibody (dAb®), antigen binding fragments, immunologically effective fragments, Fab, F(ab')2, variable fragment (Fv), disulphide linked Fv, single chain Fv or single chain variable fragment (scFv), closed conformation multispecific antibodies, disulphide-linked scFv, diabodies, TANDABS™, etc. and modified versions of any of the foregoing familiar to one of skill in the art. Alternative antibody formats include, e.g., alternative scaffolds in which the one or more CDRs of any molecules in accordance with the disclosure can be arranged onto a suitable non-immunoglobulin protein scaffold or skeleton, such as an affibody, a SpA scaffold, an LDL receptor class A domain, an avimer, or an EGF-like domain. See, e.g., Yu et al. Annu Rev Anal Chem (Palo Alto Calif) 2017 Jun. 12; 10(1):293-320.

In addition, protein engineering can be used by one of skill in the art to recombinantly generate variable regions, or graft or conjugate variable region sequences on a multi-domain and multi-function protein. Such proteins can have specific antigen binding properties, but are not typically referred to as monoclonal antibodies per-se. Protein engineering can also be used by one of skill in the art to produce recombinant, polyclonal, bispecific, bivalent, multivalent and heteroconjugate antibodies.

Figure 21:
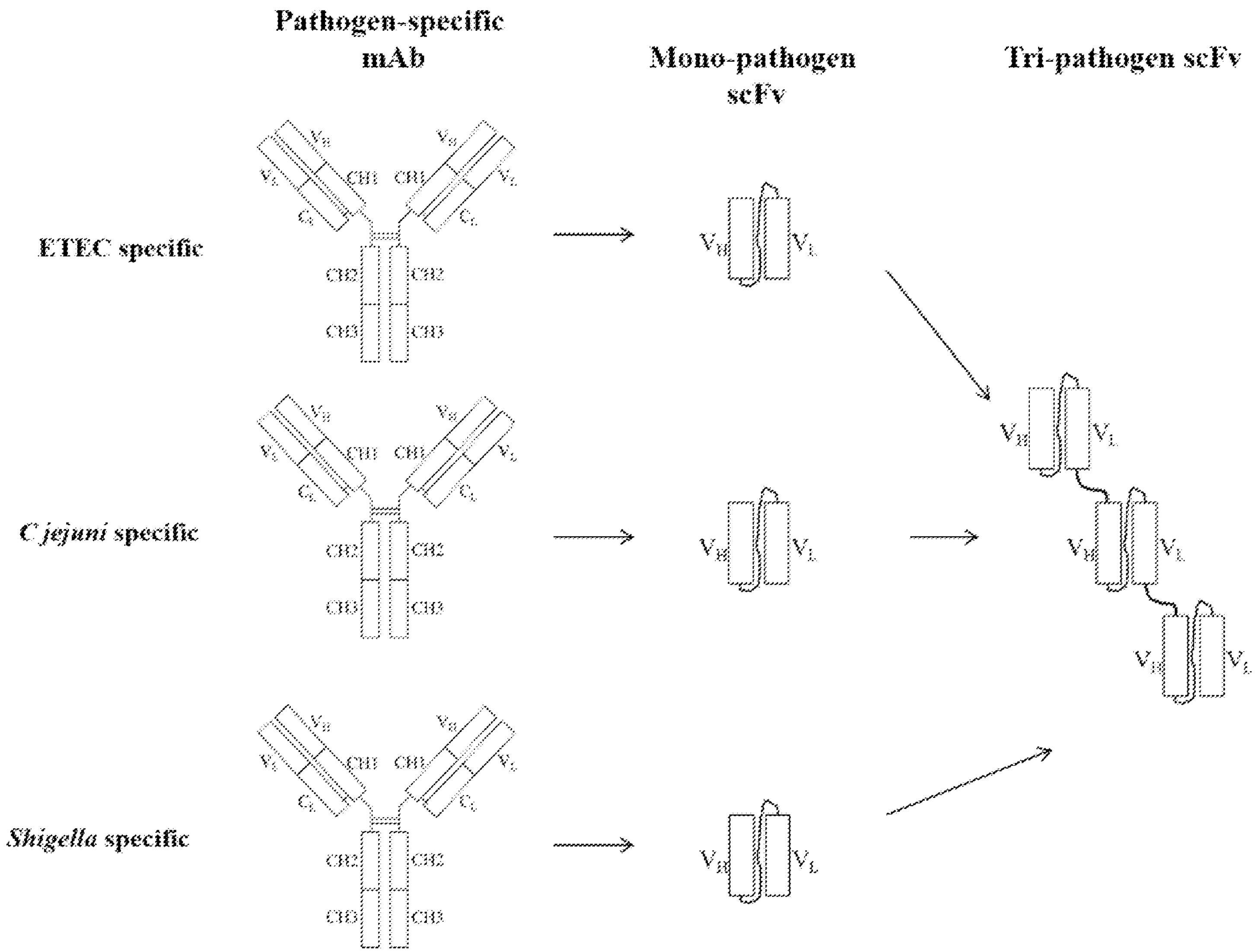
FIG. 21 is a cartoon depicting the potential application of scFvs against an enteric pathogen by linking or engineering individual scFvs. Specifically depicted is a general scheme for creating a tri-pathogen specific scFv using mono-pathogen scFvs created from pathogen-specific mAbs. As specifically depicted, the tri-pathogen scFv is directed against three different enteric pathogens, ETEC, *C. jejuni* and *Shigella.*
Figure 22:
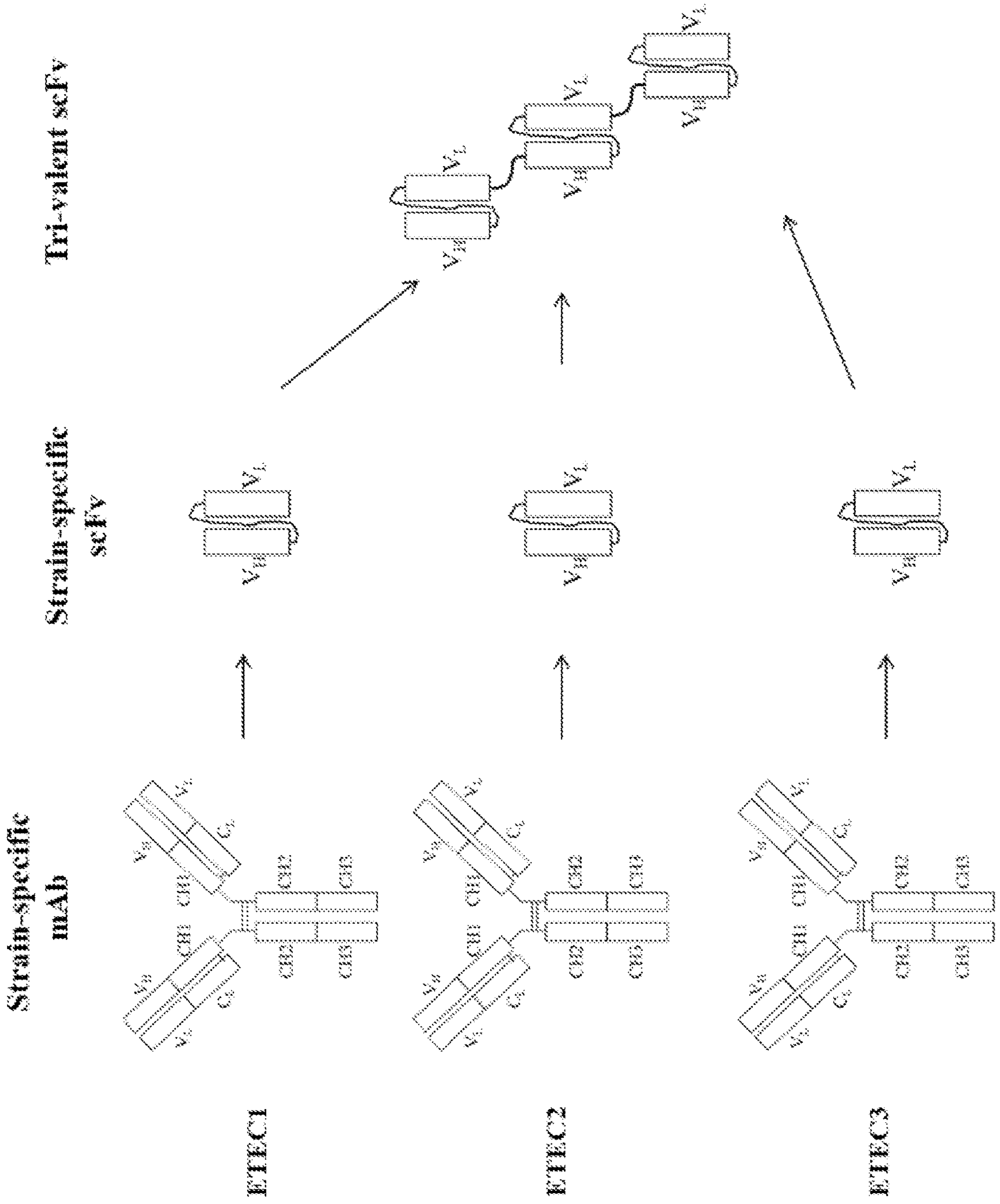
FIG. 22 is a cartoon depicting the potential application of scFv against enteric pathogen by linking or engineering individual scFvs. Specifically depicted is a general scheme for creating a tri-valent scFv using strain-specific scFvs created from strain-specific mAbs. As specifically depicted, the tri-valent scFv would be directed against three different (hypothetical) strains of ETEC.

Similarly, conventional methods and reagents may also be used by one of skill in the art to engineer and express scFv antibodies of the instant invention. As appreciated by one of skil in the art, a scFv antibody consists of variable regions of heavy (VH) and light (VL) chains, which are typically joined together by a flexible peptide linker. See, e.g., Ahnad et al., Clinical and Developmental Immunology, Vol. 2012, Article ID 980250, 15 pages, doi:10.1155/2012/980250. In particular embodiments, and as evidenced in the below examples, it is contemplated herein that scFv antibodies of the instant invention comprise the variable regions of the heavy and light chains of a murine mAbs disclosed herein, or functional fragments thereof, joined by a flexible peptide linker. It is contemplated herein that mono-pathogen scFv antibodies as well as multiple-pathogen scFv antibodies may be created, depending on the choice and number of mAbs selected for creating a scFv. See, e.g., FIG. 21. Monovalent as well as multi-valent scFvs against different strains of a pathogen may also be created, e.g., by employing one or more strain-specific mAbs such as depicted in FIG. 22 herein.

While it is contemplated herein that native proteins may be used as target antigens or immunogens to create antibodies of the instant invention, the studies described in the examples provided herein employed stabilized ETEC adhesins created using recombinant techniques incorporating "donor strand complementation" (dsc). See, e.g., methods provided in U.S. Pat. No. 9,328,150 and Poole et al., Mol. Microbiol. 63, 1372-1384 (2007). According to such experimental protocols, a recombinant ETEC adhesin polypeptide construct may be created by connecting major or minor subunits derived from the same ETEC fimbrial type using polypeptide linkers, and this structure may be stabilized by linking the C-terminal most ETEC major subunit to a donor strand region from an ETEC major subunit, which can be either homologous or heterologous to the C-terminal major subunit. Thus, an immunogenic composition can comprise a whole or an immunogenic fragment containing a donor P strand region of the ETEC fimbrial major or minor subunits.

In some construct examples, in order to avoid inadvertent association of subunits, major ETEC fimbrial subunits can contain an N-terminal deletion of 14 to 19 amino acids (indicated by subscript.) Deletion of amino acid sequence length not involved in folding also reduces the likelihood of proteolytic degradation. Thus, for example, "dsc$_{19}$CotD6xhis" refers to a recombinant donor strand complemented CotD ETEC adhesin antigen which comprises a 6 histidine residue C-terminal tag and an N-terminal deletion of 19 amino acids. Typically, the murine mAbs created using the recombinant antigens described herein do not include any epitopes containing residues from the donor strand.

One of skill in the art will appreciate that the prefix "dsc" may be used herein to distinguish recombinant antigen constructs of the instant invention from native antigens, e.g., "dscCfaE" and "CfaE", respectively. Either may be used to create an antigen binding protein, for example an antibody of the instant invention. Unless otherwise indicated herein, however, for notational simplicity, the mAbs generated against the recombinant antigen constructs of the instant invention are referred to herein in an abbreviated fashion. For example, a mAb against "dsc$_{19}$CfaE6xhis" disclosed in FIG. 12(A) is often simply referred to in the examples and data provided herein as an "anti-CfaE mAb."

It is contemplated herein that the terms "antigen binding protein", "antibody" and like terms used herein also include immunologically functional fragments thereof. Unless otherwise indicated, the terms "immunologically ftmctional fragment". "immunologically active fragment", "antibody fragment", "fragment" or like terms may be used interchangeably herein and refer to a portion of an antigen binding protein of the instant invention which comprises an amino acid sequence sufficient to specifically bind a target antigen and produce a desired effect, e.g., block or reduce the likelihood of ETEC infection to produce a therapeutic effect in a subject, and/or detect a target ETEC antigen.

As understood herein, a "derivative" of an antigen binding protein of the instant invention includes, but is not limited to, an antigen binding protein of the instant invention which has been chemically or otherwise modified using conventional methods to include a tag or other feature for a desired purpose, e.g., in order to facilitate the detection of the antigen binding protein. In another embodiment, a derivative may comprise an antigen binding protein modified to comprise one or more additional therapeutic agents. One of skill in the art is familiar with such agents and methods of creating derivatives comprising such agents. Agents which may be used with the antigen binding proteins of the instant invention include but are not limited to antibiotic agents, artificial substances such as polymers or acetates, or other biological agents such as phosphates, lipids or carbohydrates.

Figure 20:
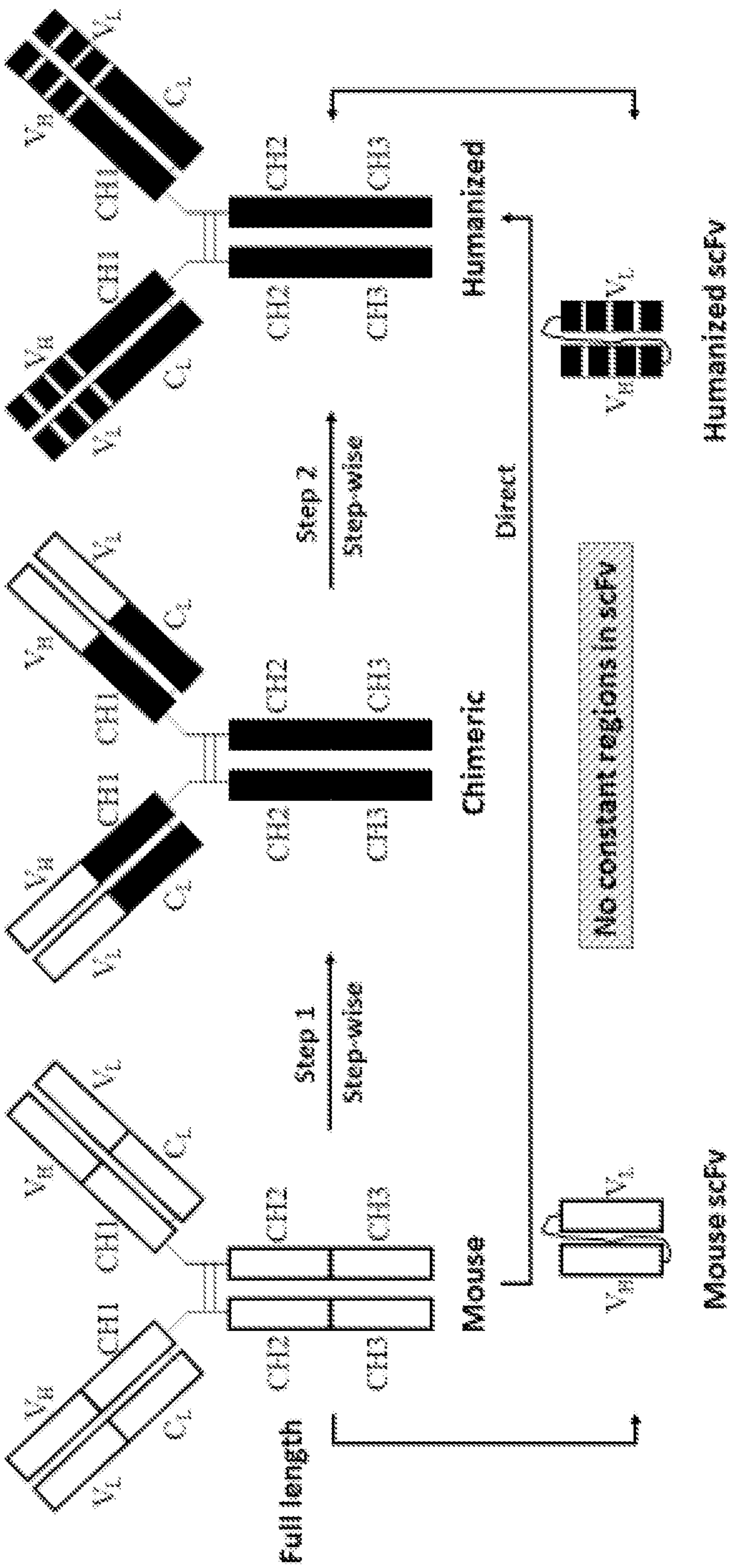
FIG. 20 is a cartoon depicting a general scheme for the step-wise humanization of a full-length mouse mAb (top series) and of a mouse scFv (bottom series). As depicted in the top series of images, Step 1 is the creation of a chimeric mAb from a mouse mAb by modifying the mouse sequences of the constant region of the mouse mAb (white blocks) to include human sequence (black blocks). Step 2 depicts the creation of the humanized mAb from the chimeric mAb by modifying the variable regions to include human sequences. In contrast, as depicted in the bottom images, the humanization of a mouse scFv does not need to include the creation of a chimeric scFv since modification of constant regions are not necessary.

In particular embodiments, the antigen binding protein of the instant invention is a chimeric antibody. Thus, in various embodiments, one of skill in the art may design one or more nucleotide sequences encoding, and amino acid sequences comprising, heavy and light chain immunoglobulin molecules, particularly sequences corresponding to the variable regions of the murine mAbs disclosed herein. In certain embodiments, sequences corresponding to CDRs are also provided. In a particular embodiment, a chimeric antibody of the instant invention includes antibodies which comprise the Fab fragment of a murine antibody disclosed herein which comprises the CDRs fused to the constant framework region of a human antibody. In particular embodiments, the antigen binding protein of the instant invention is a chimeric antibody comprising a human IgG or IgM constant region fused to mouse variable regions of an anti-ETEC monoclonal antibody disclosed herein. See e.g., FIG. 20.

In a particular prophetic embodiment, a mouse-human chimeric antibody comprising mouse variable regions of P6B8 mAb fused with constant regions of human IgG1 heavy chain and human immunoglobulin kappa light chain is contemplated herein as provided below in Example 12 and depicted in FIGS. 16(A) and 16(B). In another particular prophetic embodiment, a mouse-human chimeric monoclonal antibody comprising mouse variable regions of P5C7 mAb fused with constant regions of human IgG1 heavy chain and human immunoglobulin kappa light chain is contemplated herein and is provided below in Example 12 and depicted in FIGS. 18(A) and 18(B).

The instant invention also includes humanized antibodies based on the murine mAbs disclosed herein. A "humanized antibody" is a chimeric antibody in which a larger part of the protein is derived from human sequences. Commonly, humanized antibodies consist of 5-10% sequences derived from non-human antibodies and 90-95% sequences derived from human antibodies. Thus, in particular embodiments, it is contemplated herein that a humanized antibody of the instant invention may comprise 90-95% sequences derived from human antibodies and 5-10% sequences derived from the murine antibodies disclosed herein. In another embodiment, a humanized antibody of the instant invention may comprise the CDRs of a murine mAb disclosed herein in combination with the conserved framework region of a human antibody. In a particular embodiment, the antigen binding protein is a humanized antibody comprising a human IgG or IgM constant region fused to a humanized mouse variable regions of an anti-ETEC monoclonal antibody such as a murine mAb disclosed herein. See e.g., FIG. 20. In a particular prophetic embodiment contemplated herein, a humanized antibody may be created by fusion of humanized variable regions of P8D10 mAb with constant regions of human IgG1 heavy chain and human immunoglobulin kappa light chain and is provided below in Example 15 and depicted in FIGS. 33(A) and 33(B).

It is understood herein that one of skill in the art may create chimeric and humanized antibodies using conventional methods and materials, including employing techniques for substituting amino acids, e.g., from a murine framework that provides antigen binding specificity, in order to increase the antigen binding specificity of an antigen binding protein of the instant invention. It is also understood that the antigen binding specificity of an antigen binding protein of the instant invention can be enhanced by substituting amino acids in variable regions of an anti-ETEC antibody using conventional methods and materials, including employing amino acid substitution techniques. In order to ensure that the binding specificity is maintained, in some embodiments certain human amino acid residues may be replaced with corresponding amino acids from the equivalent murine sequences. Thus, it is contemplated herein that in some instances, murine framework residues may be included in the human framework to increase antigen binding activity.

It is understood herein that the human IgG heavy and light constant domains may be derived from any one of IgG1, IgG2, IgG3, and IgG4 subclasses of human IgG antibodies, and it may comprise one, two, or three intact or truncated constant domains (CH1-3), which may optionally be mutated to alter effector function or provide for heteromultimer formation, or modified post-translationally (e.g. glycosylation) to improve the half-life of the antibody. In certain embodiments the IgG constant region is a human IgG1 constant region.

It is also contemplated herein that human antibodies based on the nucleic acid and amino acid sequence information of the disclosed murine mAbs may be created by one of skill in the art using conventional methods. For example, mice may be used to manufacture mAbs containing human Ig fragments according to conventional methods. Techniques for creating such antibodies are found, e.g., in Carter P et al., Proc Natl Acad Sci USA. 1992 May 15; 89(10):4285-9; Almagro, J and Fransson, J. Front Biosci. 2008 Jan. 1; 13: 1619-33; and Wu H et al, J Mol Biol. 1999 Nov. 19; 294(1):151-62. Thus, in various embodiments, antigen binding proteins of the instant invention include human antibodies created based on a murine Mab of the instant invention and comprising a human IgG constant region fused to human variable regions of a monoclonal antibody that specifically binds to an ETEC adhesin protein.

While one of skill in the art will appreciate that human antibodies can be generated by immunization of a humanized mouse with ETEC antigens, or sequencing human B cells, it is also contemplated herein that human antibodies of the instant invention can be achieved by replacing amino acids in murine antibodies to make fully human antibodies; e.g., by substituting amino acids in variable regions of an anti-ETEC murine mAb using conventional methods and materials, including employing amino acid substitution techniques.

In addition, it is also contemplated herein that an antigen binding protein of the instant invention may be designed which displays cross reactivity to more than one ETEC adhesin. For example, one of skill in the art will appreciate that antibody fragments, including but not limited to Fab, Fv, and scFvs, can be designed from any murine mAb disclosed herein which retain the potency to reduce ETEC binding and/or infection. As discussed above, it is also understood that the cross reactivity of an antigen binding protein of the instant invention can be enhanced by substituting amino acids in variable regions of an anti-ETEC antibody using conventional methods and materials, including employing amino acid substitution techniques. Specifically, as discussed above, it is also contemplated herein that combinations of two or more of such antibody fragments can be engineered to create a single protein molecule which contains dual specificity (bispecific) or multiple specificity for ETEC adhesins. Such dual-specific or heterodimeric antigen binding protein may be achieved using conventional methods to engineer a single antibody molecule which comprises variable regions derived from more than one murine mAbs disclosed herein including, e.g., P8D10, P6B8, P10A7, P5C7, P2H6 and P7F9. Similarly, bivalent or multivalent antibodies having the same affinity may be created. See, e.g., methods disclosed in Huston J S et al. Methods Enzymol. 1991; 203: 46-88; and Holliger P et al., Proc Natl Acad Sci USA. 1993 Jul. 15; 90(14):6444-8. See, e.g., FIGS. 21 and 22 herein.

Figures 4A, 4B, 4C:
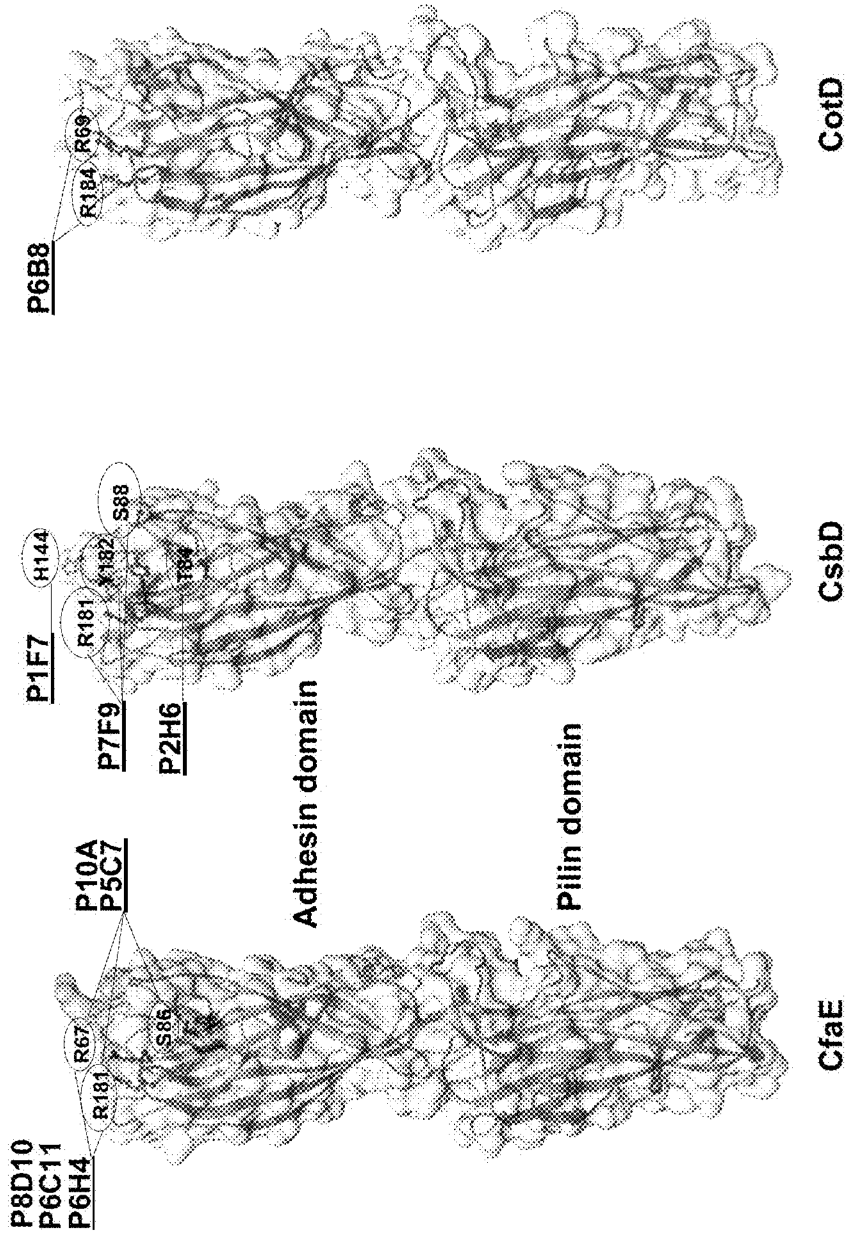
FIGS. 4(A)-4(C) depict the spatial locations of epitope residues recognized by nine anti-adhesin mAbs. Specifically.
Figure 5A:
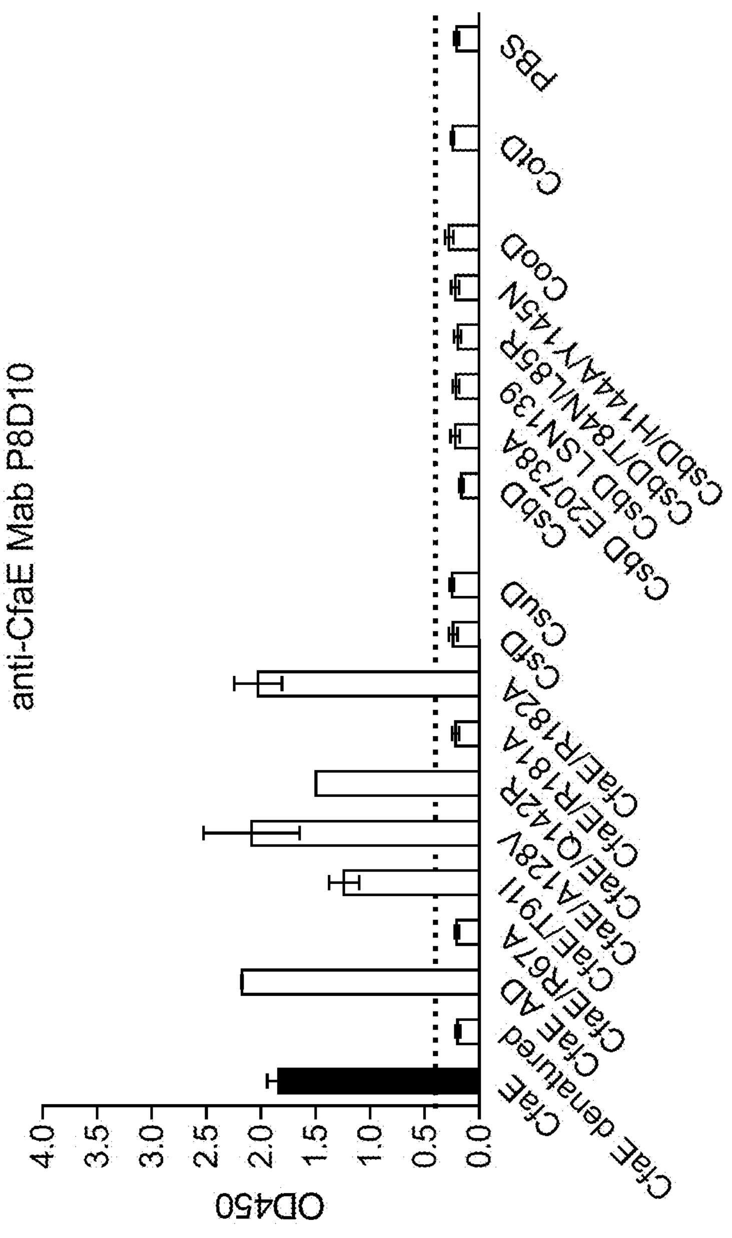
FIGS. 5(A)-5(I) depict data from anti-CfaE Mab ELISA assays performed to evaluate responses to various class 5 ETEC fimbrial adhesin variants (x axis). The responses to the immunogen CfaE are highlighted in black bars. The dashed lines represent the limit of detection in the anti-CfaE Mab ELISA assays, which equals the sum of average background of PBS buffer and three times of the standard deviation. Specifically.
Figure 5B:
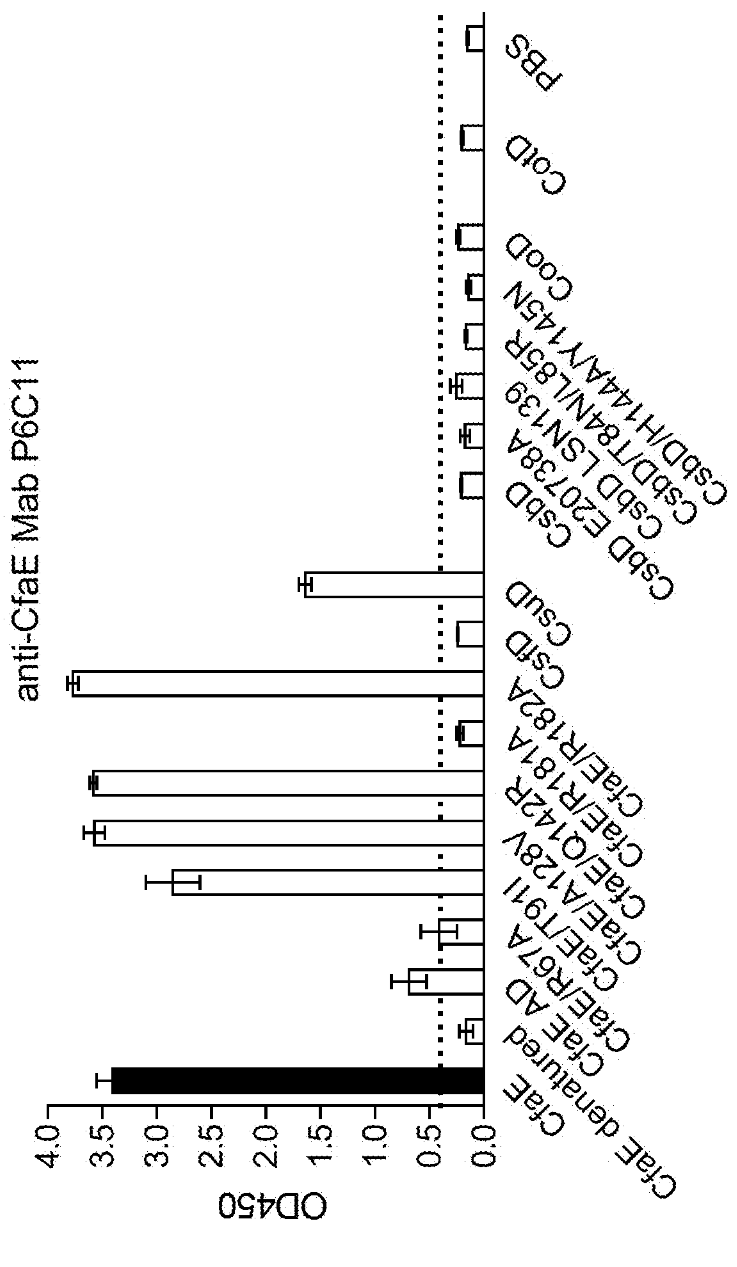
Figure 5C:
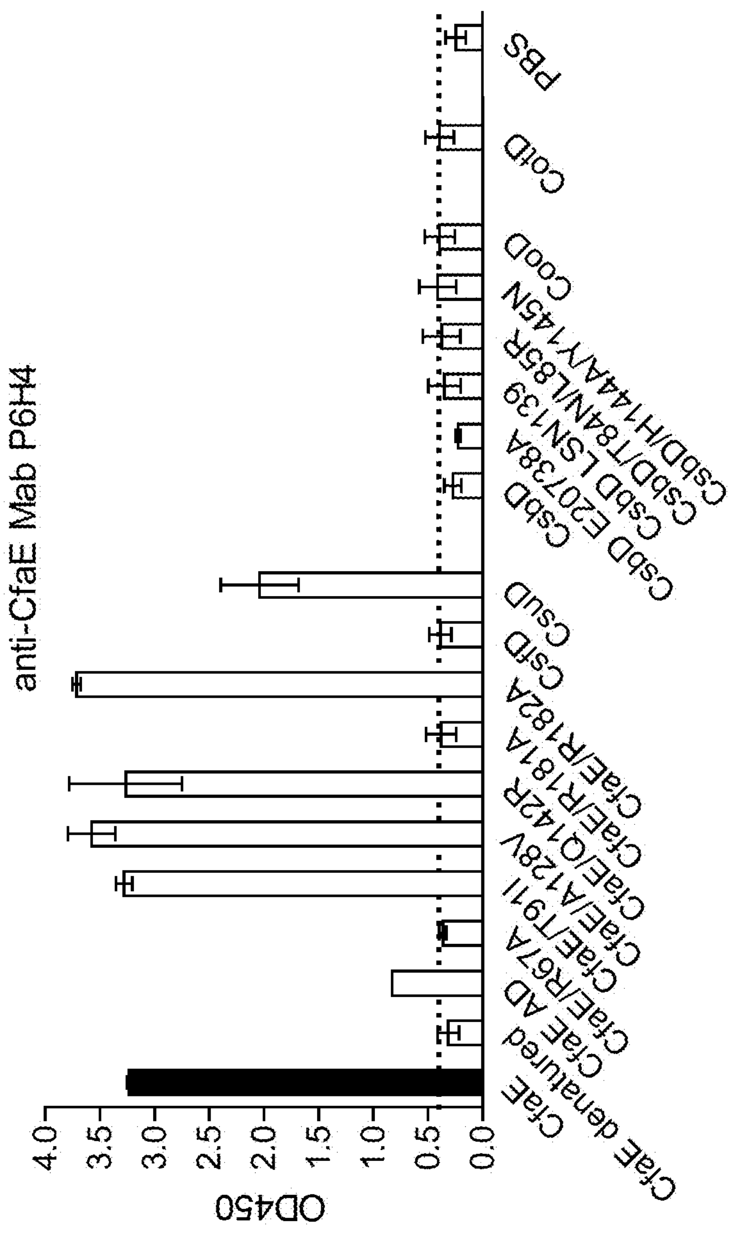
Figure 5D:
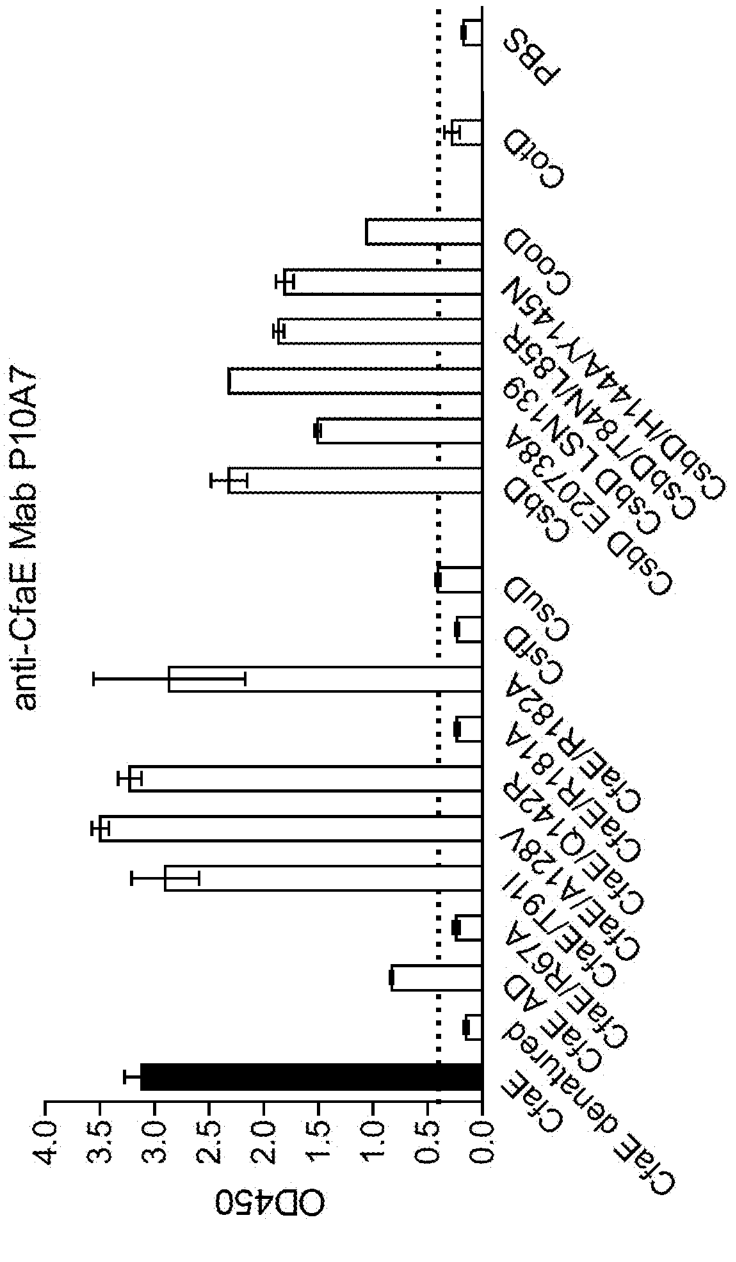
Figure 5E:
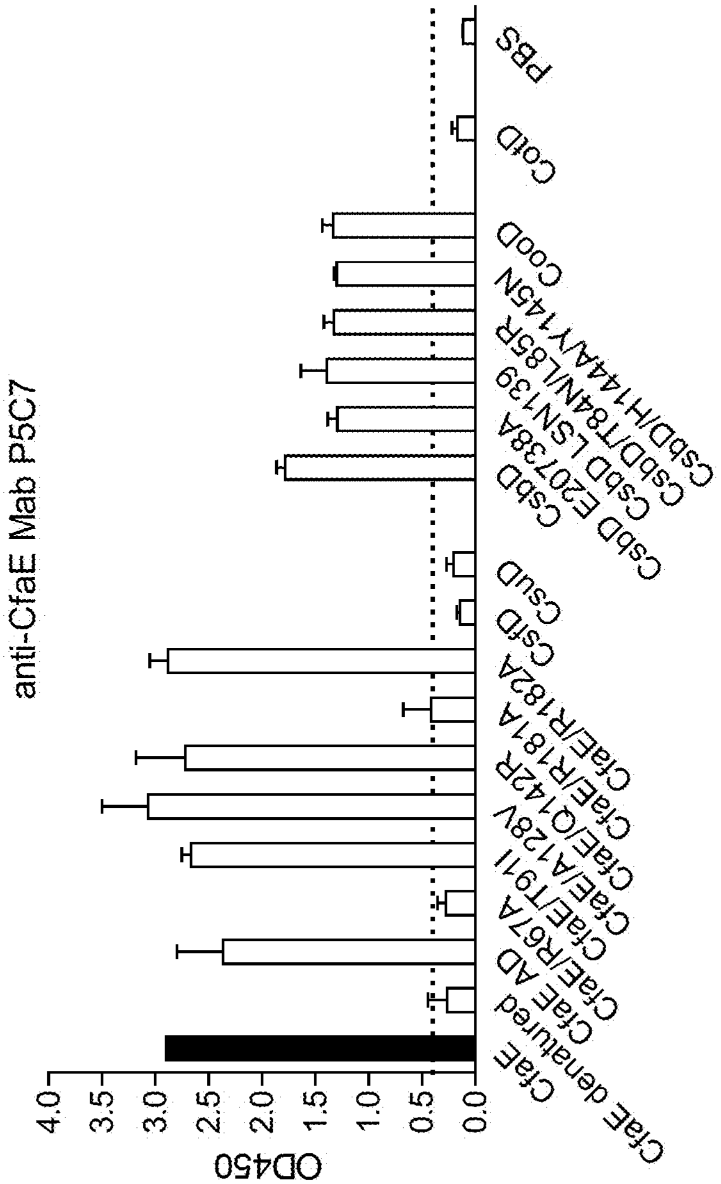
Figure 5F:
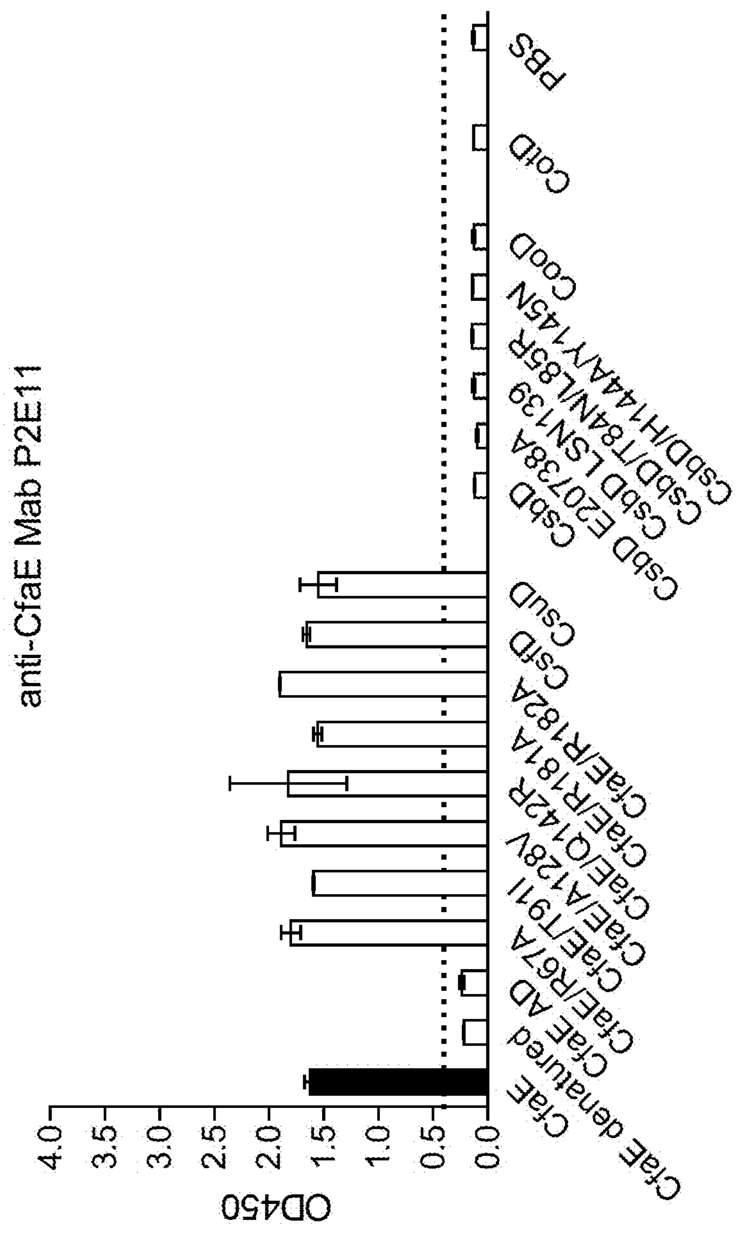
Figure 5G:
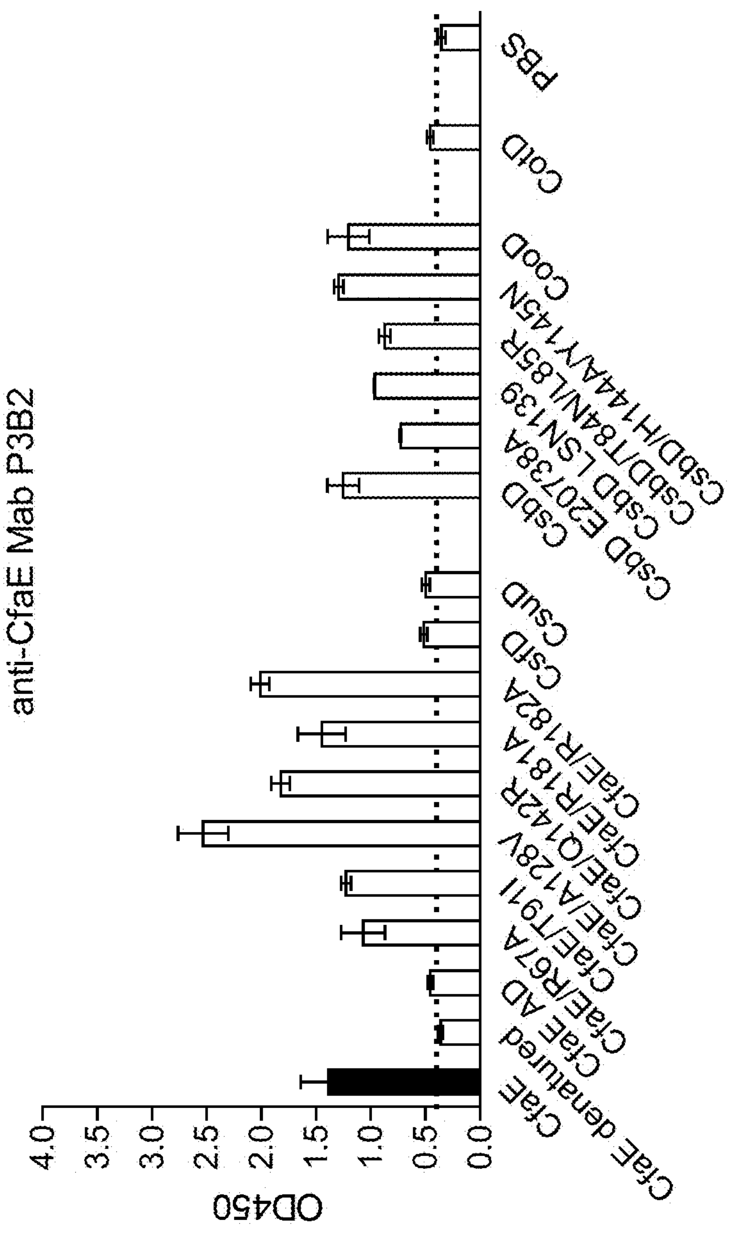
Figure 5H:
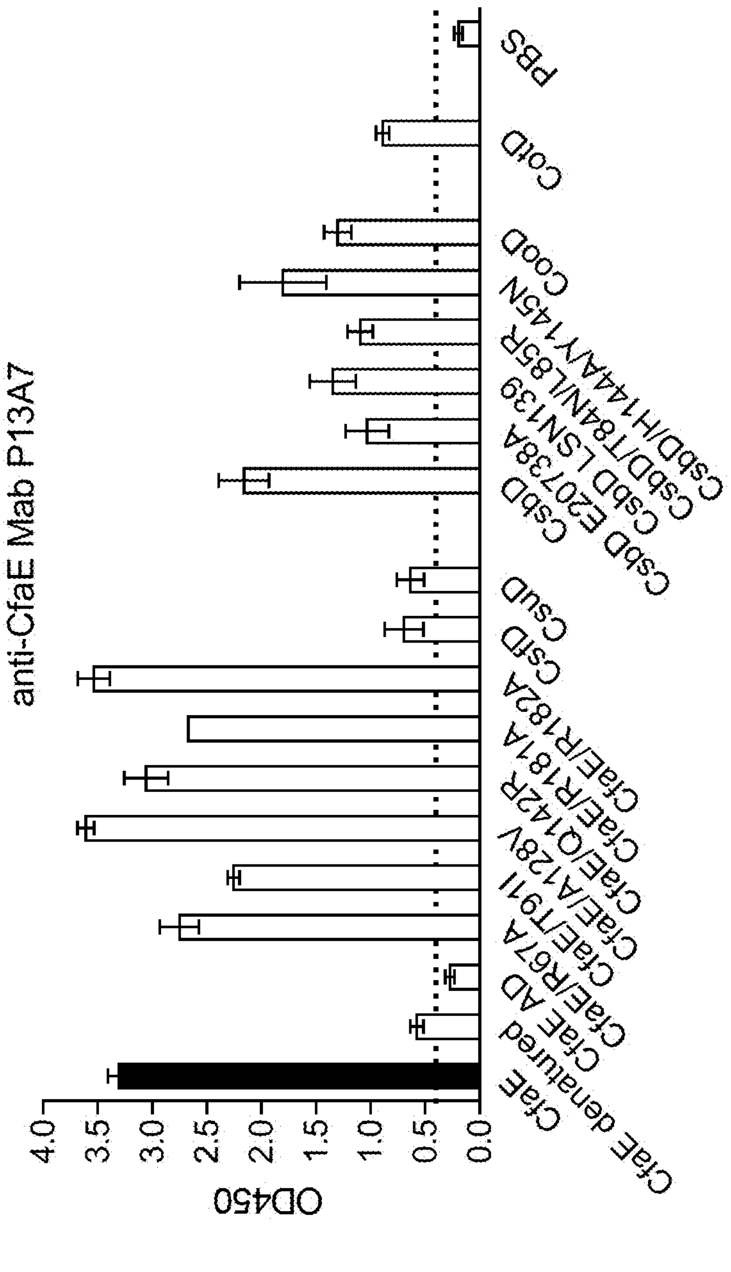
Figure 5I:
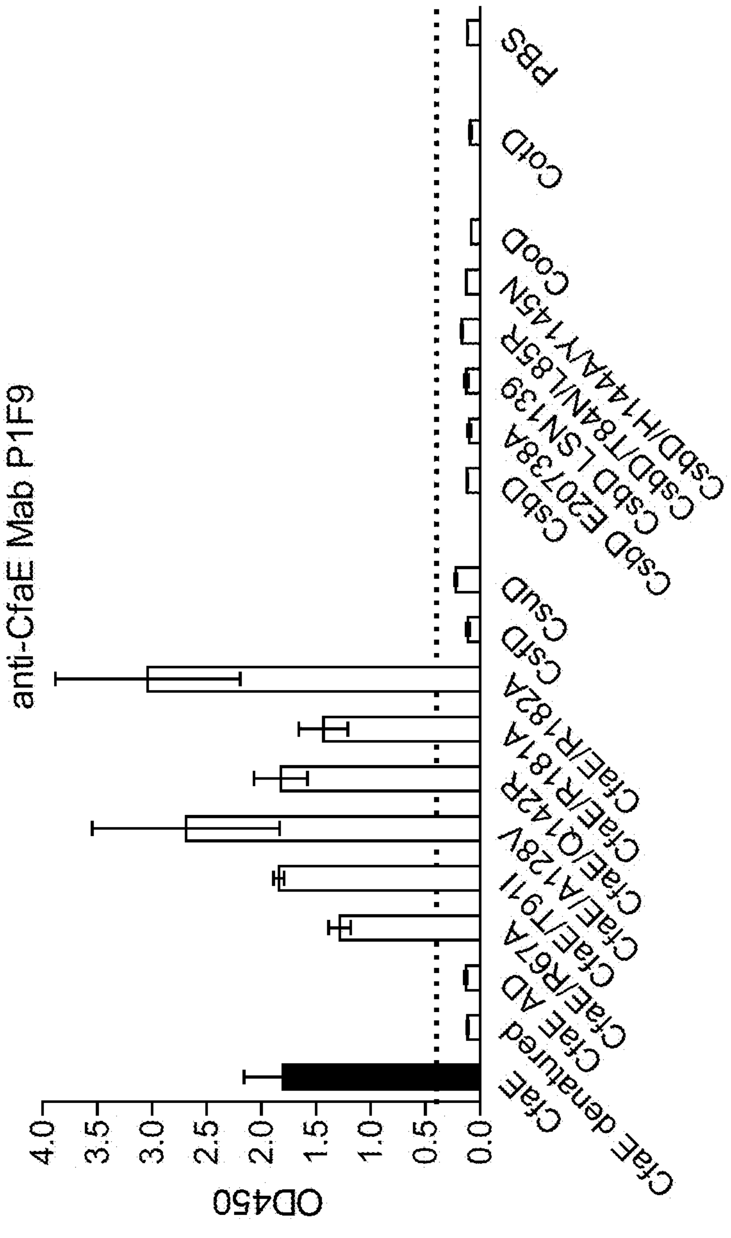

It is contemplated herein that recombinant antigen binding proteins of the instant invention may be designed to comprise three-dimensional configurations enabling high affinity binding of the specific antigen. To this end, information on particular antigen epitopes of interest is also provided herein, e.g., in FIG. 4(A)-4(C). One of skill in the art will appreciate that, based on these data, amino acid sequence substitutions may be performed to enhance the antigen binding properties of antigen binding proteins of the instant invention. For example, it is contemplated herein that in silico modeling of the three-dimensional structures of individual class 5 adhesins, individual Mabs, and complexes of the adhesins and Mabs may be performed to identify potential interacting residues between adhesins and Mabs. This may be performed by one of skill in the art using modeling software familiar to one of skill in the art. Such software includes, e.g., CHIMERA (UCSF), Discovery Studio (BIOVIA) and MODELLER (UCSF). It is contemplated herein that once epitope and sequence information of the Mabs and structure models of adhesins, Mabs, and their complexes are determined, one or more potential interacting residues in the CDR or framework regions at variable domains of the Mabs may be mutated and analyzed. For example, the mutants of Mabs or antigen binding proteins may be evaluated in hemagglutination assays for homologous and heterologous inhibition activities. See, e.g. Carter P et al., Proc Natl Acad Sci USA. 1992 May 15; 89(10): 4285-9; Almagro, J and Fransson, J. Front Biosci. 2008 Jan. 1; 13: 1619-33; Wu H et al, J Mol Biol. 1999 Nov. 19; 294(1):151-62; Morrison, S L et al PNAS USA 1984 November, 81 (21):6851-5; and Boulianne G L et al., Nature 1984 Dec. 13-19; 312(5995):643-6. NUCLEIC ACIDS In another aspect, the present invention relates to nucleic acid molecules comprising nucleotide sequences that encode an antigen binding protein of the instant invention, or an immunologically active fragment or derivative thereof. In certain embodiments, the nucleic acid molecule encodes a chimeric, humanized, or human antibody that specifically binds to a Class 5 ETEC adhesin, comprising nucleic acid sequences encoding the heavy chain of said antibody, and nucleic acid sequences encoding the light chain of said antibody, based on data for the murine mAbs provided herein. In a particular embodiment, the nucleic acid molecule encodes a chimeric, humanized, or human antibody that specifically binds to the Class 5 ETEC adhesin CotD, and which is designed based on the sequence information provided for mAb P6B8 provided in FIGS. 14(D) and 15(D). In additional particular embodiments, the nucleic acid molecule encodes a chimeric, humanized, or human antibody, as well as scFv antibodies, designed based on the sequence information provided herein for mAbs selected from the group consisting of murine mAbs P8D10, P10A7, P5C7, P2H6 and P7F9. Compositions comprising these nucleic acid molecules are also contemplated herein. Such compositions may further comprise one or more additional agents, e.g., for enhancing storage stability of such compositions or therapeutic effectiveness.

Vectors

In still another aspect, the present invention relates to a vector comprising one or more nucleic acid sequences disclosed herein, and optionally a nucleotide sequence encoding a heterologous polypeptide such as an antigenic peptide tag or enzyme, operably linked to at least one expression control sequence such as a promoter/enhancer capable of driving the expression of the nucleic acid molecules. Such vectors may be created using conventional methods, and a variety of suitable mammalian cell, insect cell, and bacterial cell expression vectors which can produce mAb or antibody fragments are familiar to one of skill in the art. Suitable vectors for the uses contemplated herein are familiar to one of skill in the art and include, e.g., a variety of commercially available vectors such as pUC19, PBR322, AbVec, and TGEX (New England BioLabs, Ipswich, MA; Addgene, Watertown, MA; BioCat GmbH, Heidelberg, Germany.) Additional commercially available mammalian expression vectors, e.g., for creating humanized antibodies of the instant invention, are familiar to one of skill in the art and include, e.g., pFUSE (InvivoGen, San Diego, CA), pTRIOZ (InvivoGen, San Diego, CA), PSF-CMV-HUIGG1 HC ((MilliporeSigma, St. Louis, MO), PSF-CMV-HUKAPPA LC ((MilliporeSigma, St. Louis, MO), and PSF-CMV-HULAMBDA LC ((MilliporeSigma, St. Louis, MO.)

Similarly, promoters and enhancers suitable for uses contemplated herein are familiar to one of skill in the art and include, but are not limited to, commercially available promotors and enhancers such as cytomegalovirus CMV promoter (Sigma-Aldrich, St. Louis, Missouri), SV40 promoter (Promega, Madison, Wisconsin), elongation factor promoter (Sigma-Aldrich, St. Louis, Missouri), polyoma enhancer, bovine growth hormone promoter, and chicken beta-actin promoter (Snapgene, Chicago, Illinois).

Host Cells

The present invention further relates to host cells which comprise at least one vector as described herein and which produce an antigen binding protein, or active fragment or derivative thereof, according to the invention. Host cells for use with the methods of the instant invention include, but are not limited to mouse myeloma cells and/or Chinese Hamster Ovary cells (CHO), CHO-S cells, NSO cells, Baby Hamster Kidney (BHK) cells, HEK293 cells; plant cells, such as tobacco, carrot and rice cells; or bacterial cells such as BL21, or insect cells such as Sf9 cells. It is contemplated herein that mammalian, e.g., human cells, may be used to create appropriately glycosylated antibodies and/or other post-translational modifications necessary for maintaining antibody function. Host cells such as these are familiar to one of skill in the art and are available from a variety of academic sources and/or commercial vendors familiar to one of skill in the art.

Hybridomas

The instant invention is also directed to hybridoma cell lines expressing the antigen binding proteins of the instant invention. In certain embodiments, a hybridoma cell line is selected from at least one of the 28 hybridoma cell lines described in Table 3.

Pharmaceutical Compositions

In another aspect, the invention relates to compositions comprising the antigen binding proteins, vectors, host cells and hybridomas of the instant invention. In particular embodiments, the compositions are pharmaceutical compositions which comprise one or more of the antigen binding proteins of the instant invention, or an immunologically active fragment or derivative thereof, alone or in combination with one or more additional pharmaceutically acceptable agents, and/or in combination with one or more pharmaceutically acceptable excipients, carriers, diluents, and/or adjuvants.

In various embodiments, such pharmaceutical compositions may comprise a mixture of antigen binding proteins of the instant invention, including one or more antigen binding proteins engineered to have affinity for more than one ETEC antigen.

In a particular embodiment, it is contemplated herein that the pharmaceutical compositions of the instant invention comprise ETEC immunogenic compositions and vaccine formulations. The terms "vaccine formulation" and "vaccine" are used interchangeably herein. One of skill in the art will appreciate that an immunogenic composition or vaccine of the instant invention may be administered to a subject in need thereof not only to enhance an immune response against ETEC, but also to provide some enhanced level of protection against ETEC infection.

As understood herein, the term "pharmaceutically acceptable" is used to refer to a non-toxic material that is compatible with a biological system such as a cell, cell culture, tissue, or organism.

Examples of pharmaceutically acceptable excipients, carriers, diluents and adjuvants are familiar to one of skill in the art and can be found, e.g., in Remington's Pharmaceutical Sciences (latest edition), Mack Publishing Company, Easton, Pa. For example, pharmaceutically acceptable excipients include, but are not limited to, wetting or emulsifying agents, pH buffering substances, binders, stabilizers, preservatives, bulking agents, adsorbents, disinfectants, detergents, sugar alcohols, gelling or viscosity enhancing additives, flavoring agents, and colors. Pharmaceutically acceptable carriers include macromolecules such as proteins, polysaccharides, polylactic acids, polyglycolic acids, polymeric amino acids, amino acid copolymers, trehalose, lipid aggregates (such as oil droplets or liposomes), and inactive virus particles. Pharmaceutically acceptable diluents include, but are not limited to, water, saline, and glycerol.

Moreover, in particular embodiments, the pharmaceutical compositions of the instant invention may optionally comprise pharmaceutically acceptable substances that can produce and/or further enhance an immune response to an antigen in a subject. These substances include, but are not limited to, adjuvants. As understood by one of skill in the art, an adjuvant can be used to increase the immunogenic efficacy of an immunogenic composition or a vaccine formulation. It may also have the ability to increase the stability of an immunogenic composition or a vaccine formulation. Thus, adjuvants are agents that enhance the production of an antigen-specific immune response as compared to administration of the antigen in the absence of the agent. Moreover, faster and longer lasting immune responses may be possible in vivo through the addition of an adjuvant to an immunogenic composition or vaccine formulation. As understood herein, in a particular embodiment, an "effective amount" of an adjuvant is that amount which is sufficient to enhance an immune response to an ETEC immunogenic composition or vaccine of the instant invention.

Adjuvants suitable for use with the immunogenic compositions and vaccines of the instant invention are familiar to one of skill in the art and are available from a variety of commercial vendors. These include, for example, glycolipids; chemokines; compounds that induce the production of cytokines and chemokines; interferons; inert carriers, such as alum, bentonite, latex, and acrylic particles; pluronic block polymers; depot formers; surface active materials, such as saponin, lysolecithin, retinal, liposomes, and pluronic polymer formulations; macrophage stimulators, such as bacterial lipopolysaccharide; alternate pathway complement activators, such as insulin, zymosan, endotoxin, and levamisole; non-ionic surfactants; poly(oxyethylene)-poly(oxypropylene) tri-block copolymers; trehalose dimycolate (TDM); cell wall skeleton (CWS); complete Freund's adjuvant; incomplete Freund's adjuvant; macrophage colony stimulating factor (M-CSF); tumor necrosis factor (TNF); 3-O-deacylated MPL; CpG oligonucleotides; polyoxyethylene ethers, polyoxyethylene esters, polyinosine-polycytidylic acid (Poly(I:C)), aluminum hydroxide (Alum), Poly[di(carboxylatophenoxy)phosphazene](PCPP), monophosphoryl lipid A, QS-21, heat labile enterotoxin (LT) toxoid, cholera toxin toxoid and formyl methionyl peptide.

In one embodiment, the adjuvant may be selected from the group consisting of antigen delivery systems (e.g. aluminum compounds or liposomes), immunopotentiators (e.g. toll-like receptor ligands), or a combination thereof (e.g., ASO1 or AS04.) These substances are familiar to one of skill in the art. In a particular embodiment, an adjuvant for use in the compositions and methods of the instant invention is selected from the group consisting of toll-like receptor ligands, aluminum phosphate, aluminum hydroxide, monophosphoryl lipid A, liposomes, and derivatives and combinations thereof. In a particular embodiment, the adjuvant may comprise a mixture of liposome, QS21 and monophosphoryl lipid A, e.g., "Army Liposomal Formulation" (ALF) adjuvant containing a synthetic monophosphoryl lipid A known commercially as 3D-PHAD™ (Avanti Polar Lipids), ALF containing QS21 (ALFQ), or ALF containing aluminum hydroxide (ALFA). See, e.g., Genito, C et al., 2017, Vaccine 35, 3865-3874; Alving, C. et al., 2012, Expert Rev Vaccines 11, 733-44; Alving, C. et al. (2012) Curr Opin Immunol 24, 310-5; Alving C. and Rao, M, (2008) Vaccine 26, 3036-3045; U.S. Pat. Nos. 6,090,406; 5,916,588.

As understood by one of skill in the art, the type and amount of pharmaceutically acceptable excipients, carriers and diluents included in the pharmaceutical compositions of the instant invention may vary, e.g., depending upon the desired route of administration and desired physical state, solubility, stability, and rate of in vivo release of the composition. For example, for administration by intravenous, cutaneous, subcutaneous, or other injection, a formulation is typically in the form of a pyrogen-free, parenterally acceptable aqueous solution of suitable pH and stability, and may contain an isotonic vehicle as well as pharmaceutical acceptable stabilizers, preservatives, buffers, antioxidants, or other additives familiar to one of skill in the art. [00100]"Additional pharmaceutically acceptable agents" for use in the methods and compositions of the instant invention are familiar to one of skill in the art and include, e.g., a variety of commercially available active pharmaceutical ingredients, including but not limited to, additional antimicrobial agents familiar to one of skill in the art. Such antimicrobial agents include "antibacterial" agents, i.e., products that can destroy or inhibit the growth of bacteria, including but not limited to ETEC. Such products include, e.g., penicillins, cephalosporins, glycopeptide derivatives, carbopenems, aminoglycosides, macrolides, tetracyclines, chloramphenicol, lincomycins, sulfonamides, metronidazole, pyrimidine derivatives, rifampicin, and quinolones.

In a particular embodiment, antibacterial agents for use in combination with the methods and compositions of the instant invention include, e.g.,: amikacin, gentamicin, tobramycin, meropenem, imipenem, cefazolin, cefepime, cefoxitin, cephalothin, ceftazidime, cefotaxime, cefoperazone, ceftriaxone, cefuroxime, levofloxacin, ciprofloxacin, nitrofurantoin, trimethoprim-sulfamethoxazole, linezolid, vancomycin, erythromycin, clindamycin, daptomycin, mupirocin, ampicillin, piperacillin, oxacillin, penicillin, mezlocillin, amoxicillin, aztreonam, sulfosoxazole, chloramphenicol, streptomycin, tetracycline, minocycline, rifampin, and silver sulfadiazine. In addition, one of skill in the art will appreciate that antibiotics such as fluoroquinolones, azithromycin, levofloxacin, rifaximin, and/or loperamide are often used in treating ETEC-related diarrhea. Such products are commercially available in a variety of forms from a variety of vendors, and therapeutically effective amounts for conventional use are familiar to one of skill in the art.

Methods of Treatment

The present invention also relates to methods for preventing or treating an ETEC infection in a subject in need thereof, comprising administering to the subject a therapeutically effective amount of at least one or more antigen binding proteins of the instant invention, and/or an immunologically active fragment, or derivative thereof. In a particular embodiment, the method comprises administering a pharmaceutical composition comprising one or more antigen binding proteins of the instant invention, e.g., an ETEC immunogenic composition or vaccine. Such administration may be with or without one or more adjuvants and/or with or without one or more additional active pharmaceutical ingredients.

It is understood herein that the pharmaceutical compositions of the instant invention, e.g., ETEC immunogenic compositions and vaccines disclosed herein, may be administered to a subject alone or in combination with other immunogenic compositions and vaccines, and/or in combination with one or more other active pharmaceutical ingredients including, e.g., other active therapeutic or immunoregulatory agents which can enhance a subject's immune response to ETEC, or to other bacteria. Such additional vaccines and active agents may be administered to a subject in any manner, e.g., before, after, or concurrently with one or more immunogenic compositions or vaccines of the instant invention.

One of skill in the art will appreciate that the methods of the instant invention encompass administration of the immunogenic compositions and vaccine formulations disclosed herein to generate immunity in a subject if later challenged by ETEC infection. It is further understood herein, however, that the compositions, vaccine formulations, and methods of the present invention do not necessarily provide total immunity to ETEC and/or totally cure or eliminate all disease symptoms.

As used herein, "treating", "treatment", and like tenns encompass reducing the severity and/or frequency of symptoms, eliminating symptoms and/or their underlying cause, preventing the occurrence of symptoms and/or their underlying cause, and improving or remediating damage. Thus, "treating" an ETEC infection refers to administering one or more antigen binding proteins of the instant invention to a subject to reduce or otherwise ameliorate the effects of an ETEC infection in the subject.

As used herein, the term "prevent", "preventing" or like terms refers to reducing the likelihood of the occurrence of an event, and does not require the 100% elimination of the possibility of an event. Thus, as understood herein, "preventing" an ETEC infection includes a prophylactic use of the antigen binding proteins of the instant invention to reduce the ability of the ETEC pathogen to establish an active infection in a subject. As understood herein, treating a subject in need thereof may encompass both prevention and treatment.

As used herein, the terms "subject", "a subject in need", "a subject in need thereof" and like terms may be used interchangeably and include an animal, including but not limited to birds and mammals, suffering from and/or susceptible to one or more ETEC infections Human beings are also encompassed in these terms. In particular, subjects in need thereof include, but are not limited to, domesticated animals as well as non-human primates and human patients.

It is contemplated herein that the pharmaceutical compositions contemplated herein may be administered to a subject in need thereof according to various regimens, i.e., in an amount and in a manner, and for a time sufficient to provide a clinically meaningful benefit to the subject. Suitable administration regimens for use with the methods of the instant invention may be determined by one of skill in the art according to conventional methods. For example, it is contemplated herein that a therapeutically effective amount of one or more antigen binding proteins of the instant invention may be administered to a subject as a single dose, or a series of multiple doses administered over a period of days, or a single dose followed by a boosting dose thereafter. In a particular embodiment, a "prime-boost" schedule may be employed, i.e., one or more earlier priming immunizations are administered followed by one or more subsequent boosting immunizations. It is contemplated herein that the same ("homologous") or different ("heterologous") vaccines may be administered in a prime-boost schedule. A "boosting dose" may comprise the same dosage amount as the initial priming dose or a different dosage amount.

As contemplated herein, an immunogenic composition or vaccine of the instant invention may be administered to a subject prior to exposure to infection, or after infection.

The administrative regimen, e.g., the quantity to be administered, the number of treatments, and effective amount per unit dose, etc. will depend on the judgment of the practitioner and are peculiar to each subject. Factors to be considered in this regard include physical and clinical state of the subject, route of administration, the intended goal of treatment, as well as the potency, stability, and toxicity of the particular composition.

As used herein, one of skill in the art will appreciate that a "therapeutically effective amount" of a pharmaceutical composition of the instant invention is that amount necessary to achieve a desired pharmacologic and/or physiologic effect in a subject (by local and/or systemic action), e.g., preventing and/or inhibiting ETEC adherence or growth in the subject. Such amounts can be readily determined by one of skill in the art. For example, therapeutically effective amounts of an ETEC immunogenic pharmaceutical composition may be gleaned by one of skill in the art in laboratory experiments, and through conventional dosing trials and routine experimentation. Therapeutically effective amounts of the pharmaceutical compositions of the instant invention may depend upon the age, weight, species (if non-human) and medical condition of the subject to be treated, and whether the antigen binding proteins are administered alone or in combination with one or more additional pharmaceutically acceptable agents, e.g., an antimicrobial agent, including but not limited to one or more additional anti-ETEC agents, and/or adjuvants.

One of skill in the art will appreciate that in some cases, a "therapeutically effective amount" may encompass more than one administered dosage amount. Indeed, when a series of immunizations is administered in order to produce a desired immune response in the subject, one of skill in the art will appreciate that in that case, a "therapeutically effective amount" may encompass more than one administered dosage amount.

As discussed above, one of skill in the art will appreciate that the antigen binding proteins of the instant invention may be administered alone, or in combination with one or more additional pharmaceutically acceptable agents, therapeutic treatments or regimens discussed herein, in any manner or combination that may be deemed therapeutically effective, e.g., before, after, or concurrently with the antigen binding proteins of the instant invention; separately in different formulations and dosage forms; at different times, and/or routes of administration, or in combination with the antigen binding proteins in a single formulation.

Various compositions, formulations, and dosage forms designed to treat ETEC infection in a subject in need thereof are contemplated herein, and may be created according to conventional methods by one of skill in the art. Indeed, it is contemplated herein that pharmaceutical compositions and dosage forms may be administered to a subject by a variety of routes according to conventional methods, including but not limited to parenteral (e.g., by intracisternal injection and infusion techniques), intradermal, transmembranal, transdermal (including topical), ocular, intramuscular, intraperitoneal, intravenous, intra-arterial, intralesional, subcutaneous, oral, sublingual, intranasal (e.g., inhalation or by aerosol administration), intracerebrospinal, intra-articular, intrasynovial, intrathecal, and topical, routes of administration.

Administration can also be by continuous infusion or bolus injections, particularly intravenous administration of one or antigen binding proteins or derivatives or fragments thereof as a bolus or by continuous infusion over a period of time, e.g., in the form of an ETEC immunogenic composition or vaccine formulation. Such compositions, formulations, dosage forms, and methods of delivery may be suitable for treating bacterial infections, e.g., on the skin, in the bloodstream, deep tissue, oral cavity, ocular cavity, gastrointestinal tract, urinary tract or any other location in a subject in which a bacterial infection may be present.

The term "dose", "dosage", "dosage form" and like terms used herein refer to physically discrete units suitable for administration to a subject, each dosage comprising a predetermined quantity of antigen binding proteins as an active pharmaceutical ingredient calculated to produce a desired response. For example, as contemplated herein, the pharmaceutical compositions of the instant invention are preferably sterile and contain an amount of the antigen binding proteins in a unit of weight or volume suitable for administration to a subject. The volume of the composition administered to a subject (dosage unit) will depend on the method of administration and is discernible by one of skill in the art. For example, in the case of an injectable, the volume administered typically may be between 0.1 and 1.0 ml, preferably approximately 0.5 ml. Amounts for clinical use can be ascertained by one of skill in the art without undue experimentation.

As discussed above, it is contemplated herein that the antigen binding proteins of the instant invention may be administered in various ways according to the methods of the instant invention, e.g., alone or in combination with one or more additional pharmaceutically acceptable agents, therapeutic treatments, or regimens, in order to enhance treatment efficacy. As one of skill in the art will appreciate, the type and amount of additional pharmaceutically acceptable agents, therapeutic treatments or regimens for use in the methods and compositions of the instant invention will depend upon the type of infection to be treated; e.g., alone, or in conjunction with one or more other pharmaceutically acceptable antimicrobial compounds.

It is contemplated herein that a therapeutically effective amount of said one or more additional pharmaceutically acceptable agents for conventional use are familiar to one of skill in the art; amounts for use in the methods and compositions of the instant invention may also be readily determined by one of skill in the art according to conventional methods. In one embodiment, it is contemplated herein that therapeutically effective amounts of an additional pharmaceutically acceptable agent, e.g., a conventional antimicrobial agent, may be reduced when administered in combination with one or more of the antigen binding proteins disclosed herein (or vice versa). In addition, it is also contemplated herein that when said one or more additional pharmaceutically acceptable agents is administered in conjunction with one or more antigen binding proteins disclosed herein, the agent may only need to be administered to a subject for a fraction of the time that said agent would typically need to be administered when administered alone (and vice versa).

Kits and Methods of Detection

It is contemplated herein that any of the antigen binding proteins of the instant invention may be used in methods and kits for detecting ETEC bacteria, ETEC fimbriae and adhesin, and even previous exposure to ETEC, or infection by ETEC according to conventional methods. For example, anti-adhesin mAbs disclosed herein can serve as positive controls or standards for diagnostic kits to see if patient sera are reactive to ETEC antigens or not. In a particular embodiment, the antigen binding proteins may be labeled to incorporate a detectable marker, e.g., a tag, fluorophore, enzyme, radioisotope or other substance familiar to one of skill in the art. In a particular example, the kit may comprise one or more containers comprising an antigen binding protein of the instant invention, detection reagents, and instruction for use thereof. The anti-adhesin antigen binding proteins can also be used to evaluate conformational stability and potency of ETEC vaccines and proteins which are based on ETEC fimbriae and adhesins. For example, as disclosed in Example 7 and Table 4, the P6B8 mAb can detect conformational epitopes of ETEC adhesin. One of skill in the art will appreciate that if vaccine antigens demonstrate diminished reactivity to the anti-adhesin antibody, e.g., due to degradation which might possibly occur during storage, a vaccine may not be as immunogenic and thus may demonstrate a loss of efficacy.

The anti-adhesin antigen binding proteins of the instant invention can also be used to quantify ETEC vaccines and proteins, which are based on ETEC fimbriae and adhesins. For example, the anti-adhesin mAbs of the instant invention can be used to quantify ETEC proteins using ELISA such as demonstrated in Example 11.

Although the invention herein has been described with reference to particular embodiments, it is to be understood that these embodiments, and examples provided herein, are merely illustrative of the principles and applications of the present invention. It is therefore to be understood that numerous modifications can be made to the illustrative embodiments and examples, and that other arrangements can be devised without departing from the spirit and scope of the present invention as defined by the appended claims. All patent applications, patents, literature and references cited herein are hereby incorporated by reference in their entirety.

EXAMPLES

As indicated below, some of the data provided in Examples 1-8 have been previously published (33, 34).

Example 1: Construction, Expression and Purification of Adhesin Proteins

The creation of the murine mAbs listed in Table 3 was previously reported (33, 34). As previously described, in order to increase stability and expression yield of ETEC adhesin, the donor strand complemented dscCsuD, dscCsfD, dscCsbD, dscCooD and dscCotD (CS14, CS4, CS17, CS1 and CS2 adhesins, respectively) were cloned into pET24 (a)+(Novagen, Darmstadt, Germany) between XhoI and NdeI sites, which was similar to the construction of dscCfaE plasmid (15). The C-terminal donor strand of each adhesin was from the N-terminal 14 to 19 residues of CsuA, CsfA, CsbA, CooA and CotA (CS14, CS4, CS17, CS1 and CS2 pilins, respectively) mature sequences. The sequences of dsc antigens are shown in FIGS. 12(A)-12(C). See also U.S. Pat. No. 9,079,945. The dscCfaE and dscCsbD served as templates for site-directed mutagenesis (QuikChange, Stratagene, La Jolla, California) to introduce point mutation(s) at the specific residues. CfaE/T91I, CfaE/A128V and CfaE/

Q142R mutants were overexpressed and purified (33). Each of these recombinant adhesin and adhesin mutant plasmids, which include an in-frame C-terminal hexahistidine tag, was transformed into *E. coli* BL21 (DE3) for expression. Cell growth, induction, harvest, lysis and protein purification were similar to the previously reported for dscCfaE (15). Briefly, the cells were grown in APS Super Broth (Difco) at 32° C. with kanamycin and induced with 1 mM isopropyl P-D-1-thiogalactopyranoside (IPTG). Cell pastes were harvested and disrupted by microfluidizer. After centrifugation of the cell lysate, the soluble proteins were purified by the nickel affinity and cation exchange chromatography sequentially. The purified proteins were pooled and concentrated. The purity and concentration of the antigens were determined by the densitometry and BCA assay (Pierce, Waltham, MA), respectively. The antigens used in the ELISA assays are listed below in Table 2:

TABLE 2

Table of Antigens used in the ELISA.

| Protein antigens | Sequence origin | Note |
|---|---|---|
| Class 5a antigens | | |
| CfaE | CFA/I (H10407) | $dsc_{19}CfaE$ (Primary*) |
| CfaE AD | CFA/I (H10407) | Adhesin domain (residues 23-202) of CfaE |
| CfaE PD | CFA/I (H10407) | Pilin domain (residues 203-383) of CfaE |
| CfaE/R67A | CFA/I (H10407) | CfaE mutant R67A |
| CfaE/T91I | CFA/I (10F2) | CfaE has an allelic variation of T911 in the CFA/I allelic strain 10F2 |
| CfaE/A128V | CFA/I (WS4437A-1) | CfaE has an allelic variation of A128V in the CFA/I allelic strain WS4437A-1 |
| CfaE/Q142R | CFA/I (SMJ344) | CfaE has an allelic variation of Q142R in the CFA/I allelic strain SMJ344 |
| CfaE/R181A | CFA/I (H10407) | CfaE mutant R181A |
| CfaE/R182A | CFA/I (H10407) | CfaE mutant R182A |
| CsfD | CS4 (BANG10-SP) | $dsc_{15}CsfD$ |
| CsuD | CS14 (WS3294A) | $dsc_{19}CsuD$ |
| Class 5b antigens | | |
| CsbD | CS17 (WS6788) | $dsc_{19}CsbD$ (Primary) |
| CsbD AD | CS17 (WS6788A) | Adhesin domain (residues 19-205) of CsbD |
| CsbD E20738A | CS17 (E20738A) | CsbD has allelic variations of N62S/S74T/T84N/L85R/H144A/Y145N/Y293H in the CS17 allelic strain E20738A |
| CsbD LSN139 | CS17 (LSN02-013966/A) | CsbD has allelic variations of L85I/H144A in the CS17 allelic strain LSN139 |
| CsbD/T84N/L85R | CS17 (WS6788) | CsbD mutant T84N/L85R |
| CsbD/H144A/Y145N | CS17 (WS6788) | CsbD mutant H144A/Y145N |
| CooD | CS1 (E24377A) | $dsc_{19}CooD$ |

TABLE 2-continued

Table of Antigens used in the ELISA.

| Protein antigens | Sequence origin | Note |
|---|---|---|
| Class 5c antigens | | |
| CotD | CS2 (C91f) | $dsc_{19}CotD$ (Primary) |
| CotD AD | CS2 (C91f) | Adhesin domain (residues 19-205) of CotD |
| CotD/R69A | CS2 (C91f) | CotD mutant R69A |
| CotD/T87A | CS2 (C91f) | CotD mutant T87A |
| CotD/K183A | CS2 (C91f) | CotD mutant K183A |
| CotD/R184A | CS2 (C91f) | CotD mutant R184A |

*Primary sequence upon which other mutant antigen sequences were based.

Example 2: Mouse Hybridoma Generation

As discussed above, "donor strand complemented" (dsc) antigens provide enhanced antigen stability and were used to construct the mAbs of the instant invention (33). Specifically, $dsc_{19}CfaE$, $dsc_{19}CsbD$ and $dsc_{19}CotD$ antigens disclosed in FIGS. 12(A)-12(C) were created according to the methods disclosed in U.S. Pat. No. 9,328,150 and Poole et al., Mol. Microbiol. 63, 1372-1384 (2007). See also (33). Briefly, nucleic acid sequences of $dsc_{19}CfaE$, $dsc_{19}CsbD$ and $dsc_{19}CotD$ were respectively cloned into pET24(a)+ plasmids between XhoI and NdeI sites, resulting pET24-$dsc_{19}CfaE$, pET24-$dsc_{19}CsbD$ and pET24-$dsc_{19}CotD$ plasmids. Each of the plasmids was transformed into BL21 (DE3) competent *Escherichia coli* cells for expression (Novagen.) BL21(DE3)/pET24-$dsc_{19}CfaE$ was grown in APS™ Super Broth media (Difco, Detroit, MI) with 50 μg/ml kanamycin at 32° C. to late logarithmic phase and induced for 3 hours with 1 mM isopropyl β-D-lthiogalactopyranoside (IPTG). Bacterial cells were harvested by centrifugation. BL21(DE3)/pET24-$dsc_{19}CsbD$ and BL21 (DE3)/pET24-$dsc_{19}CotD$ were grown and harvested in the same conditions as BL21(DE3)/pET24-$dsc_{19}CfaE$.

$dsc_{19}CfaE$ was purified by resuspending BL21(DE3)/pET24-$dsc_{19}CfaE$ cell paste in 1:4 (w/v) binding buffer A (20 mM phosphate, 500 mM sodium chloride, 50 mM imidazole, pH 7.4) with benzonase (Novagen) at 6.25 unit/ml. The bacterial resuspension was passed twice through microfluidizer (Model 1109, Microfluidic), and the cell lysate was centrifuged at 17,000 g at 4° C. for 1 hour. The supernatant was loaded onto a HisTrap HP column (Amersham Biosciences, Waltham, MA) at a flow rate of 3 ml/min, and proteins were eluted with a linear gradient to 300 mM imidazole over 20 column volumes (CVs). Fractions containing $dsc_{19}CfaE$ were pooled and diluted in 1:10 (v/v) binding buffer B (25 mM MES, pH 6.0), and loaded onto a HiTrap SP column (Amersham Biosciences) at a flow rate of 2 ml/min. The bound proteins were eluted with a linear gradient to 500 mM sodium chloride over 20 CVs. Fractions containing $dsc_{19}CfaE$ were pooled and dialyzed against phosphate buffered saline pH 6.7 overnight at 4° C.

The purification of $dsc_{19}CsbD$ was previously reported in Savarino et al, 2019 Hyperimmune Bovine Colostral Anti-CS17 Antibodies Protect Against Enterotoxigenic *Escherichia coli* Diarrhea in a Randomized, Doubled-Blind, Placebo-Controlled Human Infection Model; DOI: 10.1093/infdis/jiz135). The BL21(DE3)/pET24-$dsc_{19}CsbD$ cell paste was resuspended in 1:4 (w/v) phosphate buffered saline pH 7.4 (PBS). The bacterial resuspension was passed twice through microfluidizer (Model 1109, Microfluidic), and the cell lysate was centrifuged at 17,000 g at 4° C. for 1 hour. After the supernatant was removed, the cell pellets were washed twice by resuspension in PBS and centrifugation as described above. The washed pellets were resuspended in solubilization buffer (100 mM sodium chloride, 50 mM imidazole, 2 M urea, 20 mM sodium phosphate pH 7.4). The resuspended pellets were mixed and stirred at 30° C. for 1 hour and then centrifuged at 17,000 g for 1 hour. The supernatant was loaded onto a HisTrap FF column (Amersham Biosciences) and urea was removed from the column using a linear gradient to 100% HisTrap wash buffer (500 mM sodium chloride, 50 mM imidazole, 20 mM sodium phosphate pH 7.4) over 10 CVs. Proteins were eluted by a linear gradient to 57% HisTrap elution buffer (500 mM sodium chloride, 500 mM imidazole, 20 mM sodium phosphate pH 7.4) over 20 CVs. Fractions containing $dsc_{19}$CsbD were pooled. Purification of $dsc_{19}$CotD was identical to the purification procedure of $dsc_{19}$CsbD except for using BL21 (DE3)/pET24-$dsc_{19}$CotD cell paste.

The following mouse immunization and hybridom generation were briefly reported previously (34). Female Balb/c mice were immunized with 4 doses (5 μg per dose) of each adhesin ($dsc_{19}$CfaE, $dsc_{19}$CsbD or $dsc_{19}$CotD) at two-week intervals. Three days after the last immunization, splenocytes of the immunized mice were fused at 1:10 with mouse myeloma cell line P3NSI in the presence of polyethylene glycol. After the fused cells were incubated with HAT selective medium for 10 days in tissue culture microtiter plates, the supernatants of stable hybridomas were tested for antibody production on the ELISA plates coated with each adhesin. The culture supernatants were diluted at 1:1 ratio with phosphate buffered saline, pH 7.4 with 0.05% Tween 20 and 0.1% BSA (PBST-BSA) and added into plates. Bound antibodies were detected by incubation with goat anti-mouse IgG horseradish peroxidase conjugates diluted at 1:1500 in PBST-BSA, and the optical densities (OD) at 450 nm were measured after incubation with the ortho-phenylenediamine and peroxide substrate. The OD values of the positive hybridomas were at least 0.1 higher than those of the background level. There were 28 positive hybridomas. Nine of them were anti-dscCfaE, 11 of them were anti-dscCsbD, and eight of them were anti-dscCotD. See Table 3 for a list of the 28 hybridomas/mAbs (33).

Example 3: Monoclonal Antibody Purification

Monoclonal antibodies were purified as previously reported (33). Briefly, about 40 ml of supernatant of the hybridoma cell cultures was adjusted to pH 8.0 with sodium hydroxide and applied to 0.5 ml of the protein G resin (Genscript) at 0.5 ml/min. After washing with 15 ml of PBS, pH 7.4, the mAbs were eluted with 5 ml of 100 mM glycine, pH 2.5. The eluate was immediately neutralized by 1 M Tris, pH 8.5. The fractions containing purified mAbs were dialyzed against water, lyophilized and resuspended in PBS, pH 7.4. The final mAb concentrations were determined by the BCA assay (Pierce). See (33).

Example 4: Enzyme-Linked Immunosorbent Assay (ELISA)

ELISA procedures were performed using conventional methods as previously described (32). Briefly, antigens were diluted in the PBS, pH 7.4 and coated on a 96-well microtiter plate with 100 μl of each adhesin and mutants at 2 μg/ml. Each condition was duplicated. After the plate was incubated at 37° C. for 1 hour, each well was washed three times with 250 μl of PBS. Then each well was blocked with 250 μl of PBS with 5% fetal calf serum at 37° C. for 1 hour. After washing three times with 250 μl of PBS, 0.05% Tween 20 (PBST), each well was added 100 μl of each mouse mAb at 2 μg/ml and incubated at 37° C. for 1 hour. The plate was washed five times with 250 μl of PBST and each well was added 100 μl of goat anti-mouse IgG horseradish peroxidase-conjugated secondary antibodies and incubated at 37° C. for 2 hours. After washing three times with 250 μl of PBST, each well was added 100 μl of ortho-phenylenediamine substrates and incubated at 25° C. for 20 minutes. Optical densities (OD) were measured by a plate reader at 450 nm. See also (33) which includes a subset of data provided herein in FIGS. 5, 6, 7, and 8.

Example 5: Hemagglutination Inhibition Assay (HAT)

HAI assays were performed using conventional methods as previously described (5). The wild type class 5 ETEC strains used in this study were CFA/I (H10407), CS1 (WS1974A), CS2 (C91f), CS4 (BANG10-SP), CS14 (WS3294A), CS17 (LSNO2-013966/A), CS17 (WS6788A), and CS17 (WS4240A). Briefly, bacteria were resuspended in PBS with 0.5% D-mannose (PBSM) until the OD at 650 nm reached 40. The minimal hemagglutination titer (MHT) was determined by mixing 25 μl of each serial twofold bacterial dilution with equal volumes of 3% washed bovine erythrocytes and PBSM in the ceramic tile wells. The tile was rocked on ice for 20 minutes. The second highest bacterial dilution (one titer higher than the MHT) showing the positive mannose-resistant hemagglutination (MRHA) was used as the bacterial working solution. To determine the HAI activity or the minimum inhibition concentration (MIC) of each mAb, a serial twofold antibody dilution was made from starting concentration of 500 μg/ml, and incubated with an equal volume of the bacterial working solution at room temperature for 20 minutes. Bovine erythrocytes were then added into the wells and the tile was rocked on ice for 20 minutes. The MIC was expressed as the lowest concentration of the mAb which completely inhibited the MRHA. Data are provided in Table 5 (33). Data indicate that the mAbs against CfaE, CsbD and CotD generally have strong homologous HAI activity, whereas some heterologous HAI activities have been observed, but not as potent as homologous inhibition.

Example 6: Cross-Reactive Patterns of mAbs to Heterologous Class 5 Fimbrial Tip Adhesins The cross-reactive pattern of each mAb was examined by ELISA aiming to identify broadly reactive mAbs. The raw optical density measurements in the ELISA assays are displayed in FIGS. 1-3, and the bindings of mAbs to homologous and heterologous class 5 adhesins are summarized in Table 3 below from previously reported data. See (33).

TABLE 3

Summary of anti-adhesin mAbs reactivity to class 5 adhesins in ELISA.

| | 5a | | | 5b | | 5c |
|---|---|---|---|---|---|---|
| Mab name | CfaE | CsfD | CsuD | CsbD | CooD | CotD |
| Anti-CfaE | | | | | | |
| P8D10 | +* | −* | − | − | − | − |
| P1F9 | + | − | − | − | − | − |
| P6C11 | + | − | + | − | − | − |
| P6H4 | + | − | + | − | − | − |
| P2E11 | + | + | + | − | − | − |
| P10A7 | + | − | − | + | + | − |
| P5C7 | + | − | − | + | + | − |
| P3B2 | + | + | + | + | + | + |
| P13A7 | + | + | + | + | + | + |
| Anti-CsbD | | | | | | |
| P7C2 | − | − | − | + | + | − |
| P9A5 | − | − | − | + | + | − |
| P2H6 | − | − | − | + | + | − |
| P6G1 | − | − | − | + | + | − |
| P2A9 | − | − | − | + | + | − |
| P1F7 | − | − | − | + | + | − |
| P5A12 | − | − | − | + | + | − |
| P9D12 | − | − | − | + | + | − |
| P7F12 | − | − | − | + | + | − |
| P9E11 | + | + | + | + | + | − |
| P7F9 | + | + | + | + | + | + |
| Anti-CotD | | | | | | |
| P7F6 | − | − | − | − | − | + |
| P3F4 | − | − | − | − | − | + |
| P6B8 | − | − | − | − | − | + |
| P3D11 | − | − | − | − | − | + |
| P2B8 | − | − | − | − | − | + |
| P9G7 | − | + | + | − | − | + |
| P12A2 | + | − | + | − | − | + |
| P9A10 | + | + | + | − | − | + |

*Positive and negative reactivity of the mAbs to the adhesins in ELISA assay are indicated by "+" and "−", respectively.

Data indicate that the 28 anti-adhesin mAbs exhibited distinctive cross-reactive patterns similar to the previously reported data (33). Specifically, we observed individual adhesin specific, intra-subclass specific, inter-subclass specific and class-wide cross-reactivity. Two anti-CfaE mAbs P1F9 and P8D10 reacted only to the immunogen CfaE (FIG. 1(A), individual adhesin specific), while P6C11 and P6H4 were cross-reactive to a second class 5a adhesin CsuD (FIG. 1(B), intra-subclass specific), and P2E11 showed similar reactivity to all three class 5a adhesins (CFA/I, CS4, CS14) (FIG. 1(C), demonstrating intra-subclass specificity). Moreover, anti-CfaE mAbs P5C7 and P10A7 were cross-reactive to two class 5b adhesins, CsbD (CS17) and CooD (CS1) (FIG. 1(D), demonstrating inter-subclass specificity). Notably, two anti-CfaE mAbs P13A7 and P3B2 reacted to all tested class 5 adhesins with variable intensity (FIG. 1(E), demonstrating class-wide reactivity).

All 11 anti-CsbD mAbs were cross-reactive to CS1 adhesin CooD probably due to high sequence identity (97%) between CsbD and CooD (FIGS. 2(A)-2(D).) One anti-CsbD mAb P9E11 extended reactivity to all three class 5a adhesins (FIG. 2(C)). The other anti-CsbD mAb P7F9 was broadly reactive to all examined class 5 adhesins with strong intensities (FIG. 2(D)), (33). Five of eight anti-CotD mAbs reacted only to the immunogen CotD (FIG. 3(A)). Among the other three cross-reactive anti-CotD mAbs, P12A2 was cross-reactive to two class 5a adhesins, CfaE and CsuD (FIG. 3(B)), and P9G7 had additional reactivity to CsfD and CsuD (FIG. 3(C)); whereas the third anti-CotD mAb P9A10 was reactive to all class 5a adhesins (FIG. 3(D)).

Example 7: MAb Epitope Mapping, Epitope Feature, Domain Specificity, and Isotype Given the previously reported distinctive reactivity patterns of the 28 anti-adhesin mAbs to the class 5 adhesins discussed above, we proceeded to re-map the epitope residues of the mAbs, especially those with cross-reactivity to the heterologous adhesins. New analysis discussed below reveal errors in the previously published epitope maps of P10A7, P5C7, P2H6, and P7F9 (see Table 4.) Specifically, S86 in CfaE is a newly identified residue in the epitopes of P10A7 and P5C7. S88 and Y182 in CsbD are now identified herein as key residues in the epitope of P7F9.

We previously mapped epitope residues for each mAb by combining results from the ELISA (see data in FIGS. 5-8) and functional hemagglutination inhibition assays (see below and previously reported data in Table 5) (33.) In the ELISA assay, the identity of residues within the binding epitope was inferred by detectable difference in reactivity to the mAb between the native adhesins and adhesin allelic variants or mutants. In the functional assay, epitope-specific residues were inferred by obvious difference in inhibition concentrations of the mAb to multiple allelic strains. Specifically, since CfaE R67A and CfaE R181A were nominally reactive with anti-CfaE mAbs P8D10, P6C11, P6H4, P10A7 and P5C7 (FIG. 5(A)-5(E)), we inferred that the binding epitope of these five anti-CfaE mAbs included residues R67 and R181 in CfaE. See Table 4 below.

TABLE 4

Isotype, epitope features, domain specificity and epitope residues of anti-adhesinm Abs.

| mAb name | Isotype | Epitope features | Domain specificity | Epitope residues |
|---|---|---|---|---|
| Anti-CfaE | | | | |
| P8D10 | IgG1 | Conformational | AD# | R67, R181 |
| P6C11 | IgG2b | Conformational | AD | R67, R181 |
| P6H4 | IgG1 | Conformational | AD | R67, R181 |
| P10A7§ | IgG1 | Conformational | AD | R67, S86*, R181 |
| P5C7§ | IgG1 | Conformational | AD | R67, S86*, R181 |
| P2E11 | IgG1 | Conformational | PD# | n.d. |
| P3B2 | IgG1 | Conformational | PD | n.d. |
| P13A7 | IgG1 | Linear | PD | n.d. |
| P1F9 | IgG1 | Conformational | PD | n.d. |
| Anti-CsbD | | | | |
| P7C2 | IgG1 | Conformational | AD | n.d. |
| P9A5 | n.d. | Conformational | AD | n.d. |
| P2H6 | IgG1 | Conformational | AD | T84 |
| P6G1 | IgG1 | Conformational | AD | n.d. |
| P2A9 | IgG1 | Conformational | AD | n.d. |
| PIF7 | IgG1 | Conformational | AD | H144 |
| P9E11 | n.d. | Conformational | AD | n.d. |
| P7F9§ | IgG1 | Linear/Conformational | AD | S88, R181, Y182 |
| P5A12 | IgG1 | Conformational | AD | n.d. |
| P9D12 | n.d. | Linear | PD | n.d. |
| P7F12 | IgG1 | Linear | PD | n.d. |
| Anti-CotD | | | | |
| P7F6 | IgG1 | Conformational | AD | n.d. |
| P3F4 | IgG2a | Conformational | AD | n.d. |
| P6B8 | IgG1 | Conformational | AD | R69, R184 |

TABLE 4-continued

Isotype, epitope features, domain specificity and epitope residues of anti-adhesinm Abs.

| mAb name | Isotype | Epitope features | Domain specificity | Epitope residues |
|---|---|---|---|---|
| P3D11 | IgG1 | Conformational | AD | n.d. |
| P9A10 | IgG1 | Linear | AD | n.d. |
| P9G7 | IgG1 | Linear | PD | n.d. |
| P2B8 | IgG1 | Linear | PD | n.d. |
| P12A2 | IgG1 | Linear | PD | n.d. |

#AD stands for adhesin domain; PD stands for pilin domain.

n.d. not determined by the methods in this study.

*Indicates that the epitope residues were identified by hemagglutination inhibition assay.

§Indicates that epitope residues were partially different than previously reported (33). S86 in CfaE is a newly identified residue in the epitopes of P10A7 and P5C7. S88 and Y182 in CsbD are now identified as key residues in the epitope of P7F9.

Reanalysis of data in FIGS. 5-7 reveal that anti-CfaE mAbs P10A7 and P5C7 showed at least moderate hemagglutination inhibition activity to the CS17 WS6788A strain (see Table 5, below) but the same inhibition function was not observed to the CS17 WS4240A strain (harboring CsbD L85I allelic variation), suggesting that S86 in CfaE, sequence-aligned with L85 in CsbD (FIG. 9), is one of the epitope residues for anti-CfaE mAbs P10A7 and P5C7. As discussed in below examples, based on these data, possible future experiments include making a CfaE mutant CfaE/S86A and using the mutant in an ELISA assay to reconfirm that S86 in CfaE is one of the epitope residues for anti-CfaE mAbs P10A7 and P5C7.

TABLE 5

Functional activities of anti-adhesin mAbs measured by the minimum concentrations to inhibit hemagglutination induced by eight class 5 ETEC strains.

| | MIC‡ (ug/ml) of mAb to inhibit MRHA caused by class 5 ETEC | | | | | | | |
|---|---|---|---|---|---|---|---|---|
| | | | | 5b | | | | |
| | 5a | | | CS17 | CS17 (LSN02- | CS17 | | 5c |
| mAbs | CFA/I | CS4 | CS14 | (WS6788A) | 013966/A)§ | (WS4240A)† | CS1 | CS2 |
| Anti-CfaE | | | | | | | | |
| P8D10* | 1.2 | — | — | — | — | n.d. | — | — |
| P6C11* | 1.2 | — | — | — | — | n.d. | — | — |
| P6H4* | 1.6 | — | — | — | — | n.d. | — | — |
| P10A7* | 0.8 | — | — | 8.0 | 187.5 | — | — | — |
| P5C7* | 1.2 | — | — | 16.0 | — | — | — | — |
| P2E11 | 31 | — | — | — | — | n.d. | — | — |
| P3B2 | 3 | — | — | 12.0 | 31.3 | n.d. | 188 | — |
| P13A7 | >400 | >400 | >400 | 13.0 | >400 | n.d. | >400 | >400 |
| P1F9 | 1.5 | — | — | — | — | n.d. | — | — |
| Anti-CsbD | | | | | | | | |
| P7C2* | — | — | — | 1.0 | 1.0 | 2.0 | 4 | — |
| P9A5* | — | — | — | 4.0 | 3.9 | n.d. | 4 | — |
| P2H6* | — | — | — | 4.0 | 31.3 | 375 | 31 | — |
| P6G1* | — | — | — | 8.0 | 15.6 | n.d. | 16 | — |
| P2A9* | — | — | — | 8.0 | 15.6 | n.d. | 16 | — |
| P1F7* | — | — | — | 0.3 | — | n.d. | — | — |
| P9E11* | — | — | — | 4.0 | — | n.d. | — | — |
| P7F9* | — | — | — | — | — | n.d. | — | — |
| P5A12* | — | — | — | — | — | — | — | — |
| P9D12 | — | — | — | 63 | — | n.d. | — | — |
| P7F12 | — | — | — | — | — | n.d. | — | — |
| Anti-CotD | | | | | | | | |
| P7F6* | — | — | — | — | — | n.d. | — | 0.5 |
| P3F4* | — | — | — | — | 250 | n.d. | — | 1.0 |
| P6B8* | — | — | — | — | — | n.d. | — | 3.0 |
| P3D11* | — | — | — | — | — | n.d. | — | 16.0 |
| P9A10* | — | — | — | — | — | n.d. | — | 188 |
| P9G7 | — | — | — | — | — | n.d. | — | — |
| P2B8 | — | — | — | — | 250 | n.d. | — | 250 |
| P12A2 | — | — | — | — | — | n.d. | — | 125 |

‡The mAbs with minimum inhibition concentrations (MIC) ≤10 μg/ml, 10-100 μg/ml, 100-250 μg/ml, were defined in this study to have strong, moderate, and low functional activity, respectively.

§The CS17 LSN02-013966/A strain contains CsbD L85I/H144A allelic variation from the CS17 WS6788A strain.

†The CS17 WS4240A strain contains CsbD L85I allelic variation from the CS17 WS6788A strain.

*The mAbs were adhesin domain specific.

—The MIC was greater than 250 ug/ml.

n.d. The experiments were not performed.

Figure 6A:
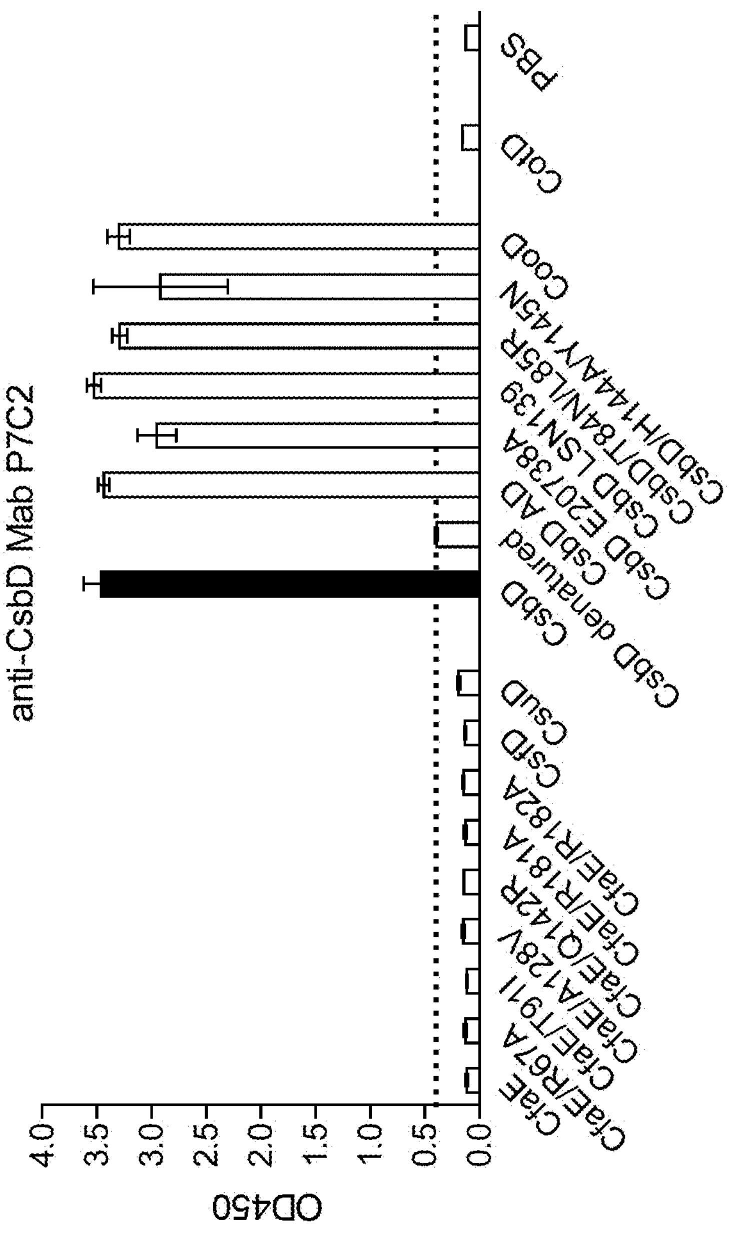
FIGS. 6(A)-6(K) depict data from anti-CsbD Mab ELISA assays performed to evaluate responses to various class 5 ETEC fimbrial adhesin variants. The responses to the immunogen CsbD are highlighted in black bars. The dashed lines represent the limit of detection in the anti-CsbD Mab ELISA assays, which equals the sum of average background of PBS buffer and three times of the standard deviation. Specifically.
Figure 6B:
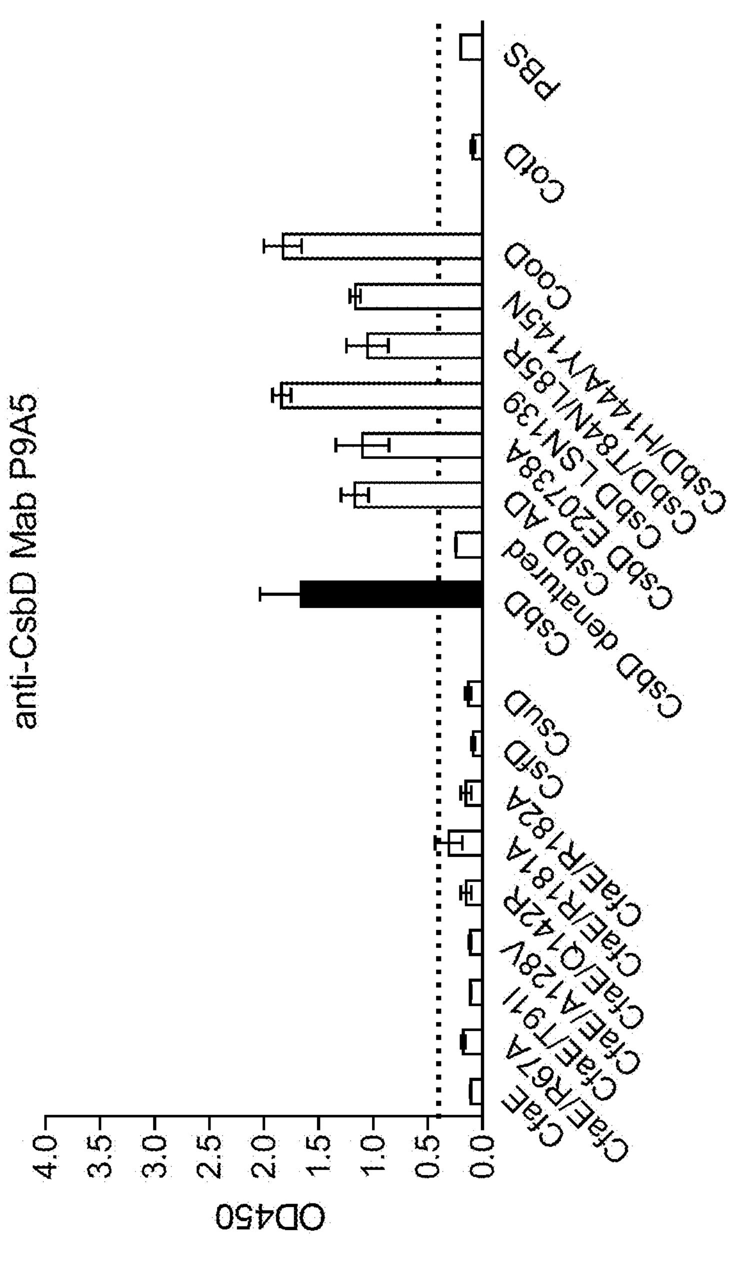
Figure 6C:
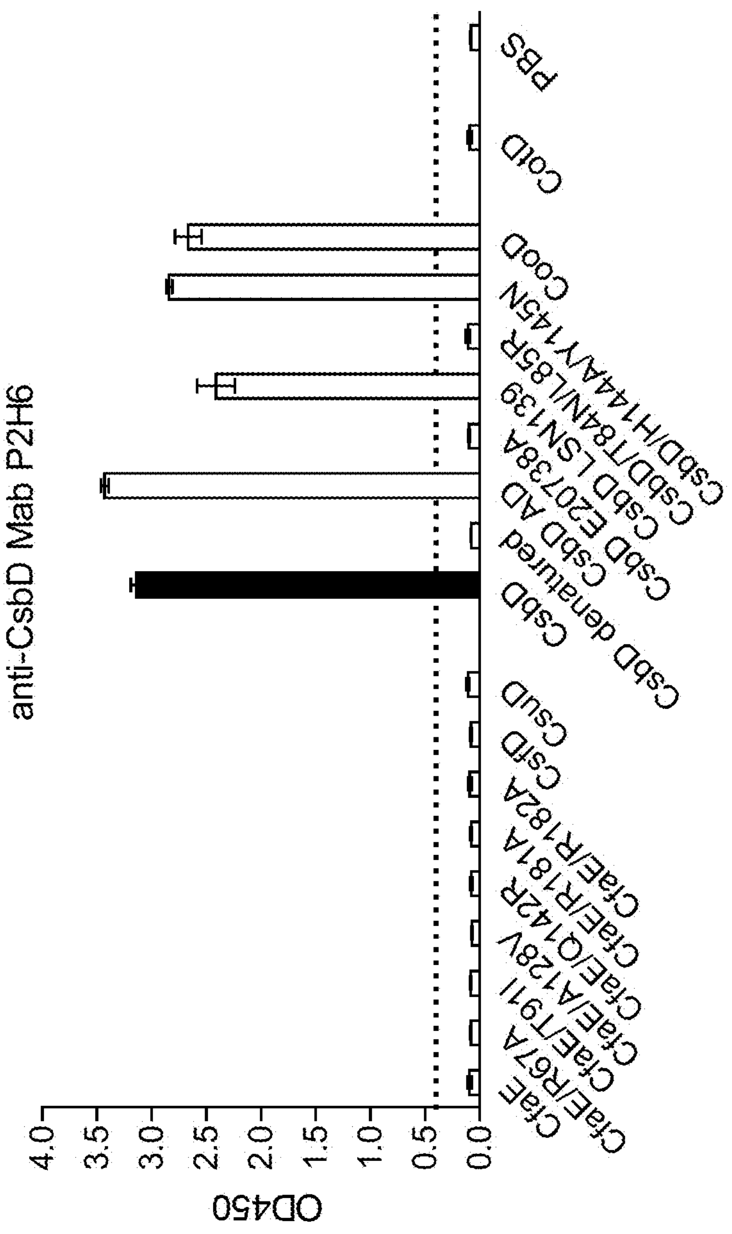
Figure 6D:
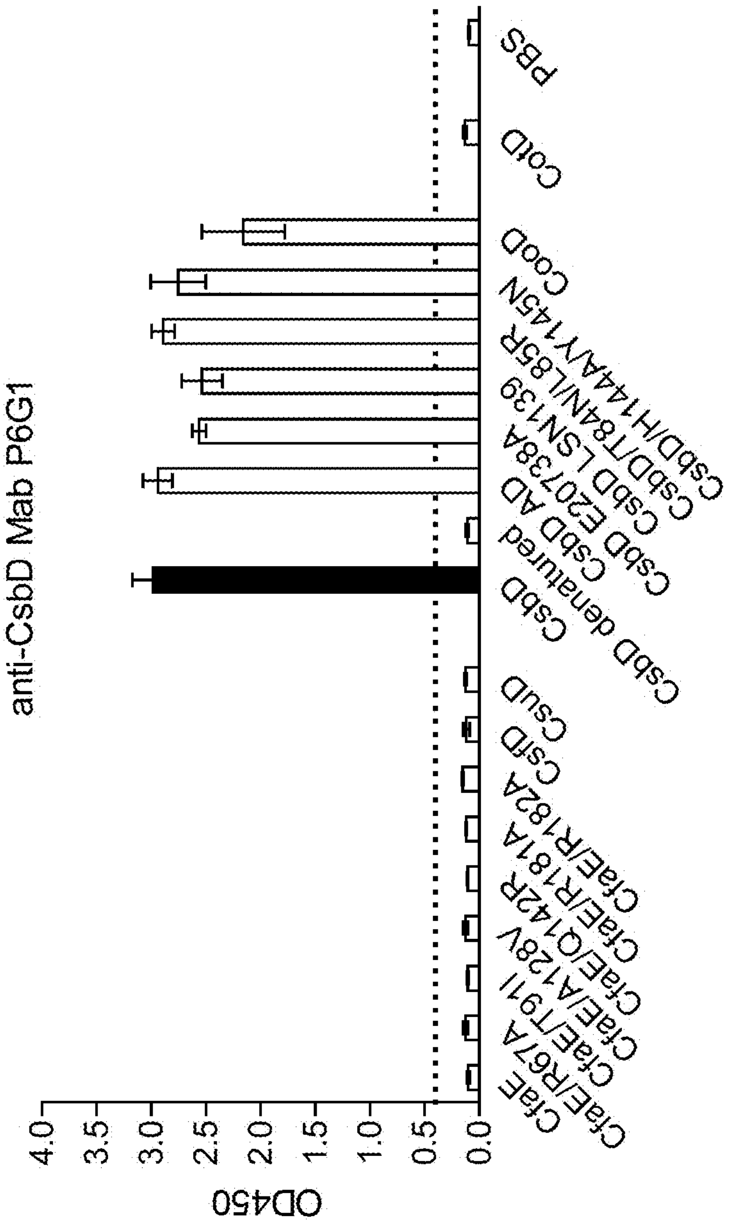
Figure 6E:
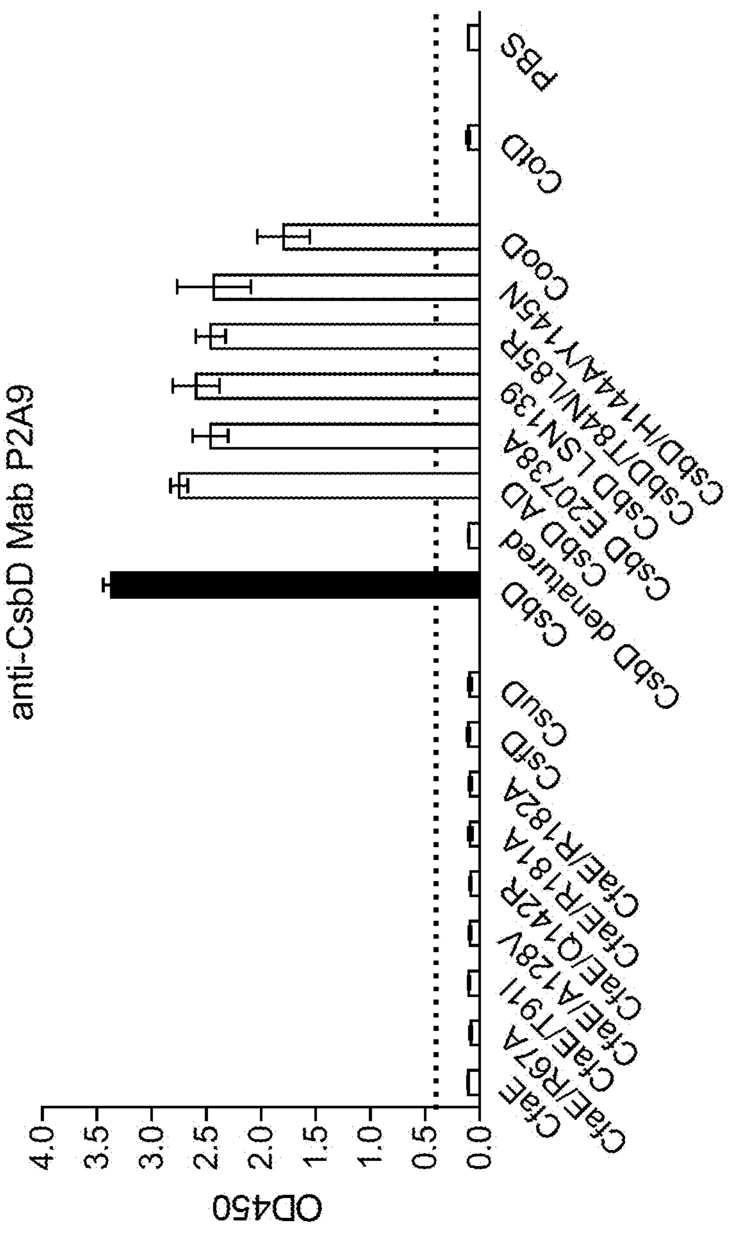
Figure 6F:
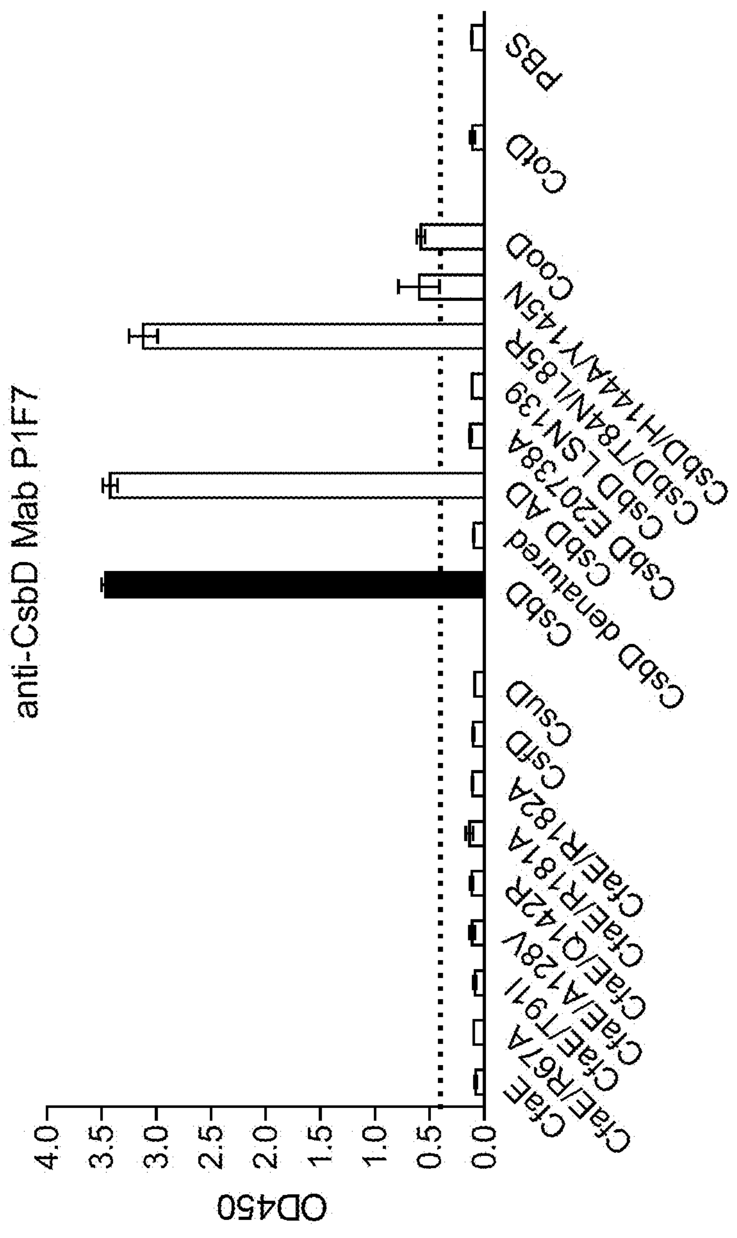
Figure 6G:
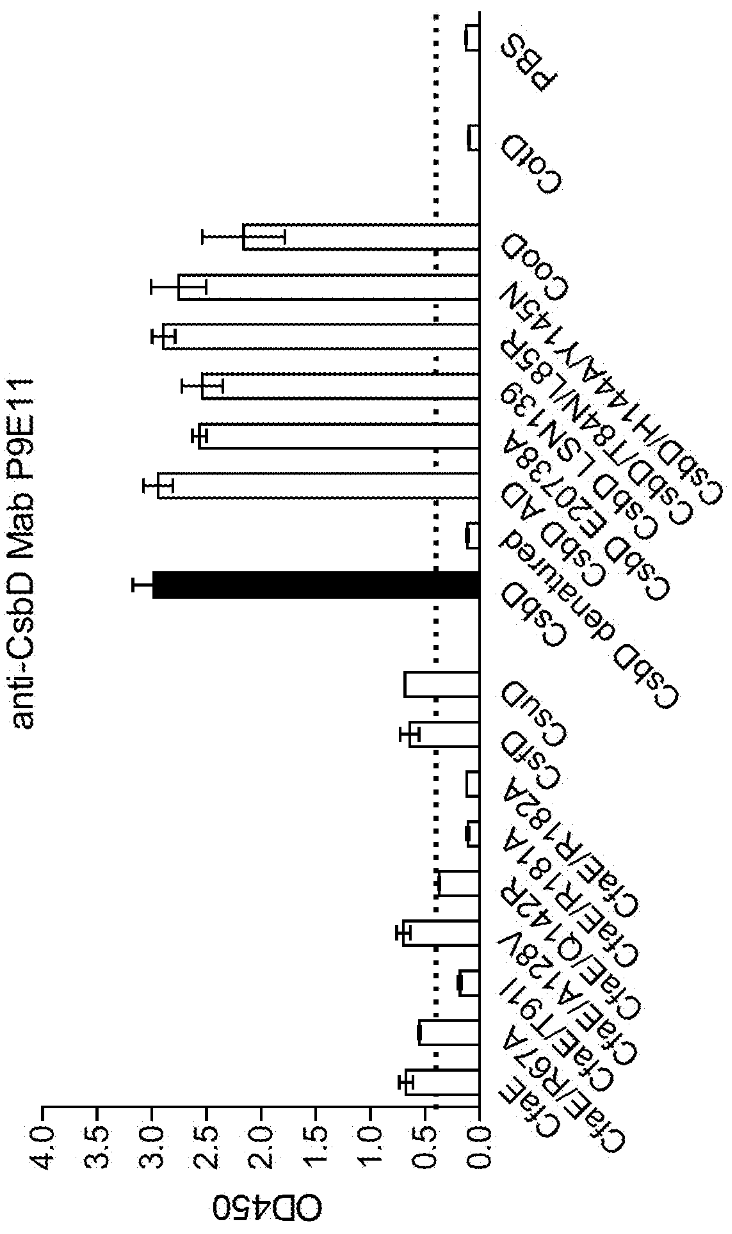

Anti-CsbD mAb P2H6 reacted less to CsbD E20738A (harboring N62S/S74T/T84N/L85R/H144A/Y145N/Y293H allelic variations) or CsbD T84N/L85R than primary CsbD, CsbD AD, CsbD LSNO2-013966/A (harboring L85I/H144A allelic variations) or CsbD H144A/Y145N (FIG. 6(C)). Additional follow on experiments contemplated herein include making a CsbD mutant CsbD/T84A and using the mutant in an ELISA assay to reconfirm that T84 in CsbD is one of the epitope residues for anti-CsbD mAbs P2H6 as previously reported (33). A second anti-CsbD mAb P1F7 reacted nominally to CsbD H144A/Y145N or CsbD L85I/H144A than primary CsbD or CsbD T84N/L85R (FIG. 6(F)), so we reasoned PIF7 epitope contained H144 residue as previously reported (33).

Figure 6H:
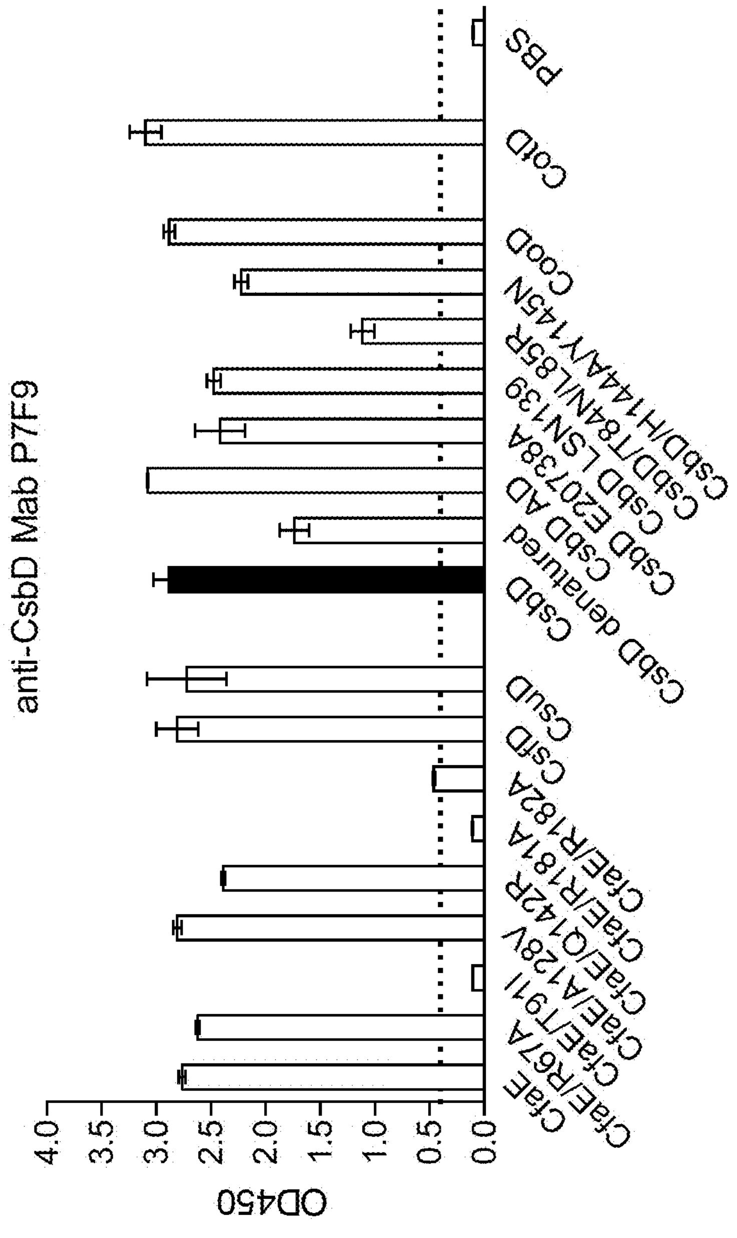
Figure 6I:
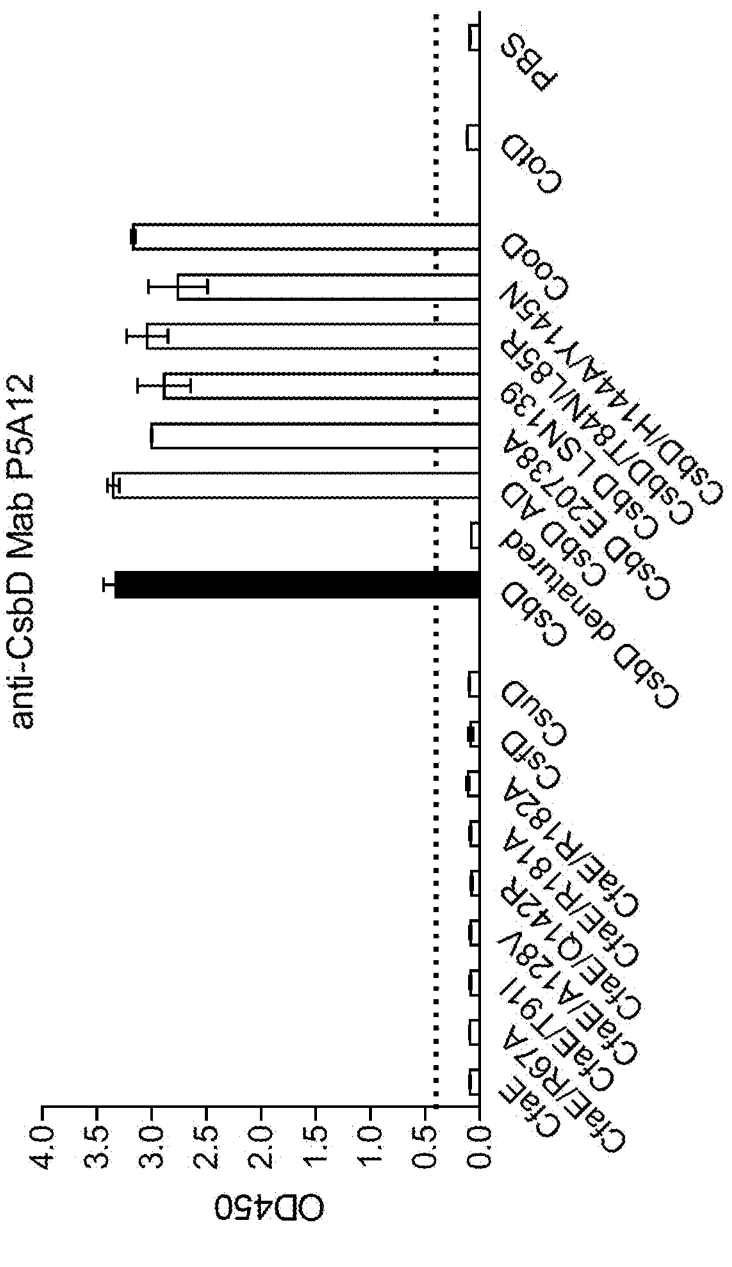
Figure 6J:
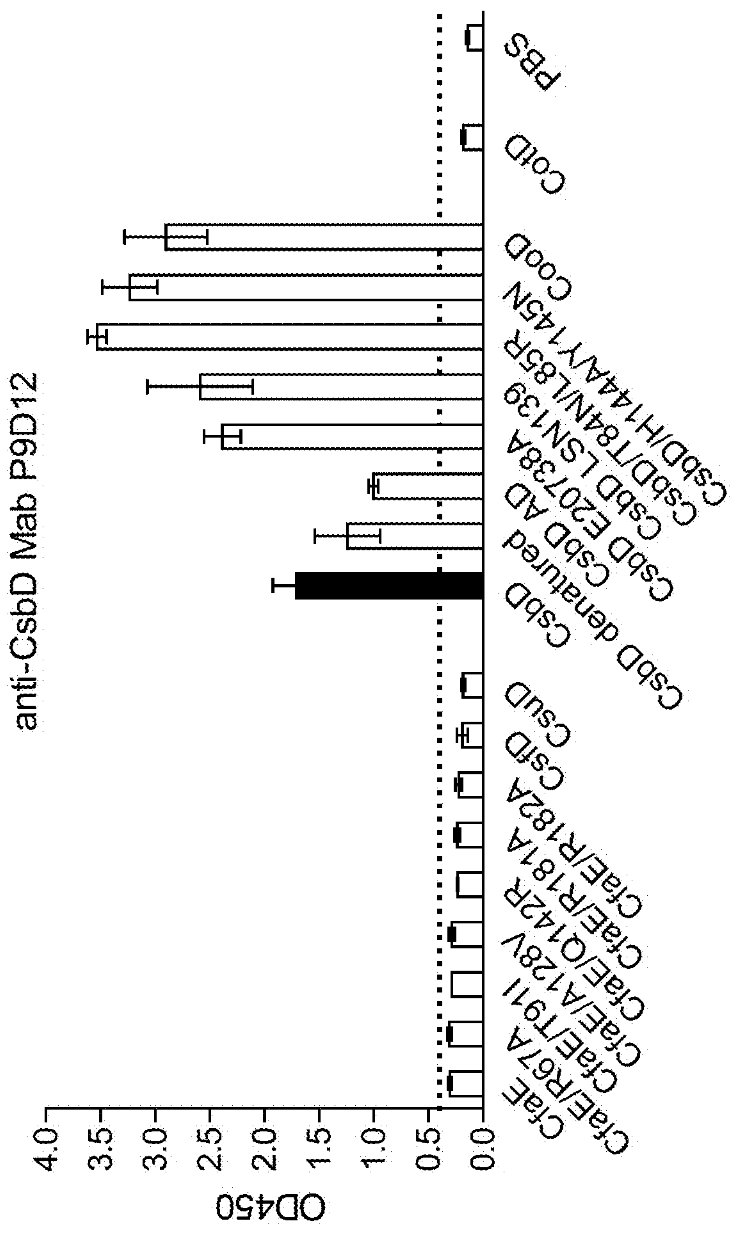
Figure 6K:
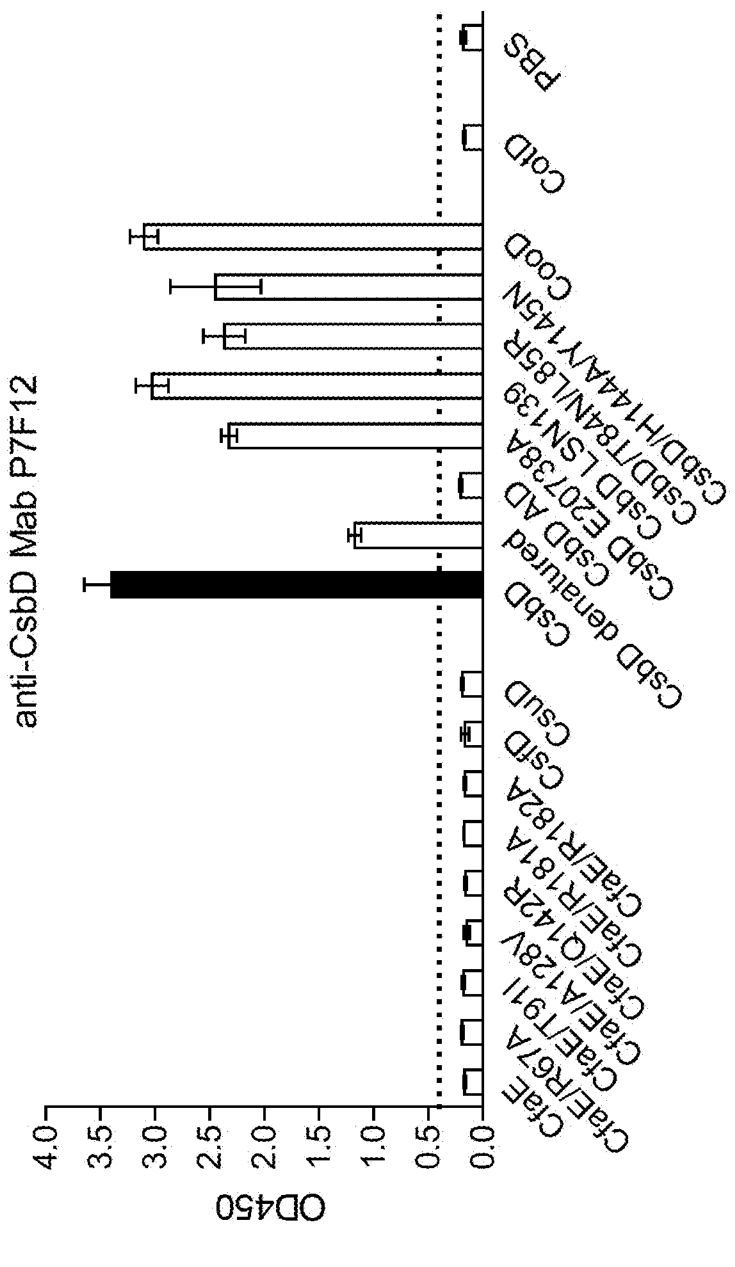
Figure 7A:
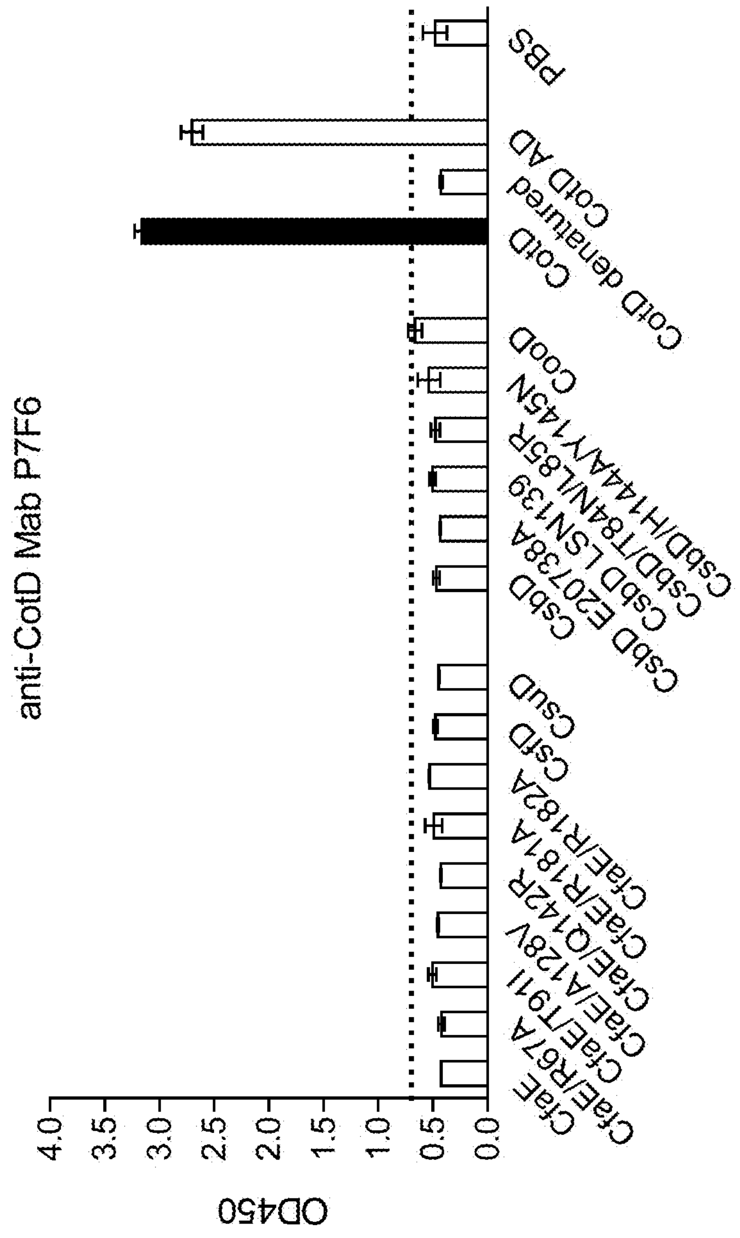
FIGS. 7(A)-(H) depict data from anti-CotD Mab ELISA assays performed to evaluate responses to various class 5 ETEC fimbrial adhesin variants. The responses to the immunogen CotD are highlighted in black bars. The dashed lines represent the limit of detection in the anti-CotD Mab ELISA assays, which equals the sum of average background of PBS buffer and three times of the standard deviation. Specifically.
Figure 7B:
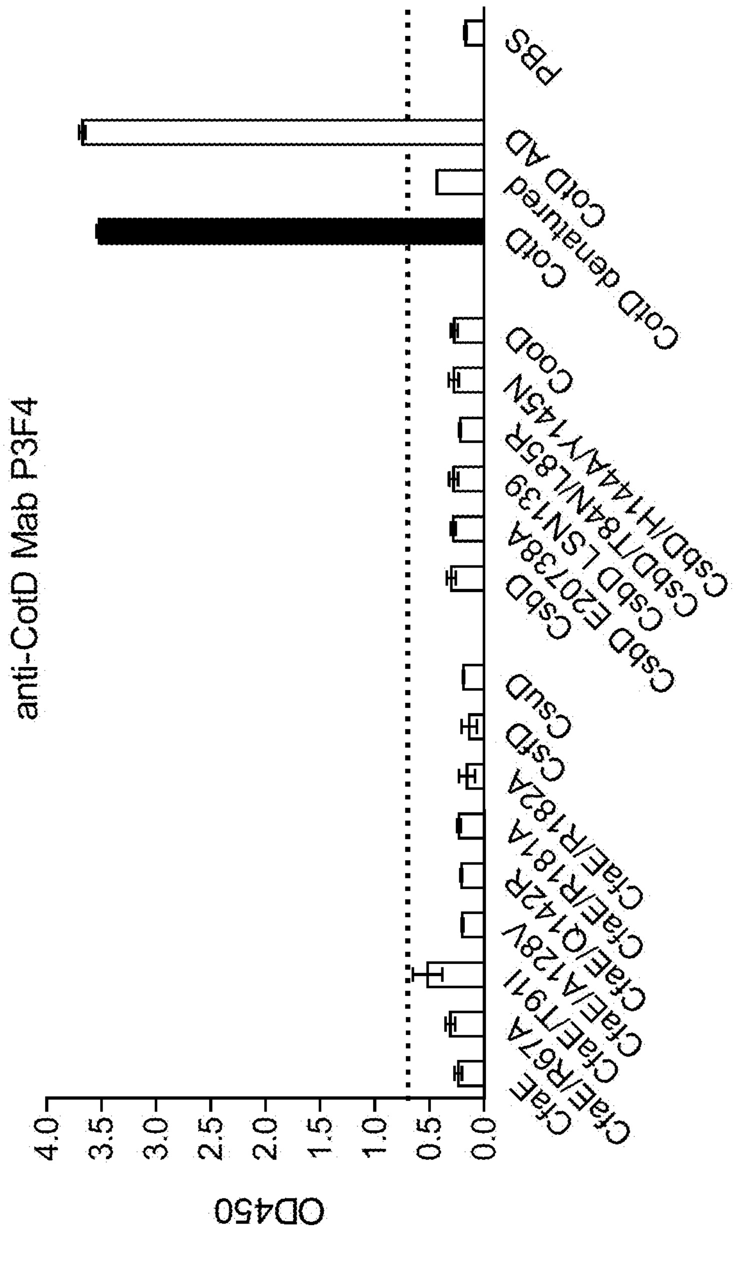
Figure 7C:
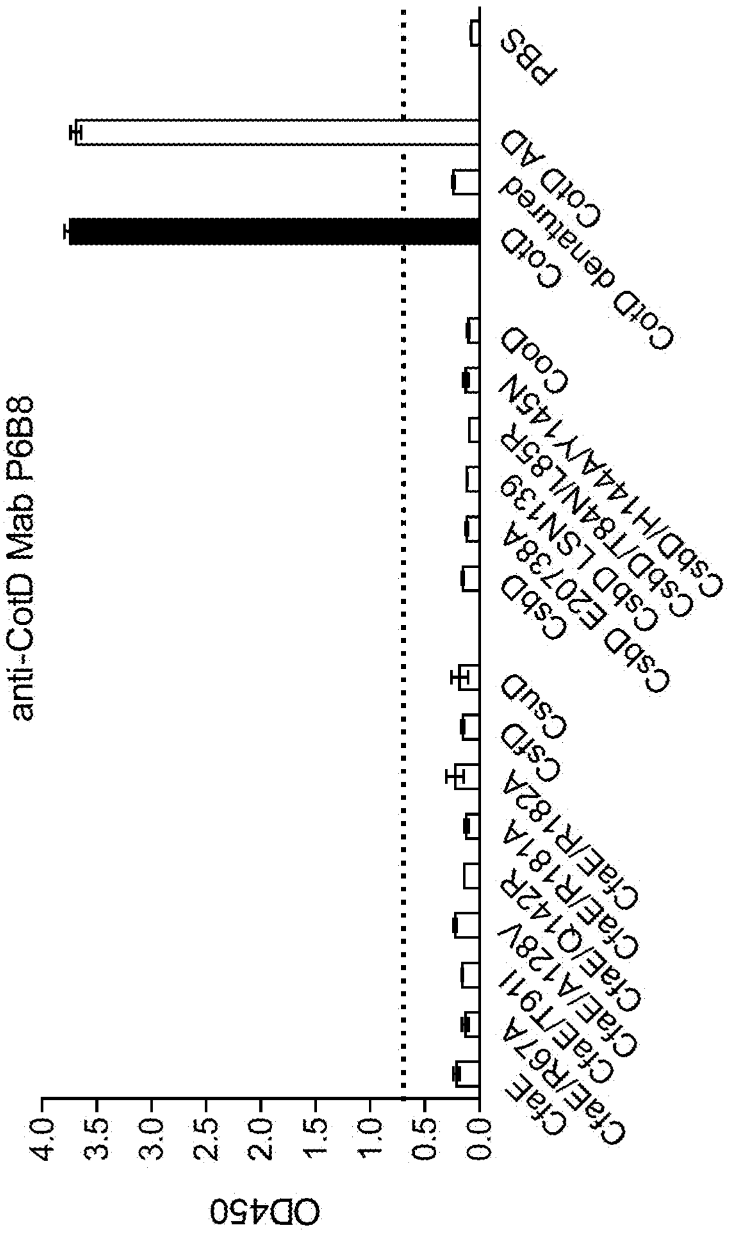
Figure 7D:
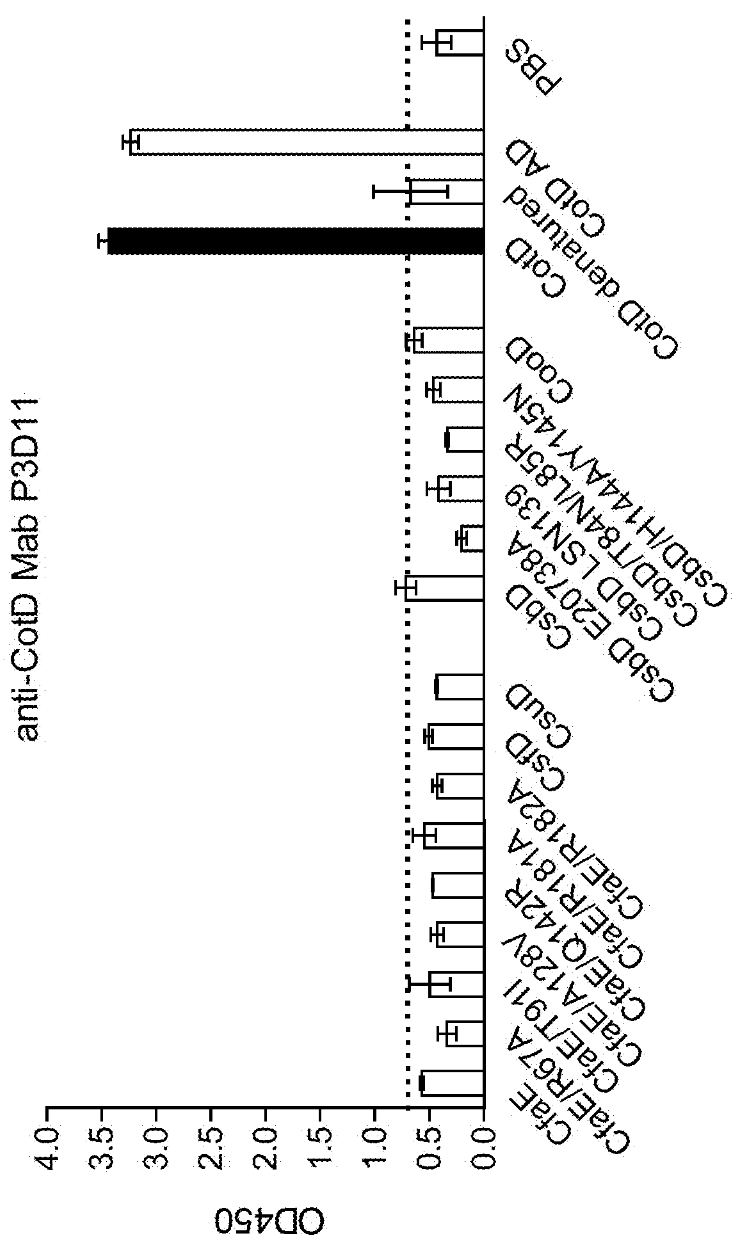
Figure 7E:
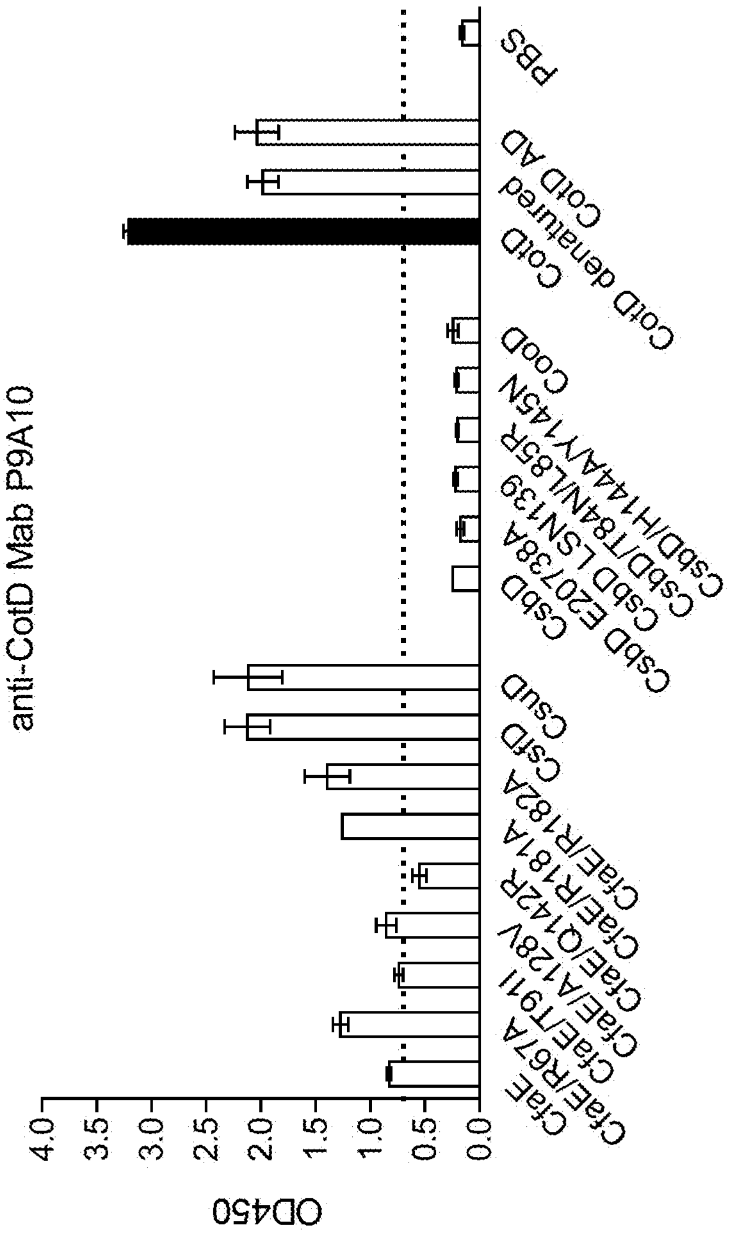
Figure 7F:
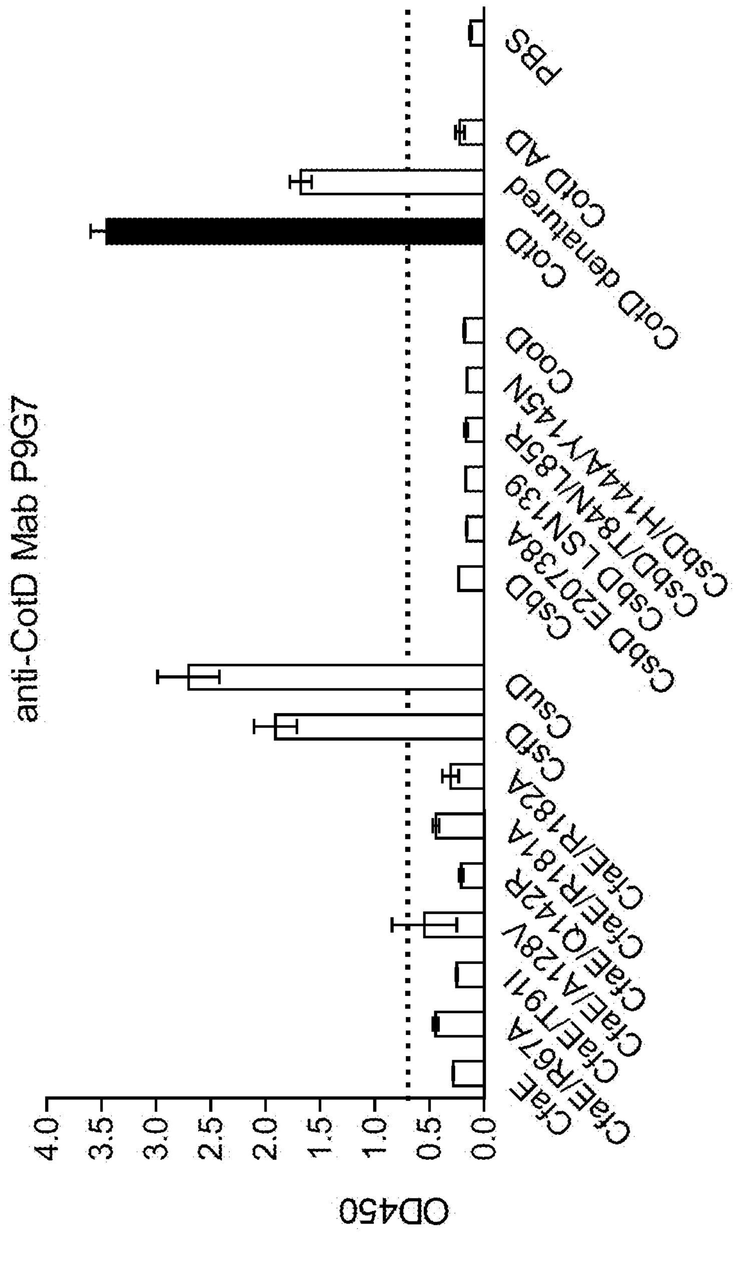
Figure 7G:
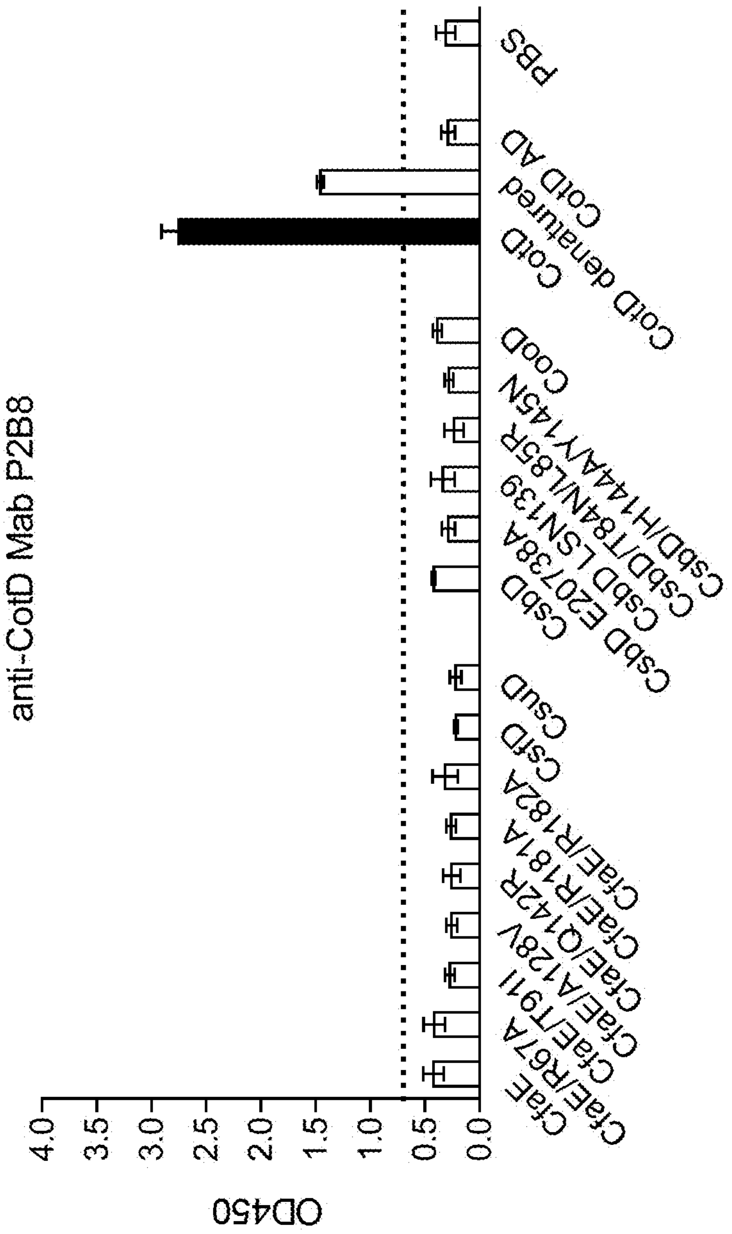
Figure 7H:
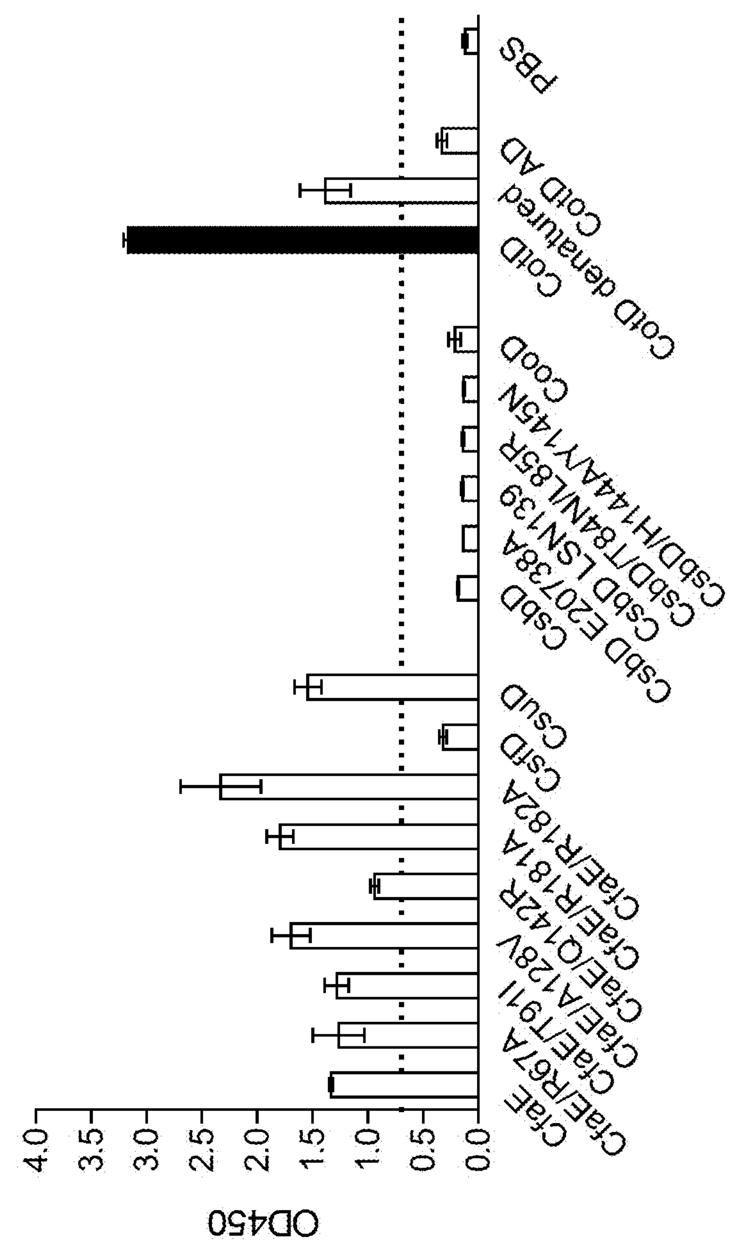
Figure 8A:
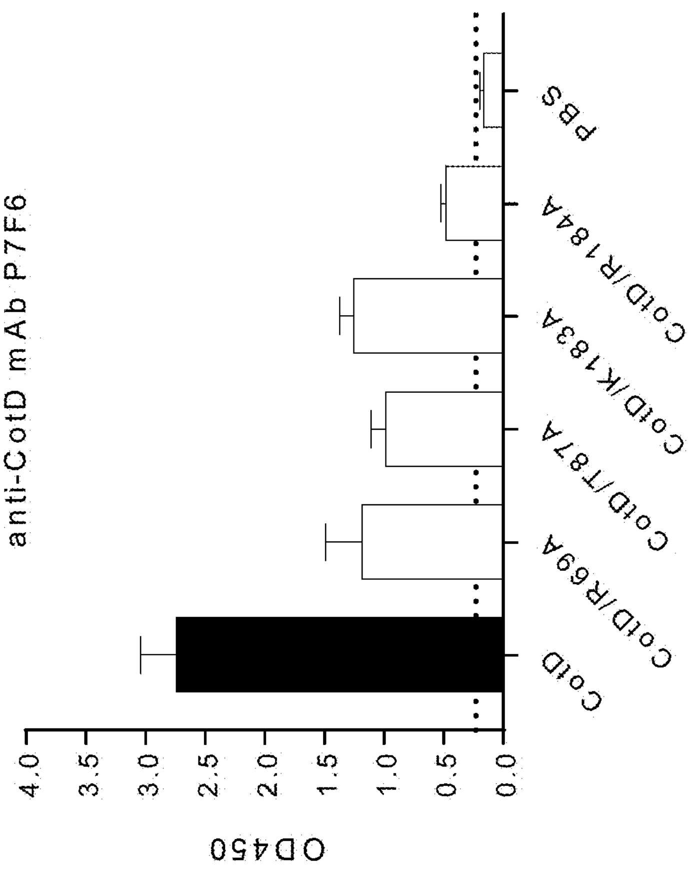
FIGS. 8(A)-(H) depict additional data from anti-CotD mAb ELISA assays performed to evaluate responses to specific CotD adhesin mutants. The responses to the immunogen CotD are highlighted in black bars. The dashed lines represent the limit of detection in the anti-CotD Mab ELISA assays, which equals the sum of average background of PBS buffer and three times of the standard deviation. Specifically.
Figure 8B:
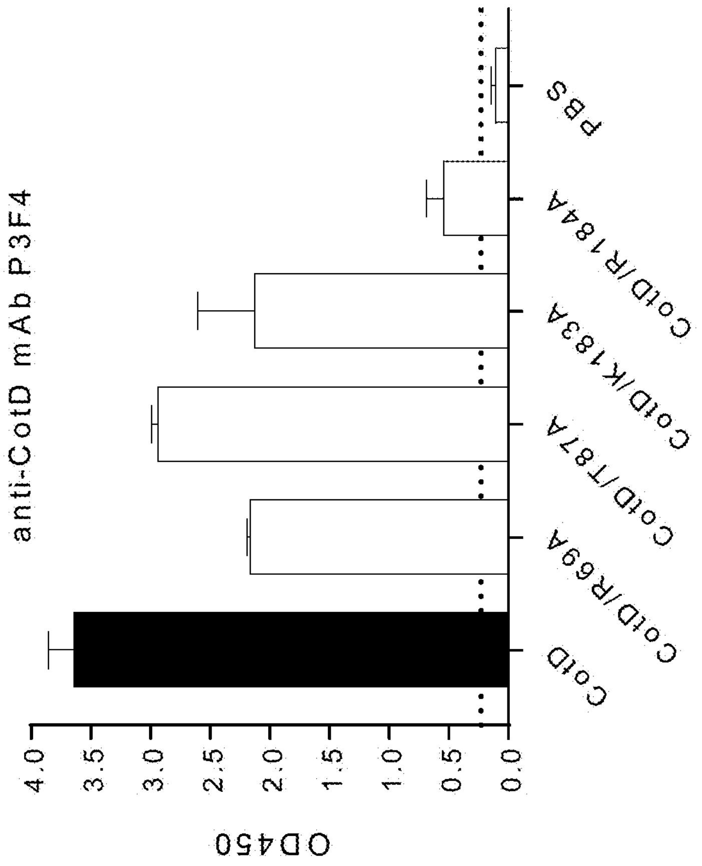
Figure 8C:
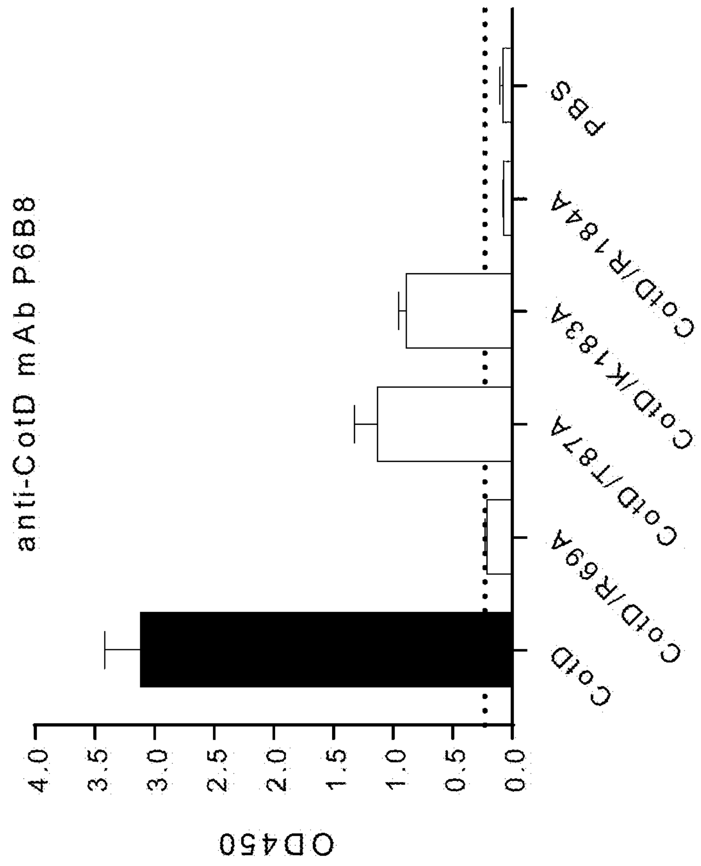
Figure 8D:
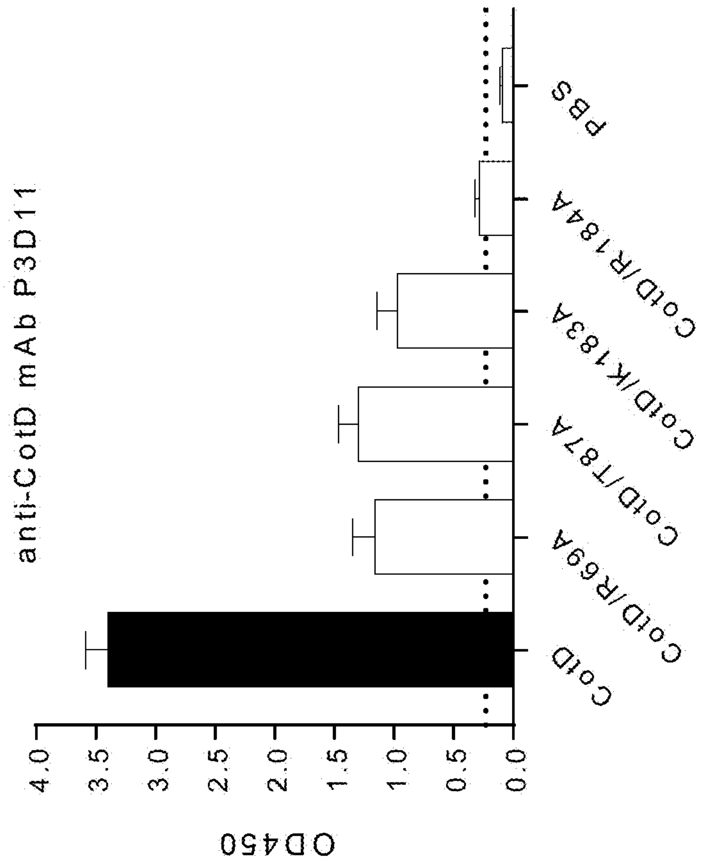
Figure 8E:
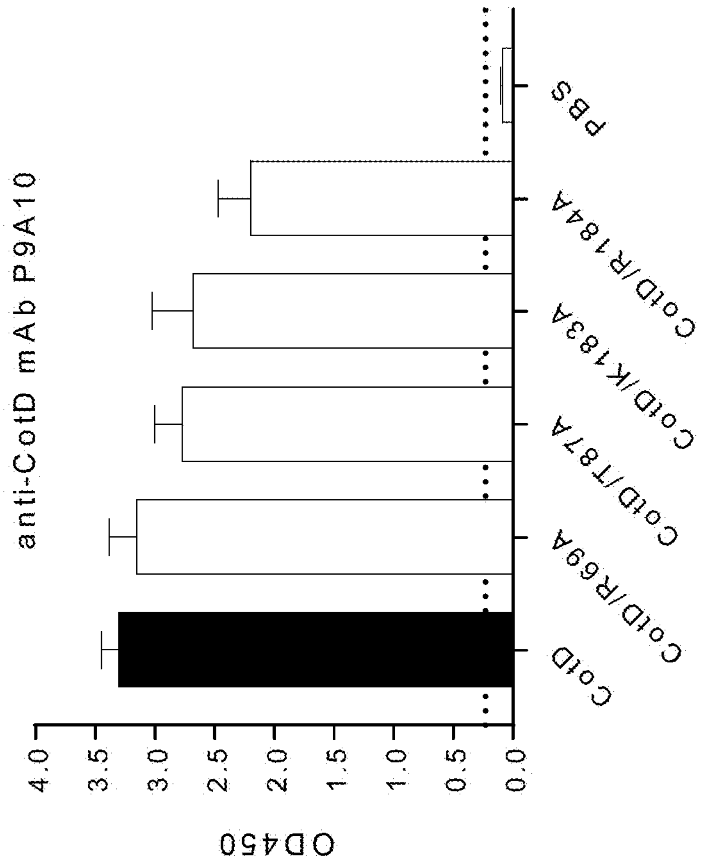
Figure 8F:
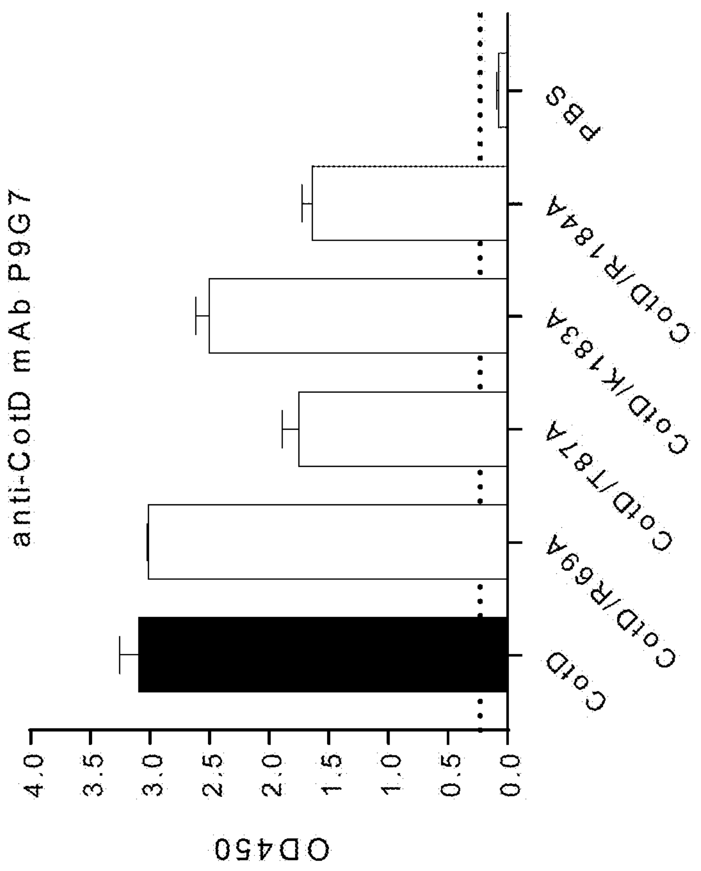
Figure 8G:
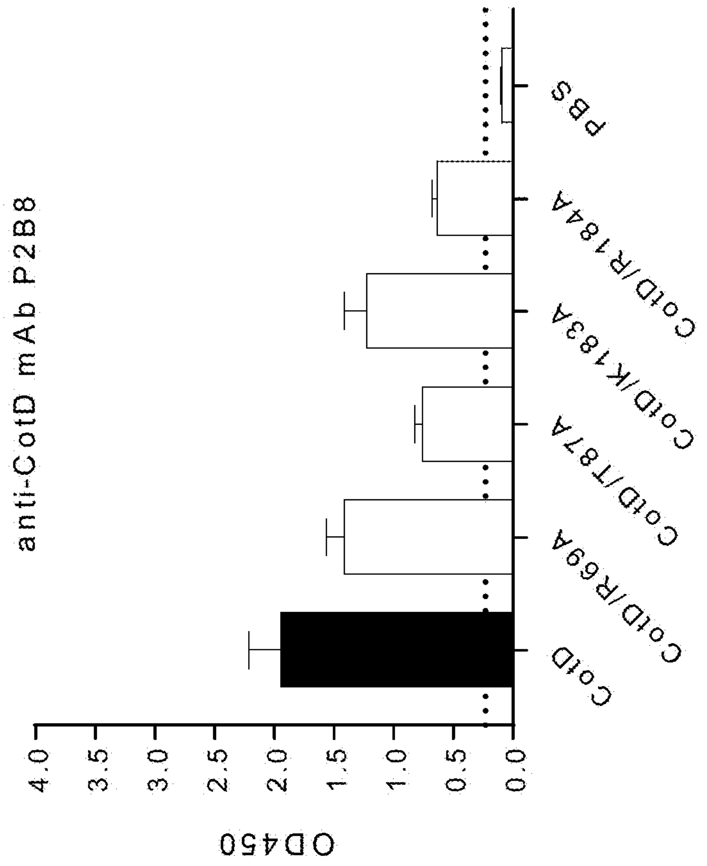
Figure 8H:
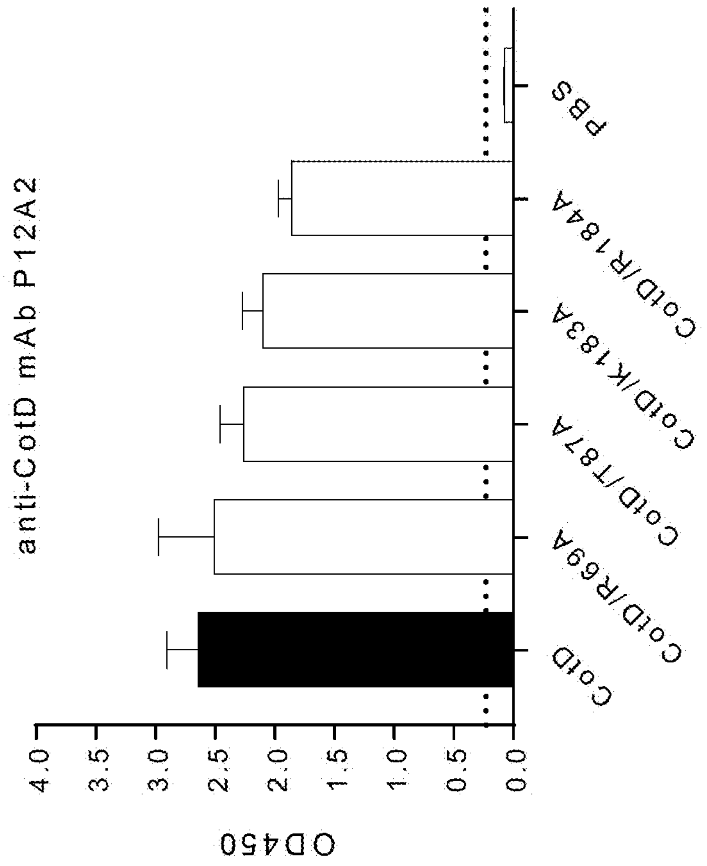

Interestingly, another anti-CsbD mAb P7F9 reacted positively to all CsbD variants, however, much less to CfaE T91V, CfaE R181A and CfaE R182A compared to primary CfaE (FIG. 6(H)); hence, P7F9 epitope included S88 (T91 in CfaE was sequence-aligned with S88 in CsbD), R181 and Y182 (primary CsbD residue 182 is a tyrosine) in CsbD. As discussed in examples below, future experiments contemplated herein include making CsbD mutants CsbD/S88A and CsbD/Y182A and using these mutants in an ELISA assay to reconfirm that S88 and Y182 in CsbD are two of the epitope residues for anti-CsbD mAbs P7F9.

In the additional anti-CotD mAb ELISA with specific CotD mutants (FIG. 8), it was discovered that the anti-CotD mAb P6B8 had nominal reactivity to CotD R69A and CotD R184A, so P6B8 epitope included R69 and R184 residues. Results are summarized in Table 4 for mAb epitope residues and are mapped on CfaE crystal structure (FIG. 4(A)), CsbD and CotD structural models (FIGS. 4(B) & 4(C)) produced using MODELLER (22) and using the CfaE structure (PDB ID 2HB0) as template. Due to the limited number of adhesin allelic variants and mutants, we were only able to infer one or more epitope residues for nine mAbs.

Figure 10:
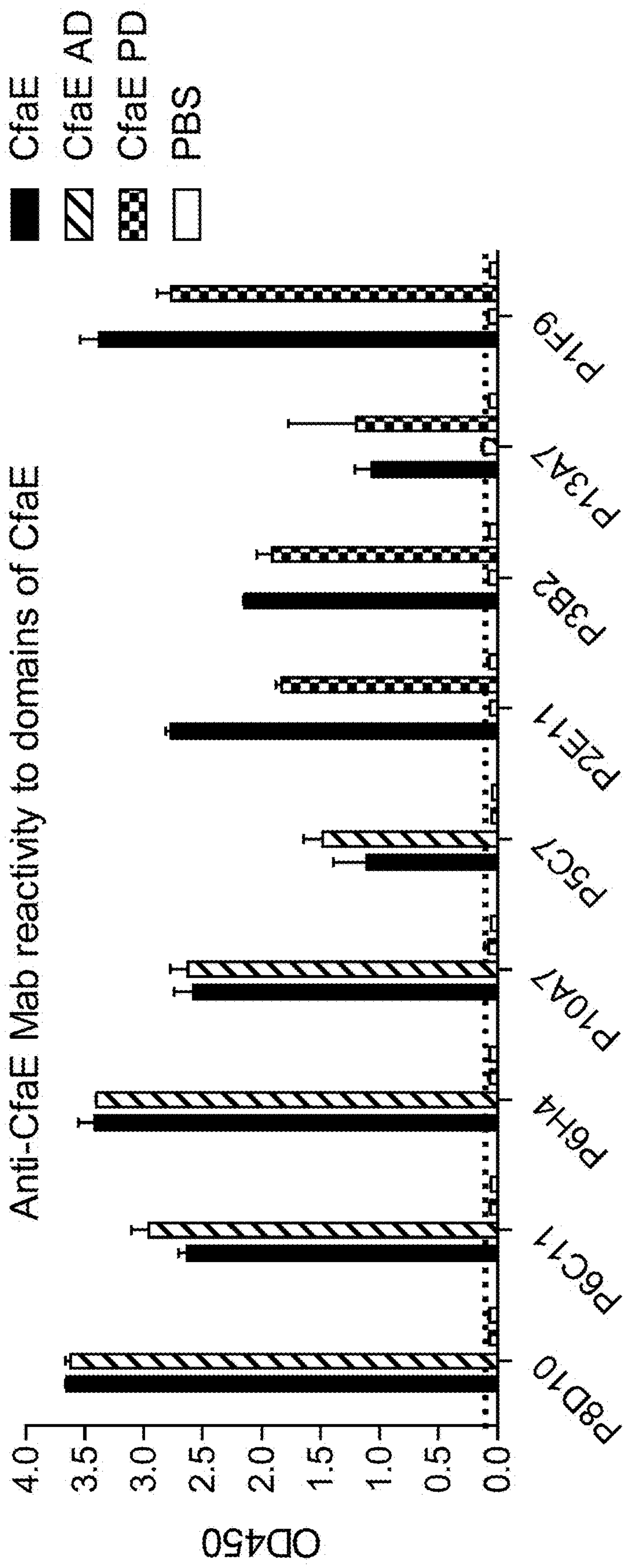
FIG. 10 depicts data from an anti-CfaE Mab ELISA performed to evaluate responses to two domains of CfaE. As depicted, "CfaE AD" refers to CfaE adhesion domain and "CfaE PD" refers to CfaE pilin domain. The responses to the immunogen CfaE are highlighted in black bars. The dashed lines represent the limit of detection in the ELISA assay, which equals the sum of average background of PBS buffer and three times of the standard deviation. All mAbs were produced against the dsc antigen construct disclosed in FIG. 12(A).

The epitope feature (conformational or linear), domain specificity and isotype of the mAbs were determined to complement the epitope analysis. When comparing to the binding to the native adhesins (immunogens) in the ELISA assays (FIGS. 5-7), twenty mAbs showed minimal binding to the heat denatured adhesins, suggesting that these recognize conformational epitopes (Table 4). Based on the reactivity of each mAb to the respective adhesin domains and mutants in the adhesin domain (FIGS. 5-7), nineteen of the 28 mAbs were adhesin domain specific (Table 4). Specifically, five of nine anti-CfaE mAbs, nine of eleven anti-CsbD mAbs, and five of eight anti-CotD mAbs were specific to the adhesin domains of CfaE, CsbD and CotD, respectively. In addition, we confirmed that the four anti-CfaE mAbs, which were not reactive to the CfaE adhesin domain, showed reactivity to the CfaE pilin domain in the ELISA assay (FIG. 10). Of 28 mAbs, 23 mAbs isotypes were determined as IgG1 by IsoQuick™ strips (MilliporeSigma, St. Louis, MO) (Table 4), consistent with mouse IgG isotype distribution (23). Based on these data, the identified key residues in the epitopes of anti-adhesin mAbs were located at or close to the receptor binding regions of the class 5 adhesin (33).

Example 8: Hemagglutination Inhibition (HAI) Activity of Anti-Adhesin mAbs

As previously reported, the presence of mAbs cross reactive to heterologous class 5 adhesins prompted us to investigate if the cross-reactivity patterns observed in the ELISA assays would be retained in the functional hemagglutination inhibition (HAI) assay. To test the potency and functional cross-reactivity of each mAb, we determined the minimum concentrations of mAbs to inhibit MRHA of bovine erythrocytes elicited by eight class 5 ETEC (Table 5) (33). Data provided therein indicate that all five anti-CfaE adhesin-domain specific mAbs (P8D10, P6C11, P6H4, P10A7 and P5C7) were very potent inhibitors of homologous ETEC (CFA/I H10407) hemagglutination with the minimum inhibition concentrations (MIC) less than 10 g/ml. Among them, P10A7 and P5C7 also showed strong or moderate functional cross-reactivity to the heterologous primary CS17 ETEC (CS17 WS6788A), suggesting the three residues (R67, S86 and R181) within epitopes of P10A7 and P5C7 were functional epitope residues shared between CfaE and CsbD. Of the four anti-CfaE pilin-domain specific mAbs, P3B2, P1F9 and P2E11 had high or moderate hemagglutination inhibition activity (HAI) against the CF-homologous strain, which was unexpected since the putative receptor-binding domain of CfaE has been localized to the adhesin domain of CfaE (24) (FIG. 4(A)). Interestingly, P3B2 even exhibited moderate and low inhibitory effects on the heterologous CS17 and CS1 strains, respectively. One anti-CfaE pilin-domain specific mAb P13A7 did not show homologous HAI activity up to 400 μg/ml, however displayed moderate heterologous HAI to the CS17 strain (33).

Among the anti-CsbD mAbs, seven of nine mAbs specific to the adhesin domain were highly potent MRHA inhibitors for the CF-homologous strain (CS17 WS6788A). These mAbs were generally less potent inhibitors for the other two CS17 strains, presumably based on allelic variation. Five CsbD mAbs, P7C2, P9A5, P2H6, P6G1 and P2A9, also showed functional cross-reactivity to the CS1 heterologous class 5b strain (Table 5), suggesting there are common functional epitopes, such as T84 in CsbD, shared between CsbD and CooD. No HAI activity of the other two adhesin-domain specific mAbs (P7F9 and P5A12) was observed to any of the eight ETEC strains within the normal range of tested concentrations (≤250 μg/ml), which was unexpected when initially reported because P7F9 was shown to be broadly reactive to all six adhesins by ELISA (Table 5) and its epitope included the conserved R181 (FIG. 4(B)). Two mAbs (P9D12 and P7F12) specific to the CsbD pilin domain had moderate or low potency in inhibiting CF-homologous MRHA, and neither of them exhibited any CF-heterologous HAI activity (33).

Among six anti-CotD mAbs specific to the adhesin domain, three of them (P7F6, P3F4 and P6B8) were high potent inhibitors of MRHA against the CS2-homologous ETEC strain; however, the other three mAbs (P3D11, P9A10 and P9G7) showed moderate or low levels of HAI to the CF-homologous ETEC strain. Two anti-CotD mAbs (P2B8 and P12A2) specific to the pilin domain displayed low HAI activity to the CS2-homologous strain. None of the anti-CotD mAbs exhibited significant functional cross-reactivity to the CF-heterologous class 5 ETEC strains (33).

Example 9: MAb P8D10 Reduced H10407 Binding to Caco-2 Cells

Caco-2 cells differentiate into an intestine tissue-like monolayer, to which ETEC has been shown strong binding. Thus, in addition to evaluating the blocking effect of mAb using erythrocytes, the more physiologically related Caco-2 cell model provides a useful assay to characterize inhibitory effects of the mAbs. Specifically, we evaluated whether the binding of H10407 ETEC to Caco-2 cells was reduced by mAb P8D10.

Figure 11:
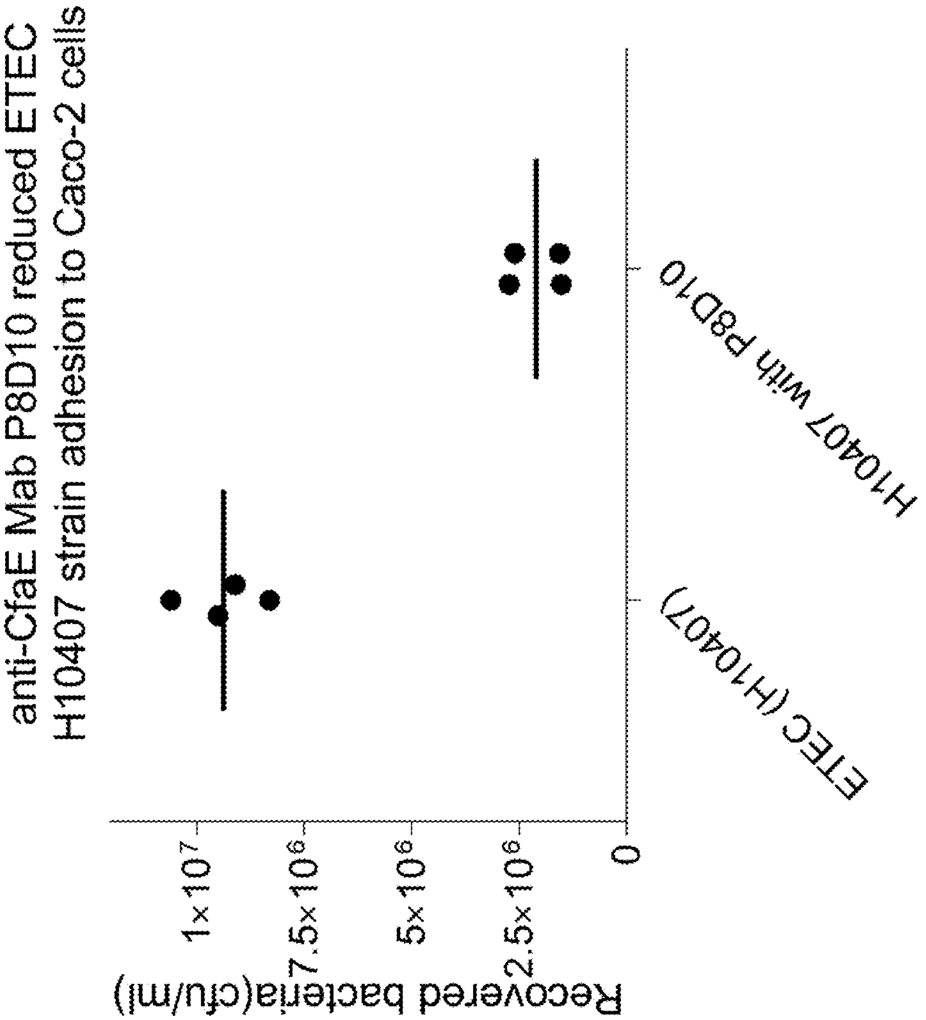
FIG. 11 depicts data showing that anti-CfaE Mab P8D10 effectively reduced the adhesion of ETEC H10407 strain to Caco-2 cells. All mAbs were produced against the dsc antigen constructs disclosed in FIG. 12(A).

Briefly, the ETEC H10407 strain was grown on CFA agar plate at 37° C. overnight. The bacteria were harvested and resuspended in phosphate buffered saline (PBS, pH 7.4) until the $OD_{650}$ reached 1.5, approximately equivalent to $1.2\times10^9$ bacteria/ml. The anti-CfaE Mab P8D10 was added into the resuspended bacteria at final concentration of 0.4 mg/ml. The bacteria alone (250 μl) and the admixture (250 μl) of bacteria and P8D10 were added into wells of Caco-2 cells, which contained 750 ul of Caco-2 growth media with 1% mannose. After the Caco-2 cell wells were incubated at 37° C. for 3 hours, the wells were carefully washed with 1 ml of PBS five times. After washing, the Caco-2 cells were detached and lysed from the wells by incubation with 1 ml of 0.1% triton X-100 at room temperature for 10 minutes. A serial 10-fold dilution of the lysed Caco-2 cells was plated on LB agar plates, which were incubated at 37° C. overnight. The recovered bacteria (bacteria bound to the Caco-2 cells) were determined by the colony forming unit (CFU) counts. Data are provided in FIG. 11 which demonstrate that the mAb P8D10 group ($2.10\times10^6$ cfu/ml) reduced the binding of ETEC H10407 strain to Caco-2 cells more than 4 times than bacteria alone group ($9.38\times10^6$ cfu/ml), suggesting the blocking effect of mAb in the intestine tissue-like Caco-2 cell model is consistent with results from previously reported hemagglutination inhibition assays.

Example 10: Antibody Variable Domain Sequencing of Hybridomas P8D10, P7C2, P9A5, P6B8, P5C7 and P1F9

Hybridoma cells P8D10, P7C2, P9A5, P6B8, P5C7, P1F9, PIF7, P7F6, and P3F4 were provided to a commercial vendor for antibody variable domain sequencing. (GenScript, Piscataway, NJ). Following the technical manual of TRIzol® Reagent (Cat. No.: 15596-026; Ambion, Foster City, CA) total RNA was successfully isolated from all of the hybridomas except hybridoma cells PIF7, P7F6, and P3F4.

Total RNA obtained from hybridomas P8D10, P7C2, P9A5, P6B8, P5C7, and P1F9 was reverse-transcribed into cDNA using either isotype-specific anti-sense primers or universal primers following the technical manual of PrimeScript™ 1st Strand cDNA Synthesis Kit (Cat. No.: 6110A; Takara, Mountain View, CA.) Antibody fragments of heavy chain and light chain were amplified according to the standard operating procedure (SOP) of rapid amplification of cDNA ends (RACE) of GenScript. Amplified antibody fragments were cloned into a standard cloning vector separately. Colony PCR was performed to screen for clones with inserts of correct sizes. The consensus sequence was provided. In each case, five clones were sequenced for each VH and VL, and all five clones expressed >99% sequence identity. The sequence and annotation information obtained for the hybridomas is provided in FIGS. 14(A)-14(F) using Kabat analysis, and 15(A)-15(F) using IMGT/NCBI IGblast, and the IMGT analysis of V (D)J junctions for each hybridoma is provided in FIGS. 16(A)-16(I).

Example 11: Quantification of ETEC Proteins Using ELISA

Figure 17A:
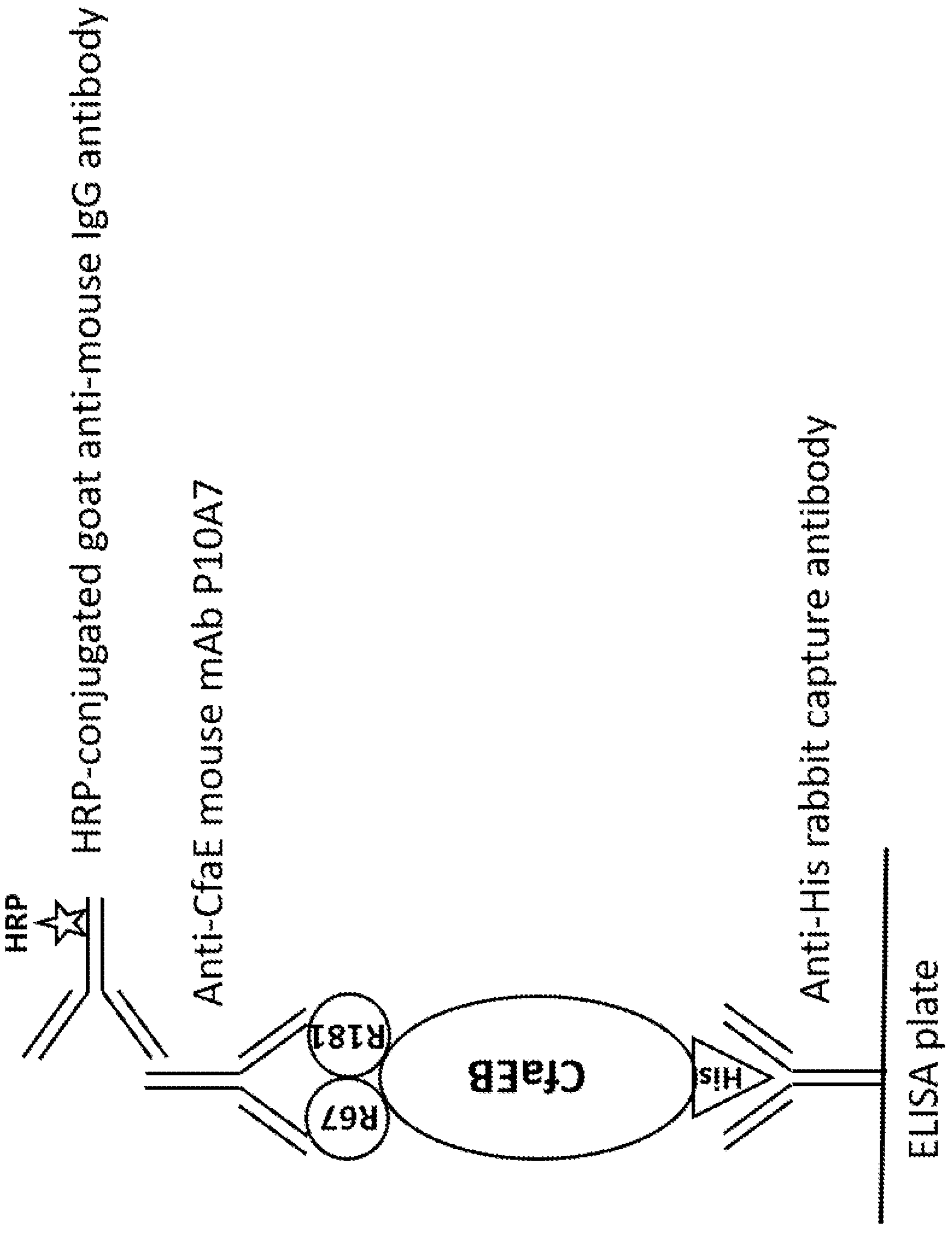
FIGS. 17(A)-17(C) depict quantification of CfaEB protein in crude cell lysate using anti-CfaE mAb P10A7. Specifically.
Figure 17B:
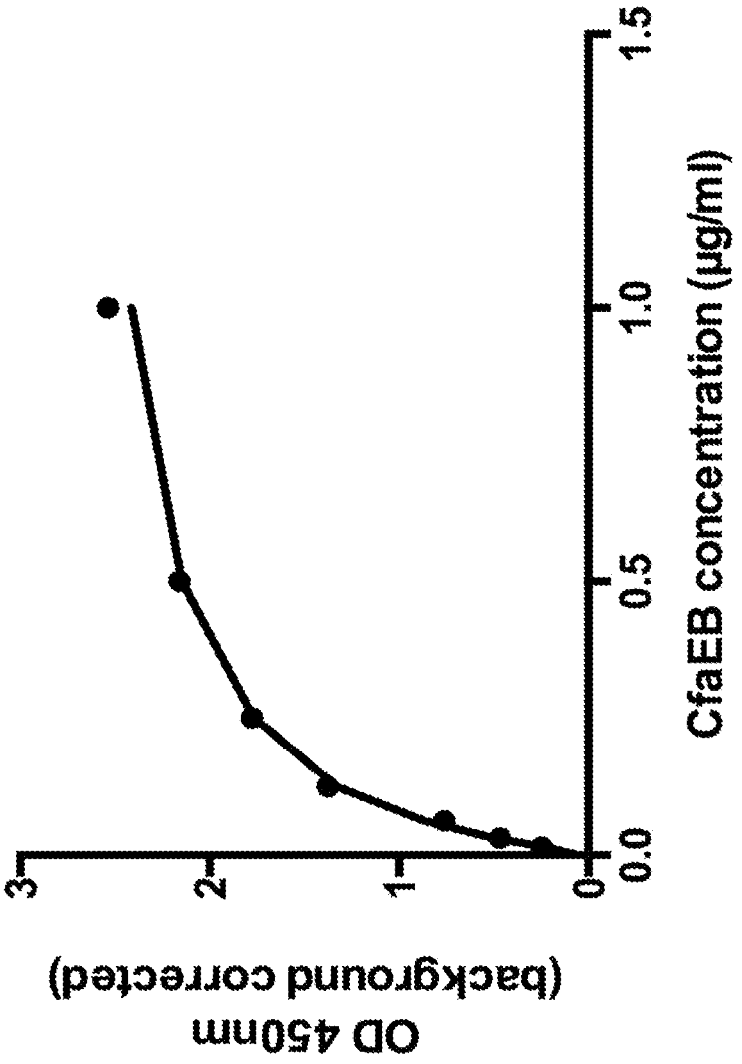

As newly reported herein, the anti-CfaE mAb P10A7 may be used to quantify CfaEB protein in crude BL21(DE3)/pET24-dsc$_{19}$CfaEB(his)6 bacterial cell lysate. This bacterial cell lysate was generated using a previously published method (10), and employing CfaEB with a C-terminal 6xHis tag. The capture ELISA principle is shown in FIG. 17(A) and is explained in detail below. Briefly, ELISA plates were coated with anti-His rabbit polyclonal antibody which can capture the 6xHis tag on the C-terminus of CfaEB. The mouse anti-CfaE mAb P10A7 can specifically recognize the R67 and R181 residues located at the top of CfaEB. The mouse mAb P10A7 is recognized and amplified by the horseradish peroxidase (HRP)-conjugated goat anti-mouse IgG detecting antibody. The substrate o-phenylenediamine dihydrochloride (OPD) was added, and the optical density (OD) was read spectrophotometrically at 450 nm. A series concentration from 0.03 ug/ml to 1.0 ug/ml of purified CfaEB was first tested and the optical density of each concentration (OD 450 nm) was plotted (black dots and curve) as shown in FIG. 17(B).

Figure 17C:
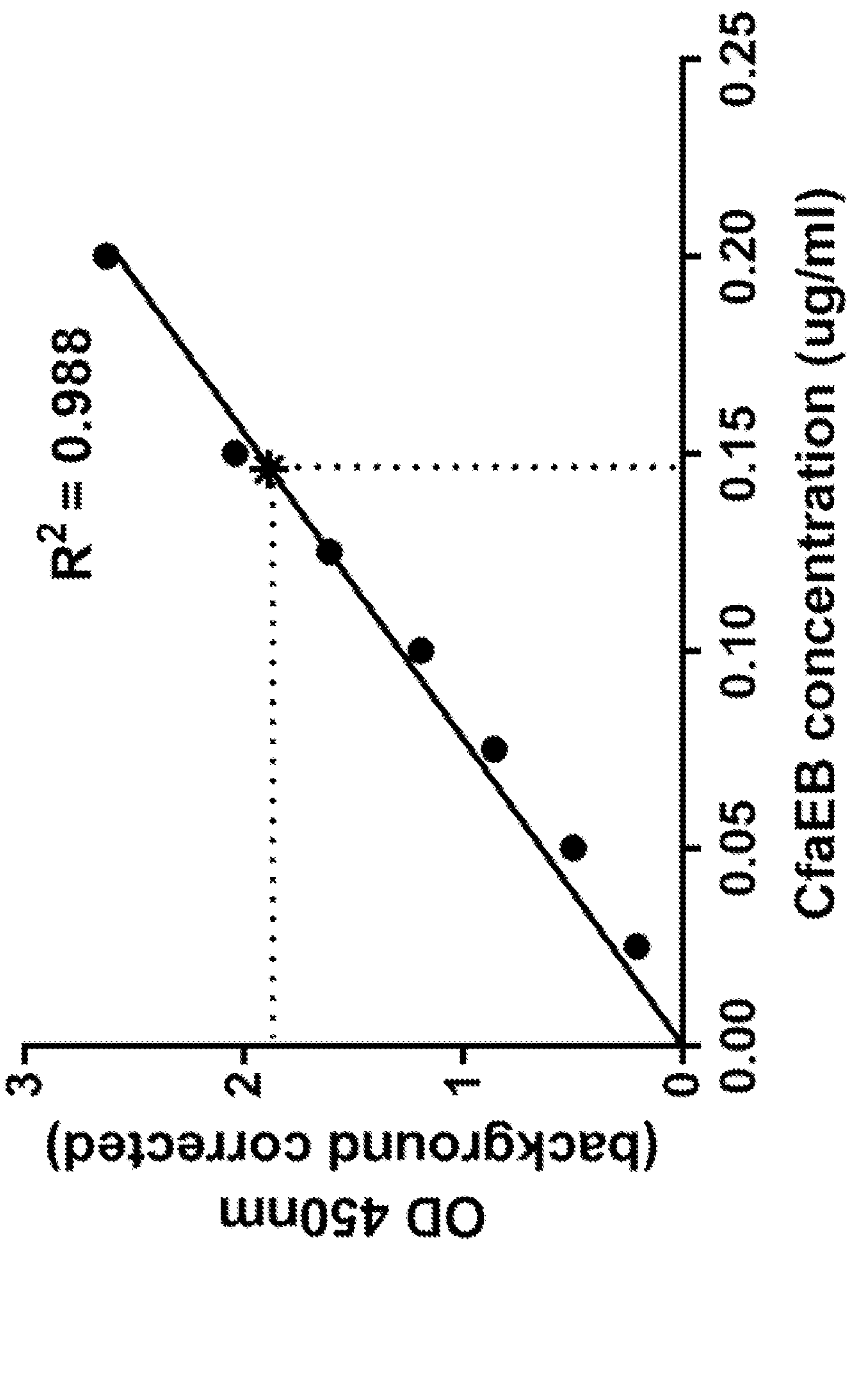

Data suggest that the OD value started to saturate at or above concentration of 0.25 ug/ml of CfaEB. A series concentration from 0.025 ug/ml to 0.2 μg/ml of purified CfaEB was also tested, and the optical density of each concentration was plotted (black dots) and fitted in a linear regression (black line) as shown in FIG. 17(C). The R2 of the fitted linear curve (standard curve) was 0.988, suggesting the goodness-of-fit between the data and the standard curve was very high. Also, a similar crude bacterial cell lysate sample containing CfaEB was diluted 3200 fold (dilution factor) in PBS buffer and was tested. The optical density of the diluted sample was plotted (black star in FIG. 17(C)) on the standard curve, and the concentration of the diluted sample was interpolated. The original concentration of CfaEB in the crude cell lysate was the product of the dilution factor and the concentration of the diluted sample.

Experimental details of ELISA: 96-well maxisorp Nunc F plastic plates were coated overnight at 4° C. with 2 μg/ml, 100 μl/well of the capture antibodies, rabbit anti-His polyclonal antibodies (Genscript, Cat. No. A00174) in phosphate buffered saline, pH 7.4 (PBS). After incubation, the plates were washed 3 times with PBS. Each well was blocked with 200 μl of 5% fetal bovine serum (FBS, Gibco) and incubated for 1 h at 37° C. After the plates were washed 3 times with PBST (PBS containing 0.05% Tween-20), a series dilution of purified CfaEB (0.03 to 1 μg/ml), a series dilution of samples (800×, 1600×, 2000×, 2400×, 3200×), and negative control were prepared in PBS, pH 7.4, and 100 μl of each was added to the wells. Each condition was triplicated and the plates were incubated for 1 h at 37° C. and subsequently washed 3 times with PBST. Each well was added with 100 μl of mouse anti-CfaE mnAb P10A7 at 2 μg/ml and incubated for 2 h at 37° C. followed by 5 times PBST washes. The plates were added with 100 μl well goat anti-mouse immunoglobulin G (IgG) horseradish peroxidase (HRP)-conjugated secondary antibody (Jackson ImmunoResearch) 1:1000 diluted in 5% FBS, and incubated for 1 h at 37° C. The plates were washed 3 times with PBST and 100 μl of substrate (1 mg/ml o-phenylenediamine (Sigma) in sodium citrate buffer (Sigma), pH 4.5 containing 0.4 μl/ml of hydrogen peroxide) were added to each well. After being incubated for 15 to 20 minutes at room temperature, the plates were measured at 450 nm on a Synergy HTX plate reader (Bio-Tek Instruments). The negative control OD value was subtracted from the OD value of samples. The mean background corrected OD value of the triplicates and the concentrations of CfaEB were plotted.

Example 12: Prophetic Production of Human-Mouse Chimeric Antibodies and Humanized Antibodies Given the sequence information of the variable regions of the murine mAbs disclosed herein, it is further contemplated herein that human-mouse chimeric mAbs comprising the variable regions of these murine mAbs and constant regions of human antibodies may be made by one of skill in the art using conventional methods. Thus, in particular embodiments, the invention includes chimeric antibodies comprising variable regions (VH and VL) of the heavy chain and light chains of a mouse mAb disclosed herein, and constant regions (CH and CL) of human IgG heavy chains and human immunoglobulin kappa light chains.

In additional particular embodiments, it is contemplated herein that a chimeric mouse-human monoclonal antibody may be designed and created by fusing mouse variable regions with constant regions of human IgG1 heavy chain and human immunoglobulin kappa light chains. Particular examples disclosed herein comprise the variable regions of murine mAbs P5C7 or P6B8 fused with constant regions of human IgG1 heavy chain and human immunoglobulin kappa light chain such as provided in FIGS. 16 and 18 herein. Briefly, as depicted therein, DNA sequences of signal sequence and variable region of P5C7 or P6B8 heavy chain may be linked to the DNA sequences of the constant region of a human IgG1 heavy chain, and the amino acid sequences of the chimeric mAb heavy chain may be translated from the DNA sequences. See, e.g., FIGS. 16(A) and 18(A). Also, the DNA sequences of signal sequence and variable region of P5C7 or P6B8 light chain may be linked to the DNA sequences of the constant region of a human immunoglobulin kappa light chain, and the amino acid sequences of the chimeric mAb light chain may be translated using conventional methods from the DNA sequences. See, e.g., FIG. 16(B) and 18(B).

Chimeric antibodies may be generated using conventional methods. See e.g., FIG. 20 which depicts a generalized scheme for doing so. For example, it is contemplated herein that the DNA sequences of signal sequences and variable regions of P5C7 or P6B8 heavy chains may be cloned into the multiple cloning site of a pFUSE-CHIg-hGle9 plasmid (InvivoGen catalog #pfuse-hchgle9), which contains an engineered constant region of human IgG1 heavy chain. The DNA sequences of signal sequence and variable region of P5C7 or P6B8 light chain may be cloned into the multiple cloning site of a pFUSE2-CLIg-hk plasmid (InvivoGen catalog #pfuse2-hclk), which contains a constant region of human immunoglobulin kappa light chain. The two resulting plasmids may then be cotransfected into host cells e.g., mouse myeloma cells and/or Chinese Hamster Ovary cells (CHO), CHO-S cells, NSO cells, Baby Hamster Kidney (BHK) cells, HEK293 cells; plant cells, such as tobacco, carrot and rice cells; or bacterial cells such as BL21, or insect cells such as Sf9 cells. It is contemplated herein that mammalian, e.g., human cells, may be used to create appropriately glycosylated antibodies and/or other post-translational modifications necessary for maintaining antibody function. Host cells such as these are familiar to one of skill in the art and are available from a variety of academic sources and/or commercial vendors familiar to one of skill in the art.

Humanized antibodies are also contemplated. For example, a humanized scFv of the instant invention may be created. Such humanized scFv may comprise a scFv with one or more CDR regions of the murine mAbs disclosed herein in a human antibody scaffold ("acceptor"). See, e.g., the scheme depicted in FIG. 20. For example, one such method of creating such humanized antibody comprises fusing the $V_H$ and $V_L$ domains of a mouse mAb disclosed herein to its respective, compatible human IgG1 constant domain backbone using conventional methods. The resulting fused coding sequences may then be subcloned into a mammalian expression vector. Commercially available mammalian expression vectors for this purpose are familiar to one of skill in the art and include, e.g., pFUSE (InvivoGen, San Diego, CA), pTRIOZ (InvivoGen, San Diego, CA), PSF-CMV-HUIGG1 HC ((MilliporeSigma, St. Louis, MO), PSF-CMV-HUKAPPA LC ((MilliporeSigma, St. Louis, MO), PSF-CMV-HULAMBDA LC ((MilliporeSigma, St. Louis, MO.) Expression of these vectors may then be achieved by transfecting these vectors into any suitable mammalian cell line, including, e.g., commercially available cell lines familiar to one of skill in the art such as CHO, CHO-S, and HEK293 cells. The expressed chimeric antibody may then be isolated from the culture supernatant and assayed for antigenic activity, e.g., in comparison with the antigenic activity of the mouse mAb, using conventional methods. See e.g., methods described in detail in Dang et al., *Clinical and Developmental immunology,* 2013; 2013: 716961. doi: 10.1155/2013/716961. Epub 2013 Sep. 2.

It is contemplated herein that construction of humanized antibodies may comprise using human acceptor frameworks as similar as possible to the murine antibody frameworks by performing standard sequence searching of available databases, e.g., the Protein Data Bank (PDFB). The human frameworks may also be modified to include residues from the murine FR regions where useful to preserve antigen-binding activity. Such structurally critical murine framework residues may be identified. e.g., using computer-assisted molecular modeling of the variable regions of the murine antibodies. See, e.g., Hou et al., Journal of Biochemistry Vol 144, Issue 1, July 2008, pp 115-120.

In additional particular embodiments, it is contemplated herein that scFv antibodies of the instant invention may be designed and created by one of skill in the art using conventional methods and reagents. For example, one of skill in the art will appreciate that a scFv antibody can be designed using conventional methods by tandemly linking the nucleic acids encoding the $V_H$ and $V_L$ regions of a mAb of the instant invention. In particular embodiments, the scFv linking format could be $V_H$-linker-$V_L$ or $V_L$-linker-$V_H$. Possible suitable linkers are familiar to one of skill in the art and include nucleic acid linkers encoding a peptide sequence which allows the scFv to retain the function of the parent mAb. Linkers of length between 15 amino acids and 20 amino acids are used.

In a particular example, possible nucleic acid linkers include nucleic acid sequences encoding a 15-amino acid peptide consisting of three repeating sequences of glycine-glycine-glycine-glycine-serine, i.e., $(GGGGS)_3$ (SEQ ID NO:97)). See, e.g., Huston, J. S. et al. Methods Enzymol 1991: 203:46-88. Additional possible linkers are familiar to one of skill in the art and include, e.g, the 18-mer (GGSSRSSSSGGGGSGGGG) (SEQ ID NO: 98) or the 20-mer (G4S4 (SEQ ID NO: 99). Linker sequences may also contain additional features designed to improve the functions of the scFv antibody. See, e.g., Andris-Widhopf, J., Steinberger, P., Fuller, R., Rader, C., & Barbas, C. F. (2011). Generation of human scFv antibody libraries: PCR amplification and assembly of light- and heavy-chain coding sequences. Cold Spring Harbor protocols, 2011(9); Schaefer, J. V, Honegger, A., & Pluckthun, A. (2010).

Construction of scFv Fragments from Hybridoma or Spleen Cells by PCR Assembly. (R. Kontermann & S. Dubel, Eds.)

```
Various leader sequences include, e.g., pelB
leader sequence
                                   (SEQ ID NO: 100)
MKYLLPTAAAGLLLLAAQPAMA
or

its variants including
                                   (SEQ ID NO: 101)
MKYLLPTAEAGLLLLAAQPAMA;

malE leader sequence
                                   (SEQ ID NO: 102)
MKKTGARILALSALTTMMESASALA
or

its variants including
                                   (SEQ ID NO: 103)
MKKTGARILALSELTTMMFSASALA;

DsbA leader sequence
                                   (SEQ ID NO: 104)
MKKIWLALAGLVLAFSASAAQ;

OmpA leader sequence
                                   (SEQ ID NO: 105)
MKKTAIAIAVALAGFATVAQA;

PhoA leader sequence
                                   (SEQ ID NO: 106)
VKQSTIALALLPLLFTPVTKA.
```

It is contemplated herein that various linkers and leader sequences may be used by one of skill in the art to design the scFvs of the instant invention.

In a particular embodiment, a prophetic P8D10 scFv antibody design and sequence are given in FIG. 19(A). As depicted therein, the scFv antibody design comprises a pelB leader sequence followed by a P8D10 murine mAb heavy chain variable domain. As depicted, a 15-mer linker of $(GGGGS)_3$ (SEQ ID NO: 97) connects the P8D10 heavy chain variable domain and a P8D10 light chain variable domain.

One of skill in the art will appreciate that various plasmid vectors and host cells may be used to express a scFv antibody of the instant invention. Indeed, scFvs are amendable to expression in prokaryotic cells (low cost production), and multipathogen or multivalent scFVs can be engineered without loss of activity. In particular embodiments, it is contemplated herein that the P8D10 scFv DNA sequence may be cloned into an expression vector including, e.g., pET vectors (Novagen), pBAD vectors (Invitrogen), pT7 vectors (Sigma), pTriEx vectors (Novagen), pLys vectors (Novagen), pCDF vectors (Novagen), pACYC vectors (Novagen), pCOLA vectors (Novagen), and other vectors previously disclosed herein. The vector harboring P8D10 scFv may then be transformed or transfected into expression cells including but not limited to BL21 cells (Novagen), BL21 (DE3) cells (Novagen), BLR cells (Novagen), BLR (DE3) cells (Novagen), HMS174 (DE3) cells (Novagen), Tuner (DE3) cells (Novagen), Origami (DE3) cells (Novagen), Rosetta (DE3) cells (Sigma), strains derived from *Escherichia coli* B strain, strains derived from *Escherichia coli* K12 strain, and other cells described herein. In a particular embodiment, it is contemplated herein that the P8D10 scFv DNA sequence may be cloned into a pET-24a plasmid vector (Novagen). The pET-24a plasmid harboring P8D10 scFv may be then transformed into BL21 (DE3) cells (Novagen). The BL21(DE3)/pET-24a-P8D10-scFV cells may be grown in Select APS media (BD sciences) with kanamycin, and the P8D10 scFv protein expression induced by addition of IPTG (Isopropyl β-d-1-thiogalactopyranoside). Another delivery vehicle for scFv could be *Lactococcus lactis* or other probiotic strains generally regarded as safe. The scFv can be expressed on the bacterial surface or secreted into the intestinal lumen. In addition to the foregoing prophetic example of a P8D10 scFV, several actual scFvs have been generated and assayed as provided in detail in the below example.

Example 13: Creation of Mouse and Humanized scFv Based on Mouse P8D10 mAb

As contemplated above, since the mouse mAb P8D10 has very potent homologous HAI activity, and its variable domains have been sequenced, this anti-CfaE mAb was chosen to make several mouse and humanized scFvs. As described in detail below, three scFvs were made based on the variable domain sequences of mAb P8D10. All three scFvs demonstrated functional activity in the HAT assay, and the two humanized scFys demonstrated more potency than the mouse scFv.

Figure 23:
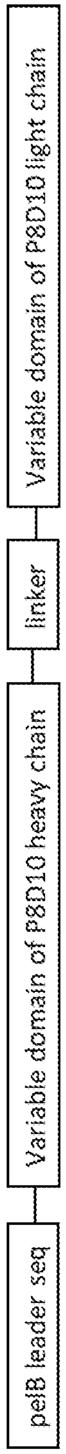
FIG. 23 depicts a cartoon of the construct of P8D10 scFvs described in Example 13. As depicted, it contains a pelB leader sequence, anti-CfaE mAb P8D10 variable domain sequences, and a “linker” (e.g., $GGGGS)_3$, (SEQ ID NO: 97)). The structure may comprise the variable domains linked in the order VH-linker-VL (also referred to herein as VHVL orVH-VL) or VL-linker-VH (also referred to herein as VLVH or VL-VH) (not depicted.)
Figure 24:
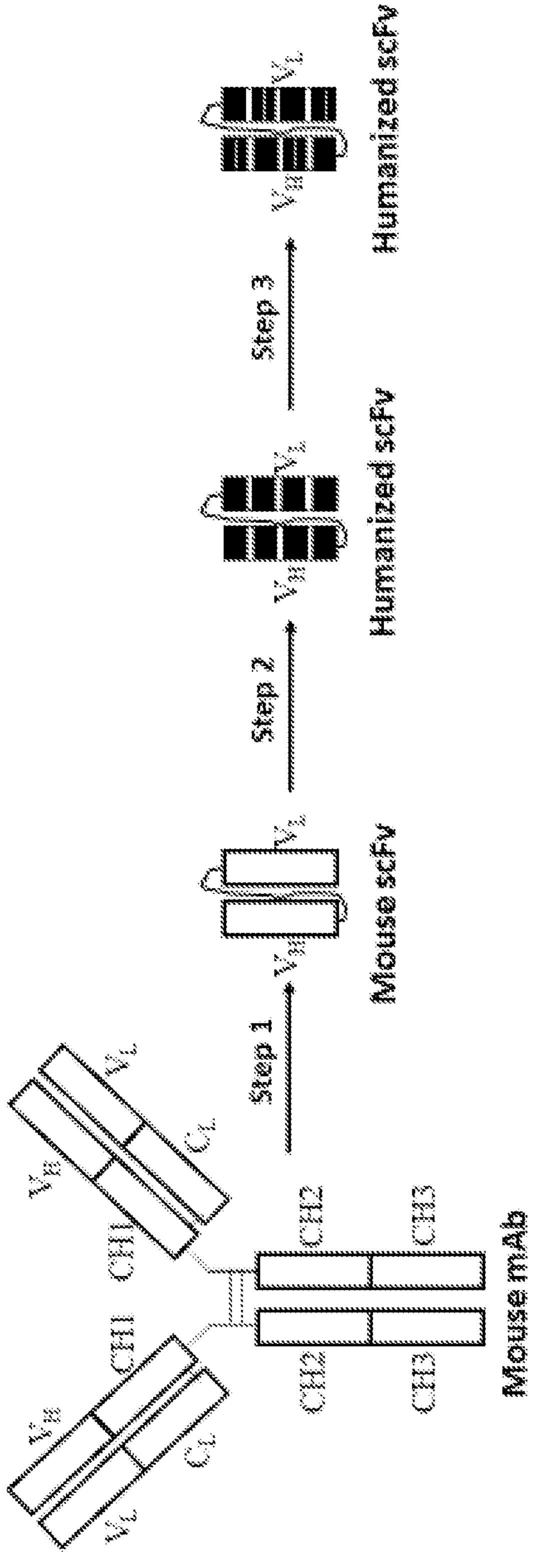
FIG. 24 is a cartoon depicting a general scheme of creating a humanized scFv based on a mouse scFV created based on a mouse mAb. As depicted, white blocks refer to mouse sequences and black blocks refer to human sequences. Step 1 depicts designing a mouse VHVL scFv using variable domain sequences from a mouse mAb and a linker. The linker is introduced between the VH and VL domains. Since each indicated step may result in total loss of activity, ideally, one can engineer and test scFv activity (e.g., using HAI) after Step 1. The goal of this step is to identify a functional scFv form, even if the HAI activity is less potent than the parent full-length mAb. The variable parameter in this step is the use of different linkers between the VH and VL domains. In Step 2, sequences of the framework regions in the mouse scFv are replaced with human sequences of framework regions. To facilitate scFv humanization in Steps 2 and 3, the mouse scFv structure is usually modeled based on the sequence alignment of available antibody structures, i.e., alignment of mouse and human Ig sequences in variable domains (not depicted here). A remedy for the potential loss of activity in Step 2 is to identify certain residues (depicted as white sticks in the black blocks) in the framework regions having contacts with residues in the complementary determining regions (CDR, depicted as narrow white blocks) based on the modeled structure, and mutating those specific human residues back to mouse residues. The specific framework residues are identified using the scFv 3D model built in Step 1.

Construct Design: Mouse and humanized scFys were created according to conventional methods. They were concurrently designed, cloned, expressed and purified. First, three scFv constructs were designed, each of which comprised a pelB leader sequence (to facilitate periplasm expression), anti-CfaE mAb P8D10 variable domain sequences (VH and VL domains), and a linker of $(GGGGS)_3$ (SEQ ID NO:97) to connect VH and VL domains. See FIG. 23 and FIG. 24.

The DNA sequences of these constructs were commercially synthesized (Eurofins Genomics, Tokyo, Japan). The synthesized nucleotide sequence for the mouse scFv (VH-VL) was initially (SEQ ID NO: 117)

"*CATATG*ATGAAATACCTATTGCCTACGGCAGCCGCTGGATTGTTATTAC

TCGCGGCCCAGCCGGCGATGGCCCAGATCCAGTTGGTGCAGTCTGGACCT

GAGCTGAAGAAGCCTGGAGAGACAGTCAAGATCTCCTGCAAGGCTTCTGG

GTATACCTTCACAAACTATGGAATGAACTGGGTGAAGCAGGCTCCAGGAA

AGGGTTTAAAGTGGATGGGCTGGATAAACACCTACACTGGACAGTCAACA

TATGCTGATGACTTCAAGGGACGCTTTGCCTTCTCTTTGGAAACCTCTGC

CAGCACTGCCCATTTGCAGATCAGCAACCTCAAAAATGAGGACGCGGCTA

CATATTTCTGTGCAAGAATGGAGTATGGTAACTACGAAAATGCTTTGGAT

TACTGGGGTCAAGGAACCTCAGTCACCGTCTCCTCAGGTGGCGGTGGCAG

CGGCGGCGGTGGTAGCGGTGGTGGCGGCAGCGACATTGTGATGACCCAGT

CTCACAAATTCATGTCCACATCAATAGGAGACAGGGTCAGCATCACCTGC

AAGGCCAGTCAGGATGTGAGTACTGCTGTAGTCTGGTATCAACAGAAACC

AGGACACTCTCCTAAACTACTGATTTATTCGGCATCCTACCGGTACACTG

GAGTCCCTGATCGCTTCACTGGCAGTGGATCTGGGACGGATTTCACTTTC

ACCATCAGCAGTGTGCAGGCTGAAGACCTGGCAGTTTATTACTGTCTACA

ACATTTTAGTACTCCTCGGACGTTCGGTGGAGGCACCAACCTGGAAATCA

AA*CTCGAG*".

This synthesized nucleotide sequence was flanked by NdeI and XhoI sites, respectively (italicized regions). An internal NdeI site (CATA TG) was inadvertently put in the nucleotide sequence initially (bold), and was later replaced with CCTATG using a commercially available site-directed mutagenesis kit according to manufacture instructions (Quikchange reaction; Agilent Technologies, Santa Clara, CA). The primers used in the Quikchange reaction were:

(SEQ ID NO: 118)
"CCTACACTGGACAGTCAACCTATGCTGATGACTTCAAGGGACGC"
and (SEQ ID NO: 119)
"GCGTCCCTTGAAGTCATCAGCATAGGTTGACTGTCCAGTGTAGG".

The resulting nucleotide sequence after the Quikchange reaction is
(SEQ ID NO: 120)
"*CATATG*ATGAAATACCTATTGCCTACGGCAGCCGCTGGATTGTTATTAC
TCGCGGCCCAGCCGGCGATGGCCCAGATCCAGTTGGTGCAGTCTGGACCT
GAGCTGAAGAAGCCTGGAGAGACAGTCAAGATCTCCTGCAAGGCTTCTGG
GTATACCTTCACAAACTATGGAATGAACTGGGTGAAGCAGGCTCCAGGAA
AGGGTTTAAAGTGGATGGGCTGGATAAACACCTACACTGGACAGTCAACC
TATGCTGATGACTTCAAGGGACGCTTTGCCTTCTCTTTGGAAACCTCTGC
CAGCACTGCCCATTTGCAGATCAGCAACCTCAAAAATGAGGACGCGGCTA
CATATTTCTGTGCAAGAATGGAGTATGGTAACTACGAAAATGCTTTGGAT
TACTGGGGTCAAGGAACCTCAGTCACCGTCTCCTCAGGTGGCGGTGGCAG
CGGCGGCGGTGGTAGCGGTGGTGGCGGCAGCGACATTGTGATGACCCAGT
CTCACAAATTCATGTCCACATCAATAGGAGACAGGGTCAGCATCACCTGC
AAGGCCAGTCAGGATGTGAGTACTGCTGTAGTCTGGTATCAACAGAAACC
AGGACACTCTCCTAAACTACTGATTTATTCGGCATCCTACCGGTACACTG
GAGTCCCTGATCGCTTCACTGGCAGTGGATCTGGGACGGATTTCACTTTC
ACCATCAGCAGTGTGCAGGCTGAAGACCTGGCAGTTTATTACTGTCTACA
ACATTTTAGTACTCCTCGGACGTTCGGTGGAGGCACCAACCTGGAAATCA
AA*CTCGAG*".

No amino acid changes resulted from the Quikchange reaction.

The synthesized nucleotide sequence for the humanized P8D10 scFv ($V_H$-$V_L$) is:

(SEQ ID NO: 121)
"*CATATG*ATGAAATACCTATTGCCTACGGCAGCCGCTGGATTGTTATTAC
TCGCGGCCCAGCCGGCGATGGCCCAGATCCAGTTGGTGCAGTCTGGATCT
GAGCTGAAGAAGCCTGGAGCGTCAGTCAAGGTCTCCTGCAAGGCTTCTGG
GTATACCTTCACAAACTATGGAATGAACTGGGTGAAGCAGGCTCCAGGAC
AGGGTTTAAAGTGGATGGGCTGGATAAACACCTACACTGGACAGTCAACC
TATGCTGATGACTTCAAGGGACGCTTTGCCTTCTCTTTGGATACCTCTGT
CAGCACTGCCTATTTGCAGATCAGCAGCCTCAAAGCTGAGGACACGGCTG
TGTATTTCTGTGCAAGAATGGAGTATGGTAACTACGAAAATGCTTTGGAT
TACTGGGGTCAAGGAACCTTAGTCACCGTCTCCTCAGGTGGCGGTGGCAG

-continued
CGGCGGCGGTGGTAGCGGTGGTGGCGGCAGCGACATTGTGATGACCCAGT
CTCCCAGCTCCCTGTCCGCATCAGTAGGAGACAGGGTCACCATCACCTGC
AAGGCCAGTCAGGATGTGAGTACTGCTGTAGTCTGGTATCAACAGAAACC
AGGAAAAGCTCCTAAACTACTGATTTATTCGGCATCCTACCGGTACACTG
GAGTCCCTGATCGCTTCACTGGCAGTGGATCTGGGACGGATTTCACTTTG
ACCATCAGCAGTCTGCAGGCTGAAGACTTCGCAACCTATTACTGTCTACA
ACATTTTAGTACTCCTCGGACGTTCGGTGGAGGCACCAAACTGGAAATCA
AA*CTCGAG*".

The nucleotide sequence of the humanized P8D10 scFv (VH-VL) is flanked by NdeI and XhoI sites in the synthesized sequence, respectively (italicized regions).

The synthesized nucleotide sequence for the humanized P8D10 scFv (VL-VH) is:

(SEQ ID NO: 122)
"*CATATG*ATGAAATACCTATTGCCTACGGCAGCCGCTGGATTGTTATTAC
TCGCGGCCCAGCCGGCGATGGCCGACATTGTGATGACCCAGTCTCCCAGC
TCCCTGTCCGCATCAGTAGGAGACAGGGTCACCATCACCTGCAAGGCCAG
TCAGGATGTGAGTACTGCTGTAGTCTGGTATCAACAGAAACCAGGAAAAG
CTCCTAAACTACTGATTTATTCGGCATCCTACCGGTACACTGGAGTCCCT
GATCGCTTCACTGGCAGTGGATCTGGGACGGATTTCACTTTGACCATCAG
CAGTCTGCAGGCTGAAGACTTCGCAACCTATTACTGTCTACAACATTTTA
GTACTCCTCGGACGTTCGGTGGAGGCACCAAACTGGAAATCAAAGGTGGC
GGTGGCAGCGGCGGCGGTGGTAGCGGTGGTGGCGGCAGCCAGATCCAGTT
GGTGCAGTCTGGATCTGAGCTGAAGAAGCCTGGAGCGTCAGTCAAGGTCT
CCTGCAAGGCTTCTGGGTATACCTTCACAAACTATGGAATGAACTGGGTG
AAGCAGGCTCCAGGACAGGGTTTAAAGTGGATGGGCTGGATAAACACCTA
CACTGGACAGTCAACCTATGCTGATGACTTCAAGGGACGCTTTGCCTTCT
CTTTGGATACCTCTGTCAGCACTGCCTATTTGCAGATCAGCAGCCTCAAA
GCTGAGGACACGGCTGTGTATTTCTGTGCAAGAATGGAGTATGGTAACTA
CGAAAATGCTTTGGATTACTGGGGTCAAGGAACCTTAGTCACCGTCTCCT
CA*CTCGAG*".

the humanized P8D10 scFv (VL-VH) is flanked by NdeI and XhoI sites in the synthesized sequence, respectively (italicized regions).

Cloning, Expression, Purification: The three P8D10 scFv were cloned, expressed and purified the same way using conventional methods and commercially available materials. Specifically, the synthesized mouse and humanized nucleotide sequences for the three P8D10 scFvs (described above) were commercially provided in pUC vectors, respectively (Eurofins Genomics, Tokyo, Japan). Each pUC vector was digested by NdeI and XhoI restriction enzymes, and the nucleotide insertion encoding the P8D10 scFv was purified and inserted into NdeI and XhoI sites of a pET-24a vector (Novagen brand, Millipore Sigma, Burlington, MA). The resulting pET-24a plasmid containing the P8D10 scfv sequence was transformed into BL21(DE3) bacterial cells (Novagen brand; Millipore Sigma, Burlington, MA). The transformed BL21(DE3) cells were grown in Select APS media (BD Biosciences, San Jose, CA) at 32° C. until the OD600 reached 0.6-0.8, and the bacterial culture was induced with 0.1 mM IPTG at 16° C. for about 18 hours. The harvested bacterial cell paste was resuspended in a buffer containing 20 mM Tris, 250 mM sodium chloride, 5 mM imidazole at pH 8.0, and microfluidized twice. The bacterial cell lysate was centrifuged for 45 minutes at 17000 g-force and 4° C. After centrifugation, the P8D10 scFv was purified from the soluble fraction of the cell lysate by a nickel affinity column, and followed by cation exchange chromatography. Briefly, after the soluble fraction of the cell lysate was loaded onto a nickel affinity column (Novagen, Burlington, MA), the column was washed by a buffer containing 20 mM Tris, 250 mM sodium chloride, 5 mM imidazole at pH 8.0, and the fractions containing P8D10 scFv were eluted by a buffer containing 20 mM Tris, 250 mM sodium chloride, 300 mM imidazole at pH 8.0. The eluate from the nickel affinity column was diluted 20 times by a buffer containing 20 mM 2-(N-morpholino)ethanesulfonic acid (MES) at pH 5.5, and the diluted solution was loaded onto a SP cation exchange column (Cytiva, Marlborough, MA). After washing the SP column with a buffer containing 20 mM MES, 50 mM sodium chloride at pH 5.5, the P8D10 scFv was eluted from the SP column with two step gradients. The first step gradient buffer was 20 mM MES, 300 mM sodium chloride at pH 5.5, and the second step gradient buffer was 20 mM MES, 400 mM sodium chloride at pH 5.5. The eluted fractions were examined on a 15% SDS-PAGE gel and fractions containing the P8D10 scFv were pooled and concentrated. Notably, FIG. 19(B) depicts the nucleotide and amino acid sequences of the generated mouse P8D10 VH-VL scFv. The amino acid sequence in FIG. 19 (B) is the same as the prophetic amino acid sequence in FIG. 19 (A). The nucleotide sequences between the two figures have one nucleotide difference.

Creation of Humanized scFvs: In order to create a 3D structural model of the mouse scFv, VH and VL amino acid sequences of mouse mAb P8D10 were individually searched against available mouse antibody structures and sequences in the Protein Data Bank (PDB) and sequence identities to the P8D10 variable sequences were ranked. See Table 6 and Table 7 below, and FIGS. 26(A) and 26(B).

TABLE 6

Ranking of amino acid sequence identity of available antibody structures and P8D10 VH sequence.

| Ranking | PDB ID | Identity (%) | Species |
|---|---|---|---|
| 1 | 1IAI (H) | 88 | Mouse |
| 2 | 2BRR (H) | 84 | Mouse |
| 3 | 1NCA (H) | 84 | Mouse |
| 4 | 3O2V (H) | 83 | Mouse |
| 5 | 2O5X (H) | 83 | Mouse |
| 6 | 6OY4 (D) | 83 | Mouse |
| 7 | 1A4J (B) | 83 | Mouse |
| 8 | 5TPW (H) | 83 | Mouse |
| 9 | 1NCB (H) | 83 | Mouse |
| 10 | 1C1E (H) | 83 | Mouse |

TABLE 7

Ranking of amino acid sequence identity of available antibody structures and P8D10 VL sequence.

| Ranking | PDB ID | Identity (%) | Species |
|---|---|---|---|
| 1 | 5I66 (B) | 93 | Mouse |
| 2 | 3IU4 (L) | 93 | Mouse |
| 3 | 6P67 (B) | 92 | Mouse |
| 4 | 2NR6 (C) | 91 | Mouse |
| 5 | 3DIF (A) | 91 | Mouse |
| 6 | 5F3B (B) | 90 | Mouse |
| 7 | 1IAI (L) | 90 | Mouse |
| 8 | 6DG2 (B) | 88 | Mouse |
| 9 | 4H20 (L) | 88 | Mouse |
| 10 | 4KQ4 (L) | 88 | Mouse |

Figure 25:
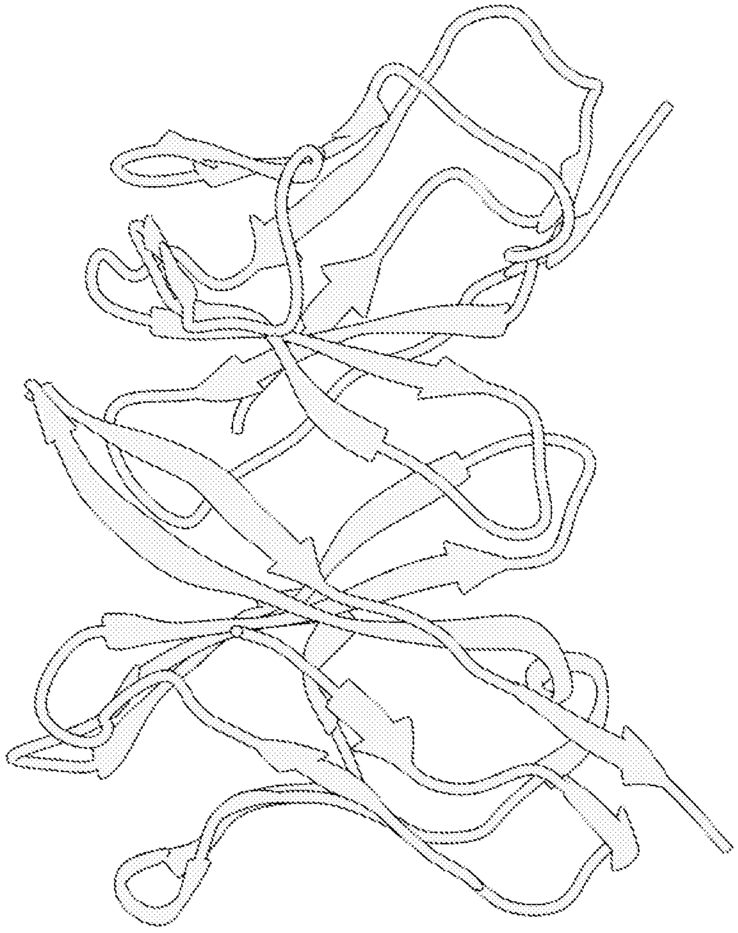
FIG. 25 depicts a Richardson diagram of the predicted structural model of mouse P8D10 VH-VL scFv. The variable heavy chain (VH) and variable light chain (VL) are indicated.
Figure 29:
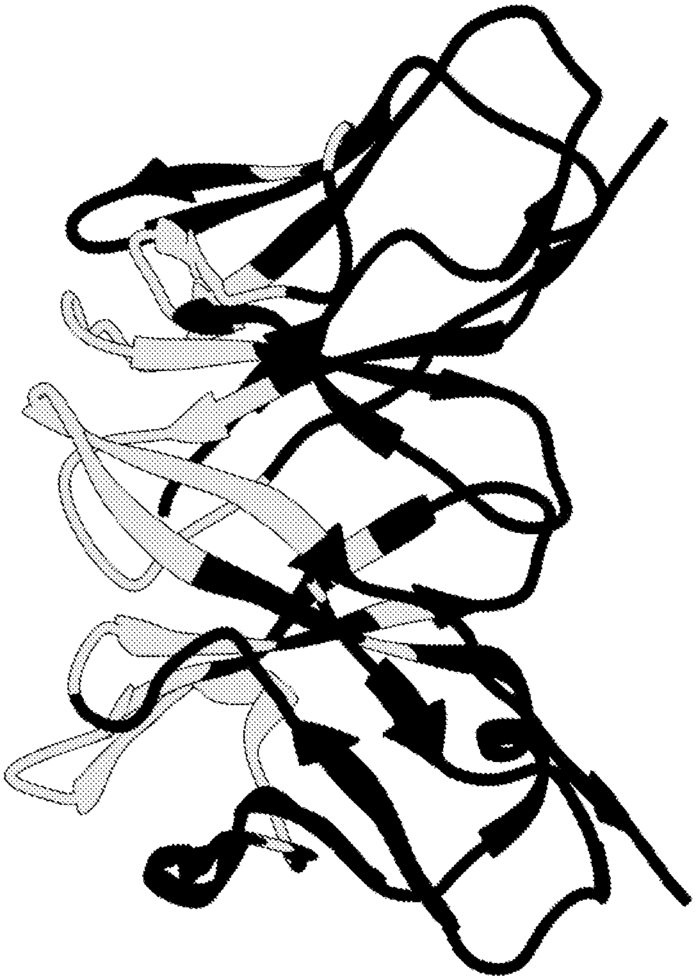
FIG. 29 depicts a Richardson diagram of the humanized P8D10 VHVL scFV. Gray sections depict mouse sequences; black sections depict human sequences. The variable heavy chain (VH) and variable light chain (VL) are indicated.
Figure 30:
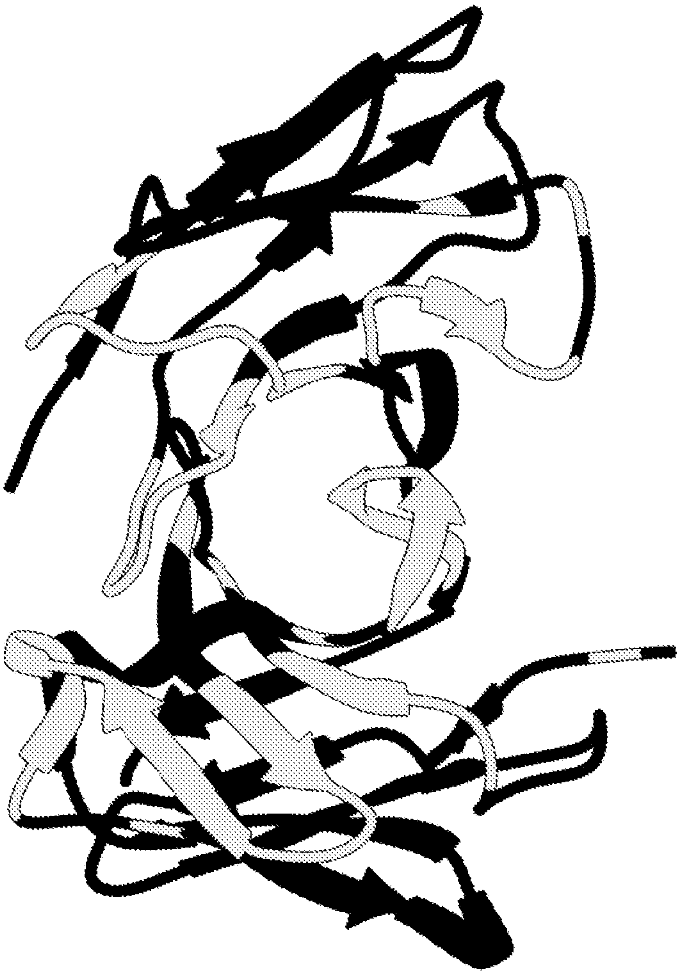
FIG. 30 depicts a Richardson diagram of a different orientation of the humanized P8D10 VHVL scFv depicted in FIG. 29. Gray sections depict mouse sequences; black sections depict human sequences. The variable heavy chain (VH) and variable light chain (VL) are indicated.

Although it is possible to model the P8D10 scFv structure by individually modeling VH and VL domains from different PDB antibodies, structural models are more accurate when both VH and VL are modeled within one PDB structure. Thus, the structure in PDB ID 1IAI was selected to make a structural model for the P8D10 mouse scFv structure (VH-VL). See FIG. 25.

To facilitate scFv humanization, the mouse P8D10 VH and VL sequences were separately searched using BlastP (https://blast.ncbi.nlm.nih.gov/Blast.cgi?PAGE=Proteins) against the non-redundant protein sequences containing human immunoglobulin (Ig) sequences. (The BlastP website has a protein database called "non-redundant protein sequences".) The top three closest human Ig variable domain sequences were identified and aligned with the P8D10 VH and VL sequences as depicted in FIG. 27(A) and FIG. 27(B), respectively. We observed that care needed to be taken when selecting "human" immunoglobulin sequences for comparison; some of the search results with high sequence identity were curated as "human origin", but they were actually mouse origin or chimeric when examined.

As depicted in FIG. 27(A) and FIG. 27(B), to create the humanized scFvs, residues in the mouse P8D10 CDR regions were kept (bold), and residues which are in the P8D10 framework regions within 5 Å of the CDR regions and different to those in the human Ig sequences, were also kept (italicized/shaded and underlined). The rest of P8D10 variable domain sequences were replaced with human Ig variable domain sequences.

Two different humanized P8D10 scFv antibodies were thus designed and are depicted in FIGS. 28(A)-(E). FIG. 28(A) depicts the amino acid sequence of the humanized P8D10 VH, and FIG. 28(B) depicts the amino acid sequence of the humanized P8D10 VL. FIG. 28(C) depicts the schematic design of humanized P8D10 VH-VL scFv construct, and P8D10 VL-VH scFv construct. FIG. 28(D) depicts the nucleotide and amino acid sequences of the humanized P8D10 VH-VL scFv, and FIG. 28(E) depicts the nucleotide and amino acid sequences of the humanized P8D10 VL-VH scFv. These constructs were cloned, expressed and purified as discussed above.

Example 14: Functional Activity of Three P8D10 scFvs

The functional activities of the three scFvs created in Example 13 were evaluated in an hemagglutination inhibition (HAI) assay according to the same protocol provided above in Example 5 with the exception that the test articles here were the full length P8D10 mAb and the three P8D10 scFv. The results (MIC) are provided in FIG. 31 and indicate that all three scFvs had functional activities in the HAI assay. The two humanized scFvs were more potent than the mouse scFv in inhibition of hemagglutination. The humanized P8D10 VLVH had the lowest minimum inhibition concentration at 1.70 ug/ml among the three P8D10 scFv.

An additional assay was employed using conventional methods and materials to evaluate the reduction of mouse residues in the humanized scFvs. Briefly, full length P8D10 mouse mAb, P8D10 mouse VH-VL scFv, P8D10 humanized VH-VL scFv and P8D10 humanized VL-VH scFv were diluted in phosphate buffered saline at pH 7.4 (PBS) and coated on a 96-well microtiter plate with 100 μl of the antibodies at two different concentrations (2 μg/ml and 5 μg/ml). Each condition was repeated two times. After the plate was incubated at 37° C. for 1 hour, each well was washed three times with 250 μl of PBS. Then each well was blocked with 250 μl of PBS with 5% fetal calf serum at 37° C. for 1 hour. After washing three times with 250 μl of PBS, 0.05% Tween 20 (PBST), each well received 100 μl of goat anti-mouse IgG horseradish peroxidase-conjugated antibodies (Jackson Immuno Research #115-035-003) and incubated at 37° C. for 2 hours. After washing three times with 250 μl of PBST, each well received 100 μl of ortho-phenylenediamine substrates (Sigma) and incubated at 25° C. for 20 minutes. Optical densities (OD) were measured by a plate reader at 450 nm.

Figure 32:
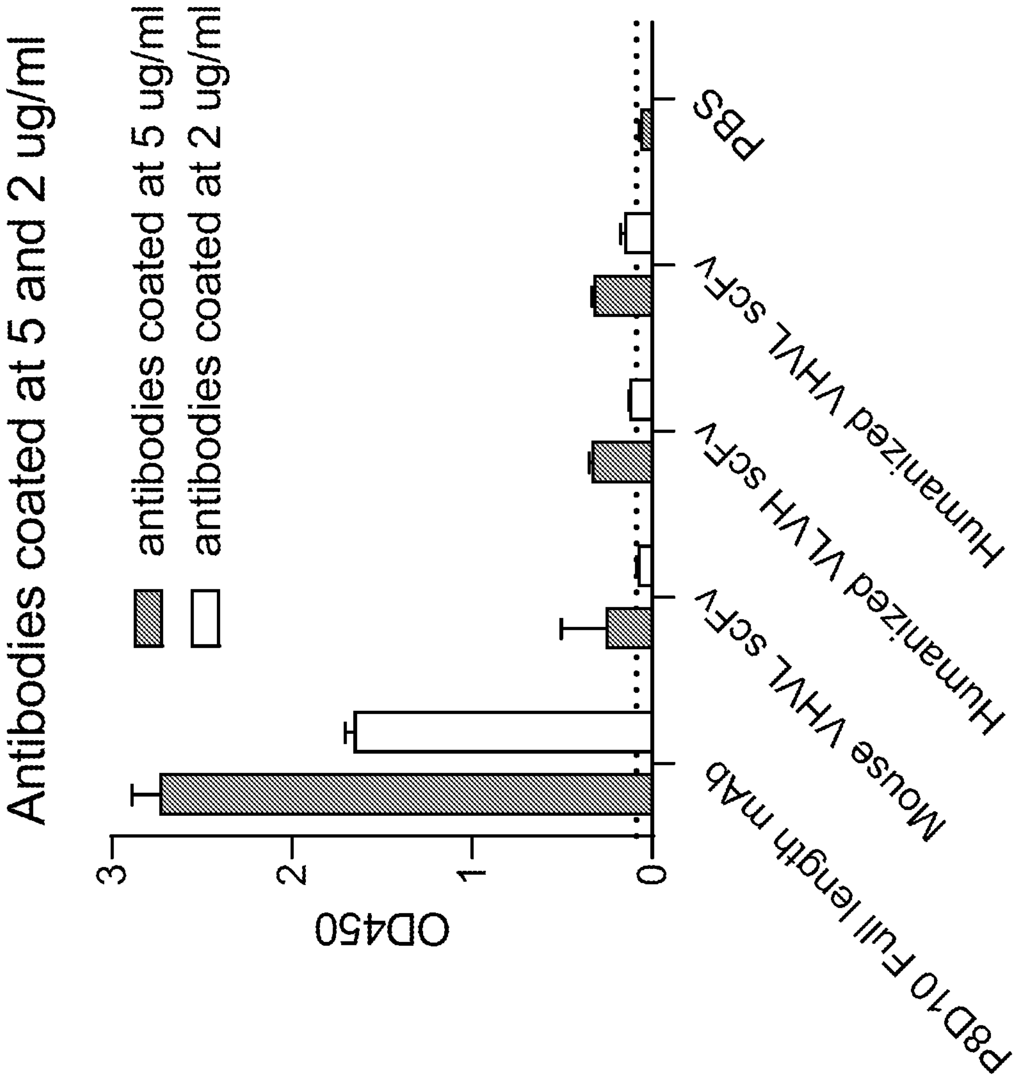
FIG. 32 depicts the results of an ELISA assay performed to evaluate the reduction of mouse residues in the humanized scFvs as detailed in Example 14. Briefly, the ELISA procedure used the indicated antibodies coated on assay plates at two different concentrations, 5 μg/ml and 2 μg/ml. The plates were washed, the wells were blocked and the plate was washed again. The plates were incubated with goat anti-mouse (IgG H+L) antibodies, and the plate was washed. The plates were incubated with OPD and the plates were read. Results indicate that the current detection antibodies target mostly on IgG Fc domains.

Results are depicted in FIG. 32 and display a reduction of OD450 from P8D10 full-length mAb to mouse and humanized scFv. These data indicate that the antibodies used in this study mostly target the mouse antibody Fc domain. Interestingly, we have also tried goat anti-mouse (Fab)2 and goat anti-human (Fab)2 antibodies, and the results were no better, suggesting that both antibodies target the constant regions in the antibodies, not the variable regions (data not shown). It is contemplated herein that additional studies may be performed to identify antibodies that may be able to more closely differentiate these mouse and humanized scFvs.

Example 15: Prophetic Full Length Humanized mAb Against CfaE

Data provided in Examples 13 and 14 herein suggest that, not only can similar humanized scFv constructs from other hybridomas disclosed herein be designed based on the example of P8D10, but also that the sequences of the two humanized P8D10 variable domains (VH and VL) disclosed herein can be grafted back onto a human Ig scaffold, and thus generate a full length humanized mAb against CfaE. Thus, in a particular prophetic embodiment, FIGS. 33(A)-33(B) herein depict the heavy chain DNA (SEQ ID NO: 113) and amino acid (SEQ ID NO: 114) sequences, and light chain DNA (SEQ ID NO: 115) and amino acid (SEQ ID NO: 116) sequences, respectively, of a prophetic humanized antibody that may be created by fusion of humanized variable regions of P8D10 mAb with constant regions of human IgG1 heavy chain and human immunoglobulin kappa light chain using materials and methods such as described in Example 12. As depicted in FIG. 33(A), the shaded sequences indicate the mAb P8D10 heavy chain signal sequence, the bold sequence is the humanized P8D10 heavy chain variable region, and the regular font represents the human IgG1 heavy chain constant region. As depicted in FIG. 33(B), the shaded sequences indicate the mAb P8D10 light chain signal sequence, the bold sequence is the humanized P8D10 light chain variable region, and the regular font represents the human immunoglobulin kappa light chain constant region.

Example 16: Future Experiments to Create Additional Anti-Adhesin mAbs

As previously reported, data provided herein for the mAb cross-reactivity patterns determined by ELISA showed individual adhesin specific, intra-subclass specific, inter-subclass specific and class-wide cross-reactivity. Specifically, among the 28 mAbs disclosed in this study, twenty-one of them cross-reacted to other class 5 adhesins, however, functional cross-reactivity was only observed in nine mAbs. Since some mAbs may cross-react with epitopes not directly involved in hemagglutination, we expected that only a subset would show heterologous HAI activity. Indeed, among mAbs with both cross-reactivity in ELISA and homologous HAI activity, the breadth of the heterologous HAI activity of each mAb was more limited than the repertoire of cross-reactivity shown by the ELISA. One example was anti-CfaE mAbs P3B2, which was cross-reactive to all other five tested class 5 adhesins, but showed heterologous HAI activity only to CS17 and CS1-ETEC. The results suggested the hemagglutination inhibition assay was more discriminating than ELISA in distinguishing subtle differences of epitopes in the class 5 adhesins recognized by the mAbs.

In addition, we previously reported that all five adhesin domain specific anti-CfaE mAbs with epitopes including the R67 and R181 residues had strong homologous HAI activity, confirming that these two residues in CfaE are essential for hemagglutination. Two adhesin domain specific anti-CsbD mAbs P2H6 and P1F7 with epitopes in the vicinity of R67 and R181, showed strong homologous HAI responses, suggesting that the upper pole region of CsbD serves as the receptor binding site, and that this may be a universal feature for all class 5 adhesins. However, one exception was anti-CsbD P7F9 mAb since it had epitope in the upper pole including R181, but had low homologous HAI activity. One possibility is that the affinity of P7F9 may be too low to elicit any HAI activity, as the affinity of mAbs to antigens such as the hemagglutinin of influenza virus (26) and the surface protein gp120 of human immunodeficiency virus (27) has been shown to be positively correlated with their functionality. The combination of low homologous HAI activity and class-wide cross-reactivity pattern in the ELISA of P7F9 may be explained by the significant primary sequence variations downstream of the R181 in the alignment of class 5 adhesins (24). P7F9 may have to spare its homologous HAI activity for the cross-reactivity.

In addition, we previously considered the receptor binding domain resides in the adhesin domain; not only were 13 out 19 adhesin-domain specific mAbs identified with strong homologous HAI activity, but also two anti-CfaE pilin-domain specific mAbs P3B2 and P1F9 had high homologous HAI activity. This observation could possibly be explained by the dynamic binding property of CfaE modulated by the interface interaction of the two domains. We previously showed that increased shear stress could activate CfaE into the high affinity binding state to the host cells (31), and partial disruption of the interface between the adhesin and pilin domains of CfaE led the activation and significant structural shift in the pilin domain (32). The mAbs specific to the pilin domain of CfaE could bind and lock the native conformation of the pilin domain, prevent structural changes under shear stress generated by the rocking in the HAI assay, and hold CfaE in the low affinity binding state, resulting in hemagglutination inhibition.

In particular, the anti-CfaE pilin-domain specific mAb P3B2 was previously shown to have HAI activity to the homologous CFA/I strain, and heterologous CS17 and CS1 strains. This mAb could have epitopes including residues in the donor strand, which is in the pilin domain and conserved across class 5 (24). This hypothesis is supported by the observation that the P3B2 mAb was reactive to a peptide within the donor strand in the peptide ELISA assay (data not shown), and the previous study suggesting that a monoclonal antibody against the N-terminal 25 residues of CFA/I subunits, which serve as the donor strand in the pilin domain, had HAI activity to CFA/I, CS1 or CS4-ETEC, and blocked those ETEC binding to the Caco-2 cells (7).

Notwithstanding the foregoing, our results with a limited number of mAbs suggests that a multivalent ETEC prophylactic or vaccine may be most effective with more than one active component due to lack of strong cross-reactive functional epitopes within class 5 adhesins. Accordingly, it is contemplated herein that future experiments may focus on creating more effective anti-adhesin mAbs as immunoprophylactic products against ETEC infection. In a particular embodiment, it is contemplated herein that such prophetic anti-adhesin mAbs would be directed to particular immunodominant epitopes on ETEC antigens. These epitopes include R67, S86, R181 in CfaE, and T84, S88, H144, R181, Y182 in CsbD, and R69, R184 in CotD disclosed herein.

In additional future studies, assays may be performed to identify additional immunodominant epitopes with competitive ELISA and potent functional epitopes with competitive HAI assay using specific mAbs and sera from human volunteers immunized with CfaE in clinical trials, e.g., clinicaltrials.gov ID NCT01644565 and NCT01922856.

It is also contemplated herein that a combination of structural, peptide-based and site-directed mutagenesis approaches may be employed for further epitope mapping. This is based on the observations summarized below.

Anti-CfaE mAbs P5C7, P6H4, P8D10, P3B2, P1F9 and P2E11: Anti-CfaE Mabs P5C7, P6H4, P8D10, P3B2, PIF9, and P2E11 displayed strong or moderate homologous functional activity (hemagglutination inhibition). The epitope of P5C7 included CfaE residues R67, S86 and R181, and P5C7 showed heterologous functional activity to one CS17 strain. The epitope of P6H4 and P8D10 included CfaE residues R67 and R181. P3B2 is a pilin-domain specific Mab. P3B2 had cross-reactivity to all six ETEC adhesins tested, and it showed heterologous functional activity to two CS17 strains and one CS1 strain. P1F9 and P2E11 are two pilin-domain specific Mabs and had homologous functional activities. Thus, experiments may be performed to gather detailed epitope information for these six Mabs. Based on these data, possible future experiments include making CfaE mutants CfaE/S85A, CfaE/S86A, CfaE/T91A, CfaE/N127A, CfaE/S138A, CfaE/H140A and CfaE/R145A, and using the mutants in ELISA assays to reconfirm that S86 in CfaE is one of the epitope residues for anti-CfaE mAbs P10A7 and P5C7, e.g., it is a residue responsible for receptor binding in a hemagglutination assay, and to identify additional epitope residues of these six Mabs.

Anti-CsbD Mabs P7C2, P9A5, P2H6, P6G1, P2A9, PIF7, P9E11 and P7F9: The seven anti-CsbD Mabs P7C2, P9A5, P2H6, P6G1, P2A9, P1F7 and P9E11 had strong homologous functional activity, and P7C2, P9A5, P2H6, P6G1 and P2A9 had heterologous functional activity to a CS1 strain. P9E11 had cross-reactivity to five ETEC adhesins. P7F9 had cross-reactivity to six ETEC adhesins. The epitope of P2H6 included CsbD residue T84. The epitope of P1F7 included CsbD residue H144. The epitope of P7F9 included CsbD residues S88, R181 and Y182. Possible future experiments include making CsbD mutants CsbD/T84A, CsbD/L85A, CsbD/S88A, CsbD/H144A, CsbD/R181A and CsbD/Y182A and using the mutants in ELISA assays to identify additional epitope residues of these eight Mabs.

Anti-CotD Mabs P7F6, P3F4 and P6B8: All three anti-CotD Mabs P7F6, P3F4 and P6B8 had strong homologous functional activity. The epitope of P6B8 included CotD residues R69 and R184. P3F4 had heterologous functional activity to a CS17 strain. Experiments may be performed to gather detailed epitope information for these three Mabs.

Epitope mapping techniques that may be performed in future include methodologies described in the above examples, and other conventional methods familiar to one of skill in the art, including, e.g., structural approaches such as X-ray crystallography, nuclear magnetic resonance (NMR), hydrogen-deuterium exchange coupled to mass spectrometry; peptide-based approaches (ELISA or phase display); and site-directed mutagenesis (a.k.a. alanine scanning or shotgun mutagenesis). For example, current hotspot residues in the epitope as described in Table 4 above were identified through site-directed mutagenesis. Specifically, two different possible approaches are contemplated and outlined below.

For certain anti-adhesin Mabs (such as anti-CfaE P8D10, P10A7; anti-CotD P6B8), a few key residues contributing to the antigen-antibody interactions are already disclosed herein. Crystallographic structures for $dsc_{19}$CfaE (PDB ID: 2HB0; Li et al., 2007 J. Biol. Chen. 282, 23970-23980) and CsbD and CotD (unpublished data) may be used to investigate other undisclosed residues in the epitope binding to the Mabs. For example, initially, the location of the known hotspot residues on the adhesin structures may be pinpointed. See, e.g., FIG. 4 which depicts CsbD and CotD structures which were in silico modeled based on CfaE structure. Amino acids in proximity to those previously identified residues can then be characterized to discover potential amino acids involving the antigen-antibody interactions. Next, each one of specific residues may be mutated into alanine, recombinant adhesin mutants made, and the reactivity of Mabs to the native adhesins and mutants compared. A new hotspot residue in the epitope is identified when the loss of Mab's reactivity to the mutant is observed compared to the Mab's reactivity to the native adhesin. The above processes (pinpoint location on the structure, analyze and identify potential residues, experimental verification) may be iterated a few times until five to eight key residues in the epitope for each Mab are identified.

Site-directed mutagenesis data provided herein did not identify hotspot residues for other anti-adhesin Mabs such as anti-CfaE P3B2; anti-CsbD P7C2, P9A5, P9E11; and anti-CotD P7F6, P3F4, due to the limited number of adhesin mutants. It is contemplated herein that future studies include constructing an overlapping peptide library for each adhesin. In a peptide ELISA assay, increased reactivity of Mabs to a peptide or a group of peptides suggests the specific peptide(s) contain residues in the epitope. These peptides may be mapped onto adhesin structures in order to define surface areas with most increased reactivity. Surface exposed residues in the specific areas then may be analyzed and evaluated as potential hotspot amino acids. Experimental verification such as making recombinant adhesin mutants, and comparing Mab reactivity to the mutants and the native adhesins, will likely confirm the qualification of the hotspot residues. The analysis of surface exposed residues and experimental verification processes may be iterated a few times until five to eight key residues in the epitope for each Mab are identified.

REFERENCES

1. Collaborators, G. B. D. D. D. (2017) 2015. *Lancet Infect Dis* 2017 September; 17(9): 909-948
2. Kotloff, K. L., et al. (2013) *Lancet* 382, 209-222
3. Porter, C. K., et al. (2017) *Mil Med* 182, 4-10
4. Gaastra, W., and Svennerholm, A. M. (1996) *Trends in microbiology* 4, 444-452
5. Anantha, R. P., et al. (2004) *Infect Immun* 72, 7190-7201
6. McConnell, M. M et al. (1989) *FEMS microbiology letters* 52, 105-108
7. Rudin, A., et al., (1994) *Infect Immun* 62, 4339-4346
8. Qadri, F., et al. (2006) *Infect Immun* 74, 4512-4518
9. Sakellaris, H., et al. (1996) *Molecular microbiology* 21, 529-541
10. Li, Y. F., et al. (2009) *Proc. Natl. Acad. Sci. USA.* 106, 10793-10798
11. Galkin, V. E., et al. (2013) *Journal of bacteriology* 195, 1360-1370
12. Sauer, F. G., et al. (1999) *Science* 285, 1058-1061
13. Choudhury, D., et al. (1999) *Science* 285, 1061-1066
14. Sakellaris, H., et al. (1999) *Proc Natl Acad Sci USA* 96, 12828-12832
15. Poole, S. T., et al. (2007) *Mol. Microbiol.* 63, 1372-1384
16. Baker, K. K., et al. (2009) *Cellular microbiology* 11, 742-754
17. Giuntini, S., et al. (2018) *Infect Immun* August; 86(8): e00355-18. (Correction published in Giuntini, S., et al. *Infect Immun* November; 86(12): e00713-18.)
18. Luiz, W. B. et al. (2015)*Infect Immun* 83, 4555-4564
19. Rollenhagen, J. E., et al. (2019) *Infect Immun* 87
20. Savarino, S. J., et al. (2017) *The Journal of infectious diseases* 216, 7-13
21. Freedman, D. J. et al. (1998) *The Journal of infectious diseases* 177, 662-667
22. Sali, A., and Blundell, T. L. (1993) *Journal of molecular biology* 234, 779-815
23. Sarvas, H. O. et al. (1983) *Mol Immunol* 20, 239-246
24. Li, Y. F. et al. (2007) *J. Biol. Chem.* 282, 23970-23980
25. Isidean, S. D. et al. (2011) *Vaccine* 29, 6167-6178
26. Kostolansky, F. et al. (2000) *J Gen Virol* 81, 1727-1735
27. Nakamura, G. R. et al., (1993) *Journal of virology* 67, 6179-6191
28. Gerhard, W. et al. (1981) *Nature* 290, 713-717
29. Wiley, D. C. et al. (1981) *Nature* 289, 373-378
30. Ekiert, D. C. et al. (2009) *Science* 324, 246-251
31. Tchesnokova, V. et al. (2010) *Mol. Microbiol.* 76, 489-502
32. Liu, Y. et al. (2013) *J Biol Chem* 288, 9993-10001
33. Shahabudin, Sakina, December 2013, "Epitope mapping and functional characterization of monoclonal antibodies against the tip-localized adhesions of CFA/I, CS17 and CS2 Class 5 fimbriae enterotoxigenic *Escherichia coli*", (Master's thesis) Pennsylvania State University, State College, PA (http://ir.upm.edu.my/find/Record/my-ump-ir.13510/Description #tabnav).
34. Sami Farid, Lanfong H. Lee, Annette L. McVeigh, Esther Bullitt, Stephen J. Savarino, "Monoclonal antibody mapping of neutralizing epitopes on the CfaE adhesin of enterotoxigenic *Escherichia coli* colonization factor antigen I", poster presented at: $4^1$ International Conference on Vaccines for Enteric Diseases, Lisbon, Portugal 2007.

What is claimed is:

1. An isolated antibody that binds to CfaE, the isolated antibody comprising complementarity determining regions (CDRs), the CDRs comprising:

CDR-L1 comprising the amino acid sequence KASQDVSTAVV (Residues 46-57 from SEQ ID NO: 112):

ii) CDR-L2 comprising the amino acid sequence SASYRYT (Residues 72-78 from SEQ ID NO: 112);

iii) CDR-L3 comprising the amino acid sequence LQHFSTPRT (Residues 111-119 from SEQ ID NO: 112):

iv) CDR-H1 comprising the amino acid sequence NYGMN (Residues 175-179 from SEQ ID NO: 112), v) CDR-H2 comprising the amino acid sequence WINTYTGQSTYADDFKG (Residues 194-210 from SEQ ID NO: 112); and vi) CDR-H3 comprising the amino acid sequence MEYGNYENALDY (Residues 243-254 from SEQ ID NO: 112).

2. The isolated antibody of claim 1, wherein said isolated antibody is selected from the group consisting of mouse, chimeric, humanized, and human monoclonal antibodies.

3. The isolated antibody of claim 1, wherein said isolated antibody is a single chain variable fragment (scFv) antibody.

4. The isolated antigen binding protein of claim 2, wherein said chimeric, humanized, and human monoclonal antibodies comprise a human IgG constant region and/or a human immunoglobulin kappa light chain.

5. The isolated antigen binding protein of claim 4, wherein said human IgG constant region is a human IgG1 constant region.

6. The isolated antibody of claim 1, wherein said isolated antibody is a humanized P8D10 VL-VH scFv antibody.

7. A composition comprising one or more of the isolated antibodies of claims 1-3, or 6.

8. The composition of claim 7, wherein said composition is a pharmaceutical composition.

9. The composition of claim 8, wherein said pharmaceutical composition is selected from the group consisting of an ETEC immunogenic composition and an ETEC vaccine formulation and optionally further comprises one or more adjuvants in an amount sufficient to enhance an immune response to the ETEC immunogenic composition and/or the ETEC vaccine formulation.

* * * * *